United States Patent
Smith et al.

(10) Patent No.: US 6,951,545 B2
(45) Date of Patent: Oct. 4, 2005

(54) INTEGRAL SAMPLE COLLECTION TIP

(75) Inventors: Dave Smith, Highland, CA (US); Mike Smith, Redlands, CA (US); Roger Tatum, Riverside, CA (US); Eric Waltzer, Riverside, CA (US); Greg Liang, Rancho Cucamonga, CA (US); Thomas J. Foley, Mission Viejo, CA (US)

(73) Assignee: Lifepoint, Inc., Ontario, CA (US)

( * ) Notice: Subject to any disclaimer, the term of this patent is extended or adjusted under 35 U.S.C. 154(b) by 0 days.

(21) Appl. No.: 10/310,658

(22) Filed: Dec. 4, 2002

(65) Prior Publication Data

US 2003/0153844 A1 Aug. 14, 2003

Related U.S. Application Data

(60) Provisional application No. 60/336,596, filed on Dec. 4, 2001.

(51) Int. Cl.⁷ ............................. A61B 5/00; B65D 81/00
(52) U.S. Cl. ..................................................... 600/573
(58) Field of Search ................................ 600/573, 309, 600/582, 584; 435/17; 514/1, 14; 546/233, 26, 27, 63, 73; 422/68.1, 55, 58, 82.01, 82.02, 82.05

(56) References Cited

U.S. PATENT DOCUMENTS

| | | |
|---|---|---|
| 3,192,954 A | 7/1965 | Gerhold |
| 3,846,075 A | 11/1974 | Cioffi |
| 3,985,155 A | 10/1976 | Nightingale |
| 4,009,005 A | 2/1977 | Johnson |
| 4,031,918 A | 6/1977 | Cagle |
| 4,151,254 A | 4/1979 | Gimovsky |
| 4,585,623 A | 4/1986 | Chandler |
| 5,028,142 A | 7/1991 | Ostoich |
| 5,050,616 A | 9/1991 | Wolf |
| 5,077,017 A | 12/1991 | Gorin |
| 5,183,740 A | 2/1993 | Ligler |
| 5,354,654 A | 10/1994 | Ligler |
| 5,354,655 A | 10/1994 | Ward |
| 6,022,326 A | 2/2000 | Tatum |
| 6,150,178 A | 11/2000 | Cesarczyk |
| 6,566,086 B1 * | 5/2003 | Al Athel et al. ............... 435/17 |
| 6,623,698 B2 * | 9/2003 | Kuo ........................... 600/573 |

FOREIGN PATENT DOCUMENTS

| | | |
|---|---|---|
| JP | 9-5322 A | 1/1997 |
| JP | 2000-9728 A | 1/2000 |

OTHER PUBLICATIONS

Matsumoto, K et al, "Simultaneous determination of glucose, ethanol and lactate in alcoholic beverages and serum by amperometric flow injection analysis with immobilized enzyme reactors" J. Biotech, 1990, vol. 14, pp. 115–126.

Linares, P. et al, "Enzymatic determination of ethanol in saliva by flow injection analysis" J. Pharm and Biomed. Analysis 1987, No. 7, pp. 701–706.

(Continued)

*Primary Examiner*—Max F. Hindenburg
*Assistant Examiner*—Brian Szmal
(74) *Attorney, Agent, or Firm*—Jones Day

(57) ABSTRACT

Assemblies are provided for collecting a sample from a mouth using an integrated sample collection tip. A sample collection assembly includes a sample collection body configured for being placed within the mouth, wherein the sample collection body includes a bore and one or more pores. The sample collection assembly further includes a conduit that disposed within the bore of the sample collection body and that is in fluid communication with the one or more pores. The conduit is bonded within the bore. The sample collection assembly can further include a hand piece that has a tip on which the sample collection body is mounted, and through which the conduit can extend. The pores can include a plurality of micropores. The sample collection body can be hydrophobic, and a hydrophilic surfactant can be disposed on the outer surface of the sample collection body.

30 Claims, 62 Drawing Sheets

OTHER PUBLICATIONS

Armbruster, D.A. et al, "Cloned enzyme donor immunoassay (CEDIA) for drugs-of-abuse screening" Clinical Chemistry 1995, vol. 41, No. 1, pp. 92–98.

Locascio-Brown, L. et al., "Flow Immunoassay Using Solid-Phase Entrapment" Analytical Chem., May 1, 1996, vol. 68, No. 9, pp. 1665–1670.

Jehanli, A. et al, "Blind Trials of an On-Site Saliva Drug Test for Marijuana and Opiates" J. Forensic Sciences 2001, vol. 46, No. 5, pp. 1214–1220.

Stone, A. et al, "Lifepoint, Inc." Wall Street Research (http://www.wallstreetresearch.org/lfpt.html) Dec. 16, 1998.

Rojas, C. "Lifepoint, Inc.: Alone at the Top?" Business Journal (http://www.busjournal.com/content/archives/mar99/corp_prof.html) Mar. 1999.

* cited by examiner

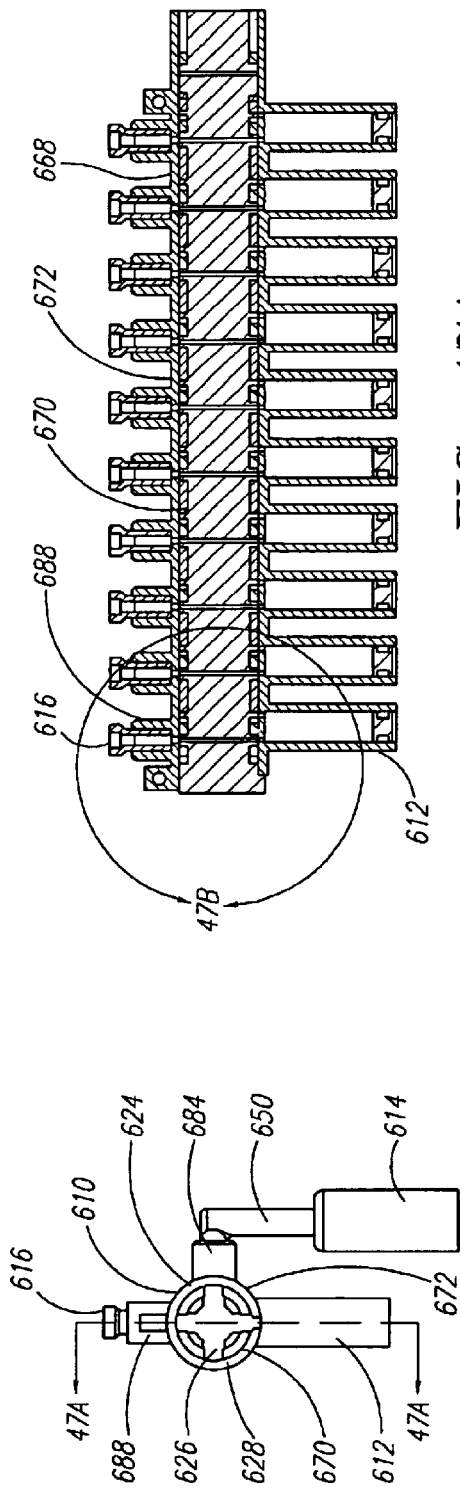
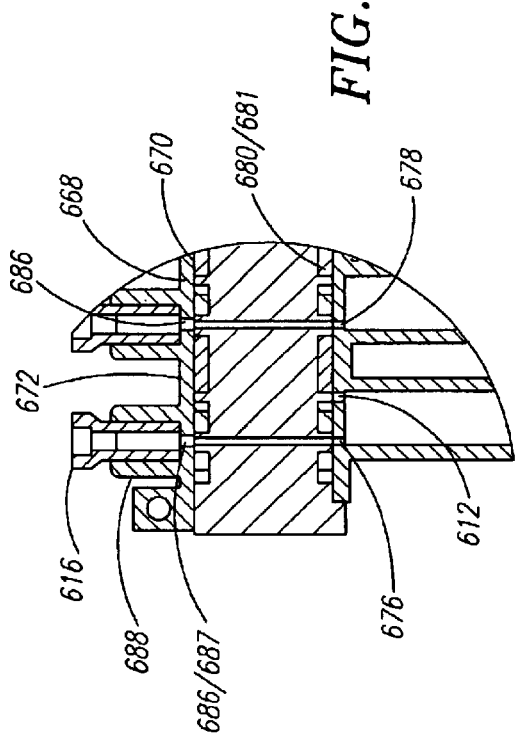
FIG. 47A
FIG. 47B
FIG. 47

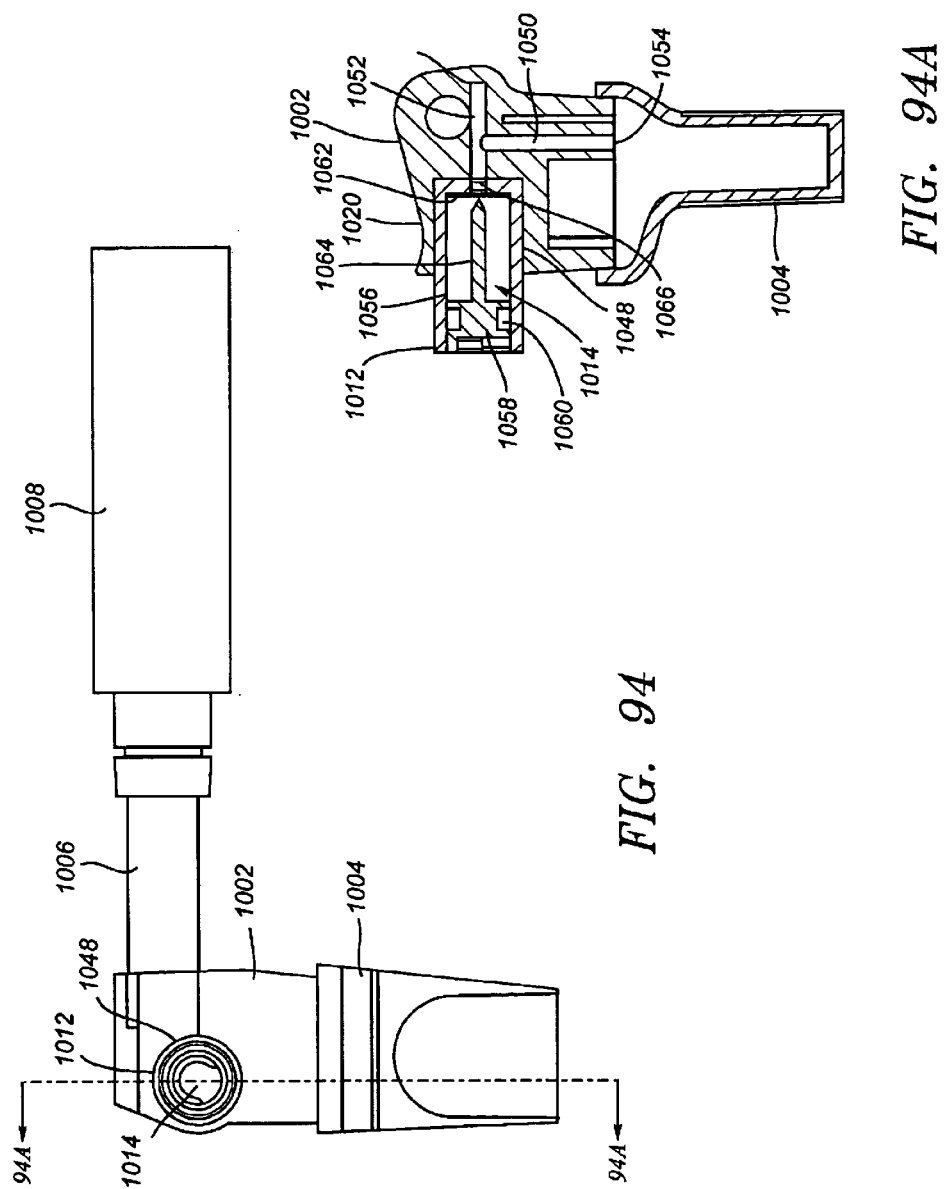

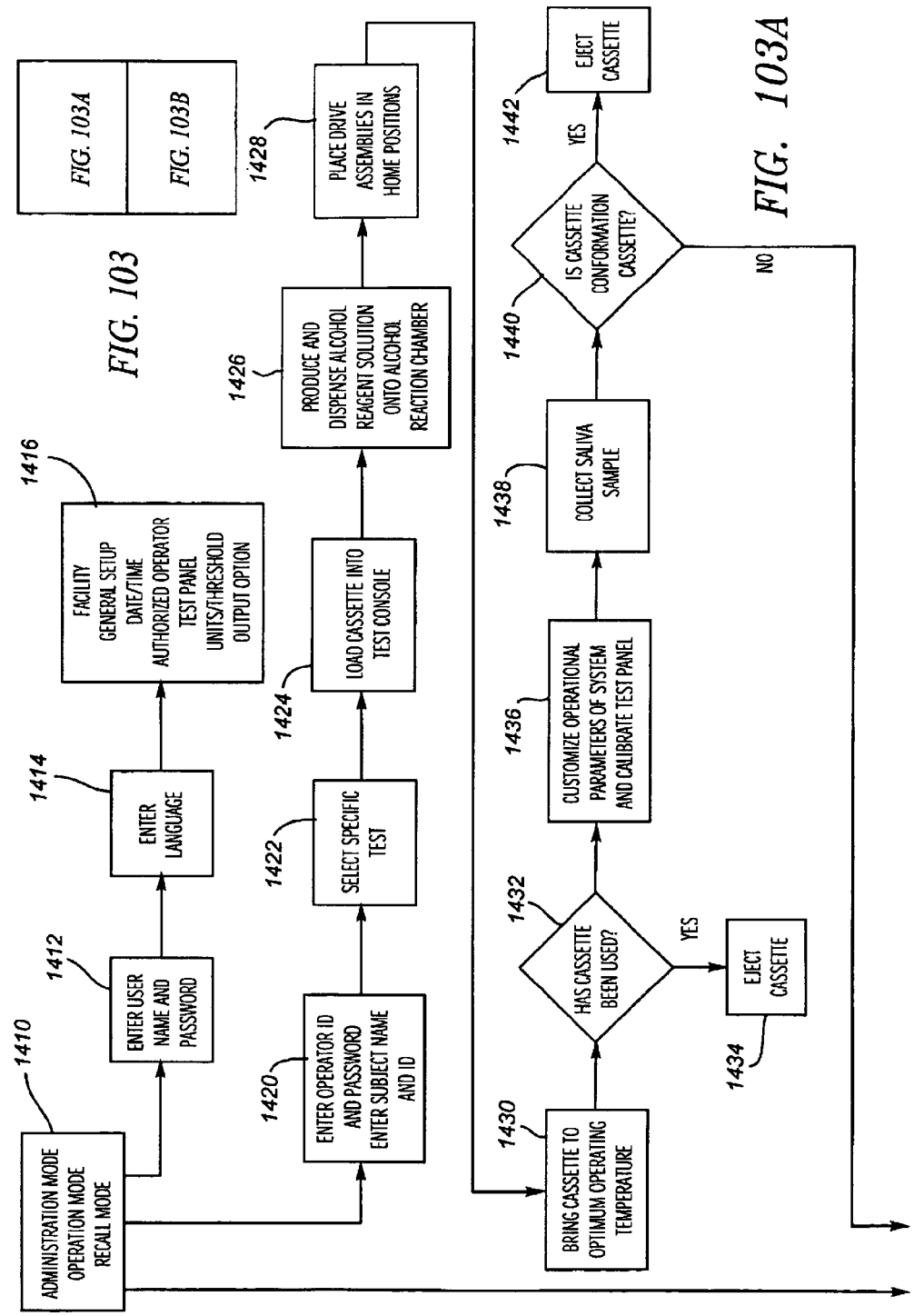

INTEGRAL SAMPLE COLLECTION TIP

RELATED APPLICATIONS

The present application claims priority under 35 U.S.C. 119(e) to U.S. Provisional Application No. 60/336,596 filed Dec. 4, 2001, which is incorporated herein by reference.

TECHNICAL FIELD OF THE INVENTION

The present inventions generally relate to systems, methods, and devices for the identification of analytes in bodily fluids, and in particular, for the identification of drugs, alcohol, and other toxic substances in saliva.

BACKGROUND OF THE INVENTION

The collection of body fluids for diagnostic analysis has long been used in medical, diagnostic, forensic, veterinary medical and other fields to test and monitor for the presence of specific molecules within the fluid. Results of such analyte testing can be used to diagnose medical conditions, and to measure the concentration of pharmaceutical and other drugs or toxic substances in a human or animal subject. Analyte test results can also be used to monitor appropriate levels of therapeutic agents, or for other purposes. A subject's oral fluids may be used to test for a wide variety of types of molecules whose concentration in saliva is related to the circulating concentration of those molecules or related metabolites of substances in the blood. (Malamud, D, *Saliva as a diagnostic fluid,* Br. Med. J., 305, 207–208 (1990); Mandel, I. D, *The diagnostic uses of saliva,* J. Oral Pathol. Med., 19, 119–125 (1990); Mandel, I. D., *Salivary Diagnosis: Promises, Promises,* Malamud, D. and Tabak, L. (eds.); *Saliva as a Diagnostic Fluid,* Vol. 694: Annals of the New York Academy of Sciences, New York: The New York Academy of Sciences (1993), pp.1–8).

Use of saliva as a medium for analysis is desirable since it can be obtained by noninvasive methods, unlike blood product collection methods that involve trained medical personnel and use venipuncture or finger-stick methods of collection. Oral fluid collection can also be done in public without requiring privacy booths, bathroom facilities, and careful subject monitoring otherwise required to avoid adulteration, sample replacement, sample dilution and other problems associated with urine collection. A number of sample collection assemblies and methods have been disclosed. For example, U.S. Pat. No. 6,022,326 issued to Tatum et al., which is fully and expressly incorporated herein by reference, describes a device and method for automatically collecting saliva from a subject through aspiration using a wand with an associated saliva collection tip and a vacuum that flows the saliva from the tip, through the wand, and into a collection chamber. After the saliva sample is collected, it is typically sent to a specialized laboratory for analysis.

Many different assay methods for measuring an analyte in a sample are known in the art. Many of such methods are immunological based, i.e., they involve measuring the binding of an antibody or antibody fragment to a complementary ligand, e.g., a drug or other molecule. Immunoassay methods, in general, are based on the competition between a specific analyte, the concentration of which is to be measured in a sample, and a known amount of tracer, which is generally the analyte or an appropriate analog antigen thereof in labeled form, with the analyte and tracer competing for a limiting number of available binding sites on a binder. U.S. Pat. Nos. 5,183,740 and 5,354,654 issued to Ligler et al., which are hereby fully and expressly incorporated herein by reference, disclose these immunoassay methods in further detail.

Typically, semi-automated or automated systems are used to load and perform immunoassay tests on the saliva samples. The majority of the systems on the market comprise a loading tray for loading multiple samples, which are not necessarily of the same nature or having the same assay performed on them. There is also a reagent tray that holds a number of reagent cartridges for the various different tests to be performed. In the machine, the samples are transferred, normally by pipetting into an assay cell, where the sample is combined with the necessary reagent or reagents. The assay cell is then transferred to a part of a machine where it can be held for sufficient time for the reagent and the sample to combine. Thereafter, the sample cell is transferred to the detector, which detects the presence of a known indicator to determine whether or not the sample contained a particular component and/or how much of that component was present in the assay.

Recent systems have employed flow injection technology, which involves combining the sample in a fluid stream that passes through a reaction column containing a support medium on which antibodies are bound and saturated with a labeled antigen. The fluid stream passes over the support media, where competition between any analytes and the labeled antigen occur. Any displaced labeled antigen passes out through the reaction chamber and into a transparent detection chamber where it is detected and quantified, e.g., by fluorescent means, as an indication of the presence and quantity of the specific analyte to be tested. U.S. Pat. Nos. 5,370,842, 5,779,978, 6,120,734, 6,159,426, as well as previously mentioned U.S. Pat. No. 5,183,740, discuss this flow injection technology in some detail.

The above-described methodologies are sufficient for some applications, e.g., those applications in which time is not critical. For other applications that require portability and/or real-time testing of the sample, e.g., in police stations, emergency rooms, etc., sending a sample to a laboratory for analysis is simply not practical. In response to the need to decrease the amount of time required to obtain test results from a sample, as well as the need to provide more convenient and less expensive diagnostic methods, there have been efforts to develop simple tests to allow unskilled persons to perform certain analytical procedures outside of the laboratory. For example, U.S. Pat. No. 5,145,789 describes a method for testing urine. As previously mentioned, however, there are various problems that are associated with urine collection and testing.

Other methods, such as those described in U.S. Pat. No. 4,703,017, 5,556,789, and 5,714,341, require a two-step process, which involves collecting the specimen, and then manually applying the collected specimen to the analytical device. Thus, at least two operations and devices are necessary with these previous methods. First, collection of the saliva specimen with some type of collection device and, second, application of the saliva specimen to the analytical device described in those inventions. Thus, these methods are disadvantageous in that they are not performed in real time and requires additional handling by users, posing a risk that errors may be unknowingly introduced into the test results.

U.S. Pat. No. 6,248,598 describes a method that collects the saliva and initiates an assay or assays of the saliva in one step. This method, however, requires the use of a saliva absorption technique, which has significant limitations, including slow collection times, risk of irreversible absorption into the carrier membrane, inability to obtain quantitative results, and a limitation of the number of different tests that can be performed on the small sample size.

There thus remains a need for improved systems, methods, and assemblies that test or facilitate in testing bodily fluids for target analytes, e.g., drugs in saliva.

SUMMARY OF THE INVENTION

Tester for Automated Identification of Analytes in Bodily Fluids

The present inventions are also directed to systems, methods, and assemblies for identifying one or more analytes within bodily fluids, such as saliva.

In accordance with a first aspect of the present inventions, a system comprises an analyte tester, an oral aspirator, a conduit that is in fluid communication between the oral aspirator and the tester, and a pump in fluid communication with the conduit. In this manner, the aspirated oral fluid can be pumped directly from the aspirator into the analyte tester for identification of one or more oral fluid analytes. In a non-limiting preferred embodiment, the analyte tester can be a flow immunoassay tester that identifies the five NIDA drugs-of-abuse, and can be configured to identify up to ten different drugs or other analytes. The analyte can also be portable, so that it can be conveniently used areas remote from laboratories. The tester may comprise a chemistry cassette and a test console configured for receiving the chemistry cassette. In this case, the conduit may be in fluid communication with the chemistry cassette. A user interface may also be provided for entering test information (e.g., a specific test selection or test panel customization) and for conveying test results (e.g., using a display or printer).

In accordance with a second aspect of the present inventions, a system comprises an analyte tester that is configured to identify one or more analytes in less than 1 ml of bodily fluid, a sample collection interface device, a conduit that is in fluid communication between the sample collection interface device and the tester, and a pump in fluid communication with the conduit. In this manner, the system can be conveniently used to test for analytes in a subject without the use of a substantial amount of bodily fluid. In a non-limiting preferred embodiment, the pump may be configured for pumping bodily fluid through the conduit at a rate of less than 200 $\mu$L/min. Although other types of bodily fluid can be collected, the sample collection interface device comprises an oral aspirator for collecting saliva from the test subject in the preferred embodiment. Other previously described features can also be incorporated into an embodiment constructed in accordance with the second aspect of the present inventions.

In accordance with a third aspect of the present inventions, a method comprises pumping an oral fluid sample from a subject to an analyte tester, and identifying one or more analytes contained in the oral fluid sample. In a non-limiting preferred method, a flow immunoassay technique can be used to semi-quantitatively or quantitatively identify the five NIDA drugs-of-abuse, and can be modified to test up to ten different drugs or other analytes. The sample can be aspirated from the test subject, and the time that it takes to complete the method can take less than ten minutes.

In accordance with a fourth aspect of the present inventions, a method comprises pumping less than 1 ml of a bodily fluid sample from a subject to an analyte tester, and identifying the one or more analytes contain in the sample.

In a non-limiting preferred method, the sample can be pumped at a rate of less than 200 $\mu$L/min. Although other types of bodily fluid can be pumped from the test subject, oral fluid can be used as the sample. Other previously described features can also be incorporated into a method performed in accordance with the fourth aspect of the present inventions.

In accordance with a fifth aspect of the present inventions, a cassette assembly comprises a chemistry cassette receivable within a test console, and a bodily fluid sample collection assembly configured for being in fluid communication with the chemistry cassette. The chemistry cassette enables the test console to identify one or more bodily fluid analytes. In a non-limiting preferred embodiment, the chemistry cassette can be a fluid immunoassay cassette, and the bodily fluid sample collection assembly can be an oral fluid sample collection assembly that includes an oral aspirator, sample collection chamber, and a conduit in fluid communication between the oral aspirator and the sample collection chamber.

Plunger-based Flow Immunoassay Assembly

The present inventions are also directed to assemblies and methods for flowing sample through a flow immunoassay assembly using one or more plungers.

In accordance with a first aspect of the present inventions, a flow immunoassay assembly comprises an immunoassay reaction chamber, a sample distribution chamber in fluid communication with the immunoassay reaction chamber, and a sample dispense plunger being movable within the sample distribution chamber to dispense the sample from the sample distribution chamber into the immunoassay reaction chamber.

In a non-limiting preferred embodiment, the flow immunoassay assembly can further include a buffer chamber in fluid communication with the immunoassay reaction chamber, and a buffer dispense plunger movable within the buffer chamber to dispense buffer from the buffer chamber into the immunoassay reaction chambers. The preferred flow immunoassay assembly can further include a read cell in fluid communication with the immunoassay reaction chamber for providing a means to measure a reaction within the reaction chamber (which may be a displacement type immunoassay reaction chamber) and a waste chamber in fluid communication with the read cell for storage of hazardous biological fluid. Upper and lower seals can be provided on the buffer chamber for storage of the buffer prior to use, in which case, the buffer dispense plunger can be provided with a stylus that is configured to puncture the upper seal when the buffer dispense plunger is moved toward the upper seal. To automate the preferred immunoassay flow assembly, it can further include a drive assembly mechanically coupled to the sample dispense plunger, and if applicable, the buffer dispense plunger.

In accordance with a second aspect of the present inventions, a flow immunoassay assembly comprises a plurality of immunoassay reaction chambers, a plurality of sample distribution chambers in fluid communication with the plurality of immunoassay reaction chambers, and a plurality of sample dispense plungers being movable within the plurality of sample distribution chambers to dispense the sample from the plurality of sample distribution chambers into the plurality of immunoassay reaction chambers.

In a non-limiting preferred embodiment, the flow immunoassay assembly can further include many of the other features described above, such as buffer chambers, read cells, a waste chamber, and a drive assembly, but can also comprise other features that facilitate the multiple flow paths. For example, the preferred flow immunoassay assembly can include a valve, such as a rotary valve, to selectively place the plurality of sample distribution chambers in fluid communication with the plurality of immunoassay reaction chambers, and if applicable, the plurality of buffer chambers in fluid communication with the plurality of immunoassay reaction chambers. The preferred flow immunoassay assembly can further include a sample/buffer mixing assembly in fluid communication with the plurality of sample distribution chambers, in which case, the mixing assembly is configured for mixing sample and buffer to form a buffered sample solution and distributing the buffered sample solution amongst the sample distribution chambers. The number of sample flow paths, i.e., the number of sample distribution chambers and corresponding immunoassay reaction chambers, can equal five or more, or even ten or more. Similarly, if applicable, the number of buffer flow paths, i.e., the number of buffer chambers and corresponding immunoassay reaction chambers, can equal five or more, or even ten or more.

In accordance with a third aspect of the present inventions, a method of analyzing a sample comprises distributing the sample into a plurality of sample distribution chambers, flowing the sample from the plurality of sample distribution chambers through a plurality of immunoassay reaction chambers by moving a plurality of sample dispense plungers within the plurality of sample distribution chambers, and measuring a reaction with each of the plurality of immunoassay reaction chambers. In a non-limiting preferred method, buffer can be flowed from a plurality of buffer chambers through the plurality of immunoassay reaction chambers by moving a plurality of buffer dispense plungers within the plurality of buffer chambers. The buffer can be flowed through the plurality of immunoassay reaction chambers prior to, during, after the sample flow, and even during sample distribution. The sample flowing through the plurality of immunoassay reaction chambers can produce a analyte detectable sample solution, in which case, the preferred method can further comprise flowing the analyte detectable sample solution through a plurality of read cells and measuring an analyte indicator, such as a labeled antigen, in the analyte detectable sample solution. The sample tested can be bodily fluid, such as saliva.

Automated Plunger-based Sample/buffer Mixing Assembly

The present inventions are also directed to assemblies and methods for mixing a sample and a buffer.

In accordance with a first aspect of the present inventions, a sample/buffer mixing assembly comprises a sample collection chamber, a buffer chamber containing a buffer, a mixing chamber, and one or more plungers. The sample collection chamber is in fluid communication with a sample collection interface device. The mixing chamber comprises a sample port adjacent the sample collection chamber, and a buffer port adjacent the buffer chamber. The one or more plungers is in fluid communication with the sample collection chamber and the buffer chamber, and can be moved to dispense the buffer from the buffer chamber into the mixing chamber via the sample port, and the sample from the sample collection chamber into the mixing chamber via the buffer port. In this manner, the dispensed sample and buffer form a buffered sample solution within the mixing chamber.

In a non-limiting preferred embodiment, the one or more plungers can include a buffer dispense plunger that is movable within the buffer chamber towards the buffer port to dispense the buffer from the buffer chamber into the mixing chamber under positive pressure via the buffer port. The one or more plungers can also include a sample dispense plunger that is movable within the mixing chamber away from the sample port to dispense the sample from the sample collection chamber into the mixing chamber via the sample port. The preferred sample/buffer mixing assembly can be automated by mechanically coupling drive assemblies to the sample and buffer dispense plungers. To ensure that the sample and buffer are mixed, a ferrous element can be provided within the mixing chamber, and a mixing motor can be magnetically coupled to the ferrous element to agitate the buffered sample solution. The preferred sample/buffer mixing assembly can also be used to mix saliva and buffer, in which case, the sample collection chamber is a saliva collection chamber.

In accordance with a second aspect of the present inventions, a method of buffering a sample comprises dispensing the sample into a mixing chamber via a sample port, dispensing buffer into the mixing via a buffer port, and mixing the sample and the buffer in the mixing chamber to form a buffered sample solution. Sample and buffer chambers are moved in fluid communication with the mixing chamber to dispense the sample and buffer within the mixing chamber.

In a non-limiting preferred method, the buffered sample solution may be dispensed from the mixing chamber via a dispense port by moving buffered sample dispense plunger in fluid communication with the mixing chamber, e.g., by moving the buffered sample dispense plunger within the mixing chamber towards the dispense port. The buffered sample solution can be mixed within the mixing chamber simply through the dispensing process, or additionally by a mixing motor. The preferred method can be automated by mechanically coupling drive assemblies to the sample and buffer dispense plungers.

In accordance with a third aspect of the present inventions, a mixing assembly comprises a first chamber containing a first solution, a second chamber containing a second solution, and a third chamber comprising a first port in fluid communication with the first chamber, a second port in fluid communication with the second chamber, and a third port. The mixing assembly further comprises a first plunger disposed within the first chamber, which is movable to dispense the first solution from the first chamber into the third chamber via the first port. The mixing assembly further comprises a second plunger disposed within the third chamber, which is movable to dispense the second solution from the second chamber into the third chamber via the second port to form a fluid mixture with the first and second solutions. The mixing assembly further comprises a third plunger disposed within the third chamber, which is movable to dispense the fluid mixture from the third chamber via the third port.

In a non-limiting preferred embodiment, the mixing assembly can be a sample/buffer mixing assembly, wherein the first, second, and third chambers can be buffer, sample collection, and mixing chambers, the first and second solutions can be buffer and sample, the first, second, and third ports can be buffer, sample, and dispense ports, and the first, second, and third plungers can be buffer, sample, and dispense plungers. The buffer port can have a seal to hold the buffer within the buffer chamber. In this case, the buffered sample dispense plunger can be provided with a stylus that punctures the seal when the buffered sample dispense plunger is moved towards the buffer port. The dispense port can also be provided with one or more through ports for allowing the buffer to flow from the buffer chamber into the mixing chamber. The buffer dispense plunger can be mated with one side of the buffered sample dispense plunger to move the buffered sample dispense plunger towards the dispense port, and the sample dispense plunger can be mated with the other side of the buffered sample dispense plunger to move the buffered sample dispense plunger towards the buffer port to puncture the seal. The mixing chamber can be in axial alignment with the buffer chamber to allow the buffer dispense plunger to engage the buffered sample dispense plunger within the mixing chamber. The buffer chamber can also have a plug that is receivable within the through port of the buffered sample dispense plunger to prevent leakage when the buffered sample dispense plunger is moved towards the dispense port to dispense the buffered sample solution. The buffer port may be a longitudinal port and the sample port may be a lateral port, in which case, one surface of the buffered sample dispense plunger may be adjacent the buffer port and the opposite surface of the buffered sample dispense plunger may be adjacent the sample port. Other previously described features can also be incorporated into an embodiment constructed in accordance with the second aspect of the present inventions.

In accordance with a fourth aspect of the present inventions, a method of mixing first and second fluid using first, second, and third chambers comprises a disposing the first fluid in a first chamber, and disposing the second fluid in a second chamber. The method further comprises moving the first plunger within the first chamber towards first port to dispense the first solution from the first chamber into the third chamber, moving a second plunger within the third chamber away from a second port to dispense the second solution from the second chamber into the third chamber to form a fluid mixture from the first and second solutions, and moving a third plunger within the third chamber towards the third port to dispense the fluid mixture from the third chamber out through the third port.

In a non-limiting preferred embodiment, the first, second, and third chambers can be buffer, sample collection, and mixing chambers, the first and second solutions can be buffer and sample, the first, second, and third ports can be buffer, sample, and dispense ports, and the first, second, and third plungers can be buffer, sample, and dispense plungers. The buffered sample dispense plunger can also be used to puncture a seal on the buffer port prior to dispensing the buffer into the mixing chamber. The buffered sample dispense plunger can be moved towards the dispense port by pushing it with the buffer dispense plunger, or moved towards the buffer port by pushing it with the sample dispense plunger. The sample and buffer can be simultaneously dispensed into the mixing chamber by moving the sample and buffer dispense plungers simultaneously. Other previously described features can also be incorporated into an embodiment constructed in accordance with the second aspect of the present inventions.

Hydrophobic/hydrophilic Sample Collection Tip

The present inventions are also directed to assemblies for collecting oral fluid from a mouth of a subject using a hydrophobic/hydrophilic sample collection tip.

In accordance with a first aspect of the present inventions, a sample collection assembly comprises a sample collection tip configured for being placed within the mouth, and a conduit in fluid communication with the sample collection tips. The sample collection tip comprises a hydrophobic interior and a hydrophilic outer surface. In this manner, the tendency of analytes within the sample to stick to the interior of the sample collection tip is minimized, while allowing wetting of the outer surface of the sample collection tip with the sample to facilitate its collection.

In a non-limiting preferred embodiment, the sample collection assembly can further include a hand piece that has a tip on which the sample collection tip is mounted, and through which the conduit can extend. The sample collection tip can have a bore in which the conduit is disposed, e.g., by bonding. The hydrophobic interior of the sample collection tip can be composed of a microporous material, such as high density polyethylene, and the hydrophobic outer surface of the sample collection can comprise a surfactant. The sample collection tip can have any suitable shape, e.g., hemi-dome shaped.

In accordance with a second aspect of the present inventions, a sample collection assembly comprises a sample collection tip configured for being placed within the mouth, and a conduit in fluid communication with the sample collection tips. The sample collection tip comprises a hydrophobic body and a hydrophilic surfactant disposed on an outer surface of the hydrophobic body. In a non-limiting preferred embodiment, the afore-described features can be incorporated into the sample collection assembly.

In accordance with a third aspect of the present invention, a sample collection assembly comprises a sample collection tip configured for being placed within the mouth, a sample collection chamber, a conduit in fluid communication with between the sample collection tip and the sample collection chamber, and a pump configured to pump sample from the sample collection tip, through the conduit, and into the sample collection chamber. The sample collection tip comprises a hydrophobic interior and a hydrophilic outer surface, which facilitates the wetting of the entire outer surface of the sample collection tip, thereby facilitating pumping of the sample. In a non-limiting preferred embodiment, the afore-described features can be incorporated into the sample collection assembly. Additionally, the pump can use relatively low air flow rates, e.g., between 5–50 ml/min at 350 mmHg absolute, to pump the sample.

Method for Accurately Mixing Sample and Buffer Solutions

The present inventions are also directed to methods for accurately mixing two solutions, e.g., buffer and sample solutions.

In accordance with an aspect of the present inventions, a method of mixing first and second fluids using first, second, and third chambers comprises selecting a fluid mixture r, providing the first chamber with a first cross-sectional area $A_1$, providing the third chamber with a second cross-sectional area $A_2$, disposing the first fluid in the first chamber, disposing the second fluid in the second chamber, moving a first plunger within the first chamber at a speed $S_1$ towards a first port to dispense the first solution from the first chamber into the third chamber, and moving a second plunger substantially simultaneously with the first plunger within the third chamber at a speed $S_2$ away from the second port to dispense the second solution from the second chamber into the third chamber, wherein $A_2S_2=A_1S_1(1+1/r)$.

In a non-limiting preferred method, the sample and buffer can be mixed, in which case, the first, second, and third chambers can be buffer, sample collection, and mixing chambers, and the first and second ports can be buffer and sample ports. The sample and buffer can be equally mixed, in which case, r=1. To effect equal mixing of the sample and buffer, $S_1 S_2$ and $2A_1 \cong A_2$, or alternatively, $A_1 \cong A_2$ and $2S_1 \cong S_2$. The mixing chamber can include a dispense port, in which case, the preferred method can further moving a third plunger, such as buffered sample dispense plunger, towards the dispense port to dispense the fluid mixture from the mixing chamber out through the dispense port, e.g., by pushing it with the buffer dispense plunger. The buffered sample dispense plunger can also be moved within the mixing chamber against the buffer port, e.g., by pushing it with the sample dispense plunger.

The buffer port may include a seal, in which case, the buffered sample dispense plunger can include a stylus that breaks the seal when the buffered sample dispense plunger is seated against the buffer port. When the sample dispense plunger is mated with the buffered sample dispense plunger, it can be adjacent the sample port, allowing the sample to flow through the sample port immediately upon movement of the sample dispense plunger. The buffered sample dispense plunger can include a through port, in which case, the buffer can be dispensed from the buffer chamber into the mixing chamber via the through port. The buffered sample solution can be mixed within the mixing chamber simply through the dispensing process, or additionally by a mixing motor. The preferred method can be automated by mechanically coupling one or more drive assemblies to the sample and buffer dispense plungers.

Flow Immunoassay Assembly With Rotary Valve

The present inventions are also directed methods and assemblies for selectively distributing and dispensing fluids using a rotary valve for purposes such as performing immunoassay testing.

In accordance with a first aspect of the present invention, a rotary valve comprises a stator and rotor disposed within the stator. The rotor is clockable between a dispense configuration, a first auxiliary dispense configuration, and a second auxiliary dispense configuration. When the rotor is clocked in the dispense configuration, it comprises a plurality of dispense channels connected between a plurality of entry dispense ports and a plurality of exit dispense ports disposed in the stator. When the rotor is clocked in the first auxiliary dispense configuration, the rotor comprises a first plurality of auxiliary dispense channels connected between a plurality of auxiliary entry dispense ports disposed on the stator and the plurality of exit dispense ports. When the rotor is clocked in the second auxiliary dispense configuration, the rotor comprises a second plurality of auxiliary dispense channels connected between the plurality of entry dispense ports and the plurality of exit dispense ports. In this manner, a fluid can be flowed through the rotary valve when the rotor is clocked in the dispense configuration, and another fluid can be flowed through the rotary valve when the rotor is clocked in either the first auxiliary or the second auxiliary dispense configuration.

In a non-limiting preferred method, the dispense configuration can be clocked substantially 90° from the first auxiliary dispense configuration and substantially 0° from the second auxiliary dispense configuration, i.e., the dispense configuration and second auxiliary dispense configuration are the same, so that a first and second fluid can be flowed through the rotary valve without requiring rotation of the rotor. The plurality of exit dispense ports can be clocked substantially 180° from the plurality of entry dispense ports and substantially 90° from the plurality of auxiliary entry dispense ports. In this case, the plurality of dispense channels can comprise a plurality of through channels connecting the plurality of entry dispense ports and the plurality of exit dispense ports. The first plurality of auxiliary dispense channels can comprise a plurality of through channels connected to the plurality of auxiliary entry dispense ports, and a plurality of substantially 90° arcuate surface channels connected between the plurality of through channels and plurality of exit dispense ports. The second plurality of auxiliary dispense channels can comprise a plurality of substantially 90° arcuate surface channels connected between the plurality of auxiliary entry dispense ports and the plurality of exit dispense ports.

In accordance with a second aspect of the present inventions, a rotary valve comprises a stator and a rotor disposed within the stator. The rotor is clockable in a distribution configuration, in which case, the rotor comprises a feed channel connecting a feed port to an entry distribution port of a first distribution port pair disposed on the stator. The rotor further comprises a plurality of distribution channels connecting an exit distribution port of each previous distribution port pair to an entry distribution port of each next distribution port pair. In this manner, fluid can be distributed amongst several chambers through a single feed port.

In a non-limiting preferred embodiment, the feed port can be clocked substantially 90° from the first distribution port pair, in which case, the feed channel comprises a through channel connected to the feed port, and a substantially 90° arcuate feed surface channel connected between the through channel and the entry distribution port of the first distribution port pair. The distribution channels can be a plurality of longitudinal surface channels that connect a rectilinear pattern of distribution port pairs. The rotor can further include a vent channel that connects an exit distribution port of the last distribution port pair with a vent port disposed on the stator. The vent port can be clocked substantially 180° from the last distribution port pair, in which case, the vent channel can comprise a first substantially 90° arcuate vent surface channel connected to the exit distribution port of the last distribution port pair, a second substantially 90° arcuate vent surface channel connected to the vent port, and a through channel connecting the first and second arcuate vent channels.

The rotor can further be clocked between the dispense configuration, first auxiliary dispense configuration, and second auxiliary configuration, as hereinbefore described. In this case, the dispense configuration may be clocked 90° from the distribution configuration, the first auxiliary dispense configuration and the distribution configuration may be clocked substantially 0° from each other, and the second auxiliary dispense configuration and dispense configuration may be clocked substantially 0° from each other. Thus, the first auxiliary dispense configuration and the distribution configuration can be the same, so that a fluid can be distributed amongst several chambers and another fluid can be dispensed without rotating the rotor, and the second auxiliary dispense configuration and dispense configuration can be the same, so that the both fluids can be dispensed without rotating the rotor.

In accordance with a third aspect of the present inventions, a flow immunoassay assembly for testing a sample comprises a plurality of sample distribution chambers, a plurality of buffer chambers, and a plurality of immunoassay reaction chambers. The flow immunoassay assembly further comprises a stator and a rotor disposed within the stator. That stator includes a plurality of entry dispense ports in fluid communication with the plurality of sample distribution chambers, a plurality of auxiliary entry dispense ports in fluid communication with the plurality of buffer chambers, and a plurality of exit dispense ports in fluid communication with the plurality of immunoassay reaction chambers. The rotor is clockable between a dispense configuration and a first auxiliary dispense configuration.

When the rotor is clocked in the dispense configuration, it comprises a plurality of dispense channels connected between a plurality of entry dispense ports (and thus, the plurality of sample distribution chambers) and the plurality of exit dispense ports (and thus, the plurality of immunoassay reaction chambers). When the rotor is clocked in the first auxiliary dispense configuration, the rotor comprises a first plurality of auxiliary dispense channels connected between the plurality of auxiliary entry dispense ports (and thus, the plurality of buffer chambers) and the plurality of exit dispense ports (and thus, the immunoassay reaction chambers). In this manner, sample can be flowed from the plurality of sample distribution chambers, through the rotary valve, and into the plurality of immunoassay reaction chambers, when the rotor is clocked in the dispense configuration, and buffer can be flowed from the plurality of buffer chambers, through the rotary valve, and into the plurality of immunoassay reaction chambers, when the rotor is clocked in the first auxiliary dispense configuration.

In a non-limiting preferred embodiment, the rotor can be further clocked in a second auxiliary dispense configuration, in which case, the rotor comprises a second plurality of auxiliary dispense channels connected between the plurality of auxiliary entry dispense ports (and thus, the plurality of buffer chambers) and the plurality of exit dispense ports (and thus, the immunoassay reaction chambers). The different configurations and ports and be clocked in relation to each other in a manner similar to that hereinbefore described, so that a buffer flow can be performed, a sample flow can be performed after clocking the rotor 90°, and then another buffer flow can be performed without clocking the rotor.

In accordance with a fourth aspect of the present inventions, a method of controlling the flow of a sample within a flow immunoassay assembly having a rotary valve, comprises flowing buffer from a plurality of buffer chambers through the plurality of immunoassay reaction chambers while the rotary valve is in a first auxiliary dispense configuration, and flowing the sample from a plurality of sample distribution chambers through the plurality of immunoassay reaction chambers while the rotary valve is in a dispense configuration. In a non-limiting preferred method, the dispense configuration comprises a sample flow configuration, and the first auxiliary dispense configuration comprises a buffer pre-wash configuration, in which case, the plurality of immunoassay reaction chambers is pre-washed with the buffer while the rotary valve is in the buffer pre-wash configuration. The buffer can also be flowed from the plurality of buffer chambers through the plurality of immunoassay reaction chambers while the rotary valve is in a second auxiliary dispense configuration, e.g., a buffer post-wash configuration.

In accordance with a fifth aspect of the present invention, a flow immunoassay assembly comprises a plurality of sample distribution chambers and a plurality of immunoassay reaction chambers. The flow immunoassay assembly further comprises a stator and a rotor disposed within the stator. The stator comprises a feed port, and plurality of distribution port pairs in fluid communication with the plurality of sample distribution chambers, with each of the distribution port pairs comprises an entry distribution port and an exit distribution port. The stator further comprises a plurality of exit dispense ports in fluid communication with the plurality of immunoassay reaction chambers. The rotor is clockable in a distribution configuration, in which case, the rotor comprises a feed channel connecting the feed port to an entry distribution port of a first distribution port pair (and thus, the first sample distribution chamber), and a plurality of distribution channels connecting an exit distribution port of each previous distribution port pair (and thus, the previous sample distribution chamber) to an entry distribution port of each next distribution port pair (and thus, the next sample distribution chambers).

In a non-limiting preferred embodiment, the stator may comprise a vent port, and the rotor may comprise a vent channel connecting an exit distribution port of the last distribution port pair (and thus, the last sample distribution chambers). To provide for sample and buffer flows, the rotor can further be clocked between the dispense configuration, first auxiliary dispense configuration, and second auxiliary configuration, as hereinbefore described. Also, the different configurations and ports can be clocked in relation to each other in a manner similar to that hereinbefore described, so that the sample can be distribution to the sample distribution chambers, the buffer can be flowed through the immunoassay reaction chambers, the sample can be flowed from the sample distribution chambers through the immunoassay reaction chambers after clocking the rotor 90°, and the buffer can be again flowed from the buffer chambers through the immunoassay reaction chambers.

In accordance with an eighth aspect of the present inventions, a method of controlling the flow of sample within a flow immunoassay assembly comprises placing a rotary valve in a distribution configuration, and flowing sample from a sample feed port into a plurality of sample distribution chambers while the rotary valve is in the distribution configuration. In a non-limiting preferred method, the sample can be cascaded into the plurality of sample distribution chambers. Air can further be vented from the plurality of sample distribution chambers via the rotary valve during the sample distribution. The sample can also be prevented from flowing through a plurality of immunoassay reaction chambers when the rotary valve is in the distribution configuration to prevent premature dispensing of the sample. The rotary valve can also be placed into dispense, first auxiliary dispense, and second auxiliary dispense configuration, e.g., sample dispense, buffer pre-wash, and buffer post-wash configurations, to effect the aforementioned sample and buffer flows through the plurality of immunoassay reaction chambers. The distribution and first auxiliary dispense configurations can be clocked substantially 0° from each other, so that the sample distribution and buffer pre-wash can be performed without rotating the rotor. Similarly, the dispense and second auxiliary dispense configuration can be clocked substantially 0° from each, so that the sample dispense and buffer post-wash can be performed without rotating the rotor.

In accordance with a seventh aspect of the present inventions, a flow immunoassay assembly comprises a plurality of sample distribution chambers, a plurality of immunoassay reaction chambers, and a rotary valve clockable between a distribution configuration to place a sample feed port in fluid communication with the plurality of sample distribution chambers, and a dispense configuration to place the plurality of sample distribution chambers in fluid communication with the plurality of immunoassay reaction chambers. In a non-limiting preferred embodiment, the flow immunoassay assembly can further comprise a plurality of buffer chambers, in which case, the rotary valve can be clockable in a first auxiliary dispense configuration to place the plurality of buffer chambers into fluid communication with the plurality of immunoassay reaction chambers, and a second auxiliary dispense configuration to further place the plurality of buffer chambers into fluid communication with the plurality of immunoassay reaction chambers. The rotary valve can be clocked in the distribution configuration to further prevent fluid communication between the plurality of distribution chambers and the plurality of immunoassay reaction chambers, and in the dispense configuration to further prevent fluid communication between the sample feed ort and the plurality of sample distribution chambers.

In accordance with an eighth aspect of the present inventions, a flow immunoassay assembly comprises a plurality of sample distribution chambers, a plurality of buffer chambers, a plurality of immunoassay reaction chambers, and a rotary valve clockable between a dispense configuration to place the plurality of sample distribution chambers into fluid communication with the plurality of immunoassay reaction chambers, and a different first auxiliary dispense configuration to place the plurality of buffer chambers into fluid communication with the plurality of immunoassay reaction chambers. In a non-limiting preferred embodiment, the rotary valve can be placed into a second auxiliary dispense configuration to further place the plurality of buffer chambers in fluid communication with the plurality of immunoassay reaction chambers.

Method of Manufacturing a Self-sealing Chamber

The present inventions are also directed to methods for manufacturing self sealing chambers by interference fitting barriers within the chambers.

In accordance with a first aspect of the present inventions, a method of substantially sealing a chamber, comprises providing a die plate through which a channel extends and a compression plate through which a tapered channel extends. The tapered channel includes a first opening and a second opening opposite the first opening. The second opening is equal to or smaller than the chamber opening. The method further comprises providing a chamber adapter that has a female portion and a passage extending therethrough The method further comprises mating the chamber adapter female portion with a compression plate male portion, and associating the chamber with the chamber adapter passage, e.g., by disposing the chamber within the chamber adapter passage. The method further comprises disposing a compressible material on the die plate and forming the barrier by pushing a pin through the compressible material into the die plate passage. The method further comprises pushing the barrier into the first tapered channel opening, through the tapered channel and into the chamber adapter passage via the second tapered channel opening. Lastly, the method further comprises pushing the barrier through the chamber adapter passage into the chamber opening.

In a non-limiting preferred method, the barrier is pushed through the compression plate tapered channel and chamber adapter passage using the pin. The passages through which the barrier passes are preferably geometrically similar, e.g., circular. In the preferred method, the barrier can be composed of a porous material, suitable for constructing an immunoassay reaction chamber. These steps can be repeated to dispose another barrier within an opening located at the other end of the chamber.

In accordance with a second aspect of the present inventions, a method of substantially sealing a chamber comprises providing a barrier having an uncompressed size larger than an opening at one of the chamber. The method further comprises providing a tool through which a tapered passage extends. The tapered passage includes a first opening and a second opening opposite the first opening. The second opening is equal to or smaller than the chamber opening. The method further comprises associating the chamber opening with the second tapered passage opening, introducing the barrier into the first tapered passage opening, and passing the barrier through the tapered passage, and into the chamber opening via the second tapered passage opening. In this manner, a barrier within an uncompressed diameter greater than the chamber opening can be placed therein and allowed to expand into a compression fit with the chamber. In a non-limiting preferred method, the aforedescribed details can be incorporated therein.

In accordance with a third aspect of the present inventions, a method of manufacturing an immunoassay reaction chamber comprises providing a hollow column with a channel, interference fitting a first porous frit within the column channel, disposing reagent within the column channel, and interference fitting a second porous frit within the column channel, wherein the reagent is contained between the first and second frits. In a non-limiting preferred method, each of the frits has an uncompressed size that is larger than the column channel, and each frit is interference fit within the column channel by disposing the frit within the column channel in a compressed stated, and allowing the frit to expand to generate a compressive force between it and the column channel. Preferably, the compressive force generated by the frit and the column channel is sufficient to hold the frit in place when fluid is flowed through the column channel. Each frit can be disposed within the column in a compressed state by associating the column channel with a tapered passage having a first opening and a second opening equal to or smaller than the column channel. The frit can then be pushed into the first tapered passage opening, through the tapered passage and into the column channel via the second tapered passage opening. The column channel can be cylindrical, in which case, the first and second frits will be circular.

In accordance with a fourth aspect of the present inventions, an immunoassay reaction chamber comprises a hollow column with a channel, a first and second porous frits interference fit within the column channel, and reagent contained within the column channel between the first and second frits. In a non-limiting preferred embodiment, each of the flits has an uncompressed size larger than the column channel, in which case, each frit can be interference fit within the column channel by a compressive force between each frit and the column channel. The column channel can be cylindrical, in which case, the first and second frits will be circular.

Rotary Valve With Compliant Lining

The present inventions are also directed to rotary valves that provide a rotor with a compliant lining.

In accordance with a first aspect of the present inventions, a rotary valve comprises a rigid hollow stator and a rotor disposed within the stator. The rotor comprises a rigid core and a compliant lining injection molded onto the rigid core, wherein the compliant lining is sealingly engaged with an inner bearing surface of the stator and comprises one or more surface channels that can be placed into fluid communication with one or more ports disposed on the stator. In a non-limiting preferred embodiment, the rigid core is composed of polycarbonate and the compliant lining is composed of polyurethane. The surface channels can be, e.g., arcuate or longitudinal surface channels. The rigid core can comprise one or more through channels, in which case, the one or more surface channels can intersect the one or more through channels to form a continuous channel.

In accordance with a second aspect of the present inventions, a rotor for a rotary valve comprises a rigid core and a compliant lining injection molded onto the rigid core, wherein the compliant lining comprises one or more surface channels. In a non-limiting preferred embodiment, the previously mentioned detailed features can be incorporated into the rotor.

In accordance with a third aspect of the present inventions, a rotary valve comprises a rigid hollow stator and a rotor disposed within the stator. The rotor comprises a rigid core including a ridge and a compliant lining injection molded onto the ridge to form a surface channel. The compliant lining is sealingly engaged with an inner bearing surface of the stator, and the surface channel can be placed into fluid communication with the flow port.

In a non-limiting preferred embodiment, the rigid core can comprise a plurality of equidistant arcuate ridges, in which case, the compliant lining can be injection molded onto the plurality of arcuate ridges to form a plurality of arcuate surface channels that can be placed into fluid communication with a plurality of flow ports disposed on the stator. The rigid core can also comprise a longitudinal ridge that intersects the plurality of arcuate ridges, in which case, the compliant lining can be injection molded onto the longitudinal ridge to form a longitudinal surface channel that can be placed into fluid communication with another flow port disposed on the stator, or even a plurality of longitudinal surface channels that can be placed into fluid communication with another plurality of flow ports disposed on the stator.

Each ridge can have a pair of opposing lateral surfaces and an adjacent circumferential surface. The compliant lining can be injection molded onto the opposing lateral surfaces of the ridge, while leaving the circumferential surface of the ridge exposed, to form the surface channel. The compliant lining can also have a surface channel stop, in which case, the ridge has another pair of opposing lateral surfaces and another adjacent circumferential surface. The compliant lining can be can be injection molded onto the other opposing lateral surface and the other adjacent circumferential surface of the ride to form the surface channel stop.

In accordance with a fourth aspect of the present inventions, a rotor for rotary valve comprises a rigid core including a ridge, and a compliant lining injection molded onto the ridge to form a surface channels. In a non-limiting preferred embodiment, the previously mentioned detailed features can be incorporated into the rotor.

Flow Immunoassay Assembly With Multiple Flow Channels

The present inventions are also directed to methods and assemblies for flowing a single sample through a plurality of immunoassay reaction chambers.

In accordance with a first aspect of the present inventions, a flow immunoassay assembly for testing a single sample, comprises a sample feed port, a plurality of immunoassay reaction chambers for performing a plurality of different assays on the sample, a plurality of sample flow channels in fluid communication between the sample feed port and the plurality of immunoassay reaction chambers, and one or more sample drive assemblies configured to pump the sample through the plurality of sample flow channels into the plurality of immunoassay reaction chambers. In this manner, several immunoassay tests can be simultaneously performed on the sample.

In a non-limiting preferred embodiment, the flow immunoassay assembly can further comprise a plurality of buffer flow channels in fluid communication with the plurality of immunoassay reaction chambers, and one or more buffer drive assemblies configured to pump the buffer through the plurality of buffer flow channels into the plurality of immunoassay reaction chambers. The preferred flow immunoassay assembly can further comprise a plurality of sample distribution chambers configured to receive the sample from the sample feed port, and a plurality of buffer chambers containing the buffer. The preferred flow immunoassay assembly can further comprise a plurality of sample dispense plungers disposed within the plurality of sample distribution chambers, and a plurality of buffer dispense plungers disposed within the plurality of buffer chambers, in which case, the one or more sample drive assemblies can have a plurality of sample dispense plunger drivers that are configured to move the plurality of sample dispense plungers within the plurality of sample distribution chambers to pump the sample, and the one or more buffer drive assemblies can have a plurality of buffer dispense plunger drivers that are configured to move the plurality of buffer dispense plungers within the plurality of buffer chambers to pump the buffer.

A valve, such as a rotary valve, can be used to selectively place the sample feed port in fluid communication with the plurality of sample distribution chambers, for selectively placing the plurality of distribution chambers in fluid communication with the plurality of immunoassay reaction chambers, and for selectively placing the plurality of buffer chambers in fluid communication with the plurality of immunoassay reaction chambers. The number of sample flow channels and buffer flow channels can be, e.g. five or more.

In accordance with a second aspect of the present inventions, a method of analyzing a single sample comprises pumping sample from a sample feed port into a plurality of sample distribution chambers, and pumping the sample from the sample distribution chambers through a plurality of immunoassay reaction chambers for performing a plurality of different assays on the sample, and measuring a reaction occurring in the plurality of immunoassay reaction chambers. In a non-limiting preferred method, a plurality of analyte detectable sample solutions are produced within the plurality of immunoassay reaction chambers, in which case, the reactions can be measured by flowing the plurality of analyte detectable sample solutions through a plurality of read cells, and measuring a plurality of analyte indicators, e.g., different labeled antigen, in the plurality of analyte detectable sample solutions. The preferred method further comprises pumping buffer from a plurality of buffer chambers through the plurality of immunoassay reaction chambers.

In accordance with a third aspect of the present inventions, a flow immunoassay assembly for testing a single sample, comprises a sample feed port, a first plurality of immunoassay reaction chambers, a first plurality of sample flow channels in fluid communication with the first plurality of reaction chambers, and a first sample drive assembly configured to pump the sample through the first plurality of sample flow channels into the first plurality of immunoassay reaction chambers. The flow immunoassay assembly further comprises a second plurality of immunoassay reaction chambers, a second plurality of sample flow channels in fluid communication with the second plurality of reaction chambers, and a second sample drive assembly configured to pump the sample through the second plurality of sample flow channels into the second plurality of immunoassay reaction chambers. In this manner, the sample flow rate and volume can be independently controlled through the first and second pluralities of sample flow channels.

In a non-limiting preferred embodiment, the flow immunoassay assembly can further include a first plurality of buffer flow channels in fluid communication with the first plurality of reaction chambers, and a first buffer drive assembly configured to pump the buffer through the first plurality of buffer flow channels into the first plurality of immunoassay reaction chambers. The preferred flow immunoassay assembly can further include a second plurality of buffer flow channels in fluid communication with the second plurality of reaction chambers, and a second buffer drive assembly configured to pump the buffer through the second plurality of buffer flow channels into the second plurality of immunoassay reaction chambers. In this manner, the buffer flow rate and volume can be independently controlled through the first and second pluralities of buffer flow channels. The preferred flow immunoassay assembly can further include many of the other features described above, such sample distribution chambers, buffer chambers, read cells, sample dispense plungers, sample dispense plunger drivers, buffer dispense plungers, and buffer dispense plunger drivers.

In accordance with a fourth aspect of the present inventions, a method of analyzing a sample comprises pumping sample through a first plurality of immunoassay reaction chambers using a first sample drive assembly, pumping the sample through a second plurality of immunoassay reaction chambers using a second sample drive assembly, and measuring a reaction within each of the first and second pluralities of immunoassay reaction chambers.

In a non-limiting preferred method, a first plurality of analyte detectable sample solutions can be produced within the first plurality of immunoassay reaction chambers, and a second plurality of result solutions can be produced within the second plurality of immunoassay reaction chambers, in which case, the reactions can be measured by flowing the first and second pluralities of analyte detectable sample solutions through first and second pluralities of read cells, and measuring first and second pluralities of analyte indicators, e.g., different labeled antigen, in the first and second pluralities of analyte detectable sample solutions. The sample can be pumped through the first and second pluralities of immunoassay reaction chambers at substantially different rates and/or different quantities. The preferred method may further comprise pumping buffer through the first plurality of immunoassay reaction chambers using a first buffer drive assembly, and pumping buffer through the second plurality of immunoassay reaction chambers using a second buffer drive assembly.

Immunoassay Chemistry Cassette Barcode for System Customization

The present inventions are also directed to assemblies, systems, and methods for using a chemistry cassette barcode to obtain information associated with the cassette.

In accordance with a first aspect of the present inventions, a barcode assembly for use with an analyte testing system comprises a barcode affixed to the chemistry cassette, and the barcode assembly further comprises a barcode reader mounted within a test console of an analyte testing system. The barcode comprises information associated with the chemistry cassette, and the barcode reader is configured for scanning the barcode when the chemistry cassette is received within the test console. In the non-limiting preferred embodiment, the barcode information can indicate a test panel contained within the chemistry cassette, e.g., the NIDA drugs-of-abuse test panel, a date of manufacture of the chemistry cassette, test calibration information, and/or information indicating whether the chemistry cassette has been previously used, e.g., a checksum code.

In accordance with a second aspect of the present inventions, a method of obtaining information within an analyte testing system comprises receiving a chemistry cassette within a test console, and scanning a barcode containing information associated with the chemistry cassette. In the non-limiting preferred method, the barcode information can indicate the previously described parameters of the system. The preferred method may further comprise preventing the chemistry cassette from being used within the test console if the barcode information indicates that the chemistry cassette has been previously used.

In accordance with a third aspect of the present inventions, a self-customizing analyte testing system comprises a test console, a chemistry cassette receivable within the test console, a barcode affixed to the chemistry cassette, a barcode reader configured for scanning the barcode, and circuitry electrically coupled to the barcode reader for modifying one or more operational parameters of the testing system based on information contained in the barcode.

In a non-limiting preferred embodiment, the barcode reader and circuitry, which can be a CPU, can be contained in the test console, and the barcode reader can be configured to scan the barcode while the chemistry cassette is received within the test console. The circuitry can be configured to modify one or more testing parameters for each analyte of a multi-analyte test panel. For example, if the barcode information comprises test calibration information, the circuitry can be configured to calibrate the test panel using the test calibration information. If the testing system comprises a flow immunoassay assembly, the circuitry can be configured to modify each of the plurality of flow channels, e.g., by modifying the flow volume or flow rate.

In accordance with a fourth aspect of the present inventions, a method of customizing an analyte testing system comprises receiving a chemistry cassette within a test console, scanning a barcode containing information associated with the chemistry cassette, and modifying one or more operational parameters based on the barcode information. In a non-limiting preferred method, the testing system can be customized by modifying one or more testing parameters for each analyte of a multi-analyte test panel as previously described. For example, a test panel can be calibrating using test calibration information obtained from the barcode, or a plurality of flow channels within a flow immunoassay assembly can be modified.

In accordance with a fifth aspect of the present inventions, a self-customizing multi-analyte flow immunoassay testing system comprises a flow immunoassay assembly, a barcode comprising information associated with the flow immunoassay assembly, a barcode reader configured for scanning the barcode, and control circuitry electrically coupled to the barcode reader. The flow immunoassay assembly comprises a plurality of flow channels corresponding to a plurality of analytes to be tested, and the control circuitry is configured to modify one or more flow channel parameters for each of the plurality of flow channels, based on the barcode information. In the non-limiting preferred embodiment, the control circuitry comprises a CPU that is configured for modifying the flow rate and/or volume of the flow channels.

In accordance with a sixth aspect of the present inventions, a method of customizing a multi-analyte flow immunoassay testing system comprises scanning a barcode comprising information associated with the flow immunoassay assembly, and modifying one or more flow channel parameters for each of a plurality of flow channels based on the barcode information. In a non-limiting preferred method, the flow rate and/or flow volume of the flow channels are modified.

Drug and Alcohol Assay Assembly

The present inventions are also directed to assemblies and methods for performing an assay on a sample for drugs and alcohol.

In accordance with a first aspect of the present inventions, a drug and alcohol assay assembly comprises a sample feed port, and immunoassay reaction chamber containing a drug reagent, and a first sample flow channel in fluid communication between the sample feed port and the immunoassay reaction chamber. The assembly further comprises an alcohol reaction chamber configured for containing an alcohol reagent, and a second sample flow channel in fluid communication between the sample feed port and the alcohol reaction chamber.

In a non-limiting preferred embodiment, the assembly can further comprise a first buffer flow channel in fluid communication with the immunoassay reaction chamber, a second buffer flow channel in fluid communication with the alcohol reaction chamber, and a reagent chamber disposed within the buffer flow channel. The reagent chamber can contain dry alcohol reagent. In this case, the alcohol reagent can comprise a reagent solution, where the reagent chamber is configured to produce the reagent solution for dispensing in the alcohol reaction chamber when buffer flows through the buffer flow channel. The drug reagent can be specific to one of the NIDA drugs-of-abuse.

In accordance with a second aspect of the present inventions, a drug and alcohol assay assembly comprises an immunoassay reaction chamber containing a drug reagent, a first sample chamber in fluid communication with the immunoassay reaction chamber, and being configured for containing sample, an alcohol reaction chamber configured for containing an alcohol reagent, and a second sample chamber in fluid communication with the immunoassay reaction chamber, and being configured for containing the sample.

In a non-limiting preferred embodiment, the assembly can further comprises a sample feed port in fluid communication with the first and second sample chamber. The preferred assembly can further comprise a sample dispense plunger disposed within the first sample chamber, and can be movable to dispense the sample from the first sample chamber into the immunoassay reaction chamber. The preferred assembly can further comprise an air flow port in communication with the second sample chamber, and can be configured to dispense the sample from the second sample chamber into the alcohol reaction chamber when air is flowed through the air flow port. The preferred assembly can further comprise a valve for selectively placing the first sample chamber in fluid communication with the immunoassay reaction chamber, and for selectively placing the second sample chamber in fluid communication with the alcohol reaction chamber. The valve can be a rotary valve, in which case, it can include a stator and a rotor disposed within the stator, wherein the second sample chamber comprises a shear valve formed within the rotor.

The preferred assembly can further comprise a first buffer chamber that contains buffer and is in fluid communication with the immunoassay reaction chamber, a second buffer chamber, and a reagent chamber in fluid communication between the second buffer chamber and the alcohol reaction chamber. In this case, the preferred assembly can further comprise a first buffer dispense plunger movable within the first buffer chamber to dispense buffer from the first buffer chamber into the immunoassay reaction chamber to hydrate dry drug reagent therein. The preferred assembly can further comprise a second a second buffer dispense plunger movable within the second buffer chamber to dispense the buffer from the second buffer chamber through the immunoassay reaction chamber to hydrate dry alcohol reagent therein, wherein a reagent solution is produced and dispensed into the alcohol reaction chamber.

In accordance with a third aspect of the present inventions, a method of performing a drug and alcohol assay, comprises flowing sample into an immunoassay reaction chamber containing a drug reagent, reacting the sample and the drug reagent, flowing the sample into an alcohol reaction chamber containing an alcohol reagent, and reacting the sample and the alcohol reagent.

In a non-limiting preferred method, the method can further comprise flowing a first buffer into the immunoassay reaction chamber to produce a hydrated drug reagent, flowing a second buffer through a reagent chamber to produce an alcohol reagent solution, and flowing the alcohol reagent solution into the alcohol reaction chamber. The sample and first buffer can be pumped into the immunoassay reaction chamber, and the sample and second buffer can be pumped into the alcohol reaction chamber.

In accordance with a fourth aspect of the present inventions, a flow immunoassay and alcohol detection assembly comprises an immunoassay reaction chamber containing a drug reagent, a first sample chamber in fluid communication with the immunoassay reaction chamber, a read cell in fluid communication with the immunoassay reaction chamber, a first energy source configured to transmit energy through the read cell, and a first energy detector configured to receive energy from the read cell. The assembly further comprises an alcohol reaction chamber configured for containing an alcohol reagent, a second sample chamber in fluid communication between the sample feed port and the immunoassay reaction chamber, a second energy source configured to transmit energy through the alcohol reaction chamber, and a second energy detector configured to receive energy from the alcohol reaction chamber. The assembly also comprises processing circuitry configured for determining a presence of a drug in the sample based on the energy received by the first energy detector, and configured for determining a presence of alcohol in the sample based on the energy received by the second energy detector.

In a non-limiting preferred embodiment, the aforedescribed features can be incorporated into the assembly. The preferred assembly can further comprise a calibrator chamber in fluid communication with the alcohol reaction chamber, and a calibrator dispense plunger movable within the calibrator chamber dispense calibrator solution having a predetermined quantity of alcohol from the calibrator chamber into the alcohol reaction chamber to react with the reagent solution. The first and second energy sources can be optical sources, and the first and second energy detectors can be optical detectors.

In accordance with a fifth aspect of the present inventions, a method of analyzing a sample comprises flowing the sample through an immunoassay reaction chamber, wherein the immunoassay reaction chamber produces a drug detectable sample solution containing a drug indicator, measuring the drug indicator, and determining a presence of a drug analyte within the sample based on the measured drug indicator. The method further comprises flowing the sample into an alcohol reaction chamber containing an alcohol reagent, wherein the alcohol reaction chamber produces an alcohol detectable sample solution containing an alcohol indicator, measuring the alcohol indicator, and determining a presence of alcohol within the sample based on the measured alcohol indicator.

In a non-limiting preferred method, the drug indicator can emit optical energy when excited, and the alcohol indicator measuring comprises optically exciting the displaced labeled antigen to emit optical energy and measuring the emitted optical energy. The alcohol indicator can exhibit an optical absorbance value at a specific optical wavelength, wherein the alcohol indicator measuring comprises transmitting optical energy through the alcohol detectable sample solution at the specified wavelength, and measuring the transmitted optical energy after it is transmitted through the alcohol detectable sample solution. The preferred method can further comprise flowing a first buffer into the immunoassay reaction chamber to produce a hydrated drug reagent, wherein the sample reacts with the hydrated drug reagent to produce the drug detectable sample solution, flowing a second buffer through a reagent chamber to produce an alcohol reagent solution, and flowing the alcohol reagent solution into the alcohol reaction chamber, wherein the sample reacts with the alcohol reagent solution to produce the alcohol detectable sample solution. The method can further comprising flowing a calibrator solution containing a predetermined quantity of alcohol into said alcohol reaction chamber to produce an alcohol detectable calibration solution containing an initial alcohol indicator, measuring the initial alcohol indicator, and calibrating the alcohol detectable sample solution.

Flow Immunoassay Scanning Assembly

The present inventions are also directed to methods and assemblies for scanning a flow immunoassay assembly.

In accordance with a first aspect of the present inventions, a flow immunoassay scanning assembly comprises a plurality of immunoassay reaction chambers, a plurality of read cells in fluid communication with the plurality of immunoassay reaction chambers, a detector having a sensing beam, and a scanning drive assembly configured to translate the detector to intersect the plurality of read cells with the sensing beam. In a non-limiting preferred embodiment, the detector comprises an optical detector, and each of the immunoassay reaction chambers contains fluorescent labeled antigen that is displaced when an analog to the fluorescent labeled antigen flows through the immunoassay reaction chamber. Thus, the fluorescent labeled antigen can be detected by the optical detector when flowed through the corresponding read cell. The detector can also be configured, such that the sensing beam intersects the plurality of read cells at an angle substantially perpendicular to the longitudinal axes of the read cells. The scanning drive assembly can be configured to translate the detector to repeatedly intersect the plurality of read cells with the sensing beam.

In accordance with a second aspect of the present inventions, a method of testing the presence of a plurality of target analytes in a sample comprises producing a plurality of immunoassay flow paths containing the sample, wherein an analyte indicator is produced in each of the plurality of immunoassay flow paths in the presence of a corresponding target analyte. The method further comprises detecting any of the plurality of analyte indicators in the plurality of immunoassay flow paths by scanning a sensing beam across the plurality of immunoassay flow paths.

In a non-limiting preferred method, the sensing beam comprises an optical sensing beam, and the analyte indicator comprises a fluorescent labeled antigen. The sensing beam can be scanned substantially perpendicular to the direction of the flow paths and repeatedly across the plurality of flow paths. The preferred method can further comprise outputting a plurality of signals based on the detection of any analyte indicators within the plurality of immunoassay flow paths, and processing the output signals to detect the present of the plurality of target analytes within the sample. The preferred method can further comprise detecting a location of each of the plurality of read cells, in which case, the detected analyte indicator is only processed when a location of a corresponding one of the plurality of read cells is detected.

In accordance with a third aspect of the present inventions, a flow immunoassay scanning assembly comprises a plurality of immunoassay reaction chambers, a plurality of read cells in fluid communication with the plurality of immunoassay reaction chambers, and a detector having a sensing beam. The flow immunoassay scanning assembly further comprises a scan head mechanism to which the detector and transmitter are mounted, and a scanning drive assembly configured to translate the detector and the transmitter to intersect the plurality of read cells with the sensing beam and energy beam.

In a non-limiting preferred embodiment, the detector can be an optical detector, and the transmitter can be an optical source, e.g., a laser, in which case, the analyte indicator can comprise fluorescent labeled antigen that is exited by the laser beam into fluorescence. The detector may be configured, such that the sensing beam intersects the plurality of read cells at an angle substantially perpendicular to the longitudinal axes of the read cells, and the transmitter is configured, such that the laser beam travels through the read cells at an angle substantially parallel to the longitudinal axes of the read cells. The scanning drive assembly can be configured to translate the detector and transmitter to repeatedly intersect the plurality of read cells with the sensing beam and energy beam. The preferred embodiment may also comprise a read cell detector fixably coupled to the scan head mechanism and configured to sense a location of each of the plurality of read cells, and processing circuitry for processing an output of the detector only when the read cell detector senses the location of each of the plurality of read cells. To facilitate detection of the read cells, read cell indicators, e.g., notches, can be spaced a distance equal to the distance in which the read cells are spaced. The scanning drive assembly can further comprise a rail that extends along the plurality of read cells, and a runner on which the scan head mechanism is fixably coupled.

In accordance with a fourth aspect of the present inventions, a method of detecting the presence of a plurality of target analytes in a sample comprises producing a plurality of immunoassay flow paths containing the sample, wherein an analyte indicator is produced in each of the plurality of immunoassay flow paths in the presence of a corresponding target analyte, exciting the plurality of analyte indicators by scanning an energy beam across the plurality of immunoassay flow paths, and detecting any of the plurality of excited analyte indicators in the plurality of immunoassay flow paths by scanning a sensing beam across the plurality of immunoassay flow paths. In a non-limiting preferred method, the sensing beam can comprise an optical sensing beam, and the energy beam can comprise an optical energy beam, such as a laser beam. The preferred method can further include scanning the sensing beam substantially perpendicular to the direction of the flow paths, and the energy beam scanned substantially parallel to the direction of the flow paths. The preferred method can further include scanning the sensing and energy beams simultaneously and repeatedly across the plurality of immunoassay flow paths.

Orthogonal Read Assembly

The present inventions are also directed to methods and assemblies for transmitting and detecting energy within a read cell.

In accordance with a first aspect of the present inventions, an orthogonal read assembly comprises an immunoassay reaction chamber, a read cell having a lumen in fluid communication with the immunoassay reaction chamber, a transmitter configured to transmit energy through the lumen, and a detector configured to sense energy emitted transversely from the lumen. In a non-limiting preferred embodiment, the transmitter can comprise an optical transmitter, such as a laser, and the detector can comprise an optical detector, e.g., a silicon diode. The optical transmitter can transmit optical energy at an oblique entry angle to the lumen, e.g., 45°, and the optical energy can be sensed by the optical detector at an angle substantially perpendicular to the lumen. The read cell can be composed of a transparent plastic and can be parallel-pipe shaped. The lumen can be cylindrically shaped and may include an optical transmission port, in which case, the optical transmitter can be configured to transmit the optical energy through the lumen via the optical transmission port.

In accordance with a second aspect of the present inventions, an orthogonal read assembly comprises an immunoassay reaction chamber containing labeled antigen that is displaced when an analog to the labeled antigen flows through the immunoassay reaction chamber, a read cell comprising a lumen in fluid communication with the immunoassay reaction chamber, a transmitter configured to transmit energy through the lumen to excite the labeled antigen to transversely emit energy from the lumen, and a detector configured to sense the transversely emitted energy from the labeled antigen. In a non-limiting preferred embodiment, any of the afore-described detail features can be incorporated into the orthogonal read assembly.

In accordance with a third aspect of the present inventions, a method of sensing an analyte within a sample comprises flowing the sample through an immunoassay reaction chamber to displace labeled antigen from the immunoassay reaction chamber, flowing displaced labeled antigen through a lumen of a read cell, transmitting energy along the lumen to excite the labeled antigen into transversely emitting energy from the lumen, and sensing the transversely emitted energy. In a non-limiting preferred method, any of the afore-described detailed features can be incorporated into the steps of the method.

Integral Sample Collection Tip

The present inventions are also directed to assemblies for collecting a sample from a mouth using an integrated sample collection tip.

In accordance with a first aspect of the present inventions, a sample collection assembly comprises a sample collection body configured for being placed within the mouth, wherein the sample collection body comprises a bore and one or more pores. The sample collection assembly further comprises a conduit that disposed within the bore of the sample collection body and that is in fluid communication with the one or more pores. In a non-limiting preferred embodiment, the conduit is bonded within the bore. The sample collection assembly can further include a hand piece that has a tip on which the sample collection body is mounted, and through which the conduit can extend. For example, the rear surface of the sample collection body can be bonded to the front surface of the sample collection tip. The one or more pores can comprise a plurality of micropores. The sample collection body can be hydrophobic, and a hydrophilic surfactant can be disposed on the outer surface of the sample collection body.

In accordance with a second aspect of the present inventions, a sample collection assembly comprises a sample collection body configured for being placed within the mouth, wherein the sample collection body comprises a bore and one or more pores. The sample collection assembly further comprises a conduit that bonded within the bore of the sample collection body and that is in fluid communication with the one or more pores. The adhesive force between the conduit and the bore is greater than the cohesive force of the sample collection body. In a non-limiting preferred embodiment, the sample collection assembly can further include a hand piece that has a tip on which the sample collection body is mounted, and through which the conduit can extend. For example, the rear surface of the sample collection body can be bonded to the front surface of the sample collection tip. The adhesive force between the rear surface of the sample collection body and the front surface of the hand piece tip can be greater than the cohesive force of the sample collection body. The one or more pores can comprise a plurality of micropores. The sample collection body can be hydrophobic, and a hydrophilic surfactant can be disposed on the outer surface of the sample collection body.

In accordance with a third aspect of the present invention, a sample collection assembly comprises a sample collection body configured for being placed within the mouth, a sample collection chamber, a conduit in fluid communication with between the sample collection body and the sample collection chamber, and a pump configured to pump sample from the sample collection body, through the conduit, and into the sample collection chamber. The sample collection body comprises a bore and one or more pores, and the conduit is bonded within the bore of the sample collection body in fluid communication with the one or more pores. The adhesive force between the conduit and the bore is greater than the cohesive force of the sample collection body. In a non-limiting preferred embodiment, the afore-described features can be incorporated into the sample collection assembly.

Alcohol Detection Assembly

The present inventions are also directed to assemblies and methods for detecting alcohol using a reconstituted reagent solution.

In accordance with a first aspect of the present inventions, an alcohol reaction assembly comprises an alcohol reaction chamber, a reagent chamber in fluid communication with the alcohol reaction chamber, and a buffer chamber in fluid communication with the reagent chamber. The alcohol reaction assembly further includes a buffer dispense plunger disposed within the buffer chamber for dispensing buffer from the buffer chamber, through the reagent chamber, and into the alcohol reaction chamber, where it hydrates dry reagent therein to produce a reagent solution. The alcohol reaction assembly further includes a calibrator chamber in fluid communication with the alcohol reaction chamber, and a calibrator dispense plunger disposed within the calibrator chamber to dispense a predetermined quantity of alcohol into the alcohol reaction chamber. The alcohol reaction assembly also includes a sample chamber in fluid communication with the alcohol reaction chamber, and being configured for containing a sample.

In a non-limiting preferred embodiment, the alcohol reaction assembly comprises buffer and calibrator drive assemblies can be mechanically coupled to the buffer and calibrator dispense plungers to automate them. The components of the alcohol reaction assembly can also be arranged in a cassette and test console. For example, the chambers and plungers can be contained with the cassette, whereas the drive assemblies can be contained within the test console. In this case, the buffer drive assembly can include a cassette loading drive assembly that is configured to load the cassette into the test console, and a buffer driver that is fixed within the test console and is configured to move the buffer dispense plunger within the buffer chamber as the cassette is being loaded into the test console. The alcohol reaction assembly can further include an air blower and air flow port in communication with the sample chamber to dispense the sample into the alcohol reaction chamber when air is pumped through the air flow port from the air blower. The alcohol reaction assembly can further include a vent port (which may be the same as the air flow port) in communication with the alcohol reaction chamber to vent air from the alcohol reaction chamber when the reagent solution and the calibrator solution are dispensed within the alcohol reaction chamber. The alcohol reaction assembly may further include a mixing drive assembly that is magnetically coupled to a ferrous element within the alcohol reaction chamber to ensure reactions proceed to completion within the alcohol reaction chamber.

In accordance with a second aspect of the present inventions, an alcohol reaction assembly comprises an alcohol reaction chamber, a reagent chamber in fluid communication with the alcohol reaction chamber, and a buffer chamber in fluid communication with the reagent chamber. The alcohol reaction assembly further includes a buffer dispense plunger disposed within the buffer chamber for dispensing buffer from the buffer chamber, through the reagent chamber, and into the alcohol reaction chamber, where it hydrates dry reagent therein to produce a reagent solution.

In a non-limiting preferred embodiment, the dry reaction in the reaction chamber comprises lyophilized alcohol dehydrogenase (ADH) and nicotinamide adenine dinucleotide (NAD). The buffer chamber can also include a seal that seals the buffer from the reagent chamber, in which case, the buffer dispense plunger can include a stylus that is configured to puncture the seal when the buffer dispense plunger is moved toward the seal. The previously described features can also be incorporated into the preferred alcohol reaction assembly.

In accordance with a third aspect of the present inventions, an alcohol detection assembly comprises an alcohol reaction chamber, a reagent chamber in fluid communication with the alcohol reaction chamber, and a buffer chamber in fluid communication with the reagent chamber. The alcohol detection assembly further includes a buffer dispense plunger disposed within the buffer chamber for dispensing buffer from the buffer chamber, through the reagent chamber, and into the alcohol reaction chamber, where it hydrates dry reagent therein to produce a reagent solution. The alcohol detection assembly further includes a sample chamber in fluid communication with the alcohol reaction chamber, and is configured for containing and dispensing a sample into the alcohol reaction chamber to produce a detectable alcohol sample solution. The alcohol detection assembly further includes an energy source that is configured for transmitting an energy beam through the alcohol reaction chamber, an energy detector configured for receiving the energy beam from the alcohol reaction chamber and outputting a signal based on the received energy beam; and processing circuitry configured for determining the presence of alcohol within the sample based on the output signal.

In a non-limiting preferred embodiment, the energy source can comprise an optical source, e.g., a light emitting diode (LED), the energy detector can comprise an optical detector, e.g., a silicon diode detector, and the processing circuitry can comprise a central processor unit (CPU). The preferred alcohol detection assembly can further comprise a splitter for splitting energy from the energy source into the energy beam and a reference energy beam that bypasses the alcohol reaction chamber, a reference energy detector for receiving the reference energy beam, and outputting a reference signal based on the reference energy beam, and a controller configured for using the reference output signal for maintaining the magnitude of the energy beam at a substantially uniform level.

The preferred alcohol detection assembly can also comprises a calibrator chamber in fluid communication with the alcohol reaction chamber, and a calibrator dispense plunger disposed within the calibrator chamber for dispensing a predetermined quantity of alcohol from the calibrator chamber into alcohol reaction chamber. In this case, the energy source can be configured for transmitting an initial energy beam through the alcohol reaction chamber, energy detector can be configured for receiving the initial energy beam from the alcohol reaction chamber, and outputting an initial signal based on the initial received energy beam, and the processing circuitry can be configured for calibrating the alcohol detection assembly based on the initial output signal. Previously described features can also be incorporated into the preferred alcohol detection assembly.

In accordance with a fourth aspect of the present inventions, a method of detecting the presence of alcohol in a sample comprises flowing buffer from a buffer chamber through a reagent chamber to produce and dispense a reagent solution into an alcohol reaction chamber, and dispensing the sample within the alcohol reaction chamber to produce an alcohol detectable sample solution. The method further comprises transmitting energy through the alcohol detectable sample solution, receiving the energy from the alcohol detectable sample solution, and determining a presence of alcohol within the sample based on the received energy.

In a non-limiting preferred method, the alcohol detectable sample solution is mixed to complete reaction between the sample and the reagent solution. The transmitted energy can be optical energy, in which case, the detectable alcohol sample solution may comprise an alcohol indicator exhibiting an optical absorbance value in the presence of the transmitted optical energy, and the presence of alcohol in the sample can be determined by determining the optical absorbance value based on the optical energy received. The alcohol indicator may be nicotinamide adenine dinucleotide with high energy hydrogen (NADH), in which case, the reagent solution may comprise alcohol dehydrogenase (ADH) and nicotinamide adenine dinucleotide (NAD), and detectable alcohol sample solution can be produced by reacting the NAD and the sample alcohol in the presence of the ADH to produce the NADH. The optical absorbance value of the alcohol indicator can be proportional to the quantity of alcohol reacted with the reagent solution, in which case, the preferred method may further comprise determining a concentration of the alcohol in the sample based on the optical absorbance value of the alcohol indicator. The preferred method may further comprise calibrating prior to dispensing the sample within the reagent solution.

In accordance with a fifth aspect of the present inventions, a method of detecting the presence of alcohol in a sample comprises flowing buffer from a buffer chamber through a reagent chamber to produce and dispense a reagent solution within an alcohol reaction chamber, and dispensing the sample within the alcohol reaction chamber to produce an alcohol detectable sample solution having an alcohol indicator. The method further comprises determining an optical energy absorbance of the alcohol indicator at a specified optical wavelength, and determining a presence of the alcohol in the sample based on the optical energy absorbance measurement.

In a non-limiting preferred method, the alcohol indicator can comprise nicotinamide adenine dinucleotide with high energy hydrogen (NADH), in which case, the reagent solution can comprise alcohol dehydrogenase (ADH) and nicotinamide adenine dinucleotide (NAD), which reacts with the sample alcohol to produce the NADH. In the preferred method, the optical absorbance value of the alcohol indicator can be proportional to a quantity of alcohol reacted with the reagent solution, in which case, the concentration of the alcohol in the sample can be based on the optical absorbance value of the alcohol indicator. The sample alcohol concentration can be determined by dispensing a predetermined quantity of alcohol from a calibrator chamber into the alcohol reaction chamber prior to dispensing the sample, thereby producing an alcohol detectable calibrator solution having a known alcohol concentration C, and measuring a first optical absorbance value $A_0$ of the reagent solution, a second optical absorbance value $A_1$ of the alcohol detectable calibration solution, and a third optical absorbance value $A_3$ of the alcohol detectable sample solution, at the specific wavelength, wherein the sample alcohol concentration is determined in accordance with the factor $C(A_2-A_0)/(A_1-A_0)$. The specified wavelength used in the preferred method to determine absorbance of the solutions can be an ultraviolet wavelength, e.g., 365 nm.

BRIEF DESCRIPTION OF THE DRAWINGS

In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 47 is a side view of the cassette portion of the sample/buffer flow assembly;

FIG. 47A is a longitudinal-sectional view taken along the line 47A—47A of FIG. 47;

FIG. 47B is a magnified view taken along the line 47B of FIG. 47A.

FIG. 94 is a front view of the cassette portion of the alcohol reaction assembly;

FIG. 94A is a cross-sectional view taken along the line 94A—94A of FIG. 94;

DETAILED DESCRIPTION OF THE PREFERRED EMBODIMENTS

Figure 1:
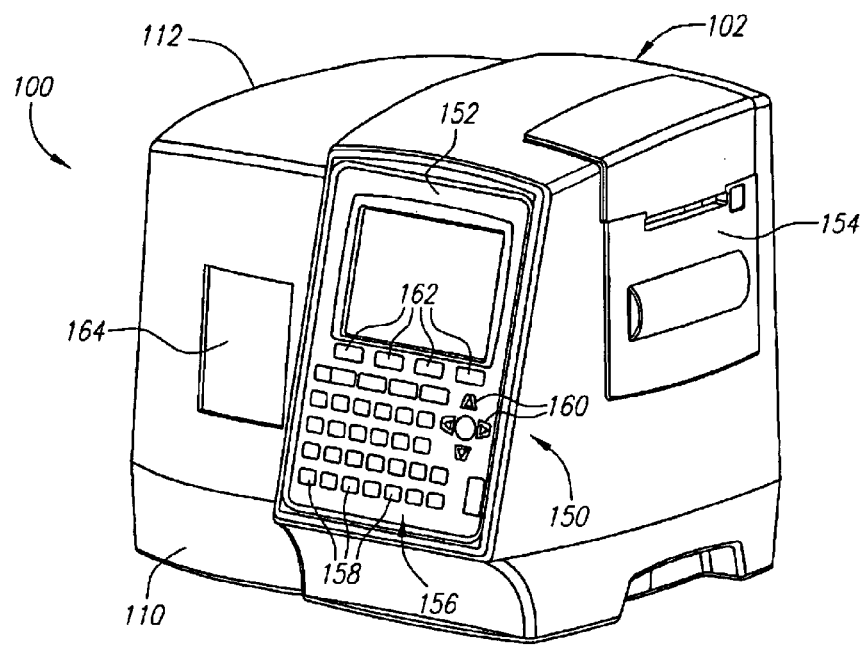
FIG. 1 is a front-right perspective view of an on-site analyte testing system constructed in accordance with a preferred embodiment of the present inventions, wherein the testing system comprises a portable test console and a loaded single-use disposable test loaded cassette assembly.

With reference to FIG. 1, an on-site analyte testing system 100 will be briefly described. The system 100 utilizes flow immunoassay technology and the collection of saliva as a specimen to screen, quantitatively, or semi-quantitatively detect the presence of any number of analytes, and specifically drugs and beverage alcohol (both illegal and legal), in a test subject. For the purposes of this specification, a test subject is any human or animal whose bodily fluids (in this case, a saliva sample) is to be collected and analyzed for drug/alcohol content using the system 100. A screening test is a test that provides for quantitation of results with sufficient accuracy and precision to permit positive determination of whether the level of analyte present in the sample is at or below a predefined cutoff level, in which case the test is declared to be a negative result, or whether the analyte is above the predefined cutoff level, in which case the test is declared to be a positive result A quantitative test is a test that provides for legally-defined quantitation of results for an analyte over a defined range (for ethanol 0.04–0.20%) at or above defined accuracy (for ethanol ≧95%) and precision (for ethanol ≧95%) levels. A semi-quantitative test is a test that provides for quantitation of results for an analyte over manufacturer-defined limits of accuracy, precision, and range of results.

The system 100 is a relatively small self-contained device, and thus, can be conveniently used in a broad range of areas, including long term therapeutic drug monitoring, disease-state testing, wellness-health screening, and all rapid diagnostic testing where a non-invasive specimen collection and/or rapid analytic result is desired. In the preferred embodiment, the system 100 can selectively provide up to ten specific immunoassay tests in a single test panel on a single, small volume, saliva sample. The system 100 manages all functions related to the running of a test on a subject, including automatic quality control validation, specimen collection, specimen adequacy test, specimen processing, reagent addition, optical readout, test result analysis and a quantitative results printout with interpretation. The system 100 automatically generates a hardcopy of the test results and interpretation to provide the necessary documentation of test results. Thus, the system 100 is fully or semi-automated in that minimal interaction by the operator is required.

The preferred embodiment of the system 100 provides the following advantages: (1) it is user friendly to non-technical personnel; (2) it collects a single specimen and generates ten test results in less than ten minutes; (3) it is non-invasive; (4) it generates blood-equivalent tests results in non-medical environments equal to centralized laboratory test results; (5) provides quantitative and evidentiary results; (6) can be customized to a broad list of applications by using multiple panels with multiple formats; (7) it is completely automated and requires no user intervention, thereby providing for legally defensible results; (8) reagents used in system can be stored for a relatively long period of time; (9) it can be applied to saliva, urine, and whole blood or plasma assays; and (10) it is portable in that it can be carried and transported by a single person and can fit into a compact place. Succinctly, the system is a highly sensitive, rapid, non-invasive, easy-to-use, on-site diagnostic tool.

The preferred system 100 generally includes a relatively small, portable test console 102 and a single-use disposable test cassette assembly 150 (shown in FIGS. 2–5), which is received by the test console 102 via a cassette port 106, as will be described in further detail below. The test console 102 includes a case 108, which contains all of the componentry (e.g., the circuitry, motors, sensors, detection and illumination devices, etc.) necessary to effect the control, electromechanical, optical, and computational functions performed on the cassette assembly 150 and essential for the analysis of the analytes within the test subject's saliva sample. In the illustrated embodiment, the case 108 is structurally divided into a bottom case portion 110 and a top case portion 112. As can be seen in FIGS. 6–11, the test console 102 also includes a main base 114, which provides the necessary support for the inner components of the console 102, integrating the assembly into a single unit. In the illustrated embodiment, the main base 114 includes a top flange 116, a bottom flange 118, and two side flanges 120 and 122, which are arranged to form a hollow three dimensional rectangular rigid structure mounted inside the bottom case portion 110. The main base further includes a distribution flange 124 on which various motors and associated components are distributed, and a pair of spacer flanges 126 to space the main base 114 from the bottom case portion 110.

Figure 2:
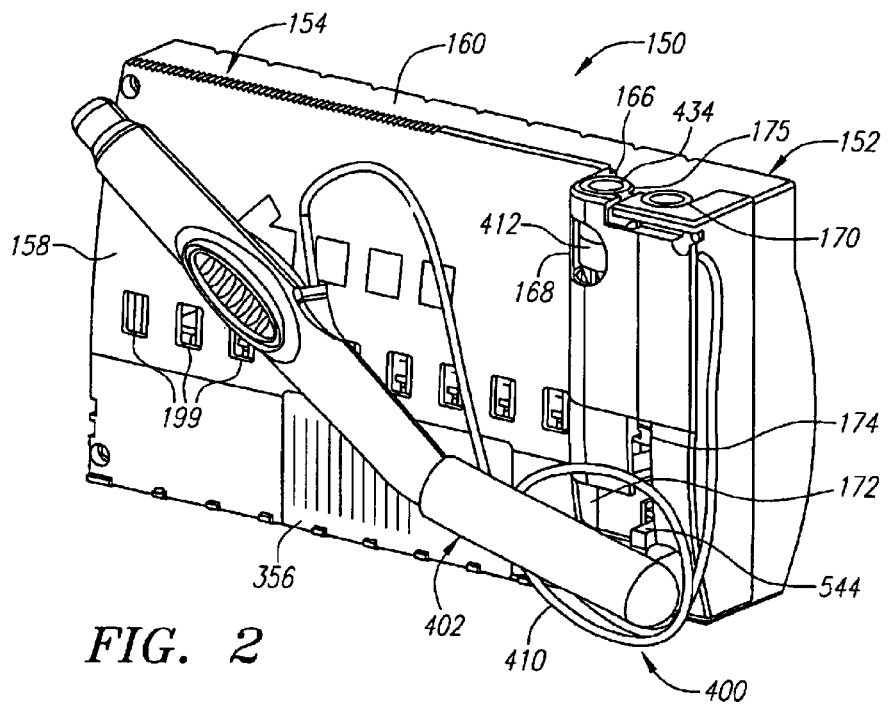
FIG. 2 is a rear-right perspective view of the cassette assembly.
Figure 3:
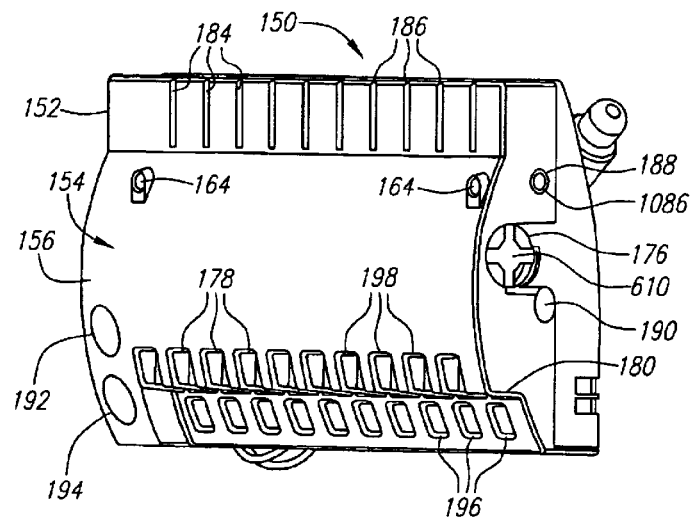
FIG. 3 is a front-right perspective view of the cassette assembly.

Referring to FIGS. 2 and 3, the cassette assembly 150 includes an external sample collection interface device, and specifically an oral aspirator 402, and an associated flexible sample collection conduit 410, which is used to collect saliva from a subject via aspiration. The cassette assembly 150 further comprises a chemistry cassette 152 that includes a case 154, which, for purposes of reference, has a front 156, rear 158, top 160, and bottom 162. The cassette case 154 houses all the chemical reagents needed to perform a panel of immunoassay tests for drugs, as well as an enzymatic test for ethanol, on the test subject's saliva sample. In the illustrated embodiment, the cassette case 154 contains pre-packaged quantities of lyophilized stable solid reagents and stabilized liquid buffer reagents having a shelf-life of twelve months under defined storage conditions. The cassette case 154 further contains all required components to provide for defined flow rate and for optical quantitation of the alcohol concentration and fluorimetric semiquantitation of the drug levels. The cassette case 154 also contains all materials, surfaces, chambers, and components that will be wetted by the saliva sample by aspiration into the chemistry cassette 152 and subsequently analyzed by the test console 102. The cassette case 154 is further designed to self-contain all chemical reagents and the biological sample after their chemical reaction, and to treat the saliva sample with an antibacterial to obviate any biological hazard of the physiological sample. Other than the chemical reagents, the chemistry cassette 152 is made entirely of common injection-molded polymers (plastics) and aluminum foil. Therefore it can be disposed of simply as solid waste.

Thus, the chemistry cassette 152, when installed within the test console 102, enables it to identify a multitude of oral fluid analytes and is available in a variety of formats to provide the various markets with the specific test panels they require. For example, the chemistry cassette 152 may provide a five drug test panel to screen or semi-quantitatively identify the National Institute on Drug Abuse (NIDA) required drugs-of-abuse, which is currently identified as cocaine, opiates (heroin, morphine, and codeine), phencyclidine (PCP), amphetamines/methamphetamines, and marijuana (tetrahydrocannabinol or THC). The chemistry cassette 152 also provides screening or semi-quantitative analysis of beverage alcohol (ethanol or EtOH). As another example, the chemistry cassette 152 may provide up to ten tests for overdose or disease panel testing. Thus, the chemistry cassette 152 can be customized to any one of a variety of applications. Thus, the combination of the test console 102 and chemistry cassette 152 provides for a fully operational flow immunoassay analyte tester.

It should be noted that a confirmation cassette, which does not perform any immunoassay tests, can be optionally used with the test console 102 to merely collect the aspirated saliva sample from the test subject. Typically, it will be used subsequent to the administration of a drug-of-abuse test on a subsequently collected saliva sample in order to confirm the results of the test. Confirmatory tests use advanced instrumentation to provide for sufficiently specific results to eliminate the possibility of interfering or cross-reacting species that might provide incorrect results, either false-positive or false-negative results, when tested with a screening test using less complex and more inexpensive technology. For example, for use by its agencies, the U.S. Government requires that screening tests for drug-of-abuse be confirmed with a test specifically incorporating gas chromatography/mass spectrometry for confirmation of results.

Having generally described the system 100, the various assemblies located in the chemistry cassette 152 and/or test console 102 will now be described. It should be noted, however, that the functional organization of this discussion into various assemblies is provided to facilitate in the understanding of the system 100, and is not meant to limit the structure of the assemblies in any way. For example, assemblies located in both the chemistry cassette 152 and the test console 102 may be divided into a cassette portion and a tester portion in the subsequent discussion. This does not mean, however, that the combination of these two portions cannot be considered a single assembly. Also, many of the components described herein bear on the functionality of several assemblies. Thus, the organization of components into a particular assembly does not mean that any such components cannot be considered a part of another assembly.

I. Electrical Assembly

Figure 12:
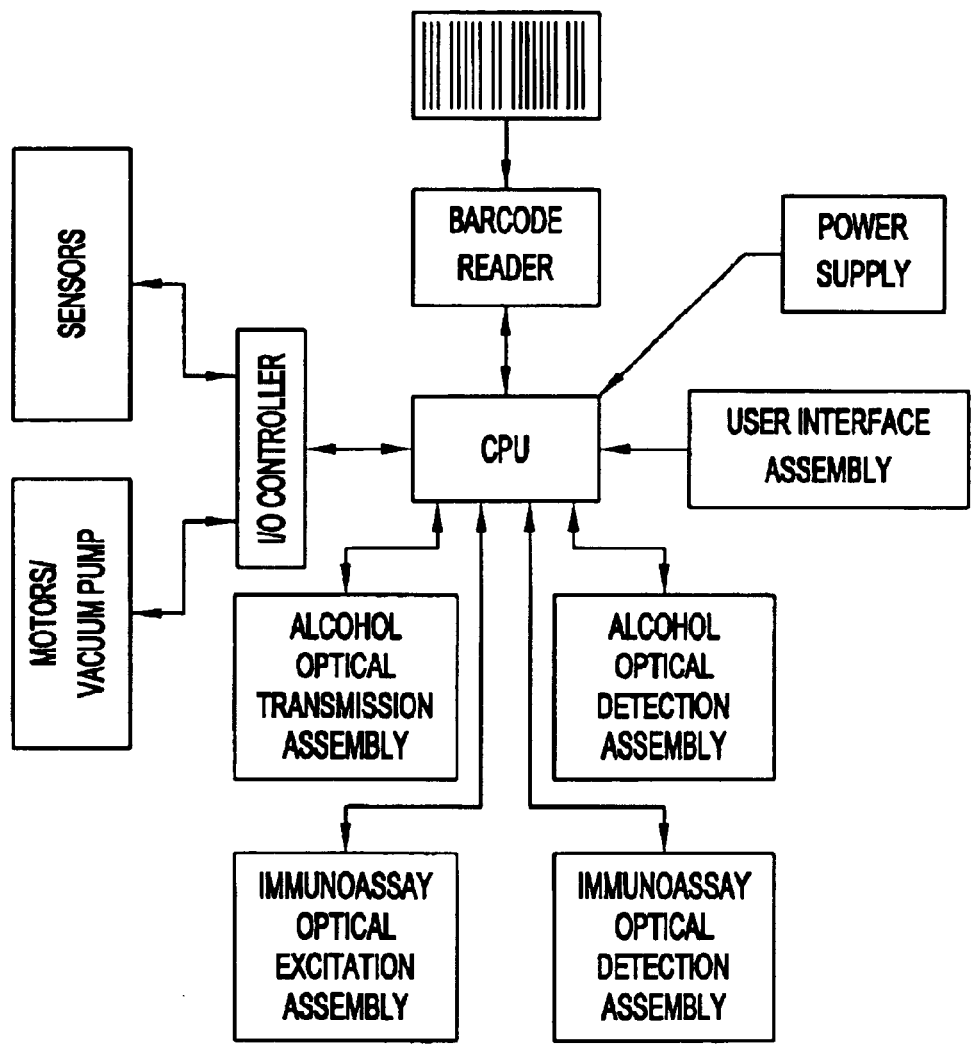
FIG. 12 is a schematic block diagram of various components of the testing system and their interaction with a central processor unit (CPU)

Referring to FIG. 12, an electrical assembly 200 provides the necessary electrical and sensing functions to the system 100. To this end, the electrical assembly 200 comprises an AC/DC power supply 202 that plugs into normal AC power mains (85–240 VAC, 50–60 Hz) and supplies a nominal single DC voltage of 12VDC (or multiple DC voltages of +5 and ±15 VDC) to the test console 102 at sufficient current to provide electrical power for all operations of the test console 102. All power requirements of the test console 102 may also be supplied by an external battery (not shown) of a sufficient ampere-hours rating to supply electrical power for all operation of the test console 102 when remote from AC supplies, such as on a ship, in an ambulance, or in a police car.

In the illustrated embodiment, the test console 102 provides sufficient internal shielding and power supply decoupling capacitors (not shown) to minimize susceptibility to external interference caused by electrostatic (ESI), electromagnetic (EMI) and radio frequency-interference (RFI) sources. The test console 102 is also sufficiently shielded and filtered to minimize generation of interference from ESI, EMI or RFI sources within the instrument. The test console 102 thus produces no more electrical noise than other common household appliances, such as television receivers or home computers. Analog and digital grounds are kept separate through the test console 102 and only joined at a single reference point within the device to minimize noise and possible error sources caused by potential ground loops within the test console 102. Similarly, all low-level, high impedance inputs are shielded and isolated to minimize noise sources within the test console 102.

The electrical assembly 200 further includes a central processor unit (CPU) 204, which controls all operations of the test console 102, with the exception of the cassette temperature controller (described below), which is under dedicated hardware control. In this regard, the CPU 204 is coupled via an input/output (I/O) controller 206 to a multitude of sensors 208 and motors 210 located throughout the test console 102. In this manner, the CPU 204 can control the motors 210 to effect the various functions performed within the test console 102, and can read the sensors 212 to determine the status of such functions. As will also be described in further detail below, the CPU 204 also performs intelligence functions, such as performing an analysis on the sample and interfacing with the operator.

II. Cassette Loading Assembly

Figure 13:
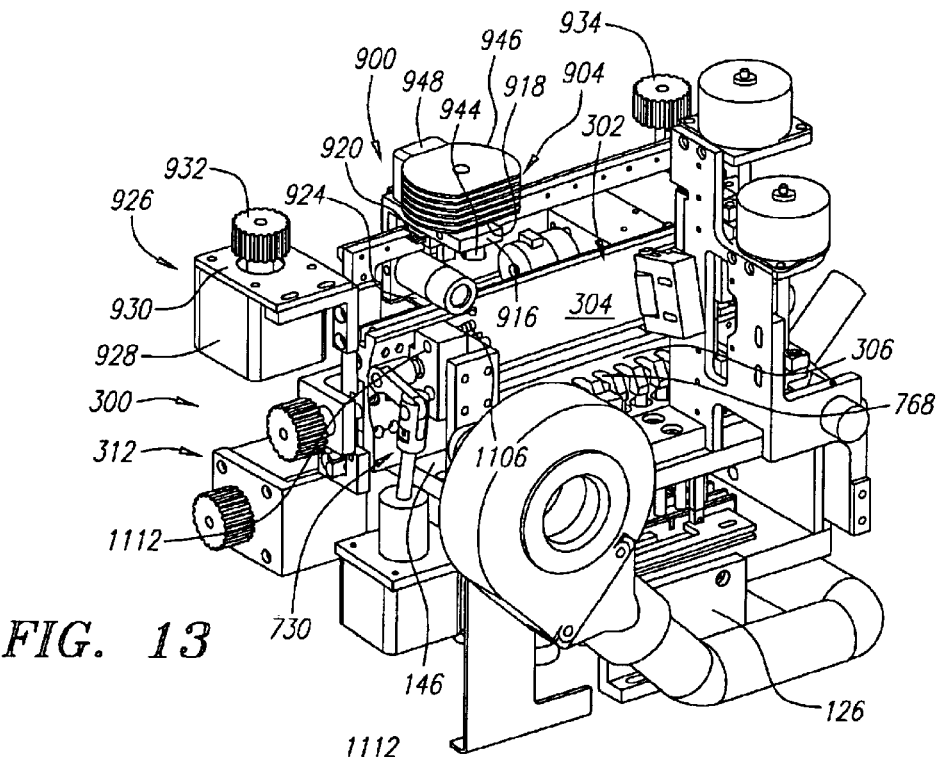
FIG. 13 is a rear-left perspective view of the inner components of the test console without the cassette assembly, wherein a cassette carriage is shown fully loaded into the test console.
Figure 14:
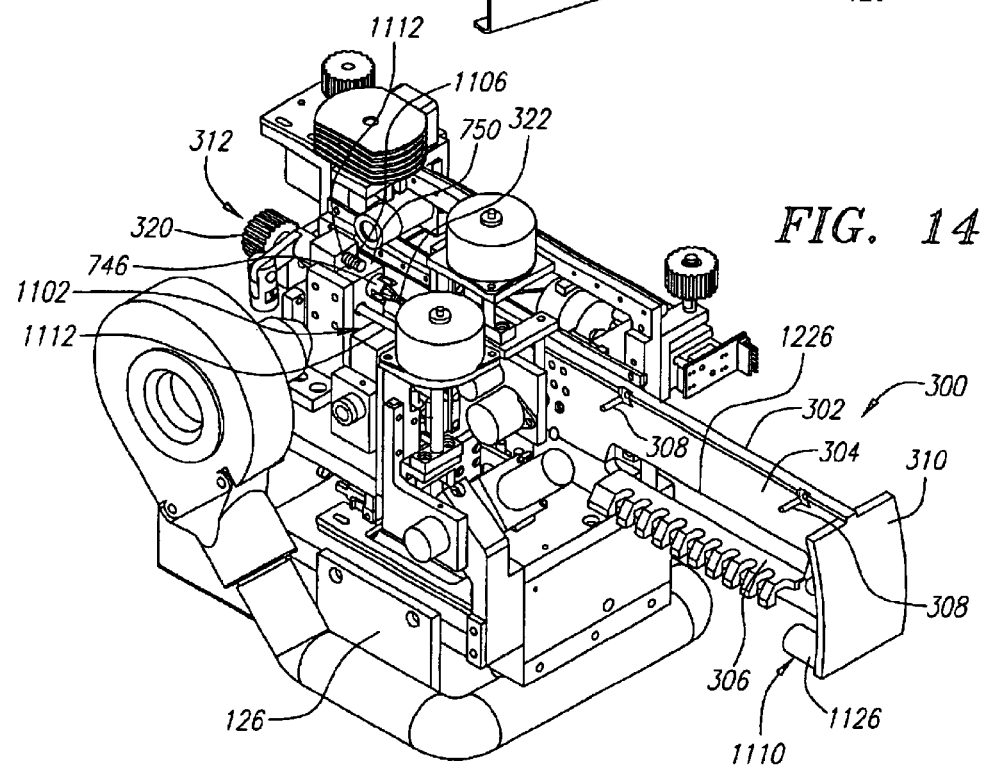
FIG. 14 is a rear-right perspective view of the inner components of the test console without the cassette assembly, wherein the cassette carriage is shown fully deployed from the test console.

Referring to FIGS. 13 and 14, the system 100 comprises a cassette loading assembly 300, the purpose of which is to allow the operator to load and unload the chemistry cassette 152 into and out of the test console 102. The cassette loading assembly 300 comprises a cassette carriage 302 for receiving the chemistry cassette 152. To this end, the cassette carriage 302 includes a front support flange 304 and a bottom flange 306, which are profiled to seat and receive the chemistry cassette 152. To ensure that the chemistry cassette 152 is firmly seated, the cassette carriage 302 comprises a pair of homing pins 308 extending from the front support flange 304, which are sized and spaced to mate with a corresponding pair of homing pin holes 164 formed in the front 156 of the cassette case 154 (see FIG. 3). As can be seen by FIGS. 13 and 14, the cassette carriage 302 linearly translates in relation to the main base 114. To this end, the cassette loading assembly 300 further includes a rail 307 (shown in FIGS. 8 and 15), which is suitably mounted on the top main base flange 116, and a mating runner 309 (shown also in FIGS. 8 and 15), which is suitably mounted to the bottom of the cassette carriage 302, thus allowing the cassette carriage 302 to smoothly ride on the main base 114 between a fully extended position (FIG. 13) and a fully closed or home position (FIG. 14). The cassette carriage 302 includes a door 310 mounted to its end, such that when the cassette carriage 302 is fully loaded, the door 310 is shut against the cassette port 106, forming a light block that substantially eliminates stray ambient light from the interior of the test console 102, the importance of which will be described in further detail below.

Figure 15:
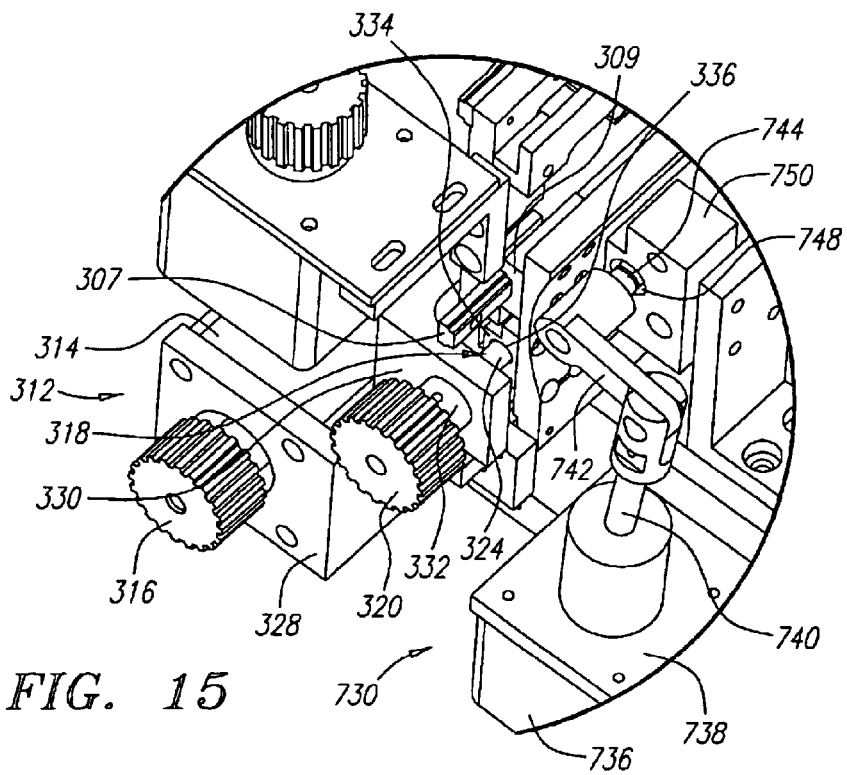
FIG. 15 is a close-up perspective view of a cassette loading assembly and a rotary valve drive assembly used in the test console.

Referring also to FIG. 15, the cassette loading assembly 300 further includes a cassette loading drive assembly 312, which automates the reciprocal movement of the cassette carriage 302 in relation to the main base 114. The cassette loading drive assembly 312 includes a rotational stepper motor 314 with an associated drive pulley 316, and a drive screw 318 with an associated idler pulley 320. The drive screw 318 includes a threaded portion 322 (best shown in FIG. 14) and opposing unthreaded portions 324 (only one shown in FIG. 13). The cassette loading drive assembly 312 further includes a drive belt (not shown) mounted around the respective drive and idler pulleys 316 and 320 for operably connecting the stepper motor 314 to the drive screw 318. The cassette loading drive assembly 312 further includes a motor mount 328 for affixing the motor 314 to the side main base flange 122, and a pair of drive screw positioners 330 (shown also in FIG. 8) having apertures 332 in which the unthreaded ends 324 of the drive screw 324 are free to respectively rotate. The drive screw positioners 330 are suitably mounted to the top main base flange 116, so that the rotating drive screw 318 is linearly fixed relative to the main base 114. The cassette loading drive assembly 312 further includes a threaded flange 334, which is suitably mounted to the exterior of the cassette carriage 302. The threaded flange 334 includes a longitudinally disposed threaded hole 336 through which the threaded portion 322 of the drive screw 318 is disposed. Thus, operation of the motor 314 rotates the drive pulley 316, which in turn rotates the idler pulley 320 and thus the drive screw 318 via drive belt. The cassette carriage 302 is then linearly translated with respect to the main base 114. Under control of the CPU 204 and I/O controller 206 (see FIG. 12), the motor 314 can be reciprocally operated to alternately translate the cassette carriage 302 between the fully loaded and fully extended positions.

Having described the structure of the cassette loading assembly 300, its operation will now be described. In its home position (FIG. 13), the empty cassette carriage 302 is fully loaded into the test console 102 and the door 310 is shut against the cassette port 106 of the test console 102 (FIG. 1). The cassette carriage 302 is ejected by semi-automatically operating (i.e., prompted by the operator) the cassette loading drive assembly 312 to fully extend the cassette carriage 302 out the cassette port 106, allowing the operator to mount the cassette 152 within the cassette carriage 302. The cassette 152 is then loaded into the test console 102 by semi-automatically operating the cassette loading drive assembly 312 to filly insert the cassette carriage 302 with the cassette 152 into the cassette port 106, returning the cassette carriage 302 to its home position. The cassette 152 can be ejected from the tester by again semi-automatically operating the cassette loading drive assembly 312 to filly extend the cassette carriage 302 and cassette 152 out the cassette port 106, allowing the operator to remove the cassette 152 from the cassette carriage 302. A fully extended cassette carriage sensor, fully inserted cassette carriage sensor, and door shut sensor (shown generally as sensors 208 in FIG. 12) are used to ensure that the afore-described steps have been fully effected.

III. Self-Customizing Assembly

Referring to FIG. 15, the system 100 comprises a self-customizing assembly 350, the purposes of which is to customize one or more operational parameters of the system as dictated by the chemistry cassette 152. To this end, the self-customizing assembly 350 comprises a barcode read assembly 352 and a customization assembly 354.

Figure 9:
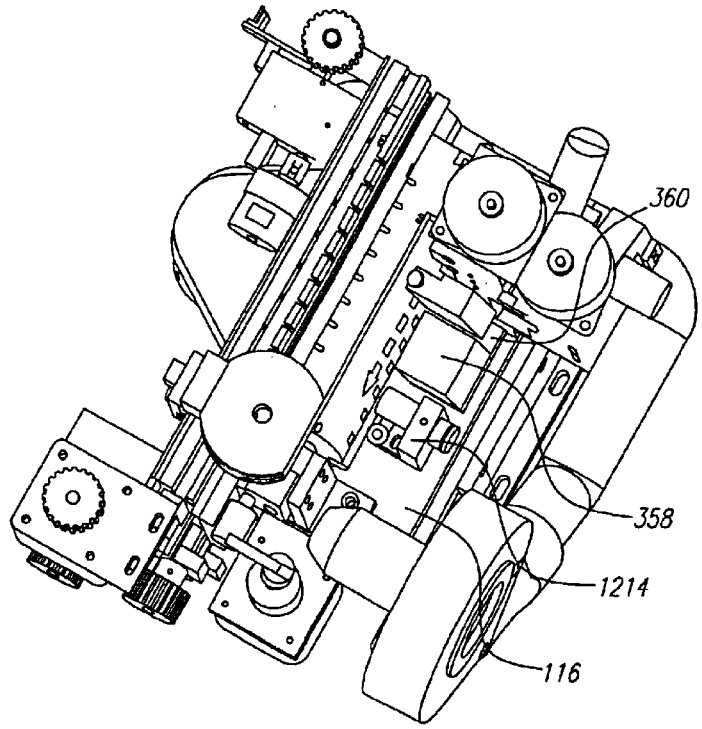
FIG. 9 is a top perspective view of the inner components of the test console with the cassette assembly.
Figure 10:
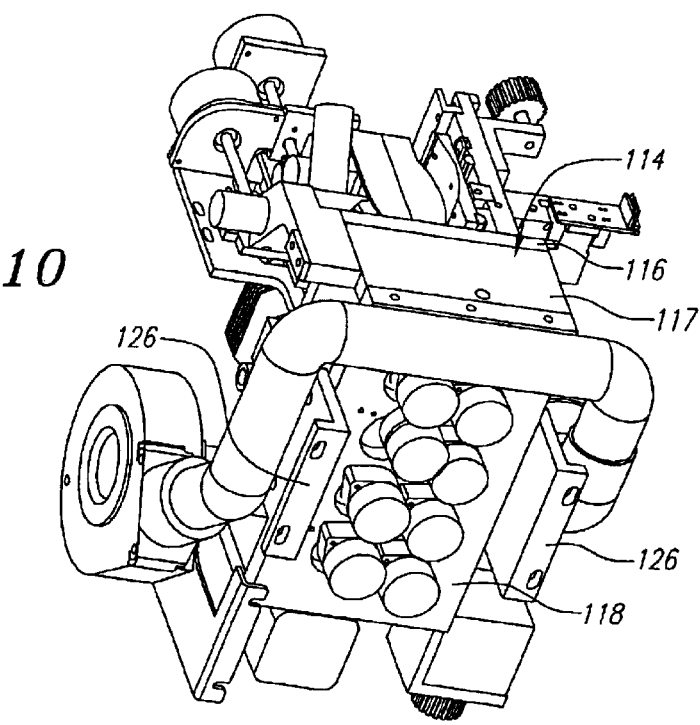
FIG. 10 is a bottom-front perspective view of the inner components of the test console with the cassette assembly.
Figure 11:
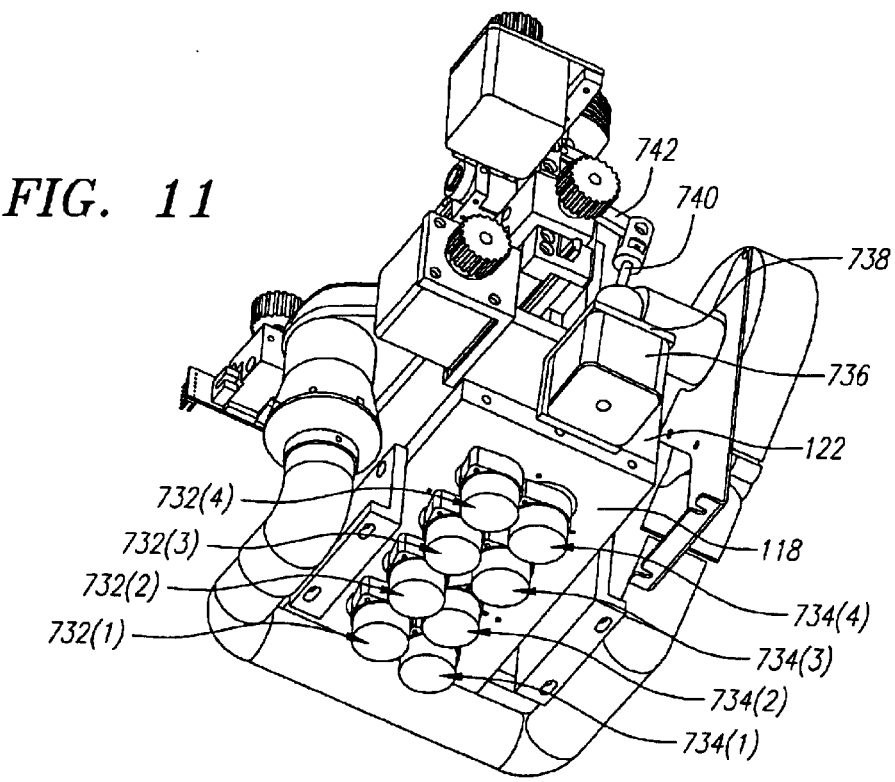
FIG. 11 is a bottom-rear perspective view of the inner components of the test console with the cassette assembly.

The purpose of the barcode read assembly 352 is to identify information associated with the chemistry cassette 152. To this end, the barcode read assembly 352 includes a unique barcode 356, which is affixed to the rear 158 of the cassette case 154 (shown in FIG. 2), and which contains information specific to the chemistry cassette 152. The barcode read assembly 352 includes a standard barcode reader 358, which is mounted to the top main base flange 116 via a mount 360, and is optically aligned with the barcode 356 when the chemistry cassette 152 is loaded within the test console 102 (FIG. 9). In the illustrated embodiment, the barcode 356 contains the following information: (1) type of cassette (e.g., NIDA drugs-of-abuse and alcohol cassette, confirmation cassette, etc.); (2) date of manufacture; (3) various lot-specific calibration information for each of the test channels; and (4) checksum code.

The customization assembly 354 comprises circuitry, and specifically the CPU 204, which is electrically coupled to the barcode reader 358 and modifies the operational parameters, and specifically the testing parameters, of the system 100 based on the barcode information. The CPU 204 can optionally modify sample flow parameters within the system 100 by, e.g., operating various motors to provide for different sample flow rates and volumes within the system 100 based on the type of cassette indicated in the barcode. Optionally, information specifically indicating the sample flow parameters can be contained within the barcode, in which case, the CPU 204 need not infer the different flow rates and volumes from the type of cassette. In addition, the CPU 204 can also calibrate a test panel using the test calibration information containing with the barcode. Further details on the customization of the system 100 will be described below.

The CPU 204 is also configured to operate the barcode reader 358 to destroy the barcode checksum code when the cassette 152 is ejected from the test console 102. Thus, if the barcode information and the checksum code do not correspond, the chemistry cassette 152 will not be able to be used, thereby preventing inadvertent or intentional reuse of an invalid cassette 152. Also, the CPU 204 will prevent use of the cassette 152 if it is expired, e.g., 12 months after the date of manufacture.

In operation, when the cassette 152 is loaded into the test console 102, the barcode reader 358 is automatically operated to read the information from the barcode 356 disposed on the cassette 152. This information is then processed by the test console 102, and specifically, the CPU 204. If the cassette 152 has expired or has been previously used, the CPU 204 will operate the cassette loading assembly 300 to eject the chemistry cassette 152. Otherwise, the CPU 204 will customize the operational parameters of the system 100 based on the barcode information. After completion of the test, the CPU 204 operate the cassette loading assembly 300 to eject the cassette 152. Additionally, as cassette 152 is ejected from the test console 102, the CPU 204 operates the barcode reader 358 to erase the checksum code from the barcode 356, so that the cassette 152 cannot be reused.

IV. Sample Collection Assembly

Figure 6:
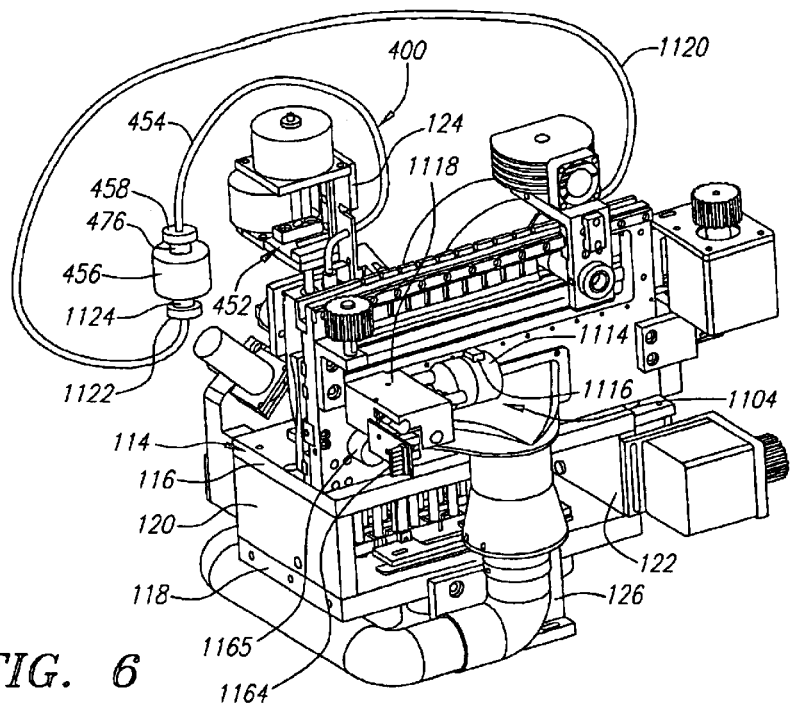
FIG. 6 is a front-left perspective view of the inner components of the test console with cassette assembly.
Figure 16:
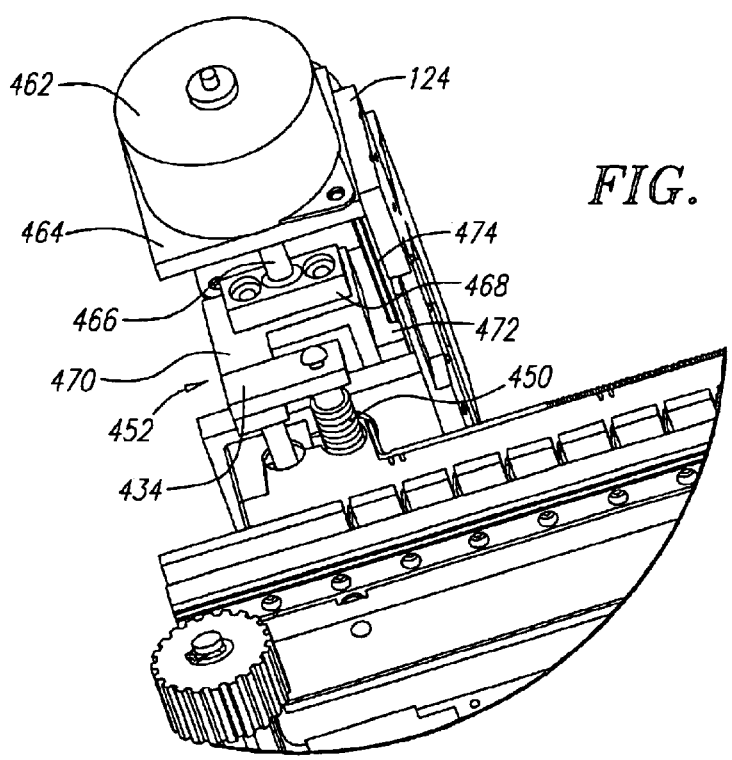
FIG. 16 is a close-up perspective view of the test console portion of a sample collection assembly, and particularly, a vacuum port drive assembly.

Referring to FIGS. 2, 6, and 16, the system 100 comprises a sample collection assembly 400, the purpose of which is to collect the required amount of saliva (in the illustrated embodiment, 350±35 μL) semi-automatically by vacuum aspiration from the mouth of the test subject. That is, the sample collection assembly 400 automatically draws saliva sample into the cassette 152, measures the total volume accumulated within the cassette 152, and notifies the operator when an adequate volume of sample has been accumulated.

A. Sample Collection Assembly—Cassette Portion

Figure 17:
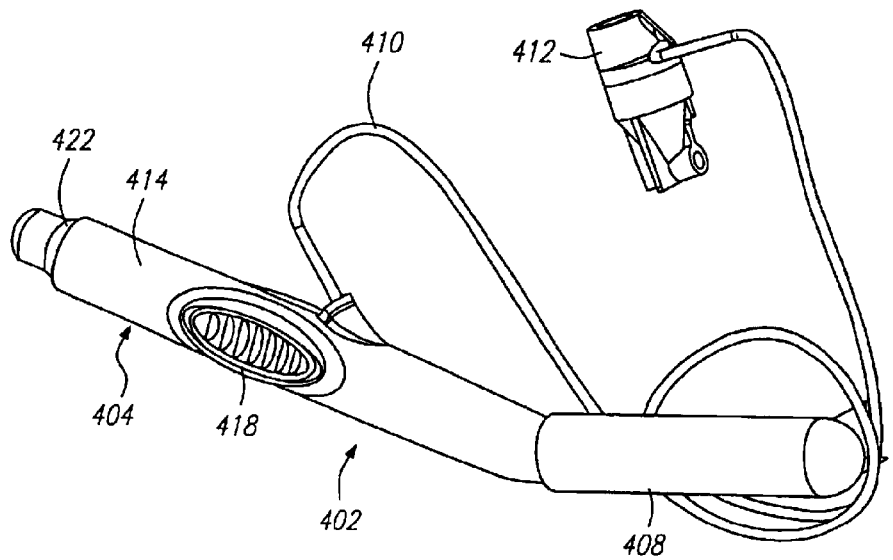
FIG. 17 is a perspective view of the cassette portion of the sample collection assembly associated, and particularly, an oral aspirator, sample collection chamber, and flexible conduit, wherein a cover/extended handle is shown used as a cover.
Figure 18:
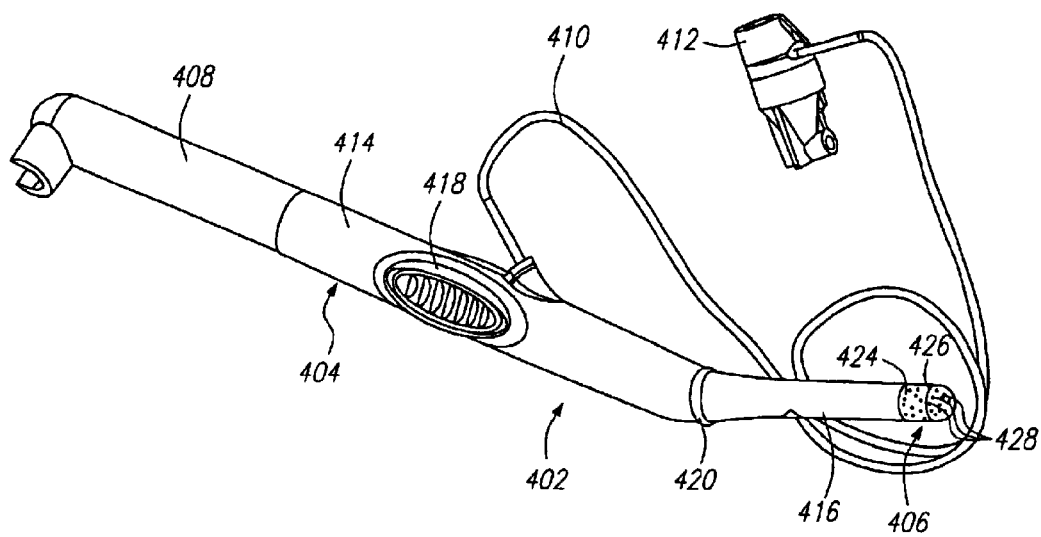
FIG. 18 is a perspective view of the oral aspirator, sample collection chamber, and flexible conduit, wherein the cover/extended handle is shown used as an extended handle.
Figure 19:
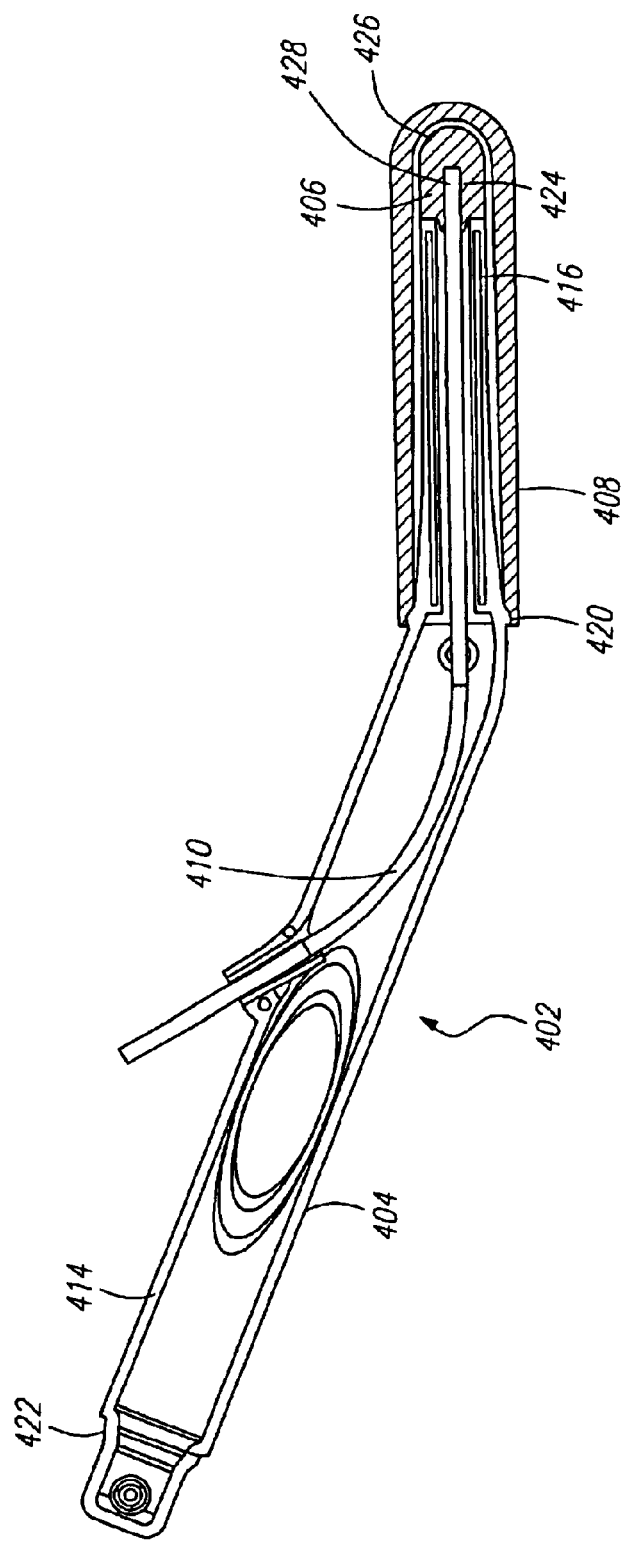
FIG. 19 is a longitudinal sectional view of the oral aspirator.

Referring specifically to FIGS. 17–19, the portion of the sample collection assembly 400 associated with the cassette assembly 150 is illustrated. The sample collection assembly 400 includes the afore-mentioned oral aspirator 402, which includes a hand piece 404, a sample collection tip 406 and a cover/extended handle 408, the afore-mentioned flexible conduit 410, and a sample collection chamber 412. As illustrated in FIG. 2, the oral aspirator 402 and conduit 410 are external to the cassette 152, whereas the sample collection chamber 412 is internal to the cassette 152.

The hand piece 404 is composed of hollow rigid or semi-rigid material of a suitable length and diameter. For example, the hand piece 404 can be composed of white-colored, injection molded ABS plastic, that is 15 cm in length, and 1 cm in diameter at a handle 414 that narrows to 0.5 cm diameter at a tip 414. To provide for the best ergonomic use of the hand piece 404 in the mouth of the test subject, the handle 414 is bent to a gentle obtuse angle, e.g., 150° at a distance of 5 cm from the tip 414, and has two opposing molded finger grips 418, e.g., 10 cm from the tip 414.

The cover/extended handle 408 is also composed of a hollow rigid or semi-rigid material of a suitable length and diameter to fit over either the tip 414 of the hand piece 404 (FIG. 17) or the handle 414 of the hand piece 404 (FIG. 18). For example, the cover/extended handle 408 can be composed of a white-colored, injection molded ABS plastic that is 5 cm in length and 1 cm in diameter. As a cover, it can be initially placed over the sample collection tip 406 to keep it clean during storage and just prior to use, and can be held in place by a positive snap-action ribbed holder 420. As an extended handle, it can be removed from the sample collection tip 406 and slipped onto the handle 414 of the hand piece 404, where it is held in place by another positive snap-action ribbed holder 422. Thus, the length of the hand piece 404 is extended in additional amount (e.g., for a total length of 19 cm to keep the test subject's and operator's fingers away from the sample collection tip 406, which will be coated with saliva. Following use, the cover/extended handle 408 can be replaced over the saliva-wetted tip 416 to prevent accidental contact of the test subject and/or operator with potentially biologically-hazardous saliva remaining on the tip 416.

The sample collection tip 406 has a size the allows it to comfortably fit within a subject's mouth, and is constructed of a non-toxic, non-analyte absorbing material. In the illustrated embodiment, the sample collection tip 406 is cylindrical in shape with a hemidome-shaped top surface, and has a length of 9 mm and a diameter of 7 mm. The sample collection tip 406 comprises a sample collection body 424 composed of a hydrophilic material, such as a fused, nontoxic, high density polyethylene (HDPE) microporous material. The outer surface 426 of the sample collection body 424 is treated with a surfactant, which reduces the surface tension of the fluid in contact with the outer surface 426. Suitable proprietary surfactants for this purpose can be obtained from Porex Corporation located in Fairburn, Ga. Thus, the interior of the microporous sample collection body 424 is hydrophobic, whereas its outer surface 426 is hydrophilic. When in contact, even partially, with a small pool of saliva in the mouth, the hydrophilic outer surface 426 of the sample collection body 424 is sufficient to cause capillary action to transport saliva into the hydrophobic interior of the sample collection body 424. It is noted that with purely hydrophobic tips, substantially the entire surface of the tip must be in contact with saliva in order to flow saliva into the interior of the tip, since exposing any portion of the hydrophobic tip surface to air would tend to draw in the less viscous air.

Thus; a relatively small applied vacuum level, e.g., 350 mmHg absolute at an air flow rate of 5–50 ml/min, has been found to be sufficient to draw saliva from the microporous sample collection tip 406 through the flexible conduit 410. This is advantageous in that a minimum air flow rate is necessary to maintain consistent oral fluid collection, since too high of a flow rate causes a greater volume of air to be transported through the system, requiring removal of greater volumes of air in the sample collection chamber 412. Also, where loss of volatile components in the saliva must be controlled, maintaining a constant, minimal flow of air through the sample collection assembly 400 at all times is advantageous.

The micropores 428 of the sample collection tip 406 are of a suitable diameter, e.g., 135 μm, to facilitate collection of the viscous saliva from the interior surface of the mouth. These micropores 428 also function as a large pore-size depth filter to prevent larger pieces of food, plaque or particles exogenous to the mouth from being aspirated into the small interior diameter of the flexible conduit 410, where they might possibly clog it and prevent aspiration of the saliva therethrough. The sample collection tip 406 is bonded to the tip 416 of the hand piece 404 with a nontoxic, medical-grade cyanoacrylate adhesive. Specifically, the rear circular surface of the sample collection tip 406 is bonded to the front surface of the hand piece tip 416, thereby sealing the rear micropores of the sample collection tip 406 and forcing air to flow from the sides and front surfaces of the sample collection tip 406, where saliva is likely to be located once the tip 406 is inserted into the mouth of the test subject for sample collection.

Also, the central axis of the sample collection tip 406 contains a bore 428 into which one end of the flexible conduit 410 is inserted and bonded with a non-toxic, non-analyte absorbing material, preferably the same as that used to bond the sample collection tip 406 to the hand piece tip 416. This double bonding with very strong adhesive causes the sample collection tip 406 to be held to the hand piece tip 416 with more adhesive force than the sample collection tip's own cohesive forces. Thus, under extreme pressure, the sample collection tip 406 will fragment rather than come loose from the hand piece 404, thereby minimizing the risk of swallowing the sample collection tip 406.

The hollow-core flexible conduit 410 is made of a suitable non-toxic hydrophobic slippery material, so that drugs, e.g., THC, will not stick to its interior surface, and the flow of viscous liquid saliva through the narrow-bore interior of the flexible conduit is facilitated. Pure polytetrafluoroethylene (PTFE or Teflon) has been found to be suitable for this purpose. To facilitate bonding of the flexible conduit 410 to surfaces, such as the bore 428 of the sample collection tip 406, the outer surface of the PTFE can be etched to a depth of a few angstroms thick with a hydrophilic surface. The inner diameter of the flexible conduit 410 is preferably selected based on the vacuum level and flow rates, while maximizing retention of volatile ethanol in the saliva sample as it is aspirated through the flexible conduit 410. An inner diameter of, e.g., 0.5 mm has been empirically found to be suitable for a vacuum level of 350 mmHg absolute and an air flow rate of between 5–50 ml/min. The thickness of the wall of the flexible conduit 410 is preferably suitable to prevent kinking, which may otherwise clog the bore of the flexible conduit 410, and thereby prevent collection of the saliva sample. Also, the specified wall thickness should provide sufficient strength to prevent most persons from being able to stretch or part the material, thereby preventing sample collection. A wall thickness of 0.50 mm has been found to be suitable for this purpose. The length of the flexible conduit 410 is preferably suitable to facilitate collection of the required volume of saliva from comfortably seated test subjects when the test console 102 is placed on a bench-top. A length of 45–60 cm has been found to be suitable for this purpose.

Figure 20:
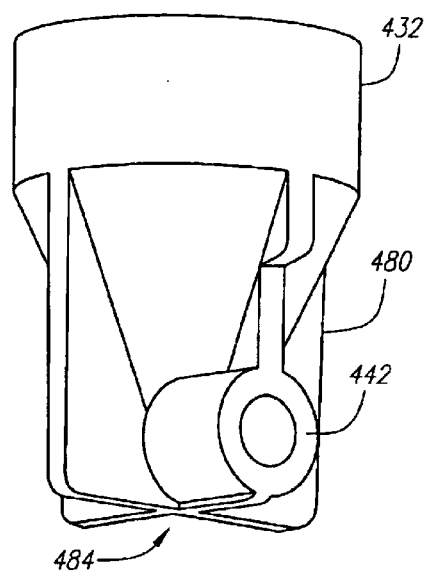
FIG. 20 is a perspective view of a bottom chamber base used to construct the sample collection chamber.
Figure 21:
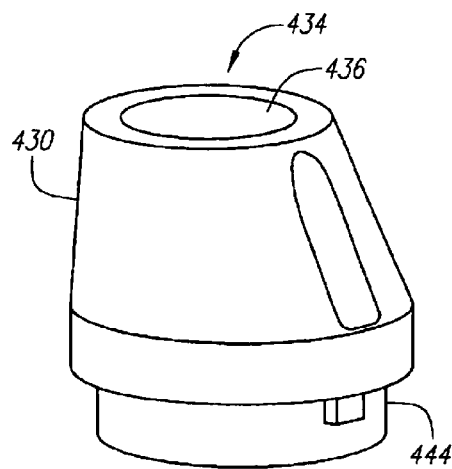
FIG. 21 is a perspective view of a top chamber cap used to construct the sample collection chamber.

Referring to FIGS. 20 and 21, the sample collection chamber 412 is composed of a suitable material, such as injection molded ABS polymer, and is formed of a top chamber cap 430 and a bottom chamber base 432, which are thermally welded together around their circumference. The top chamber cap 430 includes a self-sealing vacuum port 434 within which there is tightly disposed a hydrophobic seal 436. In the illustrated embodiment, the seal 436 is composed of a self-sealing polyethylene membrane that comprises small-diameter pores that are coated with a hydrophilic substance, such as carboxymethlcellulose. When wetted, the hydrophilic pores rapidly swell, closing the pore interiors, thereby preventing liquid from passing through the membrane. This self-sealing vacuum port 434, thus facilitates passing air, while preventing liquid or spray droplets from passing from the cassette, which contains all saliva-wetted parts of the system 100, into the test console 102, which must remain dry in order to prevent even the remote possibility of electrical shock hazard. The self-sealing vacuum port 434 also serves to keep the potentially biologically hazardous saliva from leaking out of the cassette 152 after its disposal following use.

Figure 22:
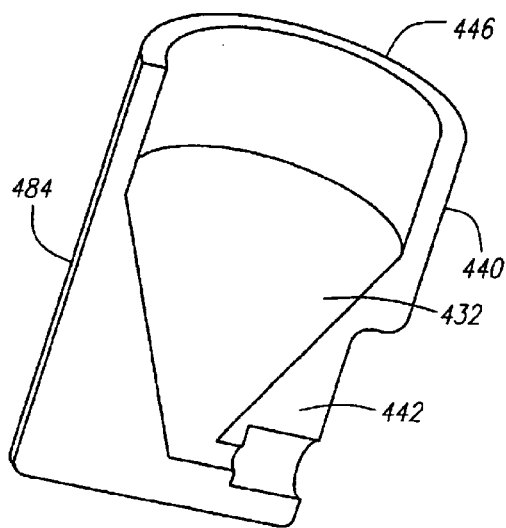
FIG. 22 is a cut-away perspective view of the bottom chamber base.
Figure 23:
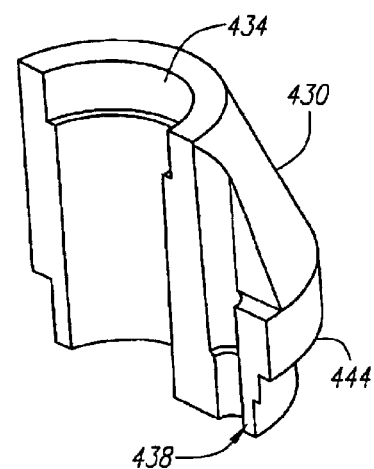
FIG. 23 is a cut-away perspective view of the top chamber cap.

Referring further to FIGS. 22 and 23, the top chamber cap 430 further includes a sample input port 438 within which the end of the flexible conduit 410 is bonded with a suitable material, such as a medical grade cyanoacrylate adhesive. The diameter of the input port 438 is of a suitable value, e.g., 1.5 mm, to facilitate a tight fit with the flexible conduit 410. The sample input port 432 leads to an internal chamber 440 within the bottom chamber base 432, which in the illustrated embodiment, has a diameter of 1 cm and holds an interior volume of 0.5 ml of saliva without wetting the self-sealing vacuum port 434. The internal chamber 440 has an inverted conical shape. Specifically, the internal chamber 440 is cylinder-shaped at its upper rim and gradually narrows to small diameter at its lower end, e.g., 0.5 mm, which leads to a sample dispense port 442 having the same diameter. So that the sample input port 438 is clocked in a predetermined rotational orientation with respect to the chamber base 432, the chamber cap 430 and chamber base 432 are provided with an alignment mechanism, and specifically a mating detent 444 and slot 446. In this manner, the portion of the flexible conduit 410 attached to the sample input port 438 will be consistently positioned adjacent a routing slot 175 formed on the top 160 of the cassette case 154, thereby allowing the flexible conduit 410 of the sample collection assembly 400 to be conveniently routed from the sample collection chamber 412 to the exterior of the cassette case 154.

B. Sample Collection Assembly—Tester Portion

Having just described the portion of the sample collection assembly 400 associated with the cassette assembly, the portion of the sample collection assembly 400 associated with the test console 102 will be discussed. Referring to FIGS. 6 and 16, the sample collection assembly 400 further includes a vacuum port connector 450, vacuum port drive assembly 452, vacuum tubing 454, vacuum pump 456 with an associated vacuum inlet filter 458, and a fluid sensor 460 (shown in FIG. 8).

The vacuum port connector 450 is composed of a compliant silicone rubber in the form of bellows, a compliant rim of which forms a tight vacuum seal when engaged with the cassette vacuum port 434. In the illustrated embodiment, the vacuum port connector 450 is 1.5 cm in length, and 1 cm in diameter, with its compliant rim 2 mm in width. The vacuum port connector 450 is engaged with the cassette vacuum port 434 by the vacuum port drive assembly 452, which includes a linear stepper motor 462 and a motor mount 464. The motor 462 is mounted to the motor mount 464, which is in turn mounted to the distribution flange 124. The vacuum port drive assembly 452 farther includes a threaded drive pin 466 rotatably coupled to the motor 462, and a threaded positioner 468 through which the drive pin 466 extends. The vacuum port drive assembly 452 further includes a first drive flange 470 affixed to the threaded positioner 468, and a second drive flange 472 on which the vacuum port connector 450 is affixed. The second drive flange 472 is mounted to the first drive flange 470, which includes a runner 474 that slidingly engages a rail 476 extending along the distribution flange 124.

Figure 5:
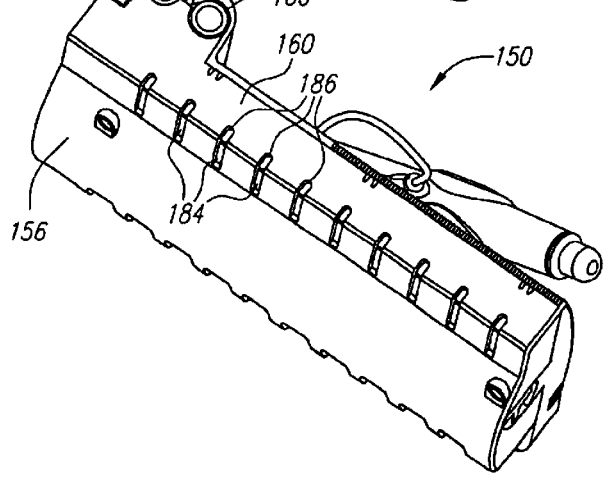
FIG. 5 is a top perspective view of the cassette assembly.

Thus, the vacuum port drive assembly 452 can be operated to lower the vacuum port connector 450 from a home position (wherein the vacuum port connector 450 is disengaged with the cassette vacuum port 434 to a pre-collection position (wherein the compliant rim of the connector 450 and the cassette vacuum port 434 coincide and provide a tight seal. As shown in FIGS. 2 and 5, a vacuum port access opening 166 is formed at the top 160 of the cassette case 154, thereby allowing the vacuum port connector 450 to engage the vacuum port 434 of the sample collection chamber 412.

The other end of the vacuum port connector 450 is connected to the vacuum tubing 454, which is composed of a suitable material, such as Tygon tubing. The vacuum tubing 454 is in turn connected to one port of the vacuum inlet filter 458, which is composed of a suitable material, such as 0.1 μm diameter port microporous hydrophilic PTFE. This prevents dust, liquid droplets, or in the event of a catastrophic failure, liquid saliva from contaminating the vacuum pump 456. The other port of the inlet filter 458 is connected to a vacuum inlet port 476 of the vacuum pump 456. In the illustrated embodiment, the vacuum pump 456 is mounted to the inside of the casing 108. Thus, the vacuum pump 456 can be operated to create negative pressure within the sample collection assembly 400.

Figure 8:
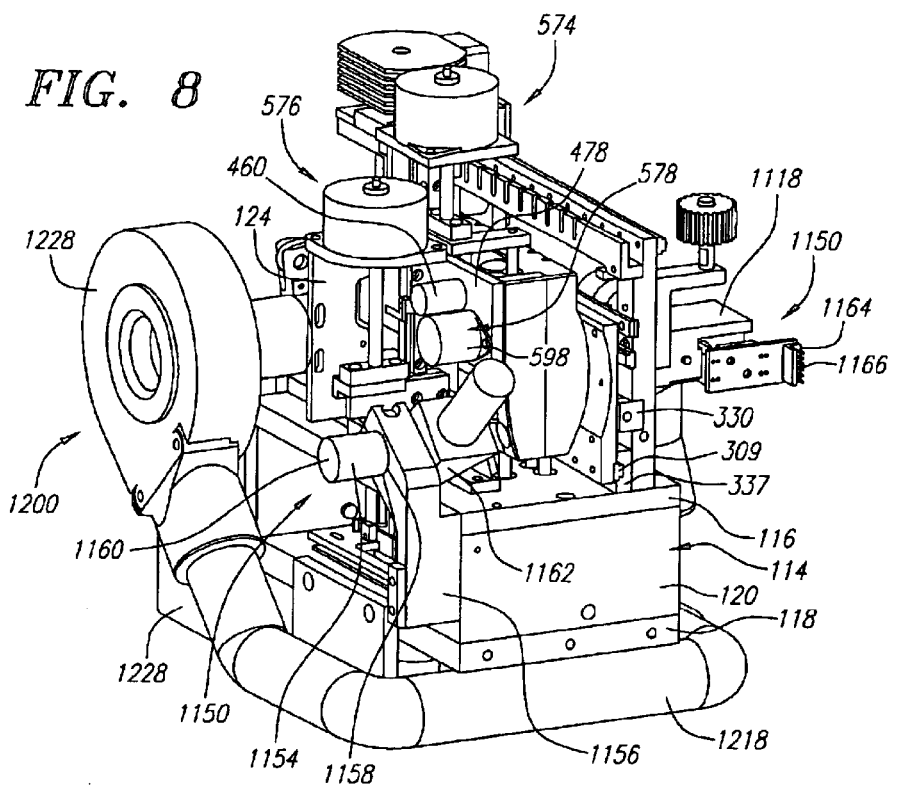
FIG. 8 is a rear-right perspective view of the inner components of the test console with the cassette assembly.

Referring to FIG. 8, the fluid sensor 460, which is used to sense when a predetermined amount of saliva sample has been collected in the sample collection chamber 412, is mounted to a mounting flange 478, which is in turn mounted to the distribution flange 124 to place the fluid sensor 460 into contact or near contact (e.g., <0.5 mm or <0.20 in) with the outside wall of the sample collection chamber 412 when the cassette 152 is fully loaded into the test console 102. In the illustrated embodiment, the fluid sensor 460 contains a 1 cm diameter sense electrode that is placed at a height, such that a volume of 350 μl saliva sample is collected at the bottom of the sample collection chamber 412. As shown in FIG. 2, a sensor access opening 168 is provided in the rear 158 of the cassette case 154 adjacent the sample collection chamber 412, thereby allowing the fluid sensor 460 to be in direct capacitive engagement with the sample collection chamber 412.

It should be noted that the vacuum port drive assembly 452 and vacuum pump 456 are all operated under control of a CPU 204 and I/O controller 206 (FIG. 12). A vacuum motor drive sensor (generally shown in FIG. 12) and the rail 474, which is indexed, are used to provide independent confirmation of the position of the vacuum port connector 450, while vacuum pressure and air flow sensors (generally shown in FIG. 12) are used to measure vacuum level and air flow rate within the vacuum pump 456.

C. Sample Collection Assembly—Operation

Having described the structure of the sample collection assembly 400, its operation will now be described. After the cassette 152 is fully loaded into the test console 102, and after the hand piece 404 is placed into the mouth of the test subject, the vacuum pump 456 is semi-automatically operated (i.e., prompted by the operator) prior to engagement of the vacuum port connector 450 with the cassette vacuum port 434. During this time, the vacuum level and flow rate are measured using the vacuum level and-flow rate sensors to determine if they fall within appropriate limits (vacuum level $\geq 200$ mmHg differential; vacuum flow rate $\geq 100$ ml/min). This measurement ensures that the vacuum pump 456 is operating properly. Simultaneous with these measurements, the vacuum port drive motor 462 is operated to move the vacuum port connector 450 downward from its home position to its pre-collection position into sealing engagement with the cassette vacuum port 434. Once the vacuum port connector 450 is in fill contact with the cassette vacuum port 434, the vacuum level and flow rate are again measured by their respective sensors and again determined to be within appropriate limits (vacuum level $\geq 300$ mmHg differential; vacuum flow rate $\geq 20$ ml/min). This measurement ensures that the cassette portion of the sample collection assembly 400 is operating properly.

If the vacuum level is less than the 300 mmHg differential, than a vacuum leak at the cassette vacuum port 434 is determined. In this case, the vacuum port connector 450 is disengaged and repositioned over the vacuum port 434. The vacuum level is again measured, and if less than the 300 mmHg differential, the vacuum port connector 450 is disengaged, and the chemistry cassette 152 is ejected from the test console 102 and then reloaded into the test console 102. The vacuum level is again measured, and if less than the 300 mmHg differential, the vacuum leak is considered fatal.

If the vacuum level is greater than the 300 mmHg differential, but the air flow rate is less than 20 ml/min, than a vacuum leak within the chemistry cassette 152 is determined, which would typically be caused by a leak within the sample/buffer mixing assembly, as will be described in further detail below. In this case, the vacuum port connector 450 is disengaged, the chemistry cassette 152 is ejected from the test console 102, and then, after prompting the operator, another chemistry cassette 152 is loaded into the test console 102. The vacuum level and air flow rate tests are then repeated for the new chemistry cassette 152. If on the other hand, the vacuum level is greater than the 300 mmHg differential, but the air flow rate is less than 20 ml/min, it is determined that the conduit 410 or sample collection tip 406 is clogged. In this case, the vacuum port connector 450 is disengaged, the chemistry cassette 152 is ejected from the test console 102, and then, after prompting the operator, another chemistry cassette 152 is loaded into the test console 102. The vacuum level and air flow rate tests are then repeated for the new chemistry cassette 152.

Once the vacuum level and air flow rate have been determined to be within the control limits, saliva collection begins. Air is drawn out of the cassette vacuum port 434, drawing a mixture of saliva sample and air into the sample collection tip 406 from the mouth of the test subject, through the flexible conduit 410, and into the internal chamber 440 of the sample collection chamber 412, where it is released from the turbulent flow conditions of the small-bore port 438 into a laminar flow within the much larger diameter internal chamber 440. Because the sample collection chamber 412 is oriented in a vertical direction along the height axis of the cassette 152, which is also held vertically by the test console 102, gravity causes the more dense liquid saliva to settle to the bottom of the internal chamber 440, while air is drawn from the top of the internal chamber 440 through the vacuum port 434 as a partial vacuum is applied thereto. The inverted conical shape of the internal chamber 440 facilitates collection of all of the liquid saliva from the sample collection chamber 412 as it funnels down to the small diameter dispense port 442.

Saliva collection is continued until the sample collection chamber 412 is filled with the predetermined quantity of saliva sample, as measured by the fluid sensor 460, or until a predetermined amount of time (in the illustrated embodiment, one minute) elapses. If one minute has expired without collecting the predetermined amount of saliva sample, the operator is prompted to readjust the sample collection tip 406 within the test subject's mouth, and saliva collection commences until the sample collection chamber 412 is filled with the predetermined quantity of saliva sample, as measured by the fluid sensor 460, or until another predetermined amount of time (in the illustrated embodiment, one minute) elapses. If the second minute has expired without collecting the predetermined amount of saliva sample, the process is repeated again. Sample collection is aborted if the third attempt at collecting the saliva fails. If, however, a predetermined quantity of saliva sample has been collected, the vacuum pump 456 is turned off, and the operator, after prompted, removes the aspirator 402 from the test subject and re-caps it.

V. Sample/Buffer Mixing Subassembly

Referring to FIGS. 8 and 24–38, the system 100 further comprises a sample/buffer mixing assembly 500, the purpose of which is to pipette predetermined volumes of collected saliva sample and buffer solution and mix them into a less viscous and higher volume buffered saliva sample solution. Mixing equal volumes of saliva sample and buffer also tends to equalize the pH and ionic strength of the saliva sample to minimize sudden changes during the immunoassay test that could cause the antibody to falsely release bound antigen in the absence of the analyte.

A. Sample/Buffer Mixing Subassembly—Cassette Portion

Figure 24:
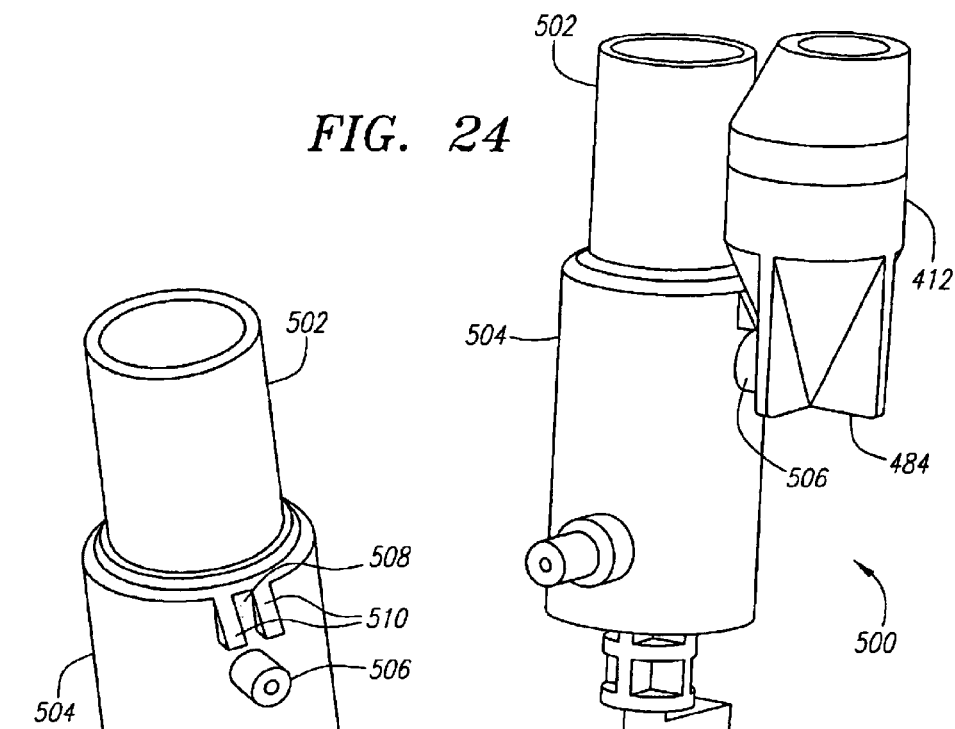
FIG. 24 is a perspective view of the cassette portion of a sample mixing assembly.
Figure 25:
FIG. 25 is a perspective view of the buffer chamber and mixing chamber of the sample mixing assembly.
Figure 26:
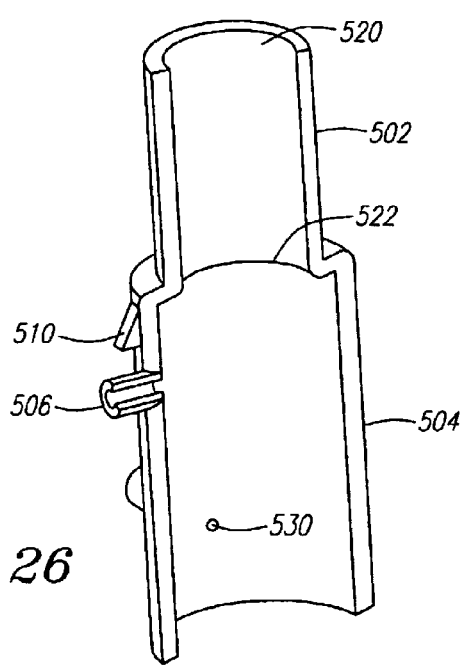
FIG. 26 is a cut-away perspective view of the buffer chamber and mixing chamber.

Referring specifically to FIGS. 24–26, the portion of the sample/buffer mixing assembly 500 that resides in the cassette 152 includes a buffer chamber 502, the previously described sample collection chamber 412, and a mixing chamber 504. In the illustrated embodiment, the buffer chamber 502 and mixing chamber 504 are combined into a cylindrically shaped unibody design composed of a suitable material, such as injection molded polypropylene polymer, but alternatively can be separate and distinct bodies that are suitably mated to each other. The buffer chamber 502 and mixing chamber 504 are in axial alignment with each other, which as will be described in further detail, facilitates interaction between plungers. The buffer chamber 502 contains a neutral buffer solution, e.g., phosphate buffered saline (PBS) buffer solution (pH 6.9), and the sample collection chamber 412 contains saliva as a result of the sample collection process. In the illustrated embodiment, the buffer chamber 502 holds 300 $\mu l$ of buffer, and as previously mentioned, the sample collection chamber 412 collects 350 $\mu l$ of saliva sample. Assuming equal parts of the buffer and saliva sample are mixed, the mixing chamber 504 holds at least 600 $\mu L$ of the mixed and buffered saliva solution.

The sample collection chamber 412 is removably affixed to the mixing chamber 504. Specifically, the sample dispense port 442 of the sample collection chamber 412 is mated with a sample inlet port 506 of the mixing chamber 504. So that an integral sample/buffer mixing assembly 500 is formed, the chamber base 432 of the sample collection chamber 412 includes a radially extending ridge 480 (shown best in FIG. 20), which mates with a slot 508 formed between two vertical radially extending ridges 510 on the buffer chamber 502, thus providing three-axis rotational stability. In addition, a chamber stand 482 is formed on the exterior of the chamber base 432 of the sample collection chamber 412, which as will be described in further detail below, rests on a ledge within the cassette 152, thereby minimizing the shearing and bending stress created at the connection between the sample dispense port 442 and the sample inlet port 506.

Figure 27:
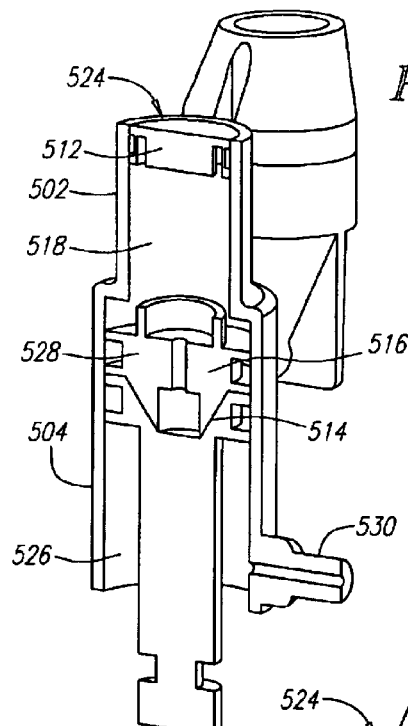
FIG. 27 is a cutaway perspective view of the sample mixing assembly shown in a home position.

Referring to FIG. 27, the mixing assembly 500 further includes a buffer dispense plunger 512, which is disposed in the buffer chamber 502, a sample dispense plunger 514, which is disposed within the mixing chamber 504, and buffered sample dispense plunger 516, which is also disposed within the mixing chamber 504. The buffer chamber 502 comprises a cylindrical bearing surface 518 with which the buffer dispense plunger 512 sealingly mates. The buffer chamber 502 comprises puncturable upper and lower seals 520 and 522 (shown in FIG. 26) at the top and bottom of the buffer chamber 502 to completely seal the buffer within the buffer chamber 502 until the mixing process has commenced. The upper and lower seals 520 and 522 prevent water vapor from escaping the confines of the buffer chamber 502 during storage of the cassette 152, and are composed of a suitable material, such as aluminum foil-lined/polymer bilayer seals. The buffer chamber 502 further includes a buffer chamber access port 524, which provides mechanical access to the buffer chamber 502.

The mixing chamber 504 comprises a plunger bearing surface 526 with which the sample dispense plunger 514 and buffered sample dispense plunger 516 sealingly mate. The mixing chamber 504 further comprises three ports: (1) a buffer port 528, which facilitates the flow of buffer from the buffer chamber 502 into the mixing chamber 504; (2) the previously described sample port 506, which is mated with the dispense port 442 of the sample collection chamber 412, and thus facilitates the flow of saliva from the sample collection chamber 412 into the mixing chamber 504; and (3) a dispense port 530, which is mated with a feed port of a flow immunoassay assembly (as will be described in further detail below), and thus facilitates the flow of buffered sample solution from the mixing chamber 504 into the flow immunoassay assembly. As illustrated, the buffer port 528 is located at the top of the mixing chamber 504, the sample port 506 is located near the top of the mixing chamber 504 but below the buffer port 528, and the dispense port 530 is located at the bottom of the mixing chamber 504. For the purposes of this specification, the buffer port 528 can be considered a longitudinal port, since it is parallel to the plunger bearing surface 526 of the mixing chamber 504. In contrast, the sample and dispense ports 506 and 530 can be considered lateral ports, since they are perpendicular to the plunger bearing surface 506 of the mixing chamber 504.

The plungers are used to dispense the buffer and sample within the mixing chamber 504 to form the buffered sample solution, and then to dispense the buffered sample solution from the mixing chamber 504. Specifically, the movement of the buffer dispense plunger 512 within the buffer chamber 502 towards the buffer port 528 dispenses the buffer from the buffer chamber 502 into the mixing chamber 504 via the buffer port 528 under positive pressure. Movement of the sample dispense plunger 514 within the mixing chamber 504 away from the sample port 506 dispenses the sample from the sample collection chamber 412 into the mixing chamber 504 via the sample port 506 under negative pressure. Movement of the buffered sample dispense plunger 516 within the mixing chamber 504 towards the dispense port 530 dispenses the buffered sample solution out of the mixing chamber 504 via the dispense port 530 under positive pressure.

The mixing assembly 500 provides for the accurate dispensing of buffer and saliva into the mixing chamber 504 in accordance with a selected fluid mixing ratio r, which in the illustrated embodiment, has been selected to be 1:1. Specifically, the cross-sectional area $A_1$ of the buffer chamber 502, cross-sectional area $A_2$ of the mixing chamber, buffer dispense plunger speed $S_1$, and sample dispense plunger speed $S_2$, are selected in accordance with the equation $A_2 S_2 = A_1 S_1 (1+1/r)$. For example, if the buffer dispense plunger speed $S_1$ and sample dispense plunger speed $S_2$ are equal, a 1:1 mixing ratio r can be achieved by providing a mixing chamber cross-sectional area $A_2$ that is twice as great as the buffer chamber cross-section area $A_1$. On the other hand, if mixing chamber cross-sectional area $A_2$ is equal to the buffer chamber cross-sectional area $A_1$, a 1:1 mixing ratio r can be achieved by providing a sample dispense plunger speed $S_2$ that is twice is great as the buffer dispense plunger speed $S_1$. In either case, the greater the ratio between the cross-sectional areas $A_2$ and $A_1$ or the greater the ratio between the plunger speeds $S_2$ and $S_1$, the more saliva is drawn into the mixing chamber 504 relative to the buffer.

Figures 32, 33:
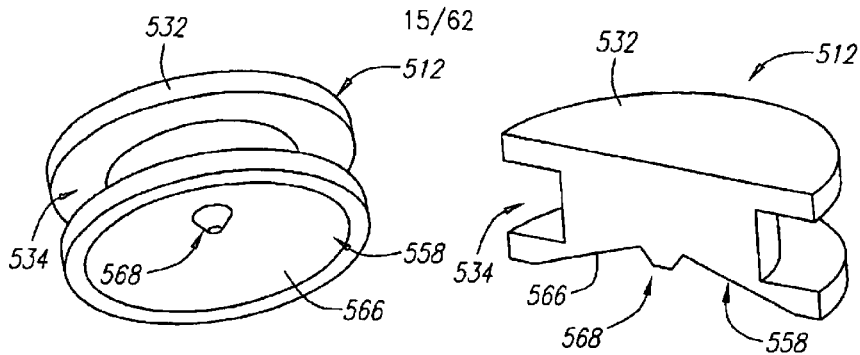
FIG. 32 is a perspective view of a buffer plunger for use in the mixing assembly.
FIG. 33 is a cutaway perspective view of the buffer plunger.

Referring to FIGS. 32–37, buffer, sample, and buffered sample dispense plungers 512, 514, and 516 will now be described. Referring specifically to FIGS. 32 and 33, the buffer dispense plunger 512 comprises a rigid plunger head 532, which includes an O-ring groove 534 for seating of an O-ring (not shown). The O-ring of the buffer dispense plunger 512 facilitates a sealing relationship between the buffer dispense plunger 512 and the bearing surface 518 of the buffer chamber 502, which preferably is coated with a silicone based substance to further facilitate this sealing relationship. Prior to use, the buffer dispense plunger S12 is completely sealed within the buffer chamber 502 between the upper and lower seals 520 and 522 As will be described in further detail below, the buffer dispense plunger 512 can be moved down within the buffer chamber 502 after the top seal 520 of the buffer chamber 502 is punctured, and then down within the mixing chamber 504 after the bottom seal 522 of the buffer chamber 502 is punctured.

Figures 34, 35:
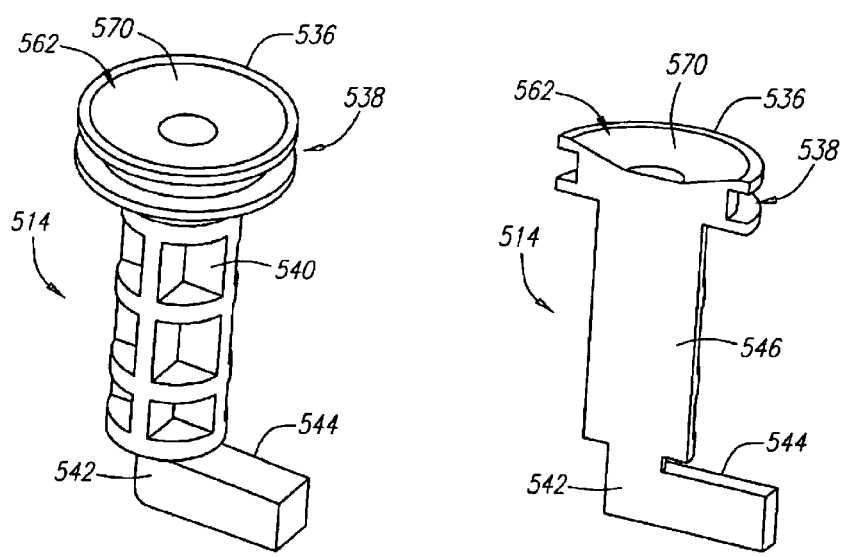
FIG. 34 is a perspective view of a sample dispense plunger for use in the mixing assembly.
FIG. 35 is a cutaway perspective view of the sample dispense plunger.

Referring specifically to FIGS. 34 and 35, the sample dispense plunger 514, like the buffer dispense plunger 512, comprises a rigid plunger head 536, which includes an O-ring groove 538 for seating of an O-ring (not shown). The O-ring of sample dispense plunger 514 facilitates a sealing relationship between the sample dispense plunger 514 and the bearing surface 526 of the mixing chamber 504, which preferably is coated with a silicone based substance to further facilitate this sealing relationship. The sample dispense plunger 514 further includes a rigid plunger body 540 and a plunger arm 542, which includes a 90° angled end 544.

As will be described in further detail below, the sample dispense plunger 514 may be moved up or down within the mixing chamber 504.

Figures 36, 37:
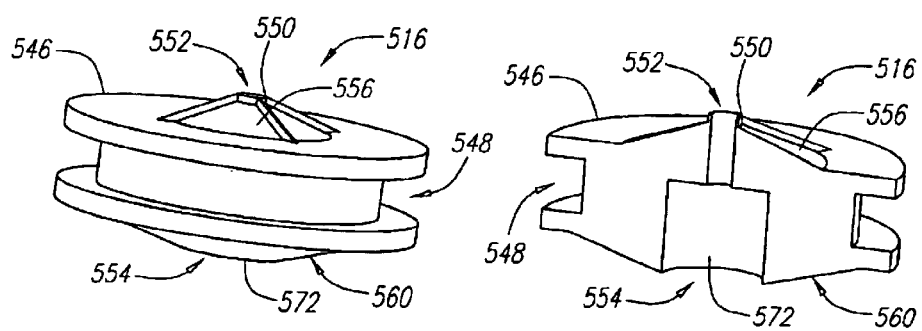
FIG. 36 is a perspective view of a buffered sample dispense plunger for use in the mixing assembly.
FIG. 37 is a cutaway perspective view of the buffered sample dispense plunger.

Referring specifically to FIGS. 36 and 37, the buffered sample dispense plunger 516, like the buffer and sample dispense plungers 512 and 514, also comprises a rigid plunger bead 546, which includes an O-ring groove 548 for seating of an O-ring (not shown). Like with the sample dispense plunger 514, the O-ring of the buffered sample dispense plunger 516 facilitates a sealing relationship between the buffered sample dispense plunger 516 and the bearing surface 526 of the mixing chamber 504. The buffered sample dispense plunger 516 further includes a stylus 550, which punctures the bottom seal 522 of the buffer chamber 502 when seated against the buffer port 528, and a through port 552, which allows buffer from the buffer chamber 502 to flow into the mixing chamber 504. The through port 552 is of a suitable size, e.g., 1 mm. The buffered sample dispense plunger 516 also comprises a ferrous element relief 554, which temporarily stores a magnetic mixing flea (not shown). The buffered sample dispense plunger 516 is moved up or down within the mixing chamber 504 with the buffer and sample dispense plungers 512 and 514. The buffered sample dispense plunger 516 serves to space the sample dispense plunger 514 a distance away from the top of the mixing chamber 504, so that it is adjacent to the sample port 506, the purpose of which will be described in further detail below.

To this end, and referring generally to FIGS. 34–37, the buffered sample dispense plunger 516 has a top thrust surface 556, which mates with a bottom thrust surface 558 of the buffer dispense plunger 512, and a bottom thrust surface 560, which mates with a top thrust surface 562 of the sample dispense plunger 514. Specifically, the bottom thrust surface 558 of the buffer dispense plunger 512 forms a stylus relief 564, which receives the stylus 550 of the buffered sample dispense plunger 516 in a complementary fashion, and a plug 566, which fits within and seals the through port 552 of the buffered sample dispense plunger 516. The top thrust surface 562 of the sample dispense plunger 514 forms a concave recess 570, which receives a convex protrusion 572 of the bottom thrust surface 560 of the buffered sample dispense plunger 516 in a complementary fashion. Thus, the buffer dispense plunger 512 can mate with and push the buffered sample dispense plunger down within the mixing chamber 504 as an integral unit, and the sample dispense plunger 514 can mate with and push the buffered sample dispense plunger up within the mixing chamber 504 as an integral unit.

B. Sample/Buffer Mixing Subassembly—Tester Portion

Figure 38:
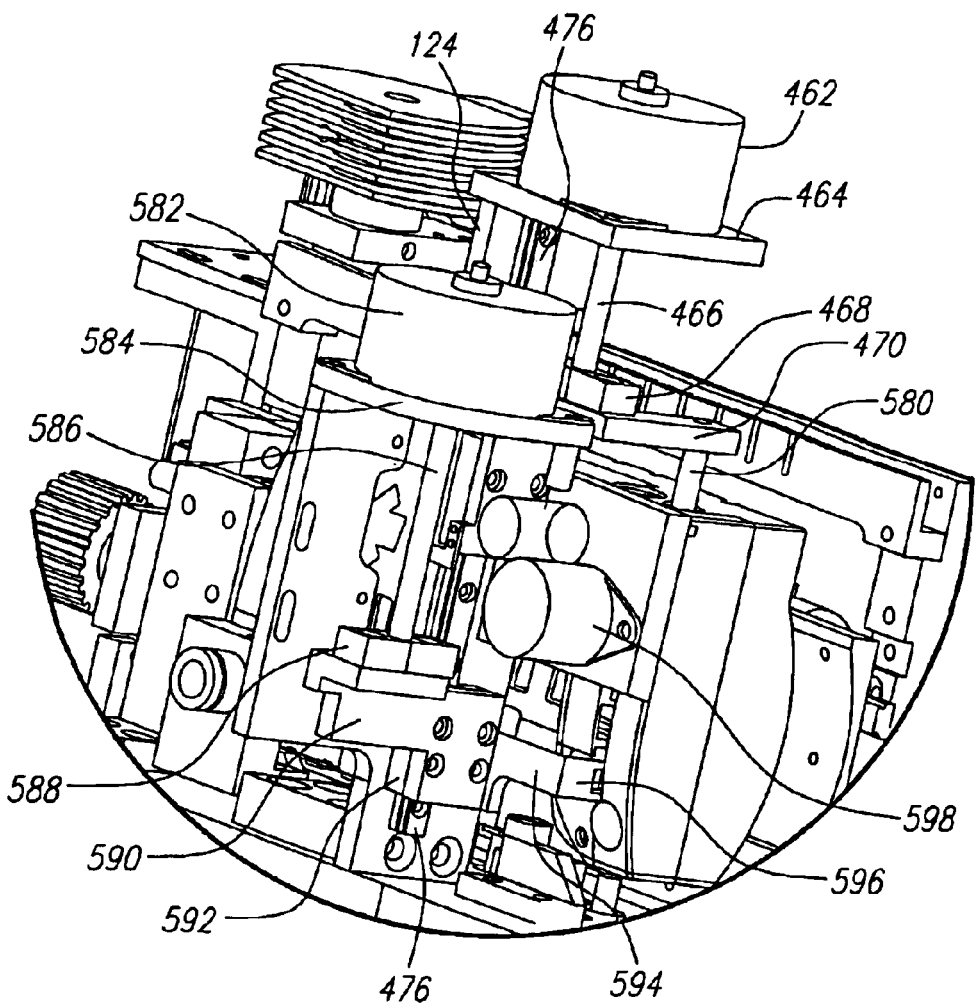
FIG. 38 is a close-up perspective view of the test console portion of the mixing assembly, and particularly, the sample and buffer drive assemblies.

Referring to FIGS. 8 and 38, the portion of the sample/buffer mixing assembly 500 that resides in the test console 102 comprises a buffer drive assembly 574, a sample drive assembly 576, and a mixing drive assembly 578.

The buffer drive assembly 574 includes the previously described linear stepper motor 462, motor mount 464, threaded drive pin 466, threaded positioner 468, and first drive flange 470. The buffer drive assembly 574 further includes a buffer driver 580 that is mounted through the first flange 470. The buffer driver 580 is aligned with the buffer chamber access port 524, so that when the buffer driver 580 is driven downward from a pre-mix position to a dispense position, it engages and pushes the buffer dispense plunger 512 downward into the buffer chamber 502 after the upper seal 520 of the buffer chamber 502 is punctured. A buffer chamber access opening 170 is formed at the top 160 of the cassette case 154 (shown in FIGS. 2 and 5), thereby allowing the buffer driver 580 to engage the buffer dispense plunger 512 within the buffer chamber 502.

The sample drive assembly 576 includes a linear stepper motor 582 and a motor mount 584. The motor 582 is mounted to the motor mount 584, which is in turn mounted to the distribution flange 124. The sample drive assembly 576 further includes a threaded drive pin 586 rotatably coupled to the motor 582, and a threaded positioner 588 through which the drive pin 586 extends. The sample drive assembly 576 further includes a first drive flange 590 affixed to the threaded positioner 588. The first drive flange 590 includes a runner 592 that slidingly engages the rail 476 extending along the distribution flange 124. The sample drive assembly 576 further includes a 9° g angled driver 594, which can be alternately driven upward and downward by the motor 582 a predetermined stepped distance. The angled sample driver 594 has a pronged tip 596, which engages the angled end 544 of the plunger arm 542 as the cassette 152 (as illustrated in FIG. 2) is loaded into the test console 102.

A horizontal access slot 172 is formed within the rear 158 of the cassette case 154 (shown in FIG. 2), terminating adjacent the angled end 544 of the plunger arm 542 to facilitate its engagement with the pronged tip 596 of the sample driver 594. When engaged, downward and upward movement of the sample driver 594 correspondingly moves the sample dispense plunger 514 downward and upward into the mixing chamber 504. A vertical access slot 174 is formed within the rear 158 of the cassette case 154 (shown in FIG. 2) adjacent the angled end 544 of the plunger arm 542, thereby allowing angled sample driver 594 to vertically displace the sample dispense plunger 514.

The mixing drive assembly 578 includes a rotary mixing motor 598, which is mounted to the mounting flange 478, and a mixing coupling (not shown) that is rotatably coupled to the mixing motor 598, which is located adjacent the mixing chamber 504 of the mixing assembly 500 when the cassette 152 is loaded into the test console 102. The mixing coupling contains two magnets (also not shown), which when rotated by the mixing motor 598 magnetically interact with the ferrous element (not shown) within the mixing chamber 504.

It should be noted that the sample drive assembly 576, buffer drive assembly 574, and mixing drive assembly 578 are all operated under control of a CPU 204 and I/O controller 206 (shown in FIG. 12), with sample and buffer motor sensors (generally shown in FIG. 12) used to provide independent confirmation of the positions of the sample and buffer drivers 580 and 594.

C. Sample/Buffer Mixing Subassembly—Operation

Referring generally to FIGS. 27–31, with general reference to FIG. 38, the operation of the mixing assembly 500 will now be described. During operation of the mixing assembly 500, the respective sample and buffer drive assemblies 574 and 576 are operated to move the buffer, sample, and buffered sample plungers 512, 514, and 516 upward and downward within the chambers of the mixing assembly 500.

Referring specifically to FIG. 27, the mixing assembly 500 is shown in its shipping or home position. The buffer is completely sealed within the buffer chamber 502 with the top and bottom seals 520 and 522 of the buffer chamber 502 yet to be punctured. The buffer dispense plunger 512 is located at the top of the buffer chamber 502, so that mixing chamber 504 contains the maximum amount of buffer. The buffered sample dispense plunger 516 is at the top of the mixing chamber 504, but is not seated against the buffer port 528, and has therefore not yet punctured the bottom seal 522 of the buffer chamber 502. The sample dispense plunger 514 is mated with the buffered sample dispense plunger 516. The O-ring of the buffered sample dispense plunger 516 seals the sample port 506 in this position to ensure that there is no vacuum leak during the previously described sample collection process.

Figure 28:
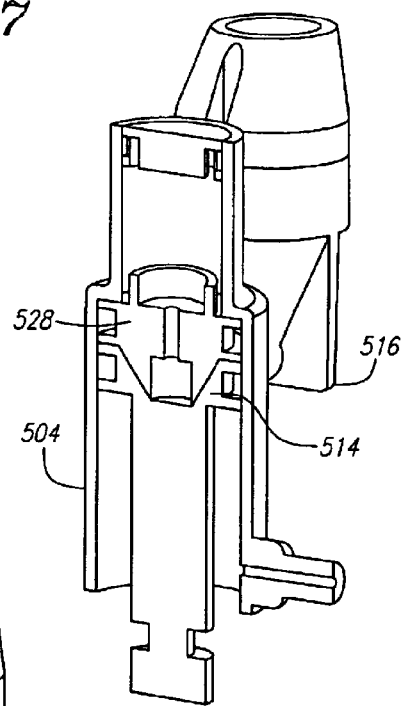
FIG. 28 is a cutaway perspective view of the sample mixing assembly shown in a pre-sample and buffer dispensing position.

Referring specifically to FIG. 28, the sample drive assembly 576 is semi-automatically operated (i.e., prompted by the operator) to move the sample dispense plunger 514, and thus the mated dispense plunger 514, upward within the mixing chamber 504 towards the buffer port 528 until the buffered sample dispense plunger 516 is seated against the buffer port 528, thereby puncturing the bottom seal 522 of the buffer chamber 502. At this point, the thickness of the buffered sample dispense plunger 516 spaces the top thrust surface 570 of the sample dispense plunger 514 a predetermined distance from the top of the mixing chamber 504, so that it is just below the sample port 506. It should be noted that at this point time, the saliva sample has already been collected in the sample collection chamber 412, and thus, the sample port 506 need not be sealed at this point.

Figure 29:
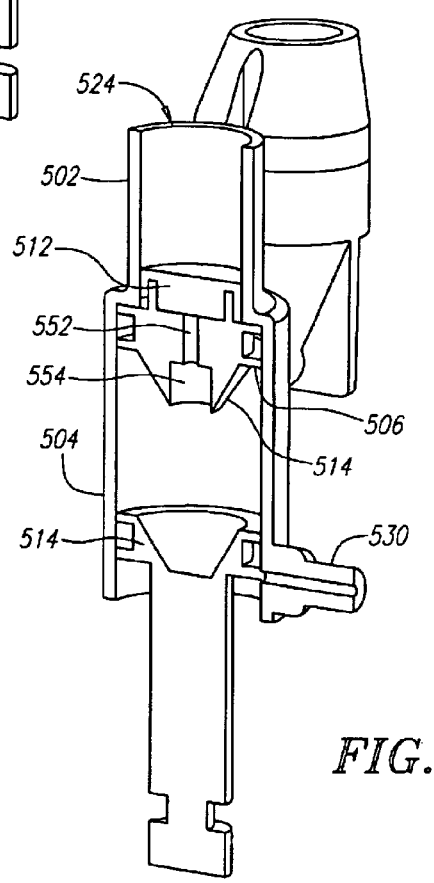
FIG. 29 is a cutaway perspective view of the sample mixing assembly shown in a buffered sample solution mixing position.

Referring specifically to FIG. 29, the buffer drive assembly 574 is then automatically operated (i.e., prompted by the CPU) to engage the buffer driver 466 with the buffer chamber access port 524, puncturing the upper seal 520, and then moving the buffer dispense plunger 512 downward within the buffer chamber 502 towards the buffer port 528. Simultaneously, the sample drive assembly 576 is operated to move the sample dispense plunger 514 downward within the mixing chamber 504 towards the dispense port 530. Thus, buffer flows from the buffer chamber 502, through the buffer port 528 and then through the through port 552 and ferrous element relief 554 of the buffered sample dispense plunger 516, into the mixing chamber 504. At the same time, saliva sample flows from the sample collection chamber 412, through the sample port 506, into the mixing chamber 504, thereby forming a buffered sample solution within the mixing chamber 504. During this dispensing process, the sample dispense plunger 514 remains above the dispense port 530, thus sealing it off from the buffered sample solution. It should be noted that partial mixing of the buffer and saliva sample occurs as they are dispensed into the mixing chamber 504.

Figure 30:
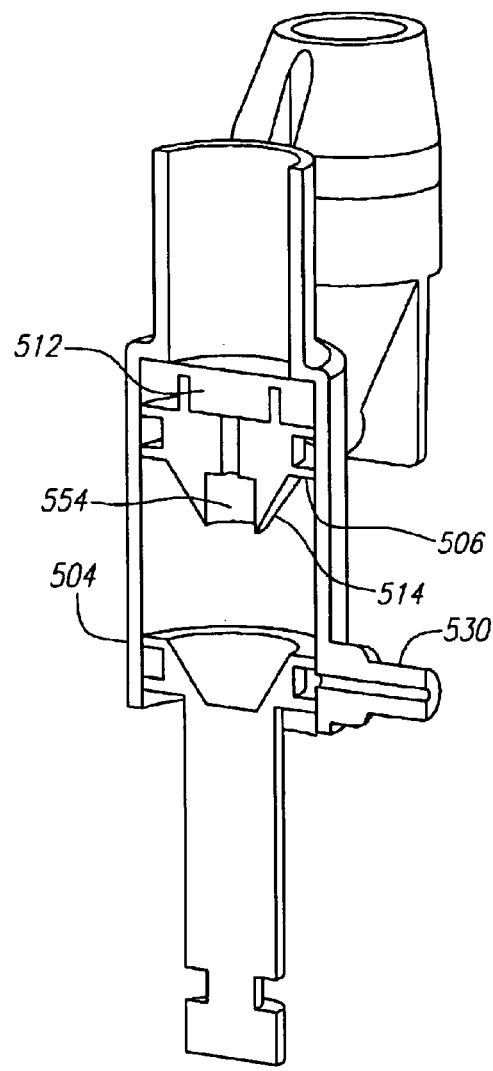
FIG. 30 is a cutaway perspective view of the sample mixing assembly shown in a pre-buffered sample solution dispensing position.

Referring specifically to FIG. 30, downward movement of the buffer dispense plunger 512 automatically ceases after the buffer dispense plunger 512 is mated with the buffered sample dispense plunger 516, and when the integral unit intersects the sample port 506 to seal it. Similarly, downward movement of the sample dispense plunger 514 ceases when the sample dispense plunger 514 is located at the bottom of the mixing chamber 564 intersecting the dispense port 530 to seal it. At this point, the ferrous element (not shown) is also released from the ferrous element relief 554 of the buffered sample dispense plunger 516 into the mixing chamber 504. The mixing drive assembly 578 is operated to rapidly move the ferrous element within the mixing chamber 504, thereby agitating, and thus, homogeneously mixing the buffered sample solution. Because the sample and dispense ports 506 and 530 are both sealed, none of the buffered sample solution leaks out the mixing chamber 504 during this enhanced mixing process.

Figure 31:
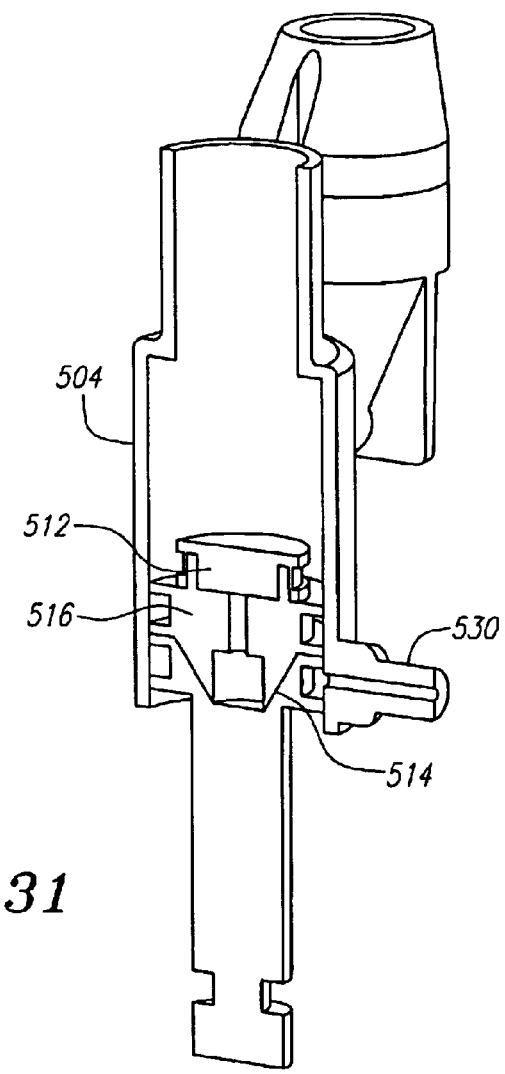
FIG. 31 is a cutaway perspective view of the sample mixing assembly shown in a post-buffered sample solution dispensing position.

Referring specifically to FIG. 31, the buffer drive assembly 574 is automatically operated again to move the buffer dispense plunger 512, and thus the buffered sample dispense plunger 516, downward within the mixing chamber 504 towards the dispense port 530. Simultaneous with this, the sample drive assembly 576 is automatically operated to move the sample dispense plunger 514 downward within the mixing chamber 504 until the entire sample dispense plunger 514 is below the dispense port 530. At this point, the dispense port 530 is exposed to the buffered sample solution within the mixing chamber 504, and downward movement of the sample dispense plunger 514 automatically ceases.

Downward movement of the mated buffer and buffered sample dispense plungers 512 and 516, on the other hand, continues, thereby dispensing the buffered sample solution from the mixing chamber 504 out through the dispense port 530. Downward movement of the mated buffer and buffered sample dispense plungers 512 and 516 continues until the buffered sample dispense plunger 516 mates with the sample dispense plunger 514, and thus when the buffered sample solution has been completely dispensed from the mixing chamber 504. Anytime prior to the ejection of the cassette 152 from the test console 102, the sample and buffer drive assemblies 574 and 576 are automatically moved back to their home positions (i.e., disengaged from the cassette 152).

VI. Flow Immunoassay Assembly

Referring generally to FIGS. 39–65, the system 100 comprises a flow immunoassay assembly 600, the purpose of which is to generate and exhibit a measurable immunoassay reaction for each targeted drug (ten in the illustrated embodiment) that is found in the buffered sample solution received from the sample/buffer mixing assembly 500. In performing this function, the flow immunoassay assembly 600 includes a sample/buffer flow assembly 602 and an immunoassay reaction assembly 604. The flow immunoassay assembly 600 comprises a plurality of sample flow channels 606 (ten in the illustrated embodiment) and a plurality of buffer flow channels 608 (ten in the illustrated embodiment), which are respectively used to flow sample and buffer therethrough in effecting the proper immunoassay reaction for each targeted drug.

A. Sample/Buffer Flow Assembly

The purpose of the sample/buffer flow assembly 602 is to provide appropriate volumes, flow rates, and flow times for continuous buffer pre-wash, sample, and buffer post-wash solutions to flow through the immunoassay reaction assembly 604.

1. Sample/Buffer Flow Assembly—Cassette Portion

Figure 39:
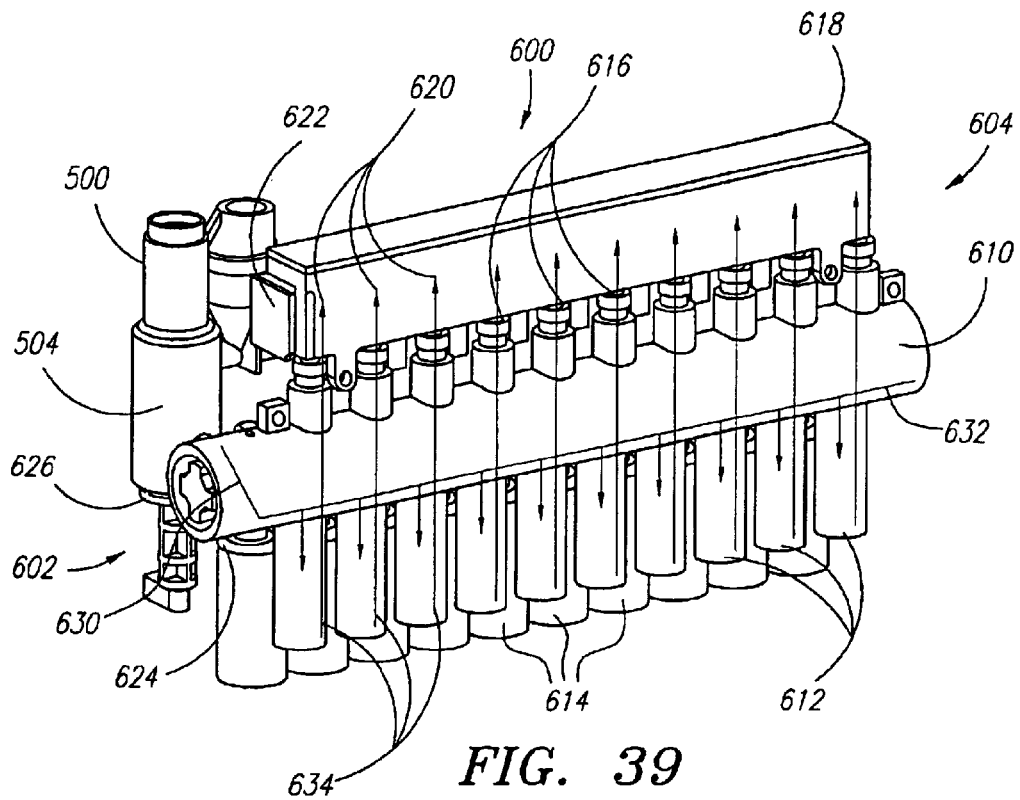
FIG. 39 is a front-left perspective view of the cassette portion of an immunoassay flow assembly.
Figure 40:
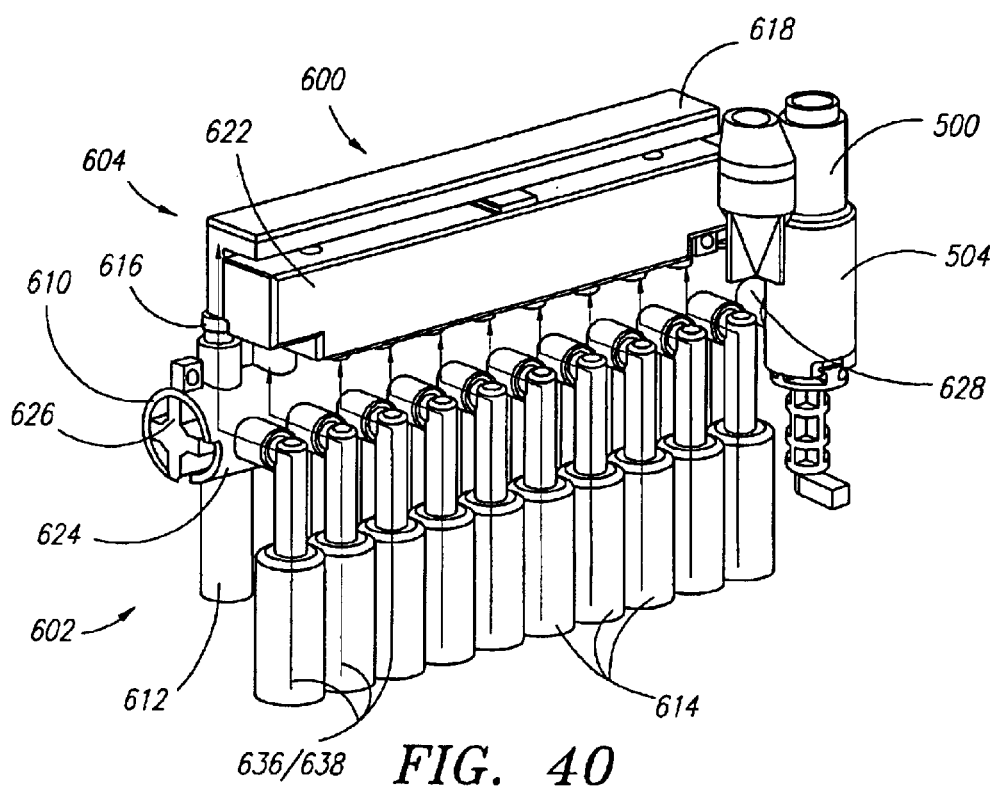
FIG. 40 is a rear-left perspective view of the cassette portion of the immunoassay flow assembly.

Referring specifically to FIGS. 39 and 40, the portion of the sample/buffer flow assembly 602 that resides in the cassette 152 includes a rotary valve 610 and an equal number (ten in the illustrated embodiment) of sample distribution chambers 612, buffer chambers 614, and a sample feed port 628. For purposes of context, the immunoassay reaction assembly 604, and specifically, an equal number of reaction chambers 616, a read cell assembly 618 comprising an equal number of read cells 620, and a waste chamber 622, are also illustrated.

The rotary valve 610 includes a generally cylindrical hollow stator 624 and a generally cylindrical rotor 626, which is inserted into the stator 624 in a rotatably sealing relationship. Preferably, the stator 624 is slightly lubricated with silicone oil to provide for a smooth rotary relationship between the stator 624 and rotor 626. The rotary valve 610 is of a suitable length to support the sample and buffer flow channels, which in the illustrated embodiment, is 13 cm. The rotor 626 can be clocked within the stator 624 to place the rotary valve 610 into a various configurations to effect predefined flow paths between the afore-described mixing chamber 504 of the mixing assembly 500 and the sample distribution chambers 612, between the sample distribution chambers 612 and the immunoassay reaction chambers 616, and between the buffer chambers 614 and the immunoassay reaction chambers 616.

In the illustrated embodiment, the rotary valve 610 can be clocked between a distribution configuration (sample distribution configuration), dispense configuration (sample flow configuration), first auxiliary dispense configuration (buffer pre-wash configuration), and second auxiliary dispense configuration (buffer post-wash configuration). In the illustrated embodiment, the sample distribution and buffer pre-wash configurations are simultaneously effected by placing the rotary valve 610 in a first position, and the sample dispense and buffer post-wash configurations are simultaneously effected by placing the rotary valve 610 in a second position clocked 90° from the first position.

Specifically, the rotary valve 610, when in the sample distribution configuration, places the sample feed port 628 in fluid communication with the sample distribution chambers 612, while preventing fluid communication between the sample distribution chambers 612 and reaction chambers 616, thus facilitating distribution of the buffered sample solution (hereinafter, sample) from the mixing assembly 500 into the sample distribution chambers 612 without prematurely exposing the immunoassay reaction chambers 616 to the sample. The rotary valve 610 also provides for proper venting of air displaced from the sample distribution chambers 612 during the distribution process. In the illustrated embodiment, a single vertical flow path 630 and a single horizontal flow path 632 accomplishes this by connecting the sample feed port 628 with the sample distribution chambers 612 using the vertical flow path 630, and connecting the sample distribution chambers 612 in series and filling them in a cascading manner using the horizontal flow path 632. In this manner, each of the sample distribution chambers 612 are filled with precisely-measured prevolumes of sample. Another single vertical flow path 634 connects the sample distribution chambers 612 to a vent port (not shown). It should be noted that for the purposes of this specification, elements are in fluid communication with each other when configured such that fluid flowing through one element correspondingly flows through the other element.

The rotary valve 610, when in the sample flow configuration, places the sample distribution chambers 612 in fluid communication with the immunoassay reaction chambers 616, while preventing fluid communication between the sample distribution chambers 612 and sample feed port 628, thus facilitating the flow of the sample from the sample distribution chambers 612 through the immunoassay reaction chambers 616, and preventing the flow of the sample out through the sample feed port 628. In the illustrated embodiment, ten parallel vertical flow paths 634 are formed between the sample distribution chambers 612 and the immunoassay reaction chambers 616 when the rotary valve 610 is in the sample flow configuration.

The rotary valve 610, when in either of the buffer pre-wash or buffer post-wash configurations, places the buffer chambers 614 in fluid communication with the immunoassay reaction chambers 616, thus facilitating the flow of the buffer from the buffer chambers 614 through the immunoassay reaction chambers 616. In the illustrated embodiment, two different sets of ten parallel vertical flow paths 636/638 are formed between the buffer chambers 614 and the immunoassay reaction chambers 616. The structure and operation of the afore-described flow paths will be described in further detail below.

In the illustrated embodiment, the sample distribution configuration is clocked 0° from the buffer pre-wash configuration, i.e., the rotary valve 610 is clocked in the same position for the distribution and buffer pre-wash configurations. Thus, the buffer can be flowed from the buffer chambers 614 through the immunoassay reaction chambers 616, and the sample can be distributed to the sample distribution chambers 612 without clocking the rotary valve 610 between the buffer dispense and sample distribution functions. Likewise, the sample flow configuration is clocked 0° from the buffer post-wash configuration, i.e., the rotary valve 610 is clocked in the same position for the sample dispense and buffer post-wash configurations. Thus, the buffer can be flowed from the buffer chambers 614 through the immunoassay reaction chambers 616, and the sample can be flowed from the sample distribution chambers 612 through the immunoassay reaction chambers 616 without clocking the rotary valve 610 between the sample dispense and buffer dispense functions. The sample flow configuration is clocked 90° from the sample distribution configuration, thus requiring movement of the rotary valve 610 when switching from the sample distribution function to the sample dispense function.

Figures 41, 42:
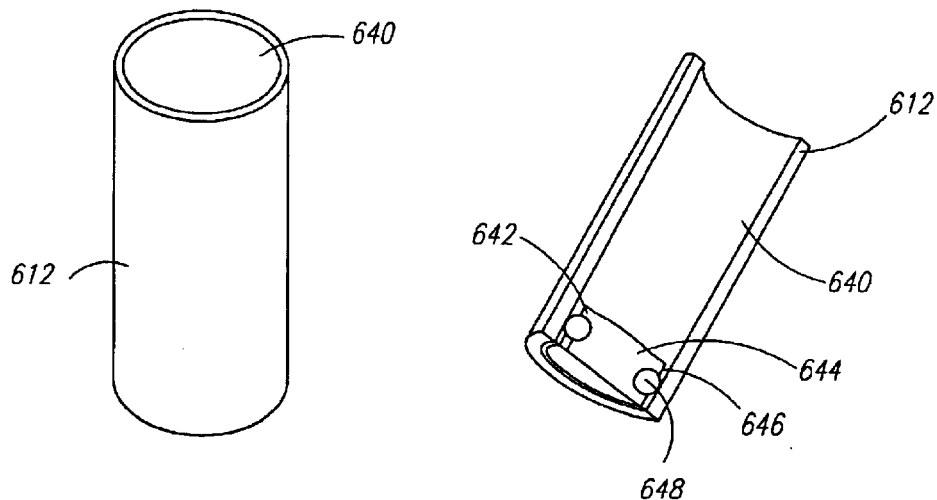
FIG. 41 is a perspective view of a distribution chamber for use in the immunoassay flow assembly.
FIG. 42 is a cutaway perspective view of the distribution chamber.

The sample distribution chambers 612, in combination, are sized to contain at least an amount equal to the entire sample dispensed from the mixing chamber 504. For example, each of the sample distribution chambers 612 has a nominal 250 µL fluid capacity. Referring now to FIG. 41, each of the sample distribution chambers 612 is cylinder-shaped and is composed of a suitable material, e.g., injection molded polycarbonate. The sample distribution chamber 612 comprises a plunger bearing surface 640 with which an associated sample dispense plunger 642 sealingly mates. Like the previously described buffer dispense plunger 512 used in the mixing assembly 500, each of the sample dispense plungers 642 comprises a rigid plunger head 644, which includes an O-ring groove 646 for seating of an O-ring 648. The O-ring 648 of the sample dispense plunger 642 facilitates a sealing relationship between the sample dispense plunger 642 and the bearing surface 640 of the sample distribution chamber 612, which preferably is coated with a silicone-based substance to further facilitate this sealing relationship. As will be described in further detail below, movement of the sample dispense plunger 642 upward within the sample distribution chamber 612 flows the sample from the sample distribution chambers 612, through the associated reaction chambers 616 and read cells 620, and into the waste chamber 622, when the rotary valve 610 is placed in the sample flow configuration.

Figures 43, 44:
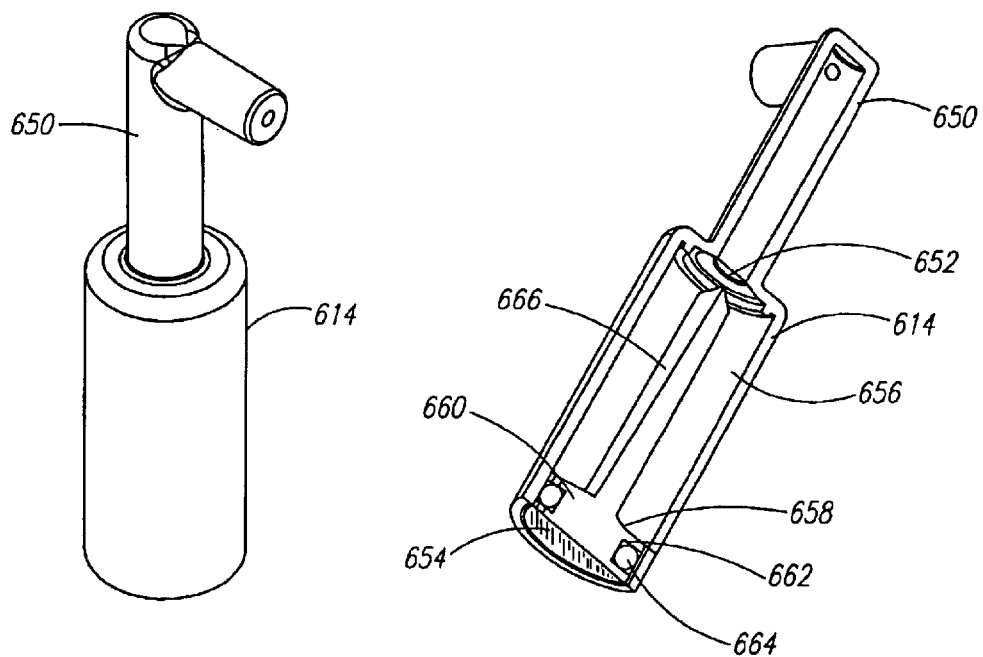
FIG. 43 is a perspective view of a buffer chamber for use in the immunoassay flow assembly.
FIG. 44 is a cutaway perspective view of the buffer chamber.
Figure 45:
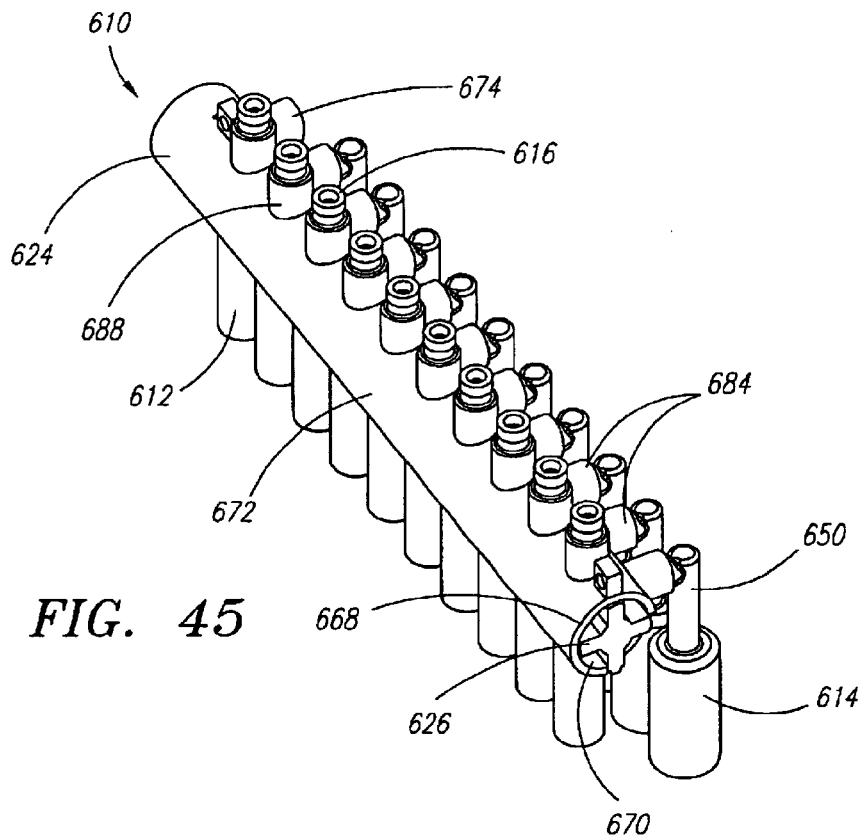
FIG. 45 is a front-right perspective view of the cassette portion of a sample/buffer flow assembly for use in the immunoassay flow assembly.
Figure 46:
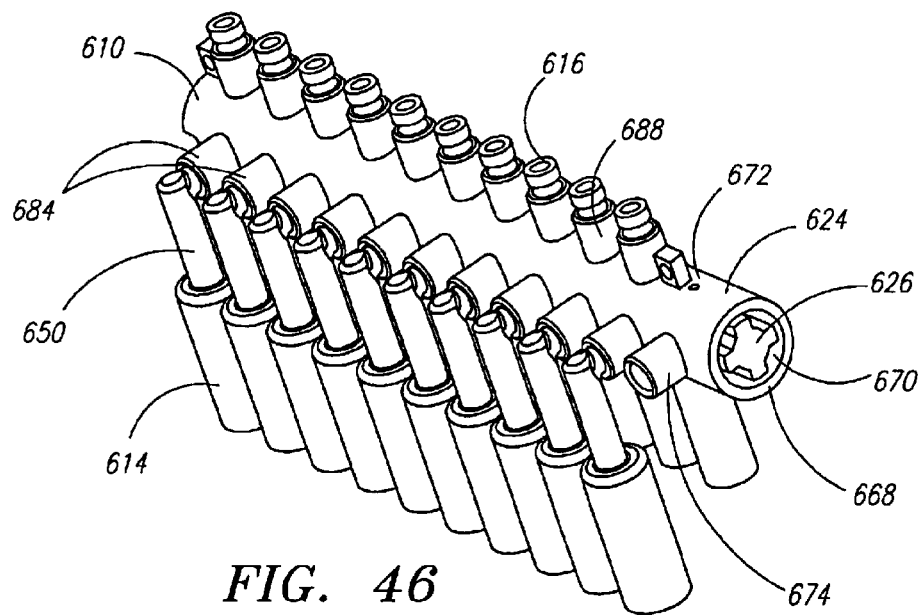
FIG. 46 is a rear-right perspective view of the cassette portion of the sample/buffer flow assembly.

Referring now to FIGS. 43 and 44, each of the buffer chambers 614 is cylindrical-shaped and is composed of a suitable material, e.g., injection molded polypropylene. Since the cassette 152 contains stabilized lyophilized enzyme and immunoassay reagents, as will be described below, it is essential to prevent migration of water vapor through the walls of the buffer chambers 614. To this end, the walls of each buffer chambers 614 are sufficiently thick and impermeable to water vapor during the storage lifetime of the cassette 152. Each buffer chamber 614 contains a suitable neutral buffer solution, e.g., phosphate buffered saline (PBS) buffer solution (pH 6.9) containing protein (0.2% BSA) and 0.05% w/v sodium azide ($NaN_3$) stabilizers, and has a capacity suitable to effectively facilitate the buffer pre- and post- wash functions. For example, each buffer chamber 614 has a capacity of 1.0 ml. Each buffer chamber 614 comprises an angled rigid tube 650, and puncturable upper and lower seals 652 and 654 bonded at the top and bottom of the buffer chamber 614 to completely seal the buffer within the buffer chamber 614 until the dispensing process has commenced. The upper and lower seals 652 and 654 prevent water vapor from escaping the confines of the buffer chamber 614 during storage of the cassette 152, and are composed of a suitable material, such as aluminum foil-lined/polymer bilayer seals.

Each of the buffer chambers 614 comprises a cylindrical bearing surface 656 with which an associated buffer dispense plunger 658 sealingly mates. The buffer dispense plunger 658, like the sample dispense plunger 642, comprises a rigid plunger head 660, which includes an O-ring groove 662 for seating of an O-ring 664 The O-ring 664 of the buffer dispense plunger 658 facilitates a sealing relationship between the buffer dispense plunger 658 and the bearing surface 656 of the buffer chamber 614. The buffer dispense plunger 658 further includes a stylus 666, which is configured to puncture the top seal 654 of the buffer chamber 614. As will be described in further detail below, movement of the buffer dispense plunger 658 upward within the sample distribution chamber 612 (after puncturing the lower seal 654), causes the stylus 666 to puncture the upper seal 654, allowing the buffer to flow from the buffer chambers 614, through the associated reaction chambers 616 and read cells 620, and into the waste chamber 622, when the rotary valve 610 is placed in the buffer pre-wash or buffer post-wash configurations.

Having already described the general function of the rotary valve 610, its detailed structure will now be described. Referring to FIG. 45–51, the stator 624 is composed of a suitable material that is able to endure the large rotary torque that will be applied in order to rotate the closely tolerenced multi-channel rotor 626 therein. In the illustrated embodiment, the stator 624 is composed of an injection-molded polycarbonate, which exhibits the required mechanical strength and rigidity. The stator 624 comprises a hollow cylindrical wall 668 having an inner bearing surface 670 with which the rotor 626 is rotatably associated, and an outer surface 672 with which a variety of chamber seats and ports are associated.

Figure 48:
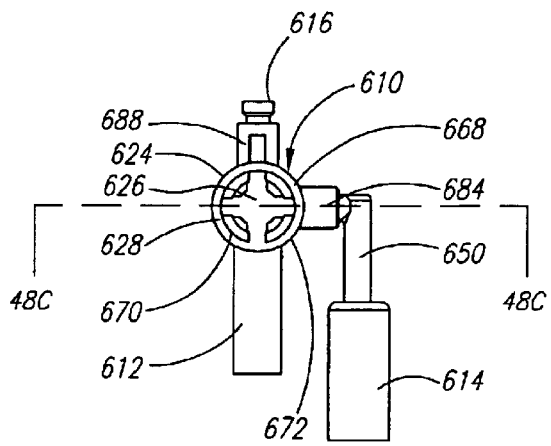
FIG. 48 is another side view of the cassette portion of the sample/buffer flow assembly.
Figure 48D:
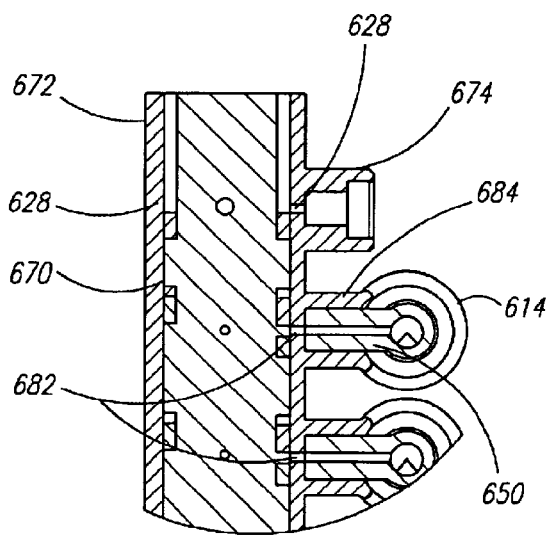
FIG. 48D is a magnified view taken along the line 48D of FIG. 48C.
Figure 48C:
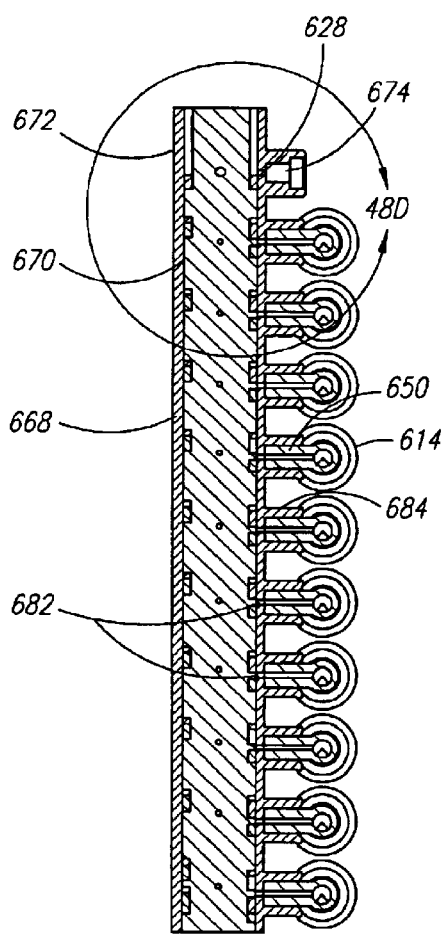
FIG. 48C is a longitudinal-sectional view taken along the line 48C—48C of FIG. 48.
Figure 49:
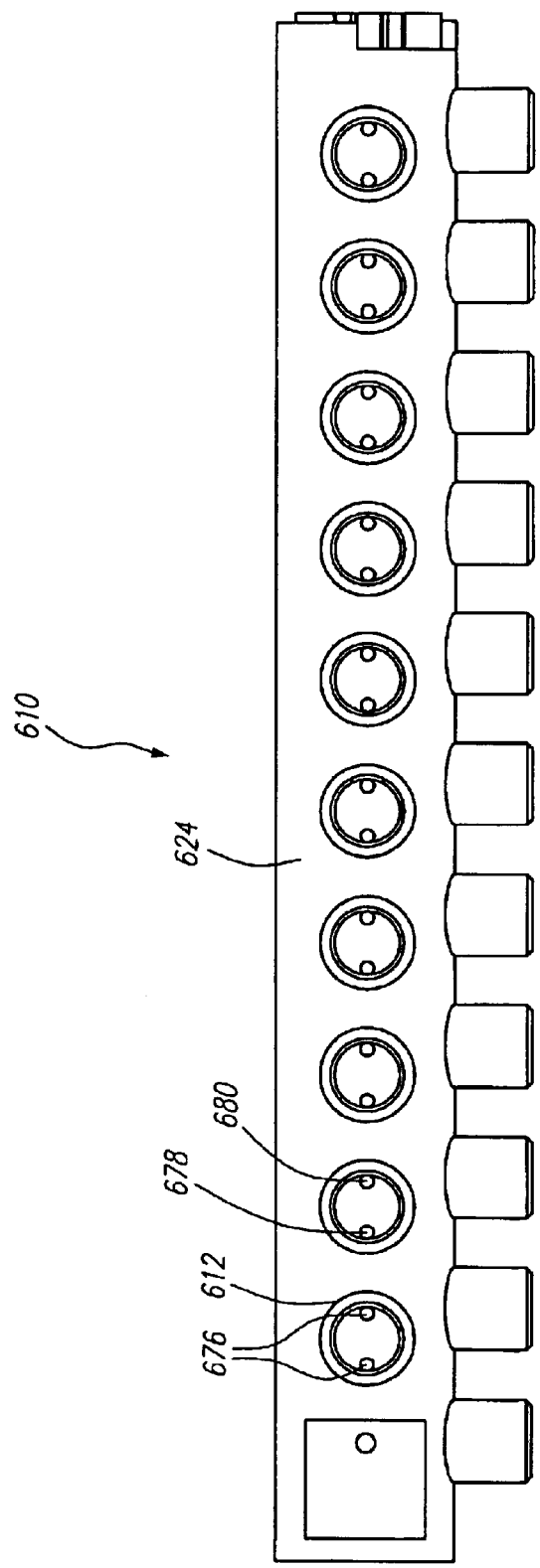
FIG. 49 is a bottom view of a rotary valve for use in the sample/buffer flow assembly.
Figure 50:
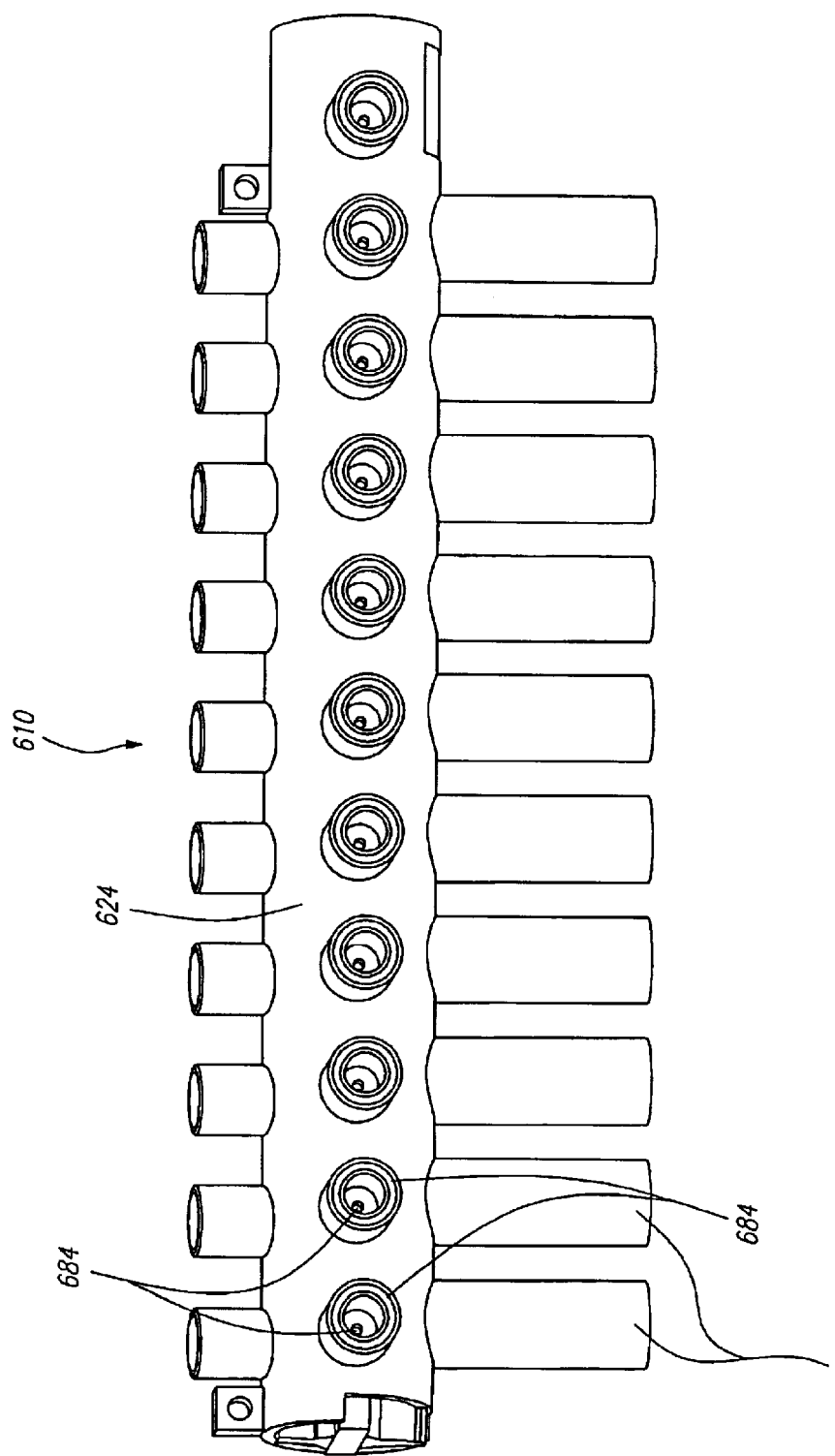
FIG. 50 is a rear-left perspective view of the rotary valve.
Figure 51:
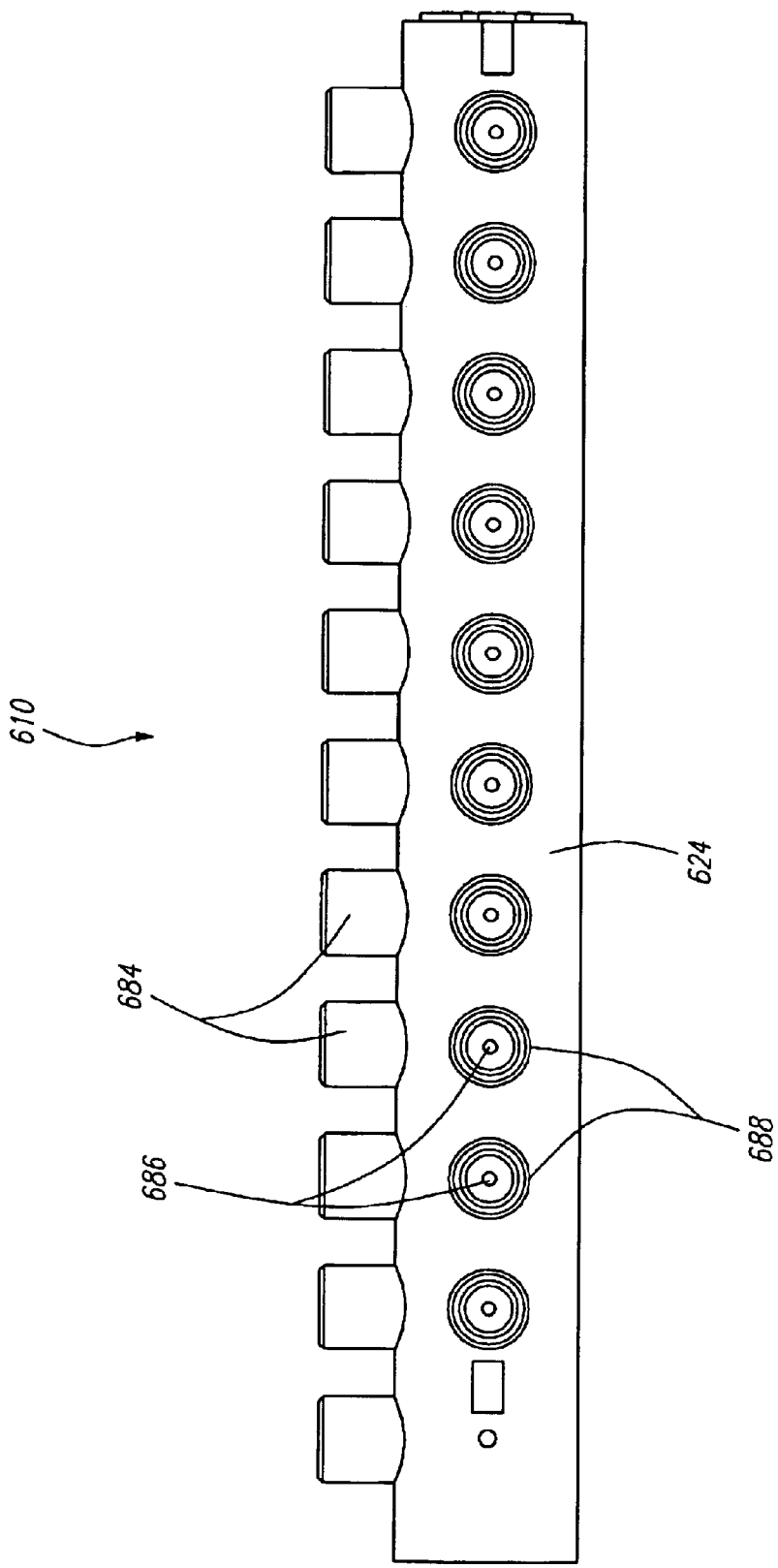
FIG. 51 is a top view of the rotary valve.

Specifically, the stator 624 comprises the afore-described sample feed port 628 (best shown in FIG. 48D), which extends through the cylindrical wall 668, and a sample feed seat 674, which extends from the cylindrical wall 668 and surrounds the sample feed port 628. The mixing chamber dispense port 530 is firmly, but removably, seated within the sample feed seat 674, thereby placing the mixing chamber 504 in fluid communication with the sample feed port 628. The stator 624 further comprises a number of distribution port pairs 676 (best shown in FIGS. 47B and 49) equal to the number of sample distribution chambers 612, which in the illustrated embodiment is ten. Each of the distribution port pairs 676 includes a entry distribution port 678 and a distribution exit port 680. The distribution port pairs 676 extend through the cylindrical wall 668 and are disposed along one side of the cylindrical wall 668 in a equidistant rectilinear fashion. In the illustrated embodiment, there are no seats for the sample distribution chambers 612, but rather the distribution chambers 612 are molded directly onto the outer surface 672 of the cylindrical wall 668 over the distribution port pairs 676, thereby respectively placing the sample distribution chambers 612 in fluid communication with the distribution port pairs 676. As will be described in further detail below, the distribution port pairs 676 facilitate distribution of the sample into the sample distribution chambers 612 in a cascading manner. It should be noted that the distribution exit ports 680 are also used as sample entry dispense ports 681 during sample flow, as will be described in further detail below.

The stator 624 further comprises a number of auxiliary entry dispense ports suffer entry dispense ports) 682 (best shown in FIGS. 48D and 50) and a number of corresponding auxiliary seats (buffer chamber seats) 684 equal to the number of buffer chambers 614, which in the illustrated embodiment is ten. The buffer entry dispense ports 684 extend through the cylindrical wall 668 and are disposed along another side of the cylindrical wall 668 in an equidistant rectilinear fashion. The buffer chamber seats 684 extend from the cylindrical wall 668 and respectively circumscribe the corresponding buffer entry dispense ports 684. The angled tubes 650 of the corresponding buffer chambers 614 are firmly, but removably, seated within the buffer chamber seats 684, thereby placing the buffer chambers 614 in fluid communication with the buffer entry dispense ports 684.

The stator 624 further comprises a number of exit dispense ports 686 and a number of exit dispense seats (reaction chamber seats) 688 (best shown in FIGS. 47B and 51) equal to the number of immunoassay reaction chambers 616. The exit dispense ports 686 extend through the cylindrical wall 668 along still another side of the cylindrical wall 668 in an equidistant rectilinear fashion. The reaction chamber seats 688 extend from the cylindrical wall 668 and respectively circumscribe the corresponding exit dispense ports 686. The corresponding reaction chambers 616 are firmly, but removably, seated within the reaction chamber seats 688, thereby placing the immunoassay reaction chambers 616 in fluid communication with the exit dispense ports 686. Significantly, it should be noted that the exit dispense ports 686 are clocked 180° from the entry distribution ports 678 and 90° from the buffer entry dispense ports 684. It should also be noted that the last exit dispense port 686 also serves as the previously mentioned vent port 687, as will be described in further detail below.

Figure 52:
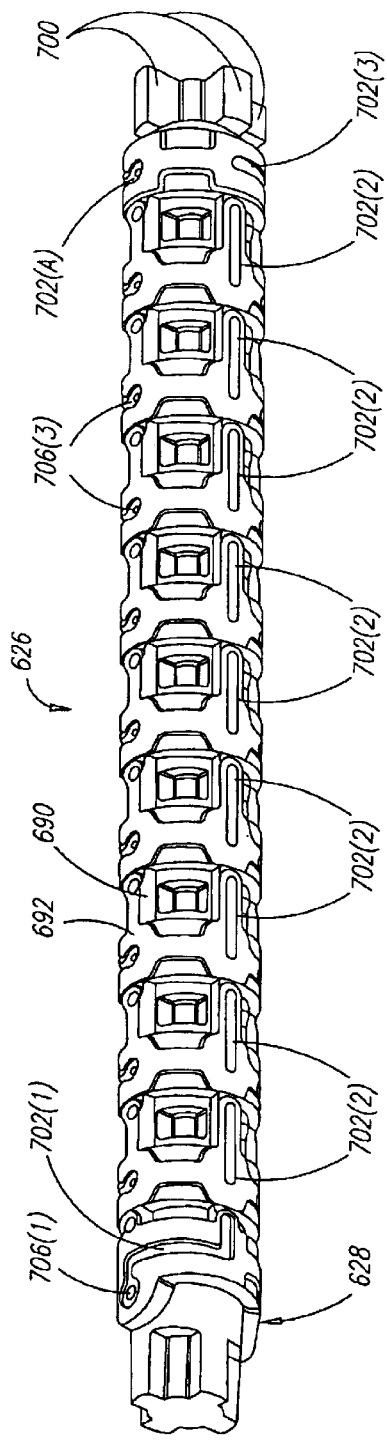
FIG. 52 is one perspective view of a rotor for use in the rotary valve.
Figure 53:
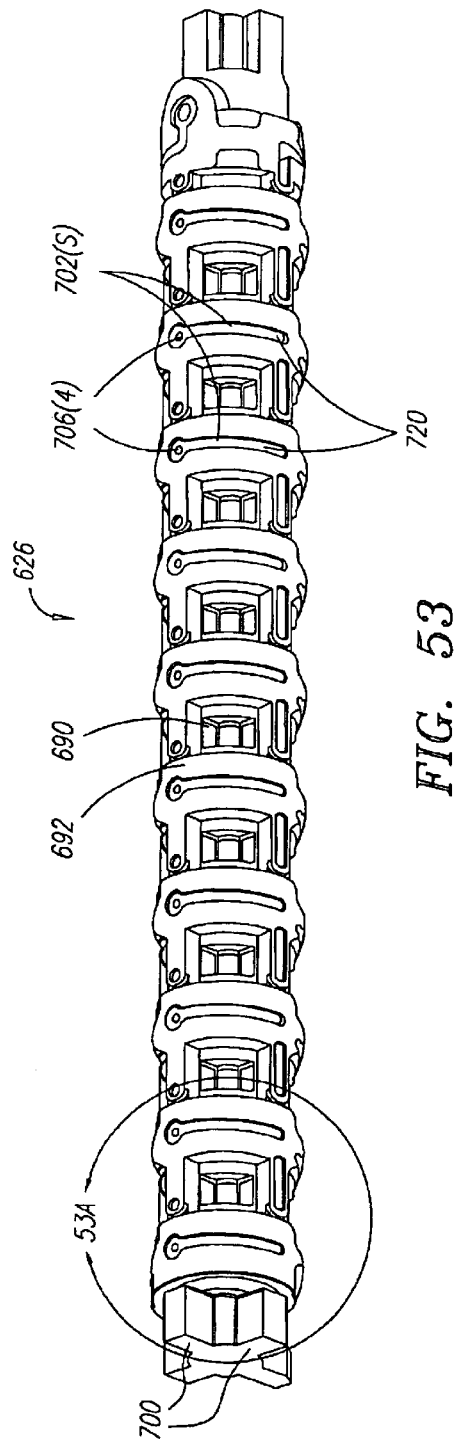
FIG. 53 is another perspective view of the rotor.
Figure 54:
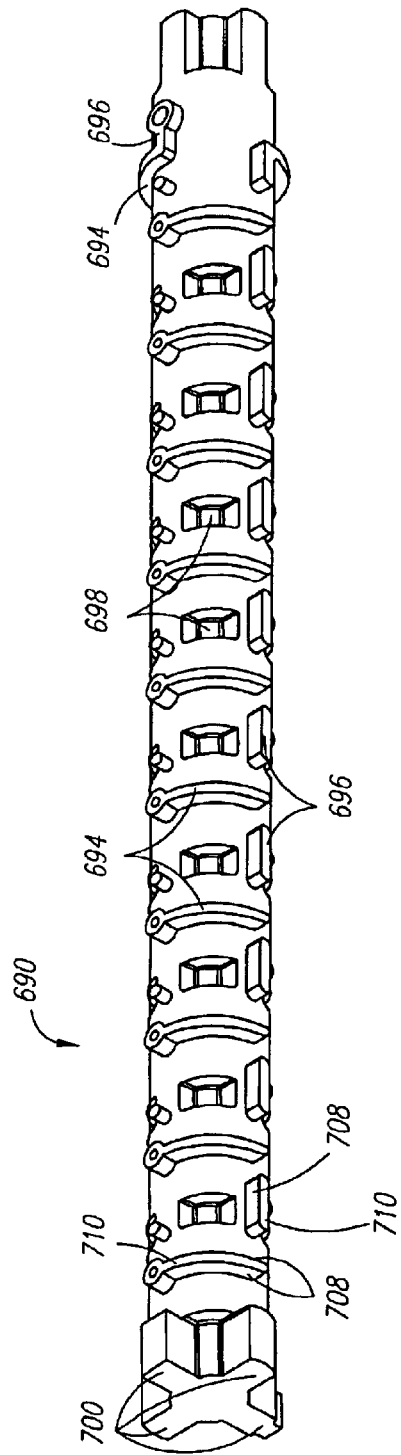
FIG. 54 is a perspective view of a rotor core used to construct the rotor.

Referring now to FIGS. 52–54, the rotor 626 comprises a honeycombed rotor core 690 and a rotor lining 692 disposed on the rotor core 690. Like the stator 624, the rotor core 690 is composed of a material that is able to endure the large rotary torque that will be applied to, which in the illustrated embodiment, is injection-molded polycarbonate. The rotor core 690 forms a number of equidistant arcuate ridges 694 and a number of longitudinal ridges 696 on which the various channels will be formed, as will be described in further detail below. The rotor core 690 further forms four radially equidistant sets of alignment apertures 698 between the arcuate and longitudinal ridges 694 and 696. These apertures 698 are engaged by the mandrel of the injection molding machine during the injection molding process. The compliant lining 692 is the portion of the rotor 626 that sealingly engages the inner bearing surface 670 of the stator 624. The compliant lining 692 is composed of a suitably compliant material, such as, polyurethane, which is injection molded over the outer periphery of the rotor core 690, and specifically, onto the various ridges formed by the honeycombed configuration of the rotor core 690. The end of the rotor core 690 forms four radially extending ridges 700 for engagement with a rotary valve drive assembly, as will be discussed in further detail below.

Figure 53A:
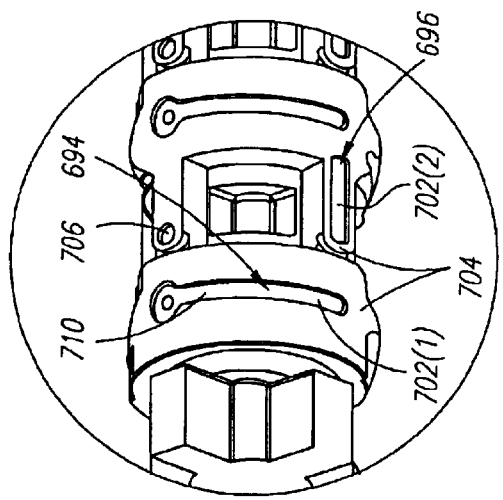
FIG. 53A is a magnified view taken along the line 53D of FIG. 53.

As will now be described, surface channels 702, surface channel stops 704, and through channels 706 associated with the rotor core 690 effect the afore-described flow paths, as specified by the various configurations in which the rotary valve 610 can be placed. Referring specifically to FIG. 53A, a compliant sealing material is formed onto the ridges of the rotor core 690. If a surface channel 702 is to be formed, the sealing material is formed on the opposing lateral surfaces 708 (shown best in FIG. 54) of the ridge 694/696, while leaving the adjacent circumferential surface 710 of the ridge 694/696 exposed. If a surface channel stop 704 is to be formed, the sealing material is formed on both the lateral surfaces 708 and the adjacent circumferential surface 710 of the ridge 694/696. Thus, when the rotor 626 is firmly disposed within the stator 624, fluid will flow within the surface channels 702 between the exposed circumferential surface of the associated ridge and the inner bearing surface 670 of the stator 624. For the purposes of this specification, the surface channels 702 associated with the arcuate ridges 694 are considered arcuate surface channels, and the surface channels 702 associated with the longitudinal ridges 696 are considered longitudinal surface channels.

During the injection molding process, the inner surface of a mandrel will be in high pressure contact with the circumferential surfaces 710 of the ridges 694/696 where surface channels 702 are to be formed. The inner surface of the mandrel will not be in contact at all with the circumferential surfaces 710 of the ridges 694/696 where surface channel stops 704 are to be formed. For purposes of alignment and stability, the mandrel will also be in contact with the apertures 698 of the rotor core 690 between the ridges 694/696. It should be noted that when forming surface channels 702 on the ridges of the rotor core 690 via injection molding, the mandrel will preferably in high pressure contact with the circumferential surface of the ridge opposite (i.e., 180°) that of the ridge on which the surface channel 702 is to be formed to ensure that the mandrel holds the rotor core 690 firmly in place during the high pressure injection molding process. Thus, unused surface channels 702 may be formed opposite the used surface channels as a result of this process. It should be noted that the injection molding process allows the rapid high volume assembly of a uniform leak-proof rotor 626 without the need for gaskets or O-rings.

The through channels 706 are formed transversely through the longitudinal axis of the rotor core 690, with one end of the through channel 706 formed through a ridge 694/696, and the other end of the through channel 706 being formed through an oppositely disposed ridge 694/696. A surface channel 702 is connected to a through channel 706 by forming the surface channel 702 adjacent an end of the through channel 706.

Referring further to FIGS. 52 and 55–57, the rotary valve 610, when clocked in the sample distribution configuration, is channeled to place the sample feed port 628 and distribution port pairs 676 of the stator 624 in fluid communication with each other, and thus, the sample distribution chambers 612 in fluid communication with the sample feed port 628. The rotor 626 is also configured to place the distribution port pairs 676 in fluid communication with the vent port 687 of the stator 624, and thus the sample distribution chambers 612 in fluid communication with the waste chamber 622. To this end, the rotor 626 comprises a feed channel 712, which connects the sample feed port 628 and the first distribution port pairs 676 to each other, and a plurality of distribution channels 714 (sample distribution channels), which connect the distribution port pairs 676 to each other. The rotor 626 further comprises a vent channel 716, which connects the last distribution port pair 676 to the vent port 687.

The feed channel 712 specifically comprises a through channel 706(1) and a 90° arcuate surface channel 702(1). One end of the through channel 706(1) connects to the sample feed port 628, and the 90° arcuate surface channel 702(1) is connected between the other end of the through channel 706 and the entry distribution port 678 of the first distribution port pair 676. The sample distribution channels 714 specifically comprise longitudinal surface channels 702(2) that connect the distribution exit port 680 of each distribution port pair 676 with the entry distribution port 678 of the next distribution port pair 676. The vent channel 716 includes a 90° arcuate surface channel 702(3), a through channel 706(2), and another 90° arcuate surface channel 702(4). One end of the 90° arcuate surface channel 702(3)

is connected to the exit distribution port 680 of the last distribution port pair 676, one end of the through channel 706(2) is connected to the other end of the 900 arcuate surface channel 702(3), and the other 90° arcuate surface channel 702(4) is connected between the other end of the through channel 706(2) and the vent port 687. It should be noted that there are preferably no channels, other than the vent channel 716, that places the sample distribution chambers 612 in fluid communication with the immunoassay reaction chambers 616 when the rotor 626 is clocked in the sample distribution configuration, thereby preventing sample from being prematurely dispensed from the sample distribution chambers 612 into the immunoassay reaction chambers 616.

Referring to FIGS. 52 and 58–60, the rotary valve 610, when clocked in the sample flow configuration, is channeled to place the sample entry dispense ports 681 (which as previously discussed coincide with the exit distribution ports 680) and exit dispense ports 686 of the stator 624 in fluid communication with each other, and thus, the sample distribution chambers 612 in fluid communication with the immunoassay reaction chambers 616. To this end, the rotor 626 comprises dispense channels (sample dispense channels) 718, and specifically through channels 706(3), which connect the corresponding sample entry dispense ports 681 and exit dispense ports 686 with each other. It should be noted that the sample dispense channels 718 are oriented in relation to the sample distribution channels 714 to correspond to the 90° clocking difference between the sample distribution and sample flow configurations.

Referring to FIGS. 53 and 61–63, the rotary valve 610, when clocked in the buffer pre-wash configuration, is channeled to place the buffer entry dispense ports 684 and exit dispense ports 686 of the stator 624 in fluid communication with each other, and thus, the buffer chambers 614 in fluid communication with the immunoassay reaction chambers 616. To this end, the rotor 626 comprises first auxiliary dispense channels 720 (buffer pre-wash channels), which connect the buffer entry dispense ports 684 and exit dispense ports 686 to each other. Each of the buffer pre-wash channels 720 specifically comprises a through channel 706(4) and a 90° arcuate surface channel 702(5). One end of the through channel 706 is connected to the corresponding buffer entry dispense port 682, and the 90° arcuate surface channel 702 is connected between the other end of the through channel 706 and the corresponding exit dispense port 686. It should be noted that the buffer pre-wash channels 720 are oriented in relation to the sample distribution channels 714 to correspond to the 0° clocking difference between the buffer pre-wash configuration and the sample distribution configuration.

Figure 64:
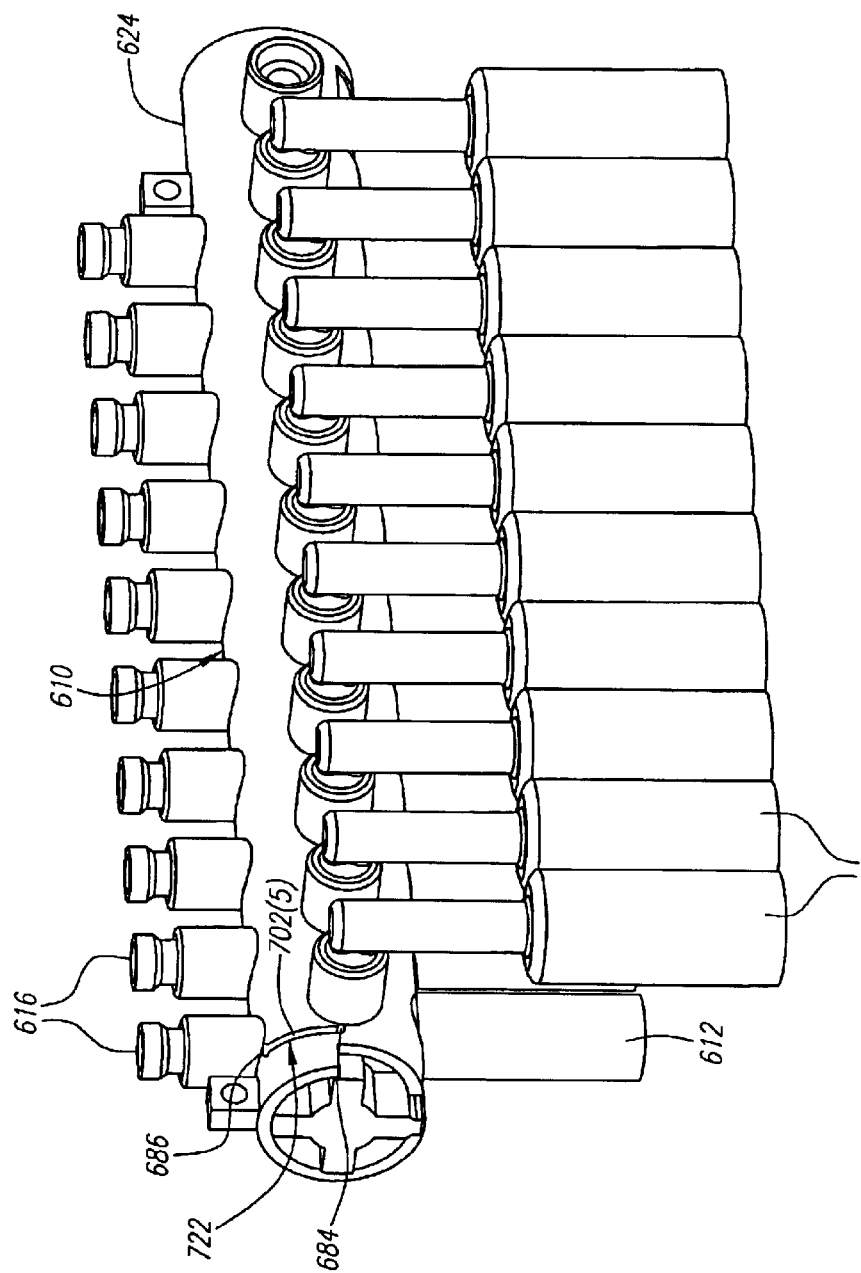
FIG. 64 is a rear-left perspective view of the cassette portion of the sample/buffer flow assembly, particularly showing the buffer dispense flow paths when the rotary valve is clocked in a buffer post-wash configuration.
Figure 65:
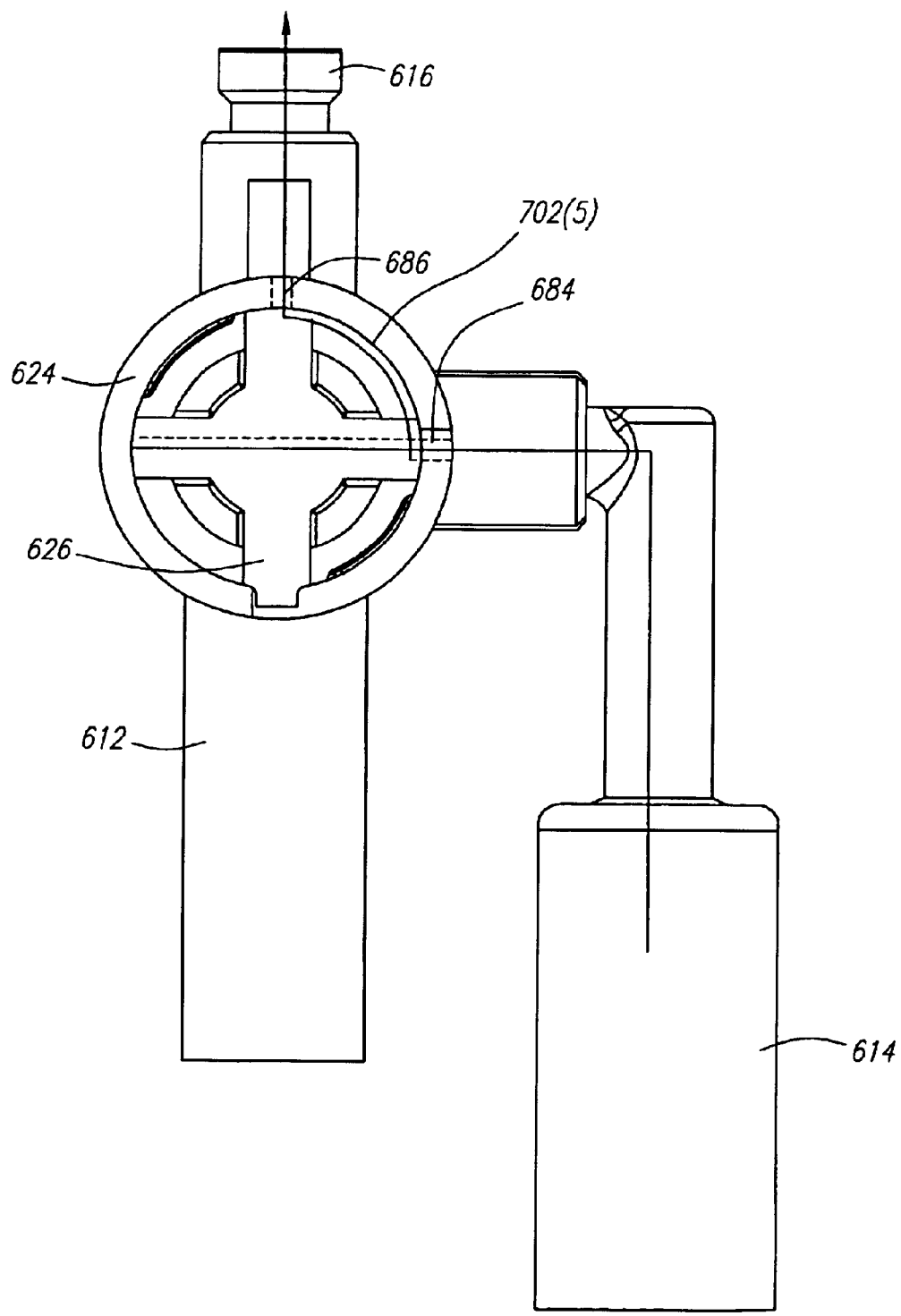
FIG. 65 is a side view of the cassette portion of the sample/buffer flow assembly, particularly showing the buffer dispense channel.
Figure 66:
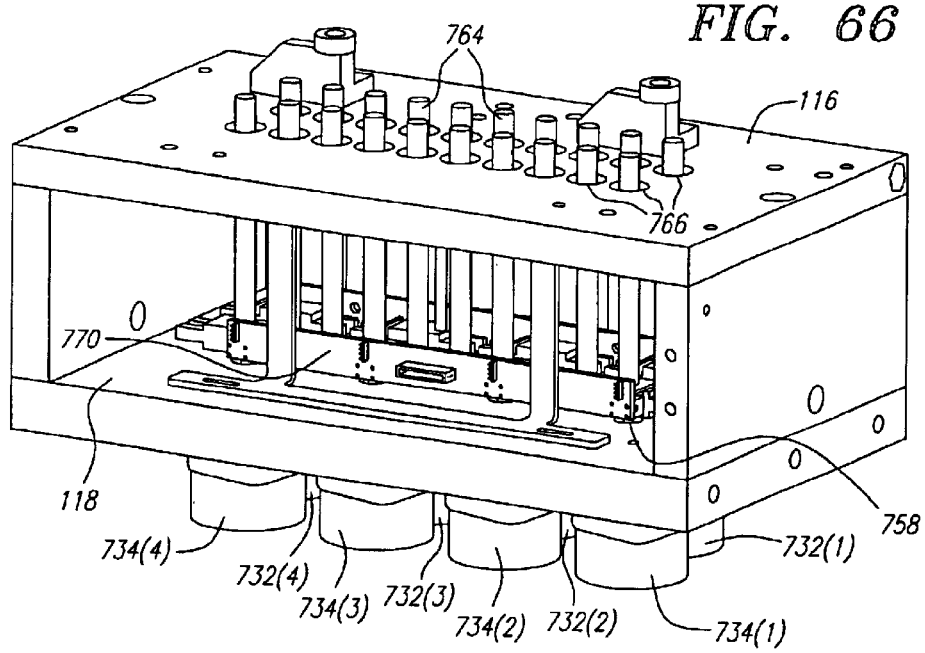
FIG. 66 is a rear-right perspective view of the test console portion of the sample/buffer flow assembly mounted within the main base of the test console.
Figure 67:
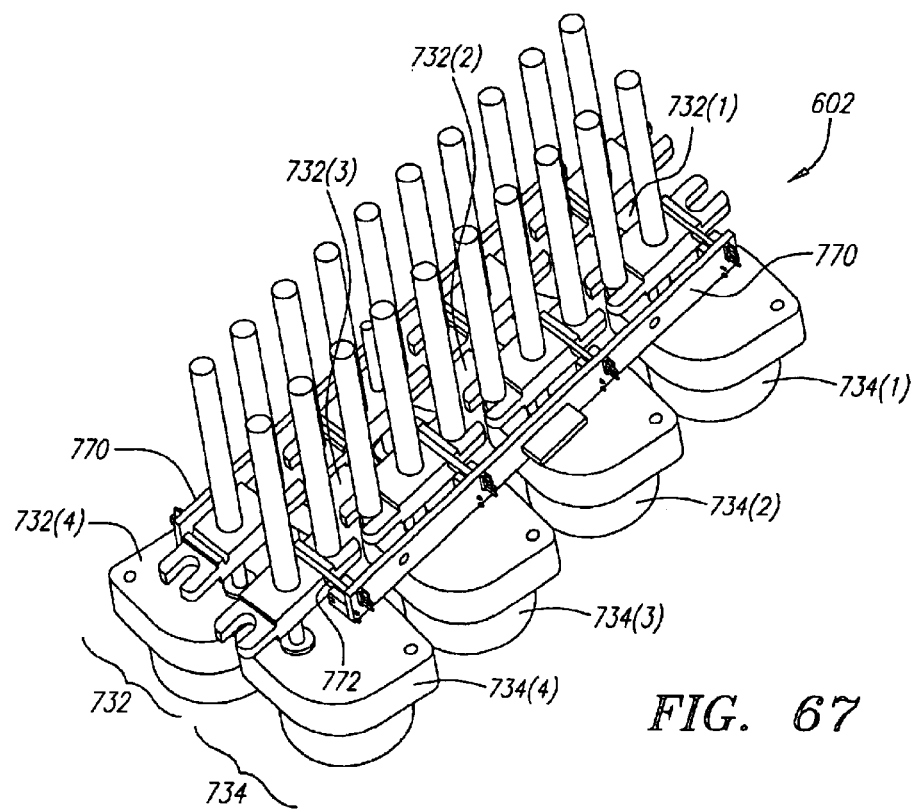
FIG. 67 is a perspective view of the test console portion of the sample/buffer flow assembly.
Figure 68:
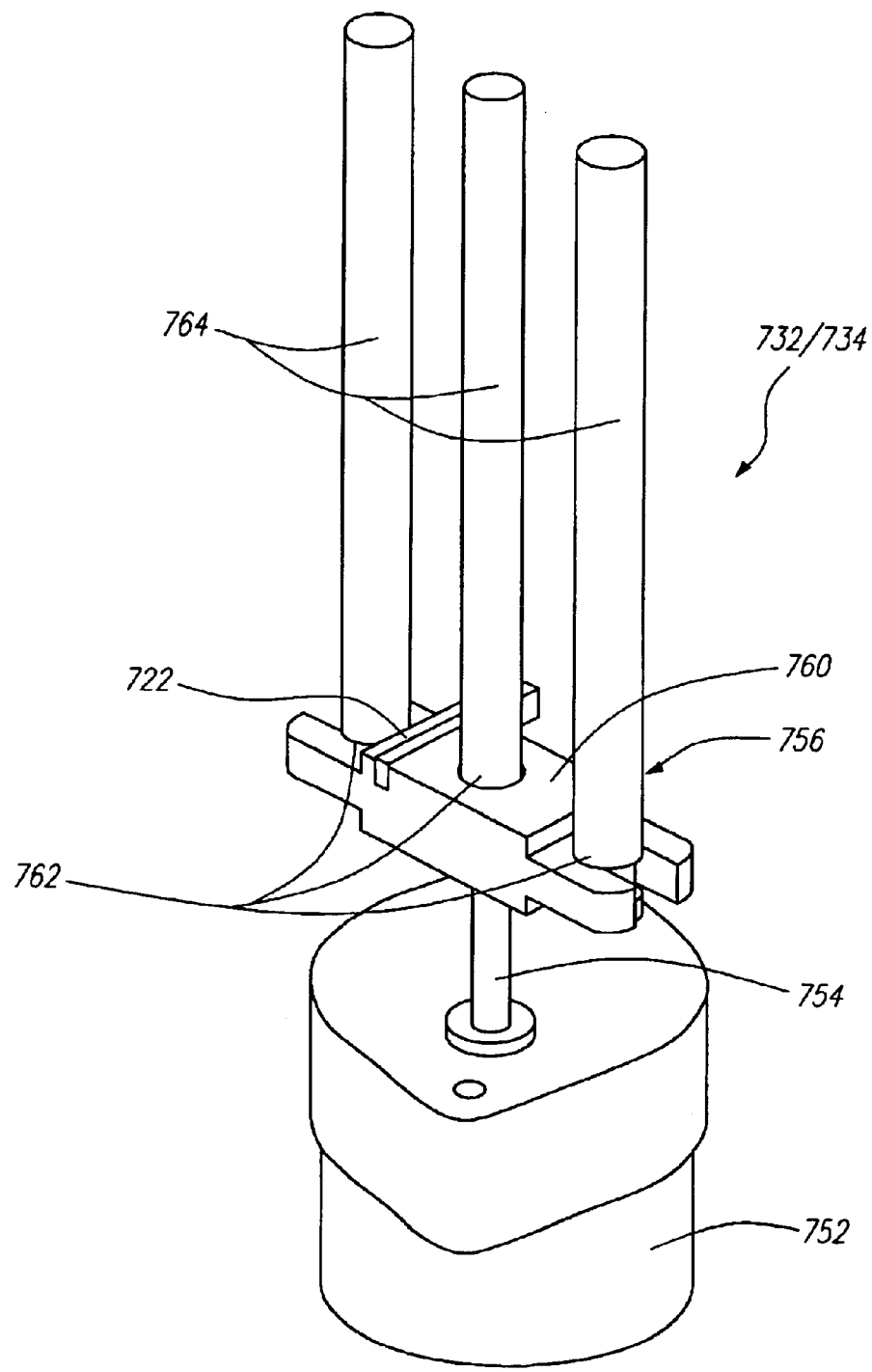
FIG. 68 is a perspective view of a motor drive assembly for use in the sample/buffer flow assembly.

Referring to FIGS. 53, 64, and 65, the rotary valve 610, when clocked in the buffer post-wash configuration, is channeled to place the buffer entry dispense ports 684 and exit dispense ports 686 of the stator 624 in fluid communication with each other, and thus, the buffer chambers 614 in fluid communication with the immunoassay reaction chambers 616. To this end, the rotor 626 comprises second auxiliary dispense channels 722 (buffer post-wash channels), which connect the buffer entry dispense ports 684 and exit dispense ports 686 to each other. Each of the buffer post-wash channels 722 specifically comprises the aforementioned 90° arcuate surface channel 702(5) connected between the corresponding buffer entry dispense port 682 and the corresponding exit dispense port 686. It should be noted that the buffer post-wash channels 722 are oriented in relation to the sample dispense channels 718 to correspond to the 0° clocking difference between the buffer post-wash configuration and the sample flow configuration.

2. Sample/Buffer Flow Assembly—Tester Portion

Having just described the portion of the sample/buffer flow assembly 602 associated with the cassette 152, the portion of the sample/buffer flow assembly 602 associated with the test console 102 will be discussed. Referring to FIGS. 11, 13–15, and 66–68, the sample/buffer flow assembly 602 further includes a rotary valve drive assembly 730, a number of sample drive assemblies 732, and a number of buffer drive assemblies 734.

Referring specifically to FIGS. 11 and 13–15, the rotary valve drive assembly 730 functions to provide the large amount of torque (in the illustrated embodiment, ≧5.5 N-m) necessary to clock the multi-channel rotary valve 610 90° from the sample distribution/buffer pre-wash configuration (its home position) and the sample dispense/buffer post-wash configuration (its actuated position). Specifically, the rotary valve drive assembly 730 comprises a linear stepper motor 736, and a motor mount 738 for affixing the linear motor 736 to the side main base flange 122. The rotary valve drive assembly 730 further includes a rotor driver 740, which is linearly displaced by the motor 736. The rotary valve drive assembly 730 further includes a crank arm 742, one end of which is hingedly connected to the rotor driver 740, and the other end of which is affixed to a rotary pin 744. The rotary pin 744 has a pronged end 746 (best shown in FIG. 14) that engages the end of the rotor 626 of the rotary valve 610 between the radially extending ridges 700.

The shaft of the rotary pin 744 rotatably extends through an aperture 748 formed in a pin alignment flange 750, which is suitably mounted to the top main base flange 116 to align the rotary pin 744 with the rotor 626 of the rotary valve 610. Thus, operation of motor 736 linearly translates the rotor driver 740, rotating the crank arm 742, and thus the rotary pin 744 and rotor 626.

It should be noted that the rotary valve drive assembly 730 is operated under control of a CPU 204 and I/O controller 206 (shown in FIG. 12), with a rotary valve home sensor (generally shown in FIG. 12) used to provide independent confirmation that the end of the rotary pin 744 rotationally aligns with the end of the rotor 626. It should be noted that the cassette case 154 comprises a rotary valve access opening 176 (shown in FIG. 3) formed on the side of the cassette case 154 adjacent one end of the rotary valve 610, thereby allowing the rotary valve drive assembly 730 to operably associate with the rotor 626 of the rotary valve 610.

Referring specifically to FIGS. 11 and 66–68, the sample drive assemblies 732 function to move the sample dispense plungers 642 upward within the respective sample distribution chambers 612. The number of sample drive assemblies 732 may vary, but in the illustrated embodiment, is four, with (1) the first sample drive assembly 732(1) being operably associated with the first two sample distribution chambers 612; (2) the second sample drive assembly 732(2) being operably associated with the next three sample distribution chambers 612; (3) the third sample drive assembly 732(3) being operably associated with the next three sample distribution chambers 612; and (4) the fourth sample drive assembly 732(4) being operably associated with the last two sample distribution chambers 612. The sample drive assemblies 732 are arranged in a rectilinear series, so that they are properly aligned with the rectilinear series of sample distribution chambers 612.

The buffer drive assemblies 734 similarly function to move the buffer dispense plungers 658 upward within the respective buffer chambers 614. The number of sample drive assemblies 732 may vary, but in the illustrated embodiment, equals four, with (1) the first buffer drive assembly 734(1) being operably associated with the first two buffer chambers 614; (2) the second buffer drive assembly 734(2) being operably associated with the next three buffer chambers 614; (3) the third buffer drive assembly 734(3) being operably associated with the next three buffer chambers 614; and (4) the fourth buffer drive assembly 734(4) being operably associated with the last two buffer chambers 614. The buffer drive assemblies 734 are arranged in a rectilinear series, so that they are properly aligned with the rectilinear series of buffer chambers 614.

Each sample/buffer drive assembly includes a linear stepper motor 752 with an associated motor driver 754, and a ganged plunger drive assembly 756. Each motor 752 is mounted to the bottom surface of the bottom main base flange 118, with the associated motor driver 754 extending through a respective aperture 758 formed through the bottom main base flange 118. The motor driver 754 includes a rotational bearing (not shown) mounted thereon adjacent the top surface of the bottom main base flange 118 for association with the ganged plunger assembly 756.

The ganged plunger assembly 756 includes a gang base 760 with a common aperture (not shown) formed at the bottom of the gang base 760 and in which the rotational bearing of the motor driver 754 is firmly mounted. The gang base 760 further includes three equally spaced sample dispense plunger drive seats 762 disposed along the center of gang base 760 opposite the common aperture 762. The ganged plunger assembly 756 further includes two or three sample/buffer dispense plunger drivers 764 seated within the respective plunger drive seats 762. The sample/buffer dispense plunger drivers 764 extend from the plunger drive seats 762 and up through apertures 766 formed through the top main base flange 116. For purposes of compactness, two sample/buffer dispense plunger drivers 764 occupy the second and third plunger drive seats 762 with respect to the first sample drive assembly 732(1); three sample/buffer dispense plunger drivers 764 will occupy all three of the plunger drive seats 762 with respect to the third sample drive assembly 732(2); three sample/buffer dispense plunger drivers 764 will occupy all three of the plunger drive seats 762 with respect to the third sample drive assembly 732(3); and two sample/buffer dispense plunger drivers 764 will occupy the first and second plunger drive seats 762 with respect to the fourth sample drive assembly 732(4).

The sample/buffer dispense plunger driver 764 extending from the second (or center) plunger drive seat 762 includes a linear bearing (not shown), and the remaining sample/buffer dispense plunger drivers 764 include a bushing (not shown), which are firmly mounted within the aperture 766 in the top main base flange 116. This arrangement prevents the sample/buffer dispense plunger drivers 764 from binding within the apertures 766 of the top main base flange 116 that may otherwise occur due to manufacturing tolerances. The apertures 766 within the top main base flange 116 align the sample/buffer dispense plunger drivers 764 with the corresponding sample dispense plungers 642 within the distribution chambers 612, such that operation of the respective sample and buffer drive assemblies 732 and 734 correspondingly engage the sample dispense plungers 642 with the sample dispense plunger drivers 764, and the buffer dispense plungers 658 with the buffer dispense plunger drivers 764. It should be noted that the sample and buffer drive assemblies 732 and 734 are considered to be in their home positions when the ends of the respective sample/buffer dispense plunger drivers 764 are below the bottom flange 118 of the cassette carriage 302, and in their pretest positions when the ends of the respective sample/buffer dispense plunger drivers 764 are disposed through apertures 768 (shown in FIG. 13) within the bottom flange 306 of the cassette carriage 302 and engaged with the respective sample and buffer dispense plungers 642 and 658 within the sample distribution and buffer chambers 612 and 614.

Thus, the ganging of the plunger drivers 764 provides flexibility in selecting different flow rates and volumes of the sample and buffer dispensed from the respective sample distribution and buffer chambers 612 and 614. For example, if the accurate testing of two or three drugs requires a relatively high volume, slow flow rate, the flow paths associated with these tests can be associated with a single gang assembly, while other flow paths can be associated with the other gang assemblies. It should be noted that the sample drive assemblies 732 and buffer drive assemblies 734 are all operated under control of a CPU 204 and I/O controller 206 (shown in FIG. 12). Sample and buffer motor assembly home and pre-test sensors (generally shown in FIG. 12) are provided to ensure that the respective sample and buffer drive assemblies 732 and 734 are placed into their home and pre-test positions when desired. In the illustrated embodiment, a pair of printed circuit boards (PCB's) 770 (one for the set of sample drive assemblies 732 and one for the set of buffer drive assemblies 734) and corresponding indicators 734 mounted to each of the gang bases 760 are used to convey this information.

It should also be noted that the cassette case 154 (shown in FIGS. 3 and 4) comprises for providing mechanical access to the sample and buffer chambers 612 and 614. Specifically, a series of ten distribution chamber access openings 178 is formed on the underside of a ledge 180 above the bottom 162 of the cassette case 154, thereby allowing the sample dispense plunger drivers 764 to engage the sample dispense plungers 642 within the sample distribution chambers 612. Likewise, a series of ten buffer chamber access openings 182 is formed on the bottom 162 of the cassette case 154, thereby allowing the buffer dispense plunger drivers 764 to engage the buffer dispense plungers 658 within the buffer chambers 614.

B. Immunoassay Reaction Assembly

Referring generally to FIGS. 69–77, the purpose of the immunoassay reaction assembly 604 is to: 1) perform a dynamic, continuous-flow immunoassay reaction on the sample in each of the drug channels; (2) present the reacted sample to scanning detector; and (3) collect and permanently store fluids that have flowed within the immunoassay reaction assembly 604. The immunoassay reaction assembly 604 comprises the afore-mentioned immunoassay reaction chambers 616, read cell assembly 618, and waste chamber 622.

Figure 69:
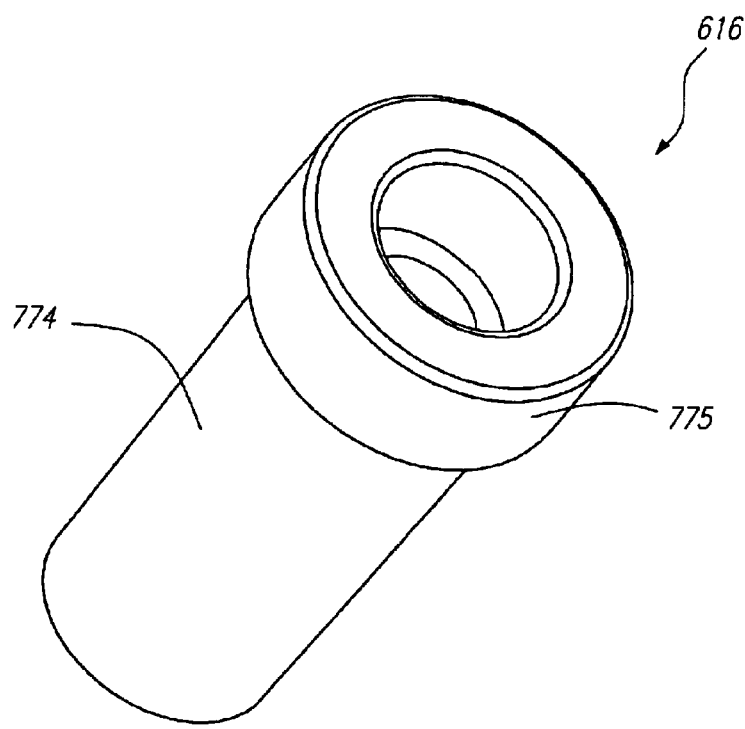
FIG. 69 is a perspective view of a reaction chamber for use in an immunoassay reaction assembly.
Figure 70:
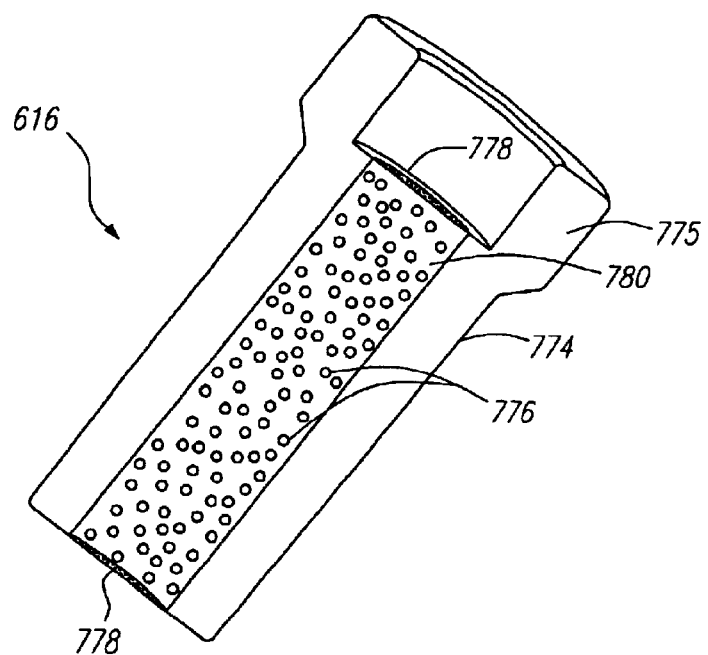
FIG. 70 is a cutaway perspective view of the reaction chamber.

Referring specifically to FIGS. 69 and 70 (close up of reaction chamber) each reaction chamber 616 is configured to provide the biochemical reaction necessary to detect analytes in the sample when flowed therethrough. It should be first noted that although the present inventions can employ various types of assays (e.g., direct binding, sandwich, and competition assays), the illustrated embodiment utilizes displacement assays to facilitate the detection of analytes in the sample. Specifically, the immunoassay reaction chambers 616 perform exchange reactions between the sample and immobilized antibody proteins, which have been previously saturated with labeled antigen (and then stabilized by lyophilization).

To this end, each immunoassay reaction chamber 616 comprises a cylindrical column 774 composed of a suitable chemically insert material, such as injection molded polypropylene polymer. The column 774 can be of any suitable size and form that allows it to compactly fit within the cassette 152. In the illustrated embodiment, the column 774 is 10 mm (0.4 in) in length and has a 2 mm (0.080 in) inner diameter channel 780. The reaction chamber 616 further comprises a read cell seat 775 in which ends of the read cells 620 will be seated, as will be described in further detail below. Each column 774 contains dried drug reagent, and specifically, a support medium that carries lyophilized antibody-antigen complexes that react in the presence of a target drug analyte. In the illustrated embodiment, the support medium comprises beads 776 that are composed of a material that is neutral to the target drug analytes, so hat a false positive or negative signal is not created. Sephacryl S-1000 beads having a 60 μm median diameter have been found to be suitable for this purpose. Among other suitable materials are silica or glass beads, hollow fibers, and activated polymers. In further embodiments, the hollow fibers or bundles of capillary tubes may serve simultaneously as the reaction chamber 616 and support medium.

The antibody-antigen complexes are formed by covalently bonding immobilized antibodies on the beads 776 for the appropriate drug to be tested. In the illustrated embodiment, approximately 10% of the active surface of each bead is covered with the antibody. The immobilized antibody is then saturated with labeled antigen, which form the drug tracer. Any suitable labeled antigen (such as, e.g., radiolabels, fluorophores, chromophores, electroactive groups, and electron spin label) can be used in the process, but in the illustrated embodiment, the labeled antigen comprises covalently bonded fluorescent CY5 dye, which excites best at 650 nm and fluoresces at 655–700 nm. The tracer-saturated antibody beads are stabilized with protein (BSA) and trehalose, and then packed as a known volume slurry into the column 774. The column 774 is washed to remove any excess labeled dye, and then lyophilized to provide for stability of one year under appropriate storage conditions. In the illustrated embodiment, each column 774 contains 3 mg of dried reagent. Further details on preparing lyophilized antibody-antigen complexes are disclosed in U.S. Pat. No. 5,354,654, entitled "Lyophilized Ligand-Receptor Complexes for Assays and Sensors," which is fully and expressly incorporated herein by reference.

In order to contain the beads 776, while allowing the flow of liquid through the reaction chamber 616, circular-shaped porous barriers or screens (frits) 778 are provided at the bottom and top of the column channel 780. The frits 778 also serve to prepare the sample by filtering out all particles larger than the pore size (in the illustrated embodiment, 30 μm) from the saliva. It is noted that larger particles (e.g., 135 μm) are initially filtered by the sample collection tip 406 of the previously described sample collection assembly 400. In the preferred embodiment, the frits 778 are advantageously self-sealing in that they are held in place by interference fit within the column channel 780.

Figure 71:
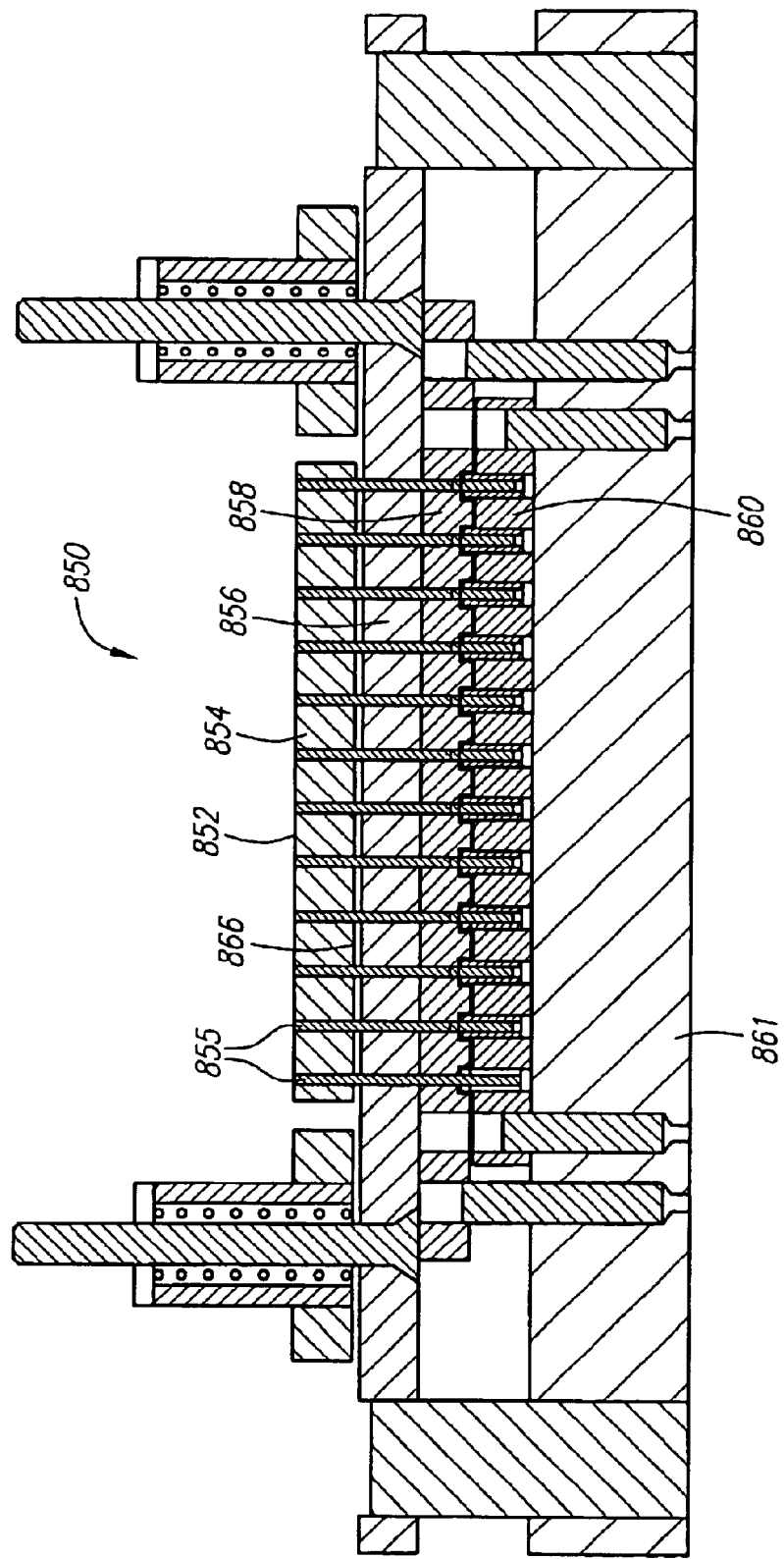
FIG. 71 is a cross-section of a frit tool assembly used to install frits within a plurality of reaction chambers.

With reference to FIG. 71, a preferred method of manufacturing the immunoassay reaction chamber 616 using a frit tool assembly 850 will now be discussed. The frit tool assembly 850 is capable of simultaneously manufacturing, compressing, and installing frits 778 within a plurality reaction columns 774, which in the illustrated embodiment, is accomplished for an 12×96 array of immunoassay reaction chambers 616. The compressed frits 778 when disposed within the column 774 are allowed to expand, thereby creating compressive forces between the first and the column channel 780. For purposes of clarification and brevity, the manufacture of only one immunoassay reaction chamber 616 will be discussed in detail.

Figure 72:
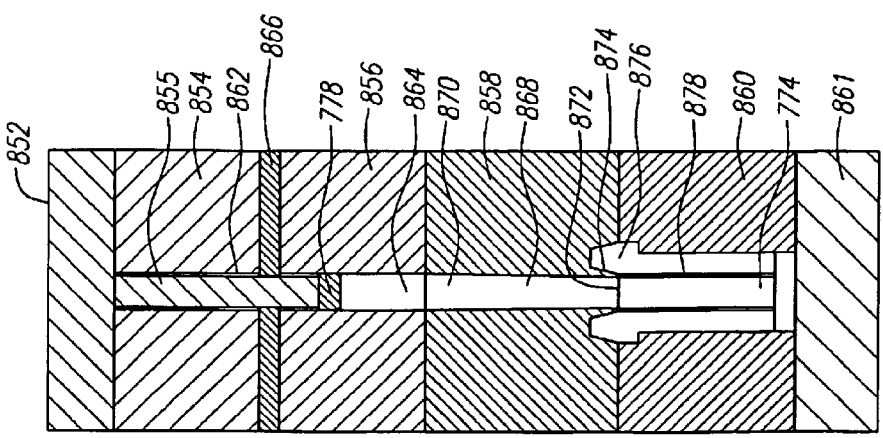
FIG. 72 is a cross-section of one bore of the frit tool assembly, particularly showing the newly cut frit within the die plate.

The frit tool assembly 850 generally comprises a punch plate 852, stripper plate 854, die plate 856, frit compression plate 858, chamber adapter plate 860, and base plate 861. The punch plate 852 includes a number of cylindrical punch plate pins 855 extending therefrom. The stripper plate 854 includes an equal number of circular passages 862 passing therethrough. Likewise, the die plate 856 includes an equal number of circular shearing passages 864 passing therethrough. Disposed between the stripper and die plates 854 and 856 is a frit material 866. As illustrated in FIG. 72, a motor assembly (not shown) operably coupled to the punch plate 852 is configured to drive the punch pins 855 (each of which has a diameter equal to the diameter of the die plate shearing passages 862) through the strip plate passages 862 and into the die plate shearing passages 864 to shear off the frits 778 within the die plate shearing passages 864. It is noted that the diameter of the uncompressed frit 778 will be approximately equal to the diameter of the die plate shearing passages 864, which in the illustrated embodiment, is 0.082 in.

Figure 73:
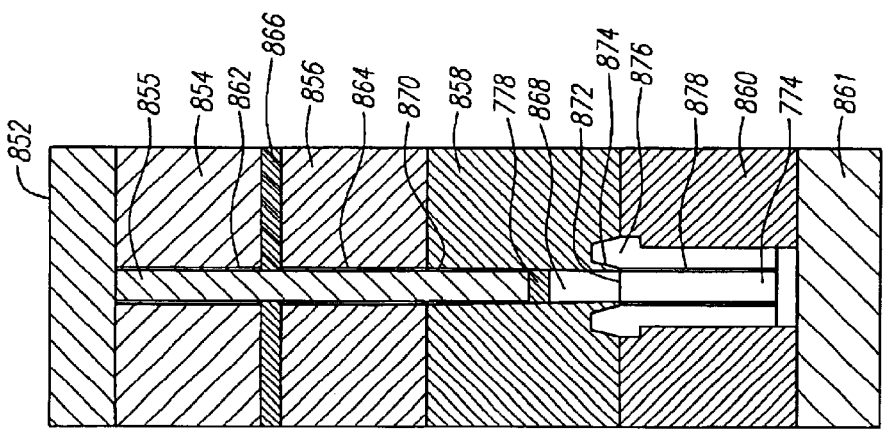
FIG. 73 is a cross-section of the frit tool assembly bore, particularly showing the frit passing through the compression plate.

The frit compressing plate 858 includes an equal number of conical passages 868 passing therethrough. The conical passages 868 have upper openings 870, which are configured to receive the newly cut frits 778 from the die plate shearing passages 864. In the illustrated embodiment, the diameters of the upper openings 870 are greater than that of the die plate shearing passages 864 to compensate for manufacturing and alignment tolerances, thereby ensuring that the upper openings 870 can receive the frits 778 from the die plate shearing passages 864. In the illustrated embodiment, the upper openings 870 have diameters of 0.084 in. The conical passages 868 naturally taper to lower openings 872, the diameters of which are less than that of the uncompressed frit 778 and column channel 780. In the illustrated embodiment, the diameters of the lower openings 872 are 0.074 in, which are less than the 0.082 in. diameters of the uncompressed frits and 0.080 in. diameters of the column channels 780. Thus, as illustrated in FIG. 73, when the punch pins 855 are further driven down into the conical passages 868 of the frit compression plate 858, the frits 778 are pushed through the conical passages 868, where they are laterally compressed by the lower openings 872.

Figure 74:
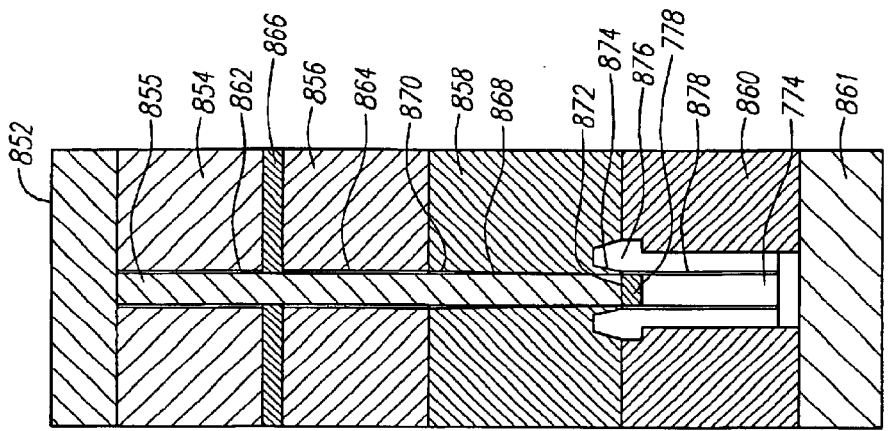
FIG. 74 is a cross-section of the frit tool assembly bore, particularly showing the frit mounted within the reaction chamber.

The frit compression plate 858 further includes an equal number of male portions 874 in which the conical passages 868 terminate. The chamber adapter 860 includes an equal number of corresponding female portions 876, which are configured to be received by the male portions 874 of the frit compression plate 858. The chamber adapter 860 further includes an equal number of cylindrical passages 878, which terminate adjacent the lower openings 872 of the frit compression plate 858. The cylindrical passages 878 are sized to firmly receive the columns 774, such that the ends of the columns 774 abut the lower passages 780 of the frit compression flange 858 when mounted therein. Thus, as illustrated in FIG. 74, when the punch pins 855 are further driven down through the cylindrical passages 878 of the chamber adapter 860, the compressed frits 778 are pushed into the column channels 780, where they expands into compression with the column channel 780 to form an interference fit.

The punch plate pins 855 are then pulled out of the chamber adapter 860, frit compression plate 858, die plate 856, and stripper plate 854, with the stripper plate 854 functioning to hold the frit material 866 in place as the punch plate pins 855 are pulled from the frit material 866. The columns 774 are then suitably flipped upside down and filled with the reagent. The afore-described process is then repeated to interference fit other frits 778 within the opposite ends of the columns 774 to form complete immunoassay reaction chambers 616, with the exception that the frit material is preferably displaced a predetermine distance to move unused frit material 866 over the shearing passages 864 of the die plate 856.

Figure 75:
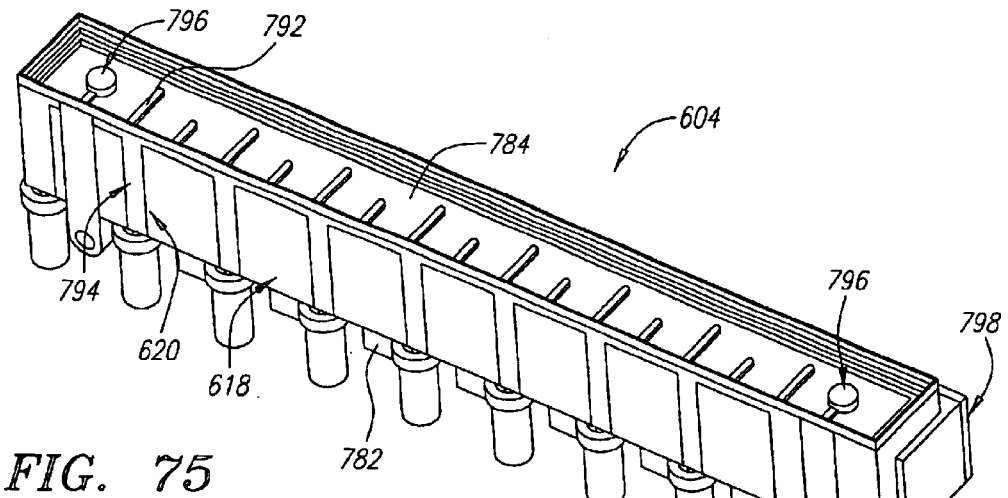
FIG. 75 is a front-right perspective view of the immunoassay reaction assembly for use in the immunoassay flow assembly.
Figure 76:
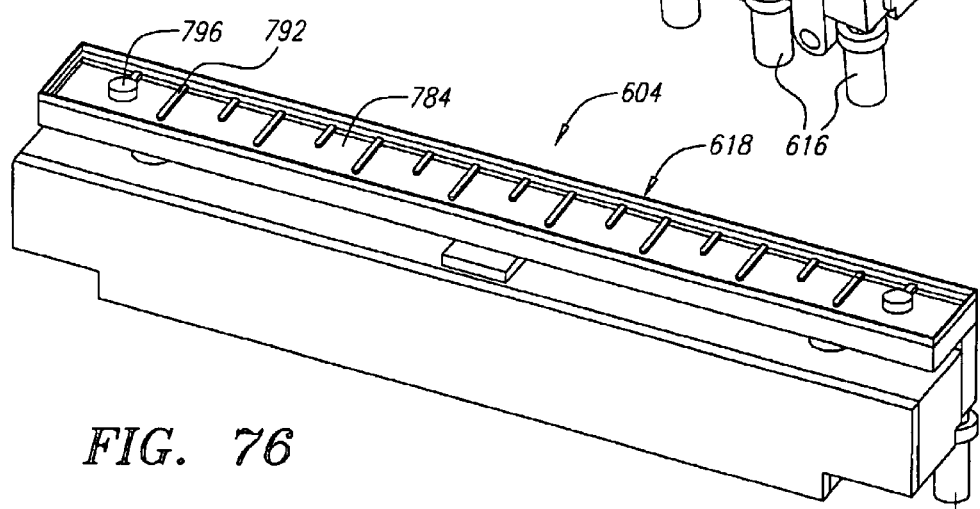
FIG. 76 is a rear perspective view of the immunoassay reaction assembly.
Figure 77:
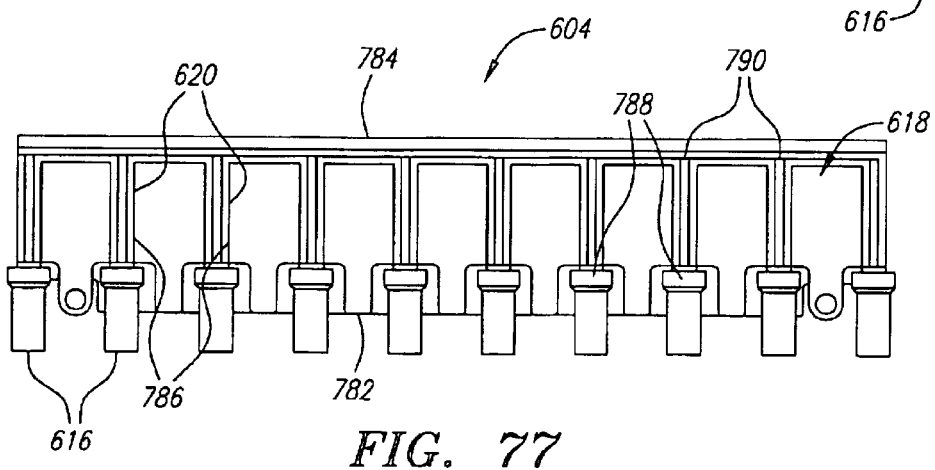
FIG. 77 is a front view of the immunoassay reaction assembly.

Referring now to FIGS. 75–77, the read cell assembly 618 is configured to present the reacted sample to a light source, where any labeled antigen will be exited into fluorescent emission, the intensity of which can be measured by a suitable detector. The read cell assembly 618 is molded from a single piece of transparent, e.g., injection molded, bubble-free, acrylic polymer, which includes vertical and horizontal disposed flanges 782 and 784.

The vertical flange 782 of the read cell assembly 618 forms the number of optical read cells 620 with internal lumens 786 (which in the illustrated embodiment, equals ten). The transparent material is selected to have especially low endogenous fluorescence (e.g., $\lambda exc=636$ nm, $\lambda em=670$ em) and no UV inhibitors or plasticizers as additives. In the illustrated embodiment, each of the molded read cells 620 is rectangular parallel-piped in shape, and has a width, depth, and length equal to 2.0 mm, 2.0 mm, and 10 mm, respectively. The read cell lumen 786 is cylindrically-shaped and has diameter of 1.0 mm. Each of the optical read cells 620 includes an input port 788 configured to be inserted into the read cell seat 775 of the corresponding reaction chamber 616. Each of the optical read cells 620 comprises an energy transmission port 790 located opposite the input port 788, which as will be described in further detail below, is used to transmit optical energy, and specifically laser energy, through the read cell lumen 786.

The horizontal flange 784 of the read cell assembly 618 forms a number of drain channels 792 (ten in the illustrated embodiment), which are in fluid communication with the optical read cells 620, and a single common drain channel 794, which is fluid communication with the drain channels 792. This common drain channel 794 is further in fluid communication with two outlet drain ports 796 that exit out the bottom of the horizontal flange 784 into the waste chamber 622.

The fluorescent labeled antigens are excited by transmitting laser energy down the longitudinal axis of the read cell lumen 786 using a light source, and specifically a laser, thereby exciting any labeled antigen into fluorescence. Thus, the laser beam enters the optical read cell 620 through the energy transmission port 790 and penetrates down the longitudinal axis of the read cell lumen 786, illuminating the sample stream, as well as the wall of the read cell lumen 786, with the laser light. The fluorescent emission within the optical read cell 620 is then detected by a detector, the intensity of which is indicative of the quantity of the target drug analyte within the sample, thereby allowing the sample to be quantitatively analyzed. It should be noted that the transmission of laser energy down the longitudinal axis of the optical read cell 620, as opposed to perpendicular to the longitudinal axis of the cell 620, allows the detector to view a greater quantity of the labeled antigen at one time, thereby increasing the accuracy of the measurement and subsequent analysis of the sample.

In order to quantitate low-intensity fluorescent photons within the labeled antigen, stray light must be eliminated from the cassette 152. The test console 102, which surrounds the cassette 152, provides the first level of stray light protection and removes 99% of ambient light. Each optical read cell 620 is masked by an optical read slit 184 formed on the front 156 of the cassette case 154 (shown in FIGS. 3–5). In the illustrated embodiment, this slit 184 is 1.2 mm in width and 10 mm in length. The end of each optical read cell 620 is also masked by an optical excitation aperture 186 formed on the top 160 of the cassette case 154 (shown in FIGS. 3 and 5). The cassette case 154 is also manufactured from light-absorbing dark pigmented plastic, and together with the optical read slits 184 and optical excitation apertures 186, eliminates 99% of the remaining stray ambient light from the exterior environment. No exposed source of red light, such as red-colored light emitting diodes (LEDs), are contained within the test console 102. At the top and sides of the optical read cell 620, a highly light-absorbent black plastic light shield 798 with interior baffles is used to absorb as much of the scattered light beam and unwanted fluorescent light as possible. Only multiple reflections from black and dark surfaces of the light shield and cassette case 154 can cause stray light. Thus, the undesirable channel-to-channel stray light pickup is minimized.

The waste chamber 622 is configured to collect and permanently store the buffer- and saliva-containing sample fluids, so that they cannot leak from the confines of the cassette case 154. The cassette 152 can then be disposed of simply as solid waste without hazard from leakage of potentially biologically hazardous saliva samples. The waste chamber 622 is composed of a suitable leak proof material, such as black polycarbonate, and is configured to be nested within the angled read cell assembly 618. The waste chamber 622 includes a pair of drain inlet ports 799 that positionally correspond with, and are configured to receive, the drain outlet ports 796 of the read cell assembly 618. The waste chamber 622 includes a self-sealing vent port (not shown) within which there is tightly disposed a hydrophobic seal (not shown). In the illustrated embodiment, the seal is composed of a self-sealing polyethylene membrane that comprises small-diameter pores (e.g., 25 $\mu$m diameter) that are coated with a hydrophilic substance, such as carboxymethlcellulose. When wetted, the hydrophilic pores rapidly swell, closing the pore interiors, thereby preventing liquid from passing through the membrane. This self-sealing vent port, thus facilitates passing air, while preventing the biologically hazardous saliva from leaking out of the cassette 152 after its disposal following use. Further, the buffer dispensed during buffer pre- and post-wash contain a 0.05% solution of sodium azide (NaN3) antibacterial preservative to prevent the growth of bacteria in the fluid medium.

C. Flow Immunoassay Assembly—Operation

Having described the detail structure of the flow immunoassay assembly 600, its detailed operation will now be described. When the cassette 152 is loaded into the test console 102, the recess formed within the end of the rotary pin 744 engages the ridged end of the rotor 626 of the rotary valve 610 (FIG. 38). Additionally, the sample and buffer drive assemblies 734 and 736 (FIG. 66) are automatically (i.e., prompted by the CPU) moved from their home positions to their pre-test positions, such that the sample dispense plunger drivers 764 are engaged with the respective sample dispense plungers 642 (FIG. 78), and the buffer dispense plunger drivers 764 are engaged with the respective buffer dispense plungers 658 (FIG. 79). For purposes of brevity, only one sample dispense plunger 642 and one buffer dispense plunger 658 is shown engaged with the respective plunger drivers 764.

Figure 55:
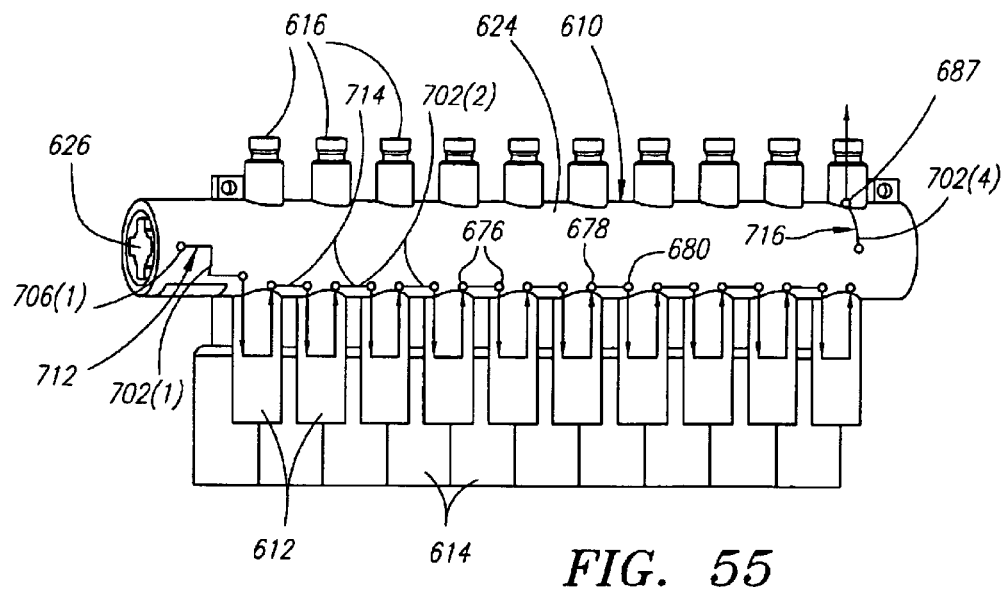
FIG. 55 is front-left perspective view of the cassette portion of the sample/buffer flow assembly, particularly showing sample distribution and venting flow paths when the rotary valve is clocked in a sample distribution configuration.
Figure 56:
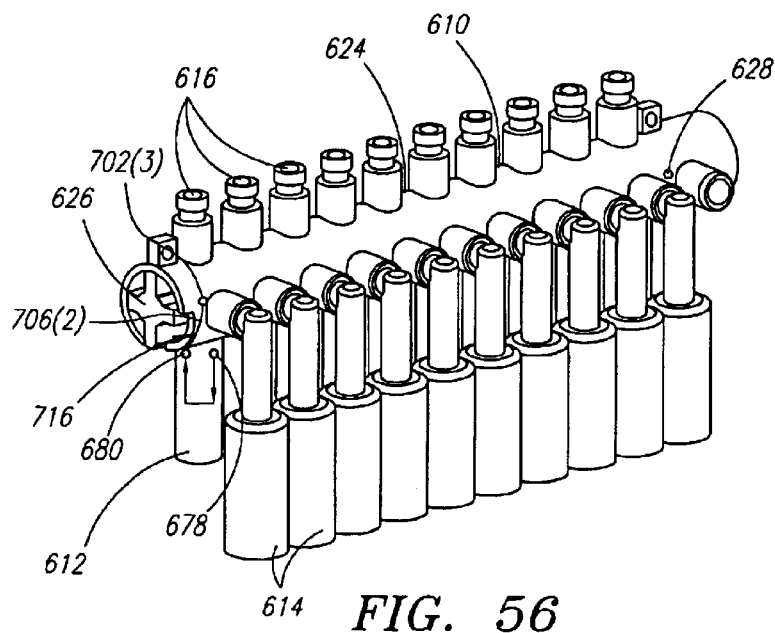
FIG. 56 is rear-left perspective view of the cassette portion of the sample/buffer flow assembly, particularly showing the sample and distribution venting flow paths when the rotary valve is clocked in the sample distribution configuration.
Figure 57:
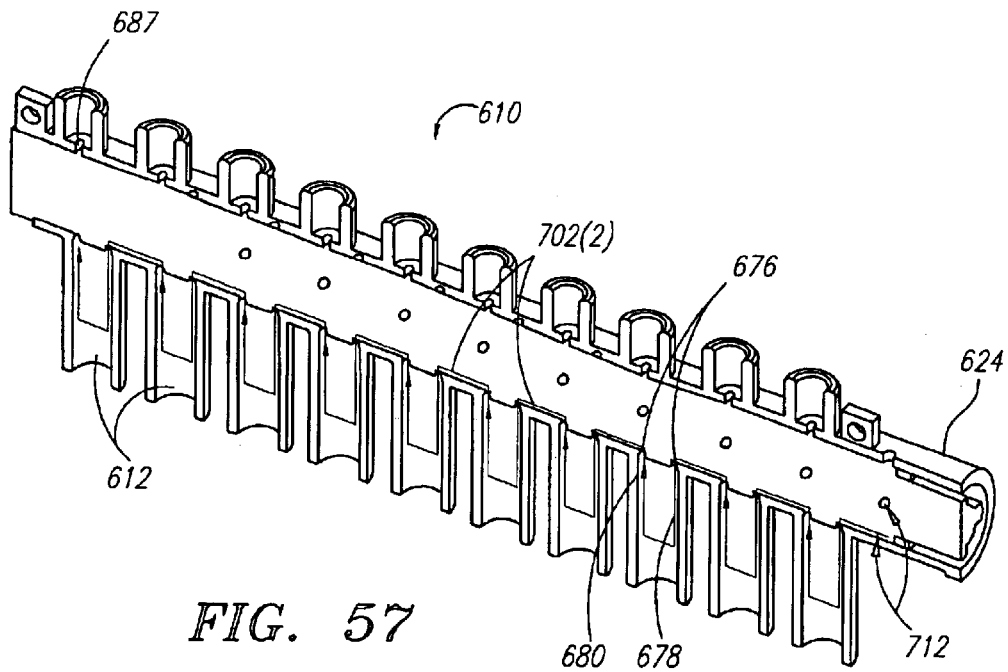
FIG. 57 is a longitudinal-sectional view of the rotary valve, particularly showing distribution channels.
Figure 58:
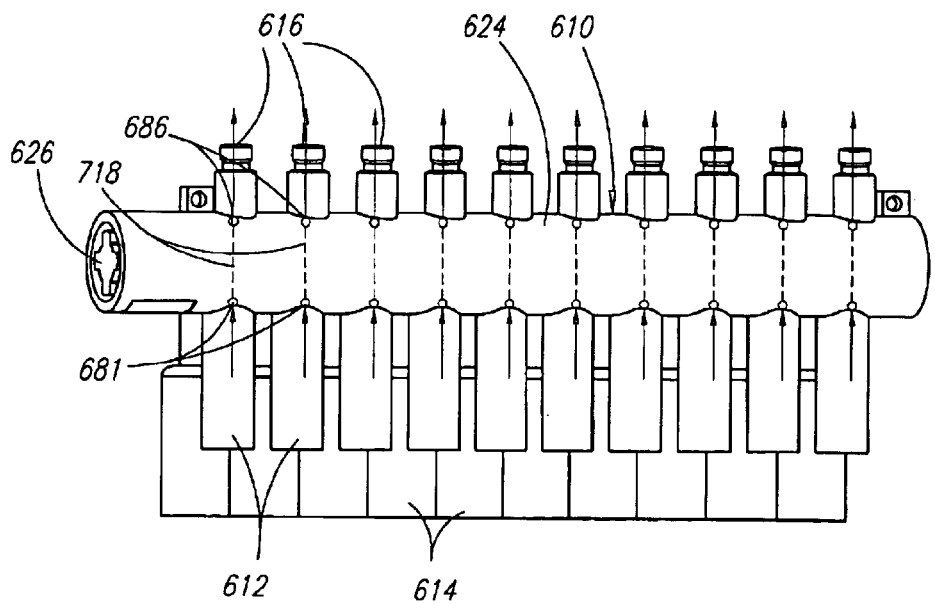
FIG. 58 is a front-left perspective view of the cassette portion of the sample/buffer flow assembly, particularly showing sample dispense flow paths when the rotary valve is clocked in a sample flow configuration.
Figure 59:
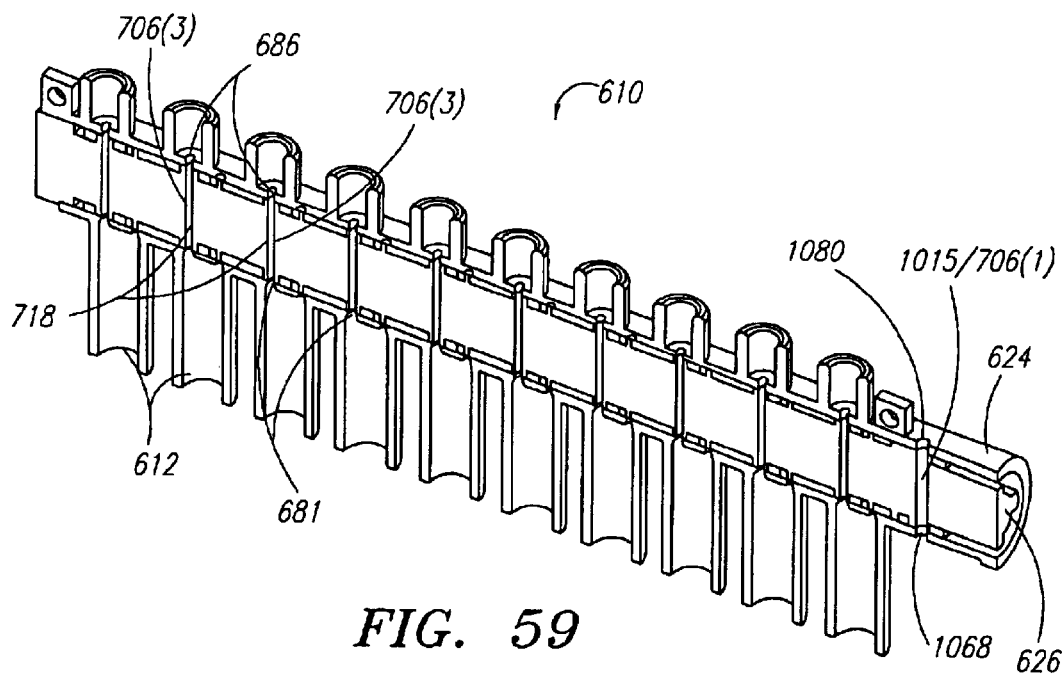
FIG. 59 is a longitudinal-sectional view of the rotary valve, particularly showing sample dispense channels.
Figure 60:
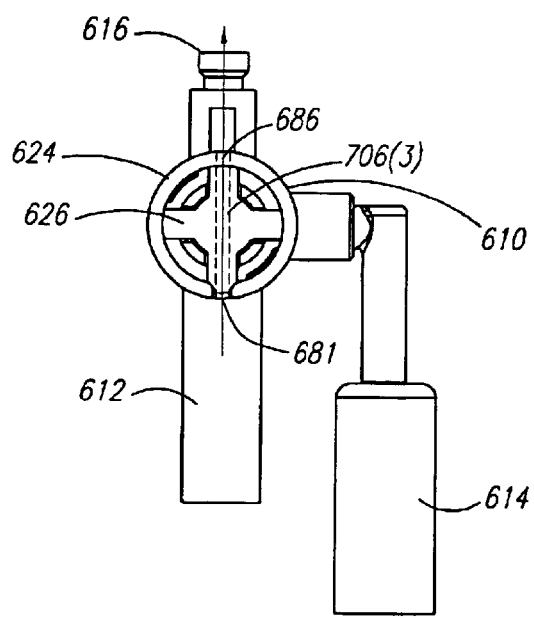
FIG. 60 is a side view of the cassette portion of the sample/buffer flow assembly, particularly showing a sample dispense channel.
Figure 61:
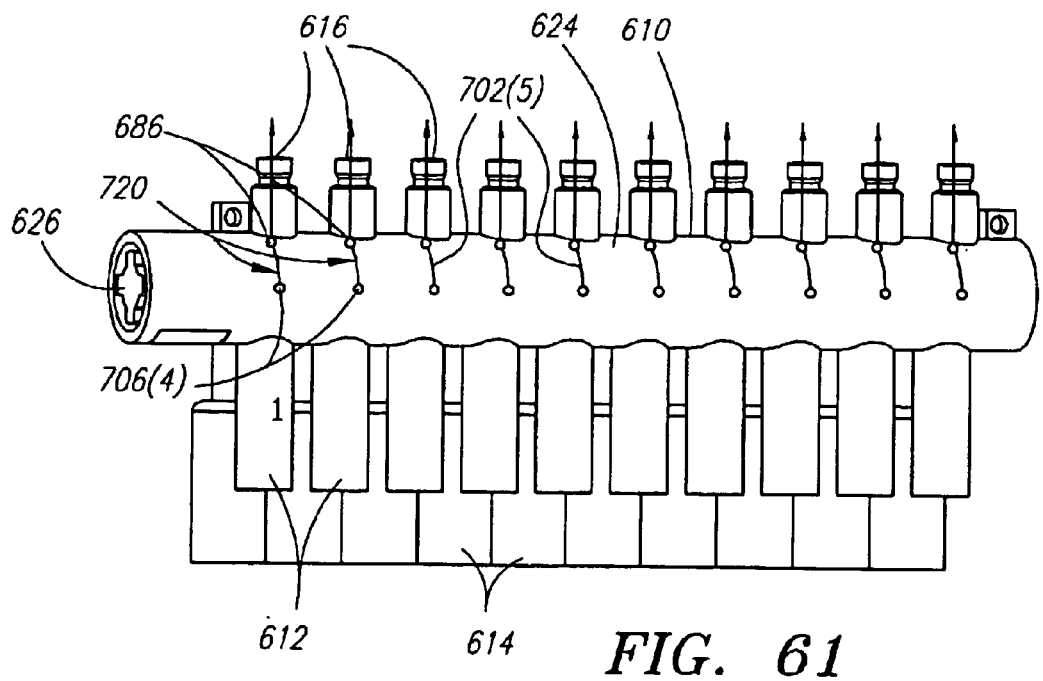
FIG. 61 is a front-left perspective view of the cassette portion of the sample/buffer flow assembly, particularly showing buffer dispense flow paths when the rotary valve is clocked in a buffer pre-wash configuration.
Figure 62:
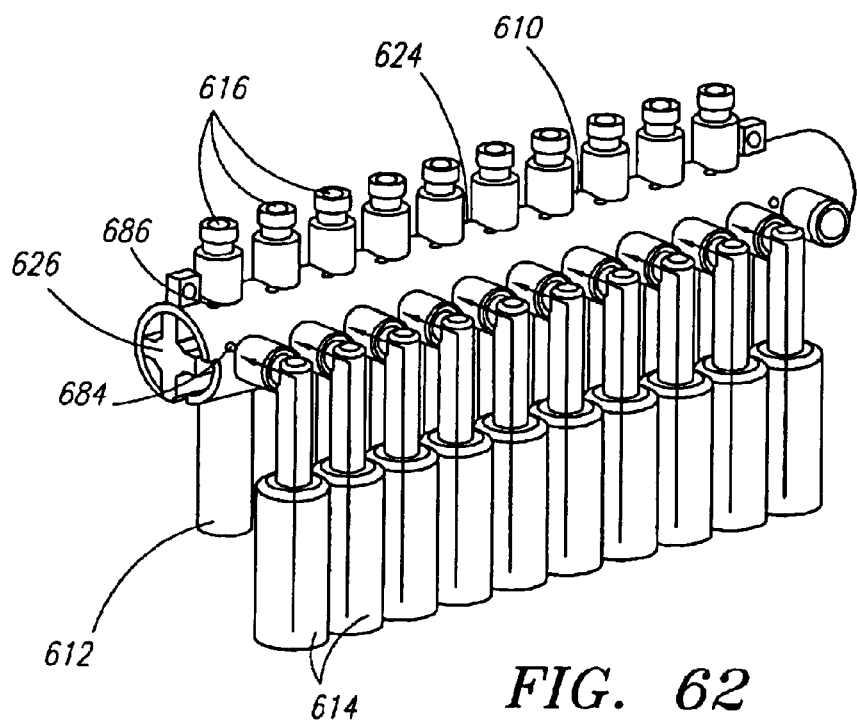
FIG. 62 is a rear-left perspective view of the cassette portion of the sample/buffer flow assembly, particularly showing the buffer dispense flow paths when the rotary valve is clocked in the buffer pre-wash configuration.
Figure 63:
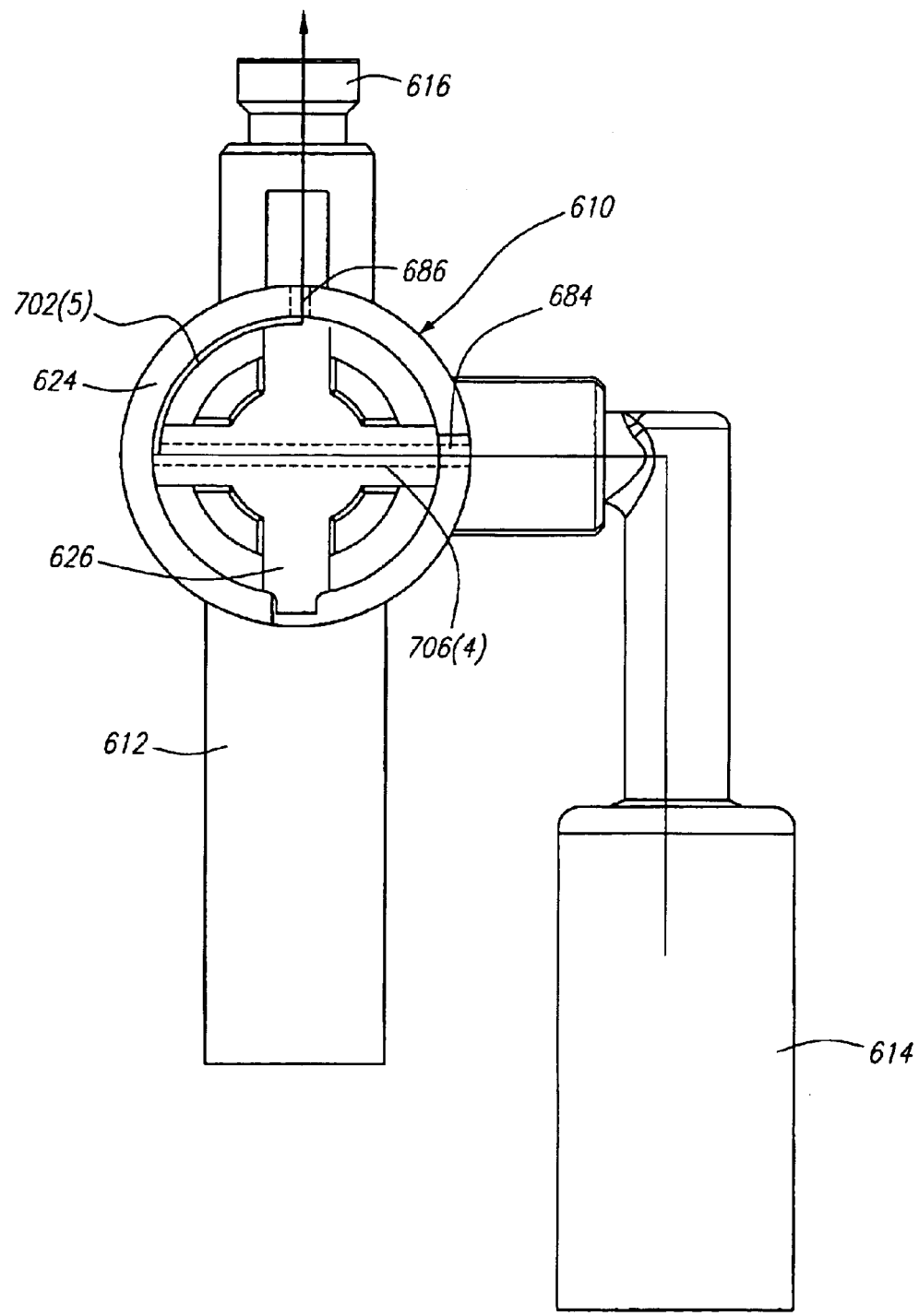
FIG. 63 is a side view of the cassette portion of the sample/buffer flow assembly, particularly showing the buffer dispense channel.
Figure 78:
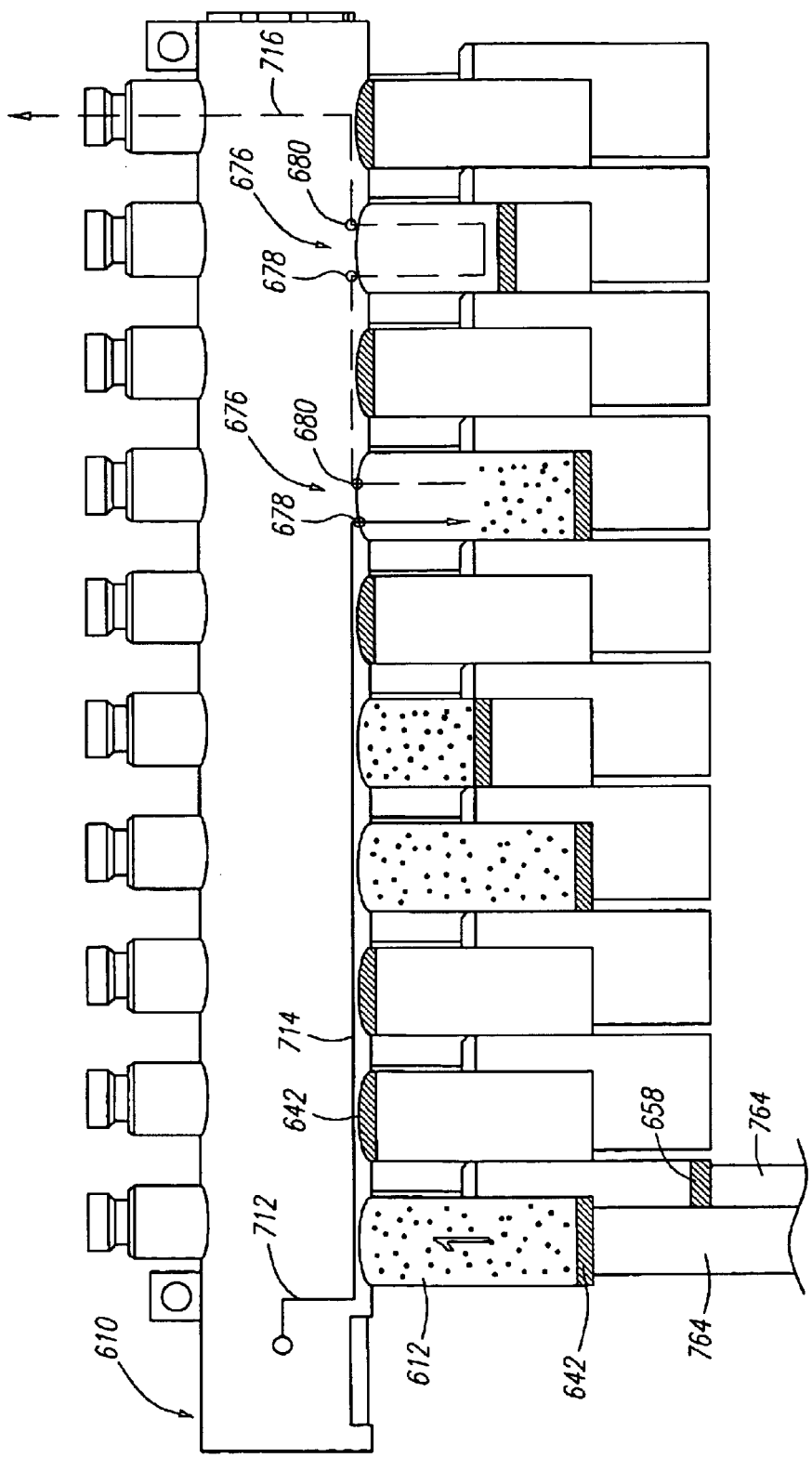
FIG. 78 is a front view of the immunoassay flow assembly, particularly showing the filling of the distribution chambers with sample during the sample distribution process.
Figure 79:
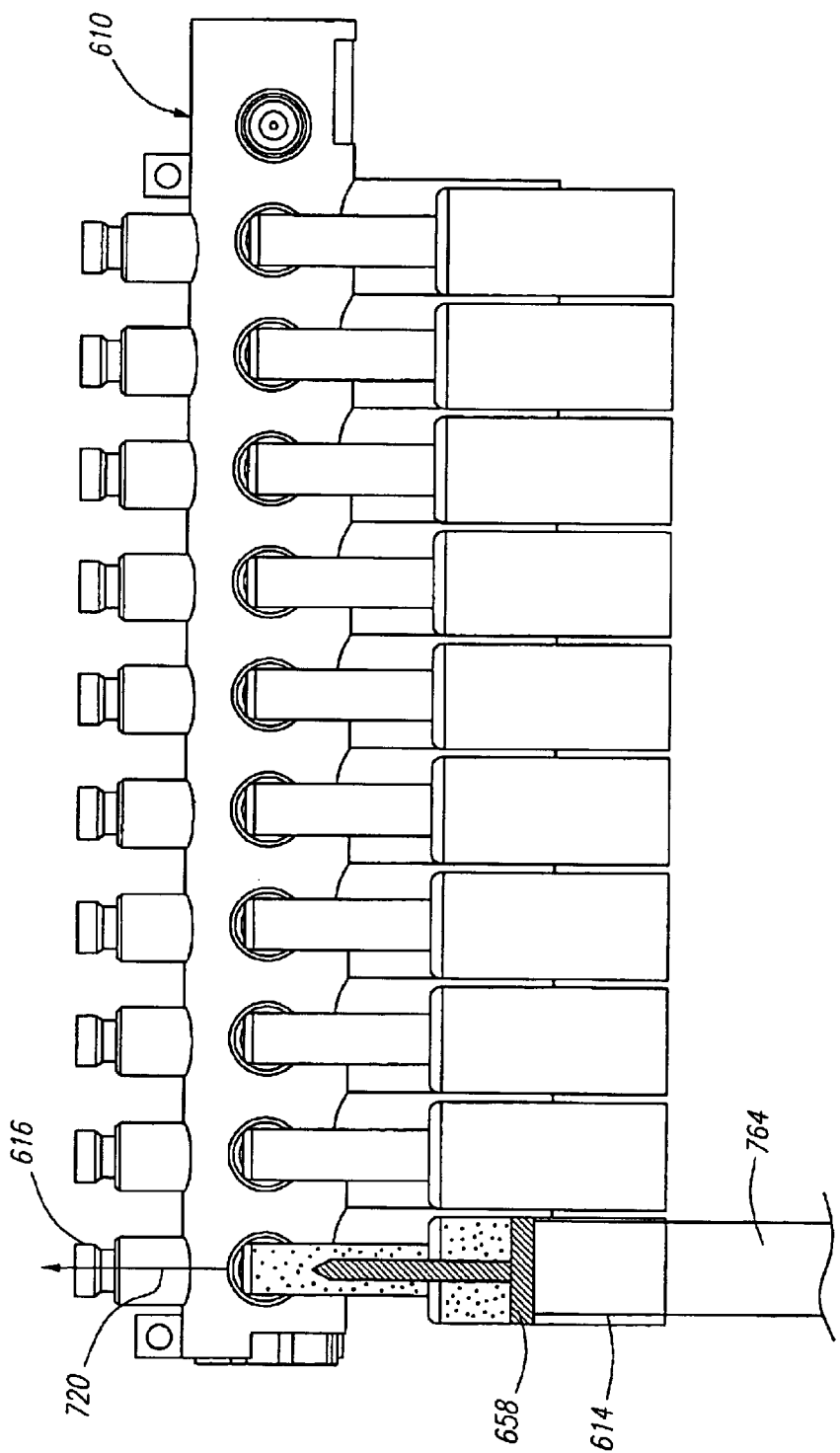
FIG. 79 is a rear view of the immunoassay flow assembly, particularly showing the dispensing of buffer from the buffer chambers during the buffer pre-wash process.
Figure 80:
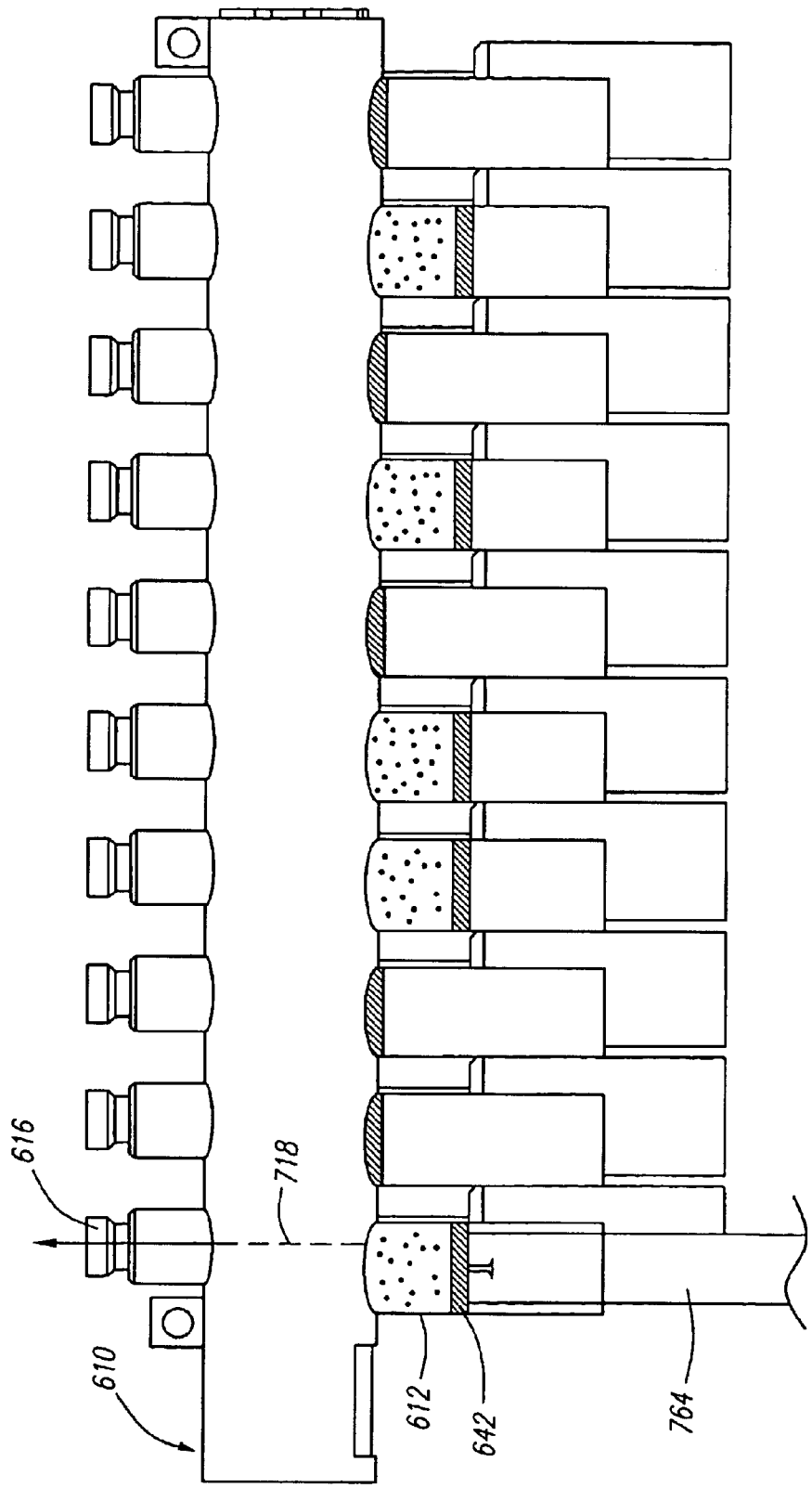
FIG. 80 is a front view of the immunoassay flow assembly, particularly showing the dispensing of sample from the distribution chambers during the sample dispense process.

Turning to FIGS. 55, 56, and 78, the sample distribution is performed in order to fill the sample distribution chambers 612 prior to flowing the sample through the immunoassay reaction chambers 616. Specifically, the rotary valve 610 is first placed into the sample distribution configuration, and the sample is pumped from the dispense port 530 of the mixing assembly 500 into the sample feed port 628, which as previously described, is accomplished by operating the buffer drive assembly 574 associated with the buffered sample dispense plunger 516 of the mixing assembly 500. It should be noted that the rotary valve 610 is preferably manufactured and stored in the sample distribution/buffer pre-wash configuration, in which case, the rotary valve drive assembly 730 need not be operated to clock the rotor 626 prior to the sample distribution process.

It should also be noted that, during the manufacturing process, the sample dispense plungers 642 are preferably pushed all the way to the top of those sample distribution chambers 612 (blanked out) that will not be used. For example, if the five drugs-of-abuse are to be tested, the remaining five sample distribution chambers 612 will be blanked out. In the illustrated embodiment, distribution chambers 2–3, 6, 8, and 10 are shown blanked out. In this manner, the sample is not distributed into unused sample distribution chambers 612, and thus wasted. To allow the sample to traverse across blanked out sample distribution chambers 612, a divot (not shown) is preferably made in the top of each sample dispense plunger 642 to ensure fluid communication between the entry and exit ports 678 and 680 of the distribution port pair 676 associated with any blanked out sample distribution chamber 612. In the case where a sample distribution chamber 612 need not be completely filled, the corresponding sample dispense plunger 642 can be pushed up into the sample distribution chamber 612 a predefined distance as dictated by the amount of sample that will be dispensed from the sample distribution chamber 612. In the illustrated embodiment, the sample dispense plungers 642 are shown displaced a predetermined distance from the bottoms of the distribution chambers 5 and 9.

Optionally, the sample drive assemblies 732 associated with the sample distribution chambers 612 to be blanked out or partially filled are operated under control of the CPU 204 and I/O controller 206 (FIG. 12) to push the sample dispense plungers 642 up into those sample distribution chambers 612 the required distance, such that the amount of sample distributed into each sample distribution chamber 612 is performed in accordance with a quantity of sample required for the corresponding sample flow channel, if any. This information can be derived from the barcode affixed to the chemistry cassette 152. If the sample drive assemblies 732 are operated to adjust the sample dispense plungers 642, it is preferable that those sample distribution chambers 612 that are to be filled with the same quantity of sample should be associated with the same sample drive assembly 576.

During sample distribution, the sample flows from sample feed port 628, through the feed channel 712 and into the first distribution chamber 612 via the entry distribution port 678 of first distribution port pair 676. Once the first distribution chamber 612 fills up, the sample flows out through the exit distribution port 680, through the sample distribution channel 714, and into the next available distribution chamber 612 via the entry distribution port 678 of the next distribution port pair 676. This cascading process continues until the last available distribution chamber 612 is filled with the sample. FIG. 78 illustrates that distribution chamber 7 is currently being filled, with distribution chambers 1, 4, and 5 having already been filled, and distribution chambers 2, 3, and 6 being blanked out. During the sample distribution process, air is vented from the sample distribution chambers 612. Specifically, as the sample distribution chambers 612 are being filled with the sample, the remaining air with each distribution chamber 612 is forced out through the corresponding exit distribution port 680, through the sample distribution channel 714 and into the next available distribution chamber 612 via the next entry distribution port 678. The air within the last available distribution chamber 612 is forced out the exit distribution port 680, through the vent channel 716, through the corresponding reaction chamber 616 and read cell 620, and into the waste chamber 622. As illustrated, since distribution chamber 7 is currently being filled and distribution chambers 8 and 10 are blanked out, air (dashed line) escapes from the exit distribution port 680 of distribution chamber 7, into and out of the entry distribution port pair 676 of distribution chamber 9, and out through the vent channel 716.

Referring to FIGS. 61–63 and 79, buffer pre-wash is performed to (1) rehydrate the immobilized antibody proteins, thereby conditioning the stabilized lyophilized column to be ready to accept liquid sample and kinetically release labeled antigen for each of the assays in response to the presence of any drug molecules in the sample; (2) wash away nonspecifically bound labeled antigen and other unwanted molecules (such as trehalose stabilizing agent); (3) pre-equilibrates the column with buffer of the appropriate pH and ionic strength in preparation for the sample; and (4) provides a convenient means to calibrate the fluorescent read out from the read cell assembly 618. It should be noted that the buffer pre-wash can be performed at any time in relation to the sample distribution process, but preferably is accomplished prior to the sample dispensing process.

At the beginning of the buffer pre-wash, the rotary valve 610 is placed into the buffer pre-wash configuration, which in the illustrated embodiment, is the same as the sample distribution configuration. Thus, the distribution and buffer pre-wash can be conveniently accomplished simultaneously, or at the least, the rotary valve 610 need not be rotated between sample distribution and buffer pre-wash. In any event, the buffer drive assemblies 734 are automatically operated, placing the buffer dispense plunger drivers 764 into contact with the buffer dispense plungers 658 after puncturing the bottom seals 654, and thereafter pushing the buffer dispense plungers 658 up within the buffer chambers 614, puncturing the top seals 652 with the styluses 666. The buffer is dispensed out of the buffer chambers 614, through the rigid tubes 650, buffer entry dispense ports 684, buffer pre-wash channels 720, and exit dispense ports 686. The buffer then flows through and conditions the immunoassay reaction chambers 616, where the afore-described preconditioning takes place, through the optical read cells 620, where the buffer is exposed to laser light and its corresponding fluorescence is measured to calibrate the read out, and then finally into the waste chamber 622, where the buffer is permanently stored.

The flow of buffer through the immunoassay reaction chambers 616 is of a suitable flow rate and volume. For example, for the drugs-of-abuse, a buffer pre-wash using a buffer volume of 400 $\mu$l at a flow rate of 400 $\mu$l/min has been found to be suitable. In this case, it will take 60 seconds to complete the buffer pre-wash.

Turning to FIGS. 58–60 and 80, the sample flow is performed in order to flow the sample through the immunoassay reaction chambers 616. The purpose of the sample flow is to expose the immunoassay reaction chambers 616 to any drug present within the sample. Thus, the sample, which may contain drug-of-abuse molecules, flows past the bound, antibody-antigen complex, causing an exchange reaction between the labeled antigen and the unbound drug molecules. Since the native drug antigen molecules bind more tightly to their corresponding antibody molecules, than the more bulky labeled antigen molecules, the reaction chamber 616 preferentially exchanges the labeled antigen with the real drug-of-abuse molecules. The net result is an increase in the concentration of fluorescent labeled antigen.

Specifically, the rotary valve 610 is automatically clocked 90° from the sample distribution configuration (buffer pre-wash configuration) into the sample flow configuration (buffer post-wash configuration). The sample drive assembly 734 is automatically operated, pushing the sample dispense plungers 642 up within the sample distribution chambers 612. The sample is dispensed out of the sample distribution chambers 612, through the sample entry dispense ports 681 (which are the same as the exit distribution ports 680), dispense channels 718, and exit dispense ports 686. The sample then flows through the immunoassay reaction chambers 616, where the exchange immunoassay reaction occurs, through the optical read cells 620, where the sample is exposed to laser light and its corresponding fluorescence is measured, and then finally into the waste chamber 622, where the sample is permanently stored. The sample flow is performed until the entirety of the sample has been emptied from the sample distribution chambers 612. It should be noted that the construction of the rotary valve 610 allows the sample to be injected as a contiguous band into the buffer flow, i.e., it prevents, or at least minimizes, the amount of air introduced into the flow that may otherwise be caused by the operation of a traditional valve between the buffer pre-wash and sample dispense processes.

The flow of the sample through the immunoassay reaction chambers 616 is of a suitable flow rate and volume. For example, a flow rate of 100 $\mu$l/min for all of the drug-of-abuse, and sample volumes of 50 $\mu$l, 50 $\mu$l, 100 $\mu$l, 250 $\mu$l, and 50 $\mu$l for cocaine, opiates (heroin, morphine, and codeine), phencyclidine (PCP), amphetanies/methamphetamines, and marijuana (tetrahydrocannabinol or THC), respectively, has been found to be suitable. Thus, in this case, it will take about 2 ½ minutes to complete the sample dispense process. It is noted that the sample distribution chambers 612 corresponding to the 50 $\mu$l and 100 $\mu$l sample volumes will be partially filled, in which case, the sample dispense plungers 642 will have been pushed up within these sample distribution chambers 612 either during the manufacturing process or by operation of the corresponding drive assemblies 734 and 736. For example, assuming a 250 $\mu$l capacity, a sample dispense plunger 642 will be pushed up ⅘ of the way for a sample distribution chamber 612 that will be partially filled with 50 $\mu$l of sample and ⅗ of the way for a sample distribution chamber 612 that will be partially filled with 100 $\mu$l of sample. Optionally, the sample drive assemblies 732 can be operated under control of the CPU 204 and I/O controller 206 (FIG. 12) to move the sample dispense plungers 642 at different speeds, thus effecting different flow rates for the sample flow channels. The information on the desired flow rates for the sample flow channels can be derived from the barcode affixed to the chemistry cassette 152.

Figure 81:
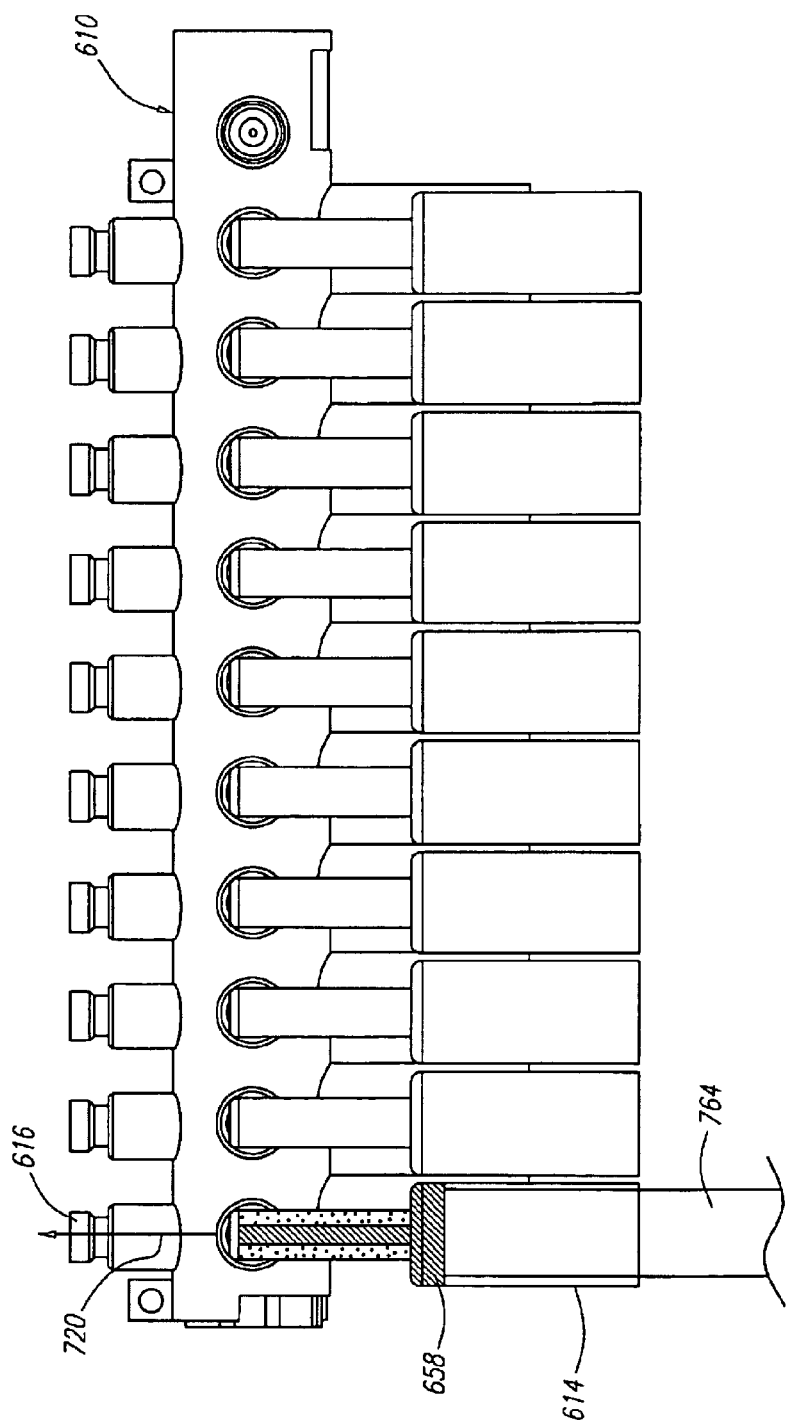
FIG. 81 is a rear view of the immunoassay flow assembly, particularly showing the dispensing of buffer from the buffer chambers during the buffer post-wash process.
Figure 82:
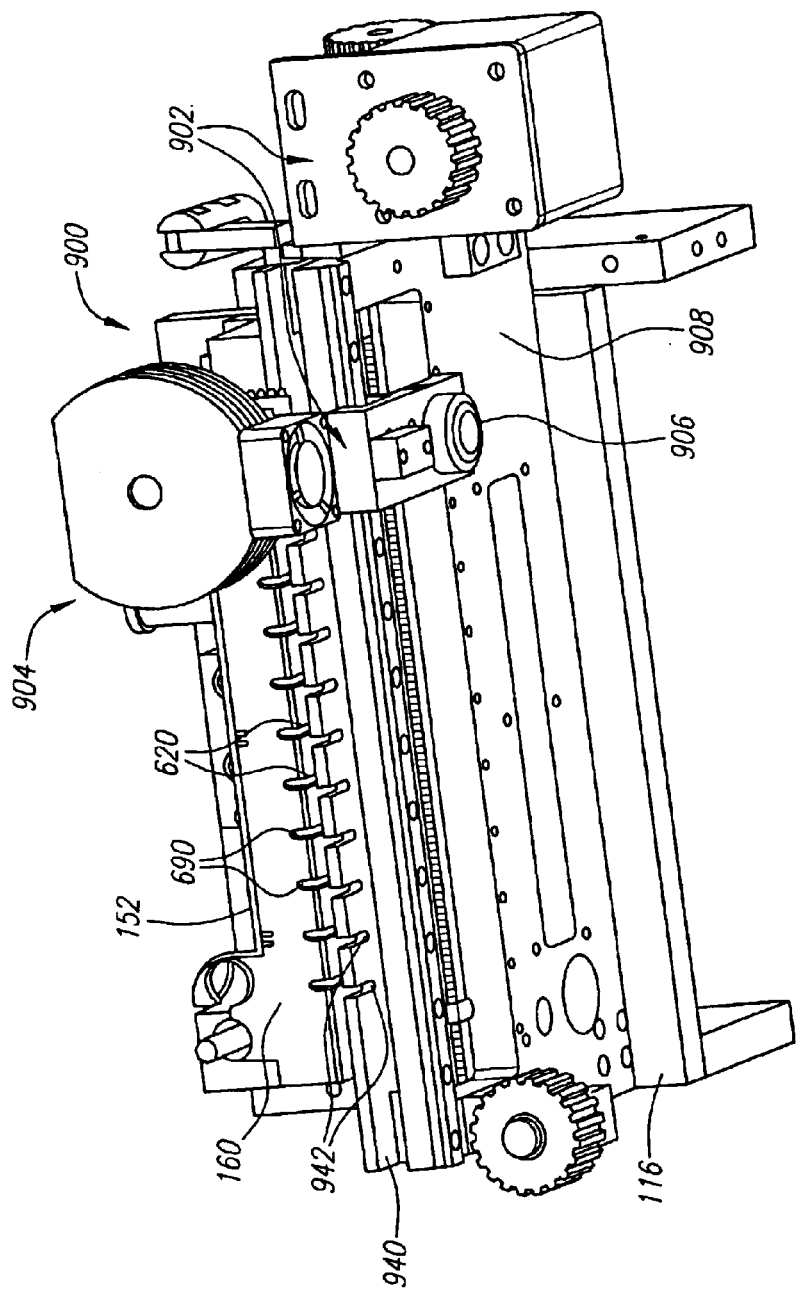
FIG. 82 is a top perspective view of the immunoassay scanning assembly and associated cassette for use within the test console.
Figure 83:
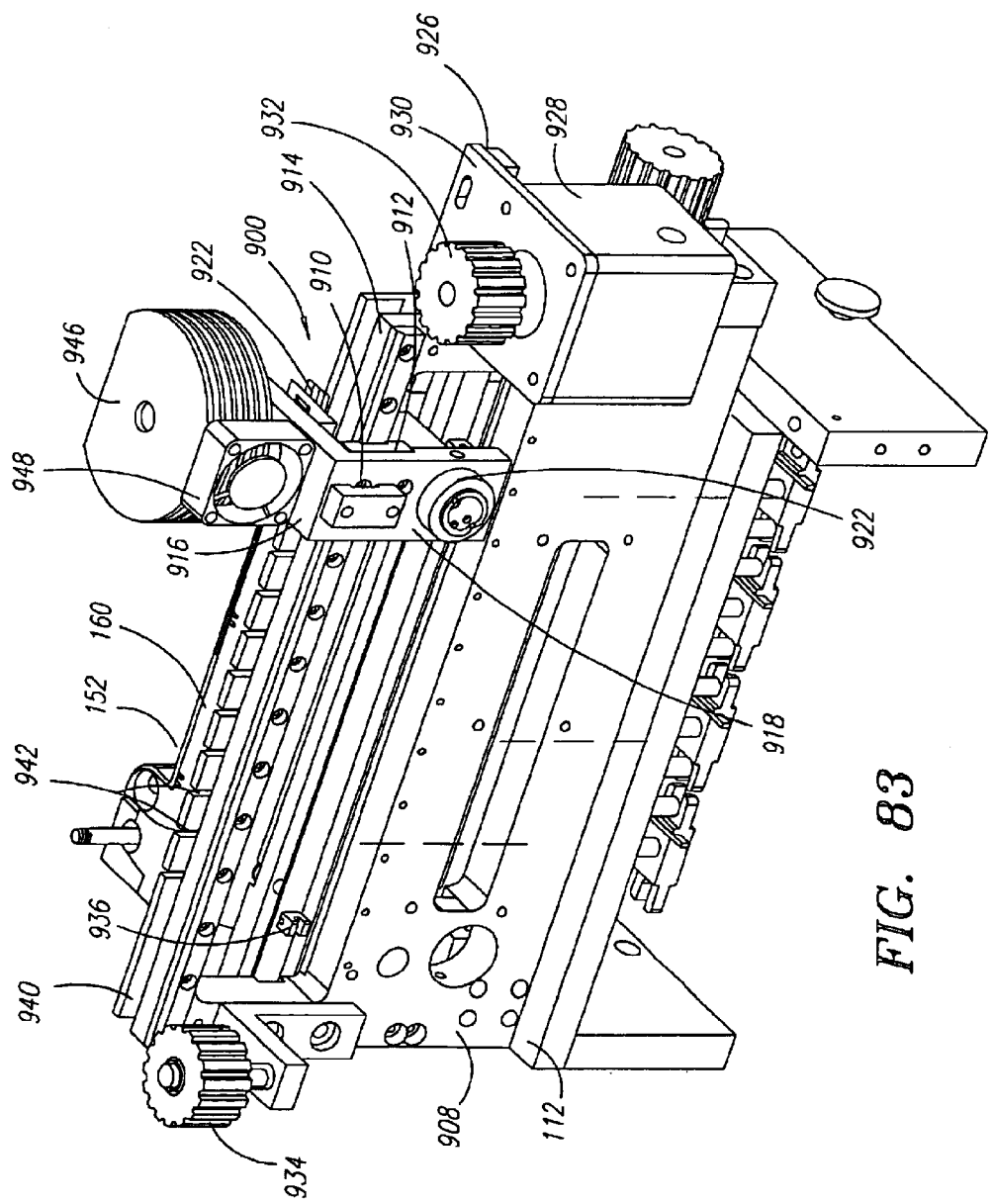
FIG. 83 is a front-right perspective view of the immunoassay scanning assembly, particularly showing a scanner head mechanism in an end position.
Figure 84:
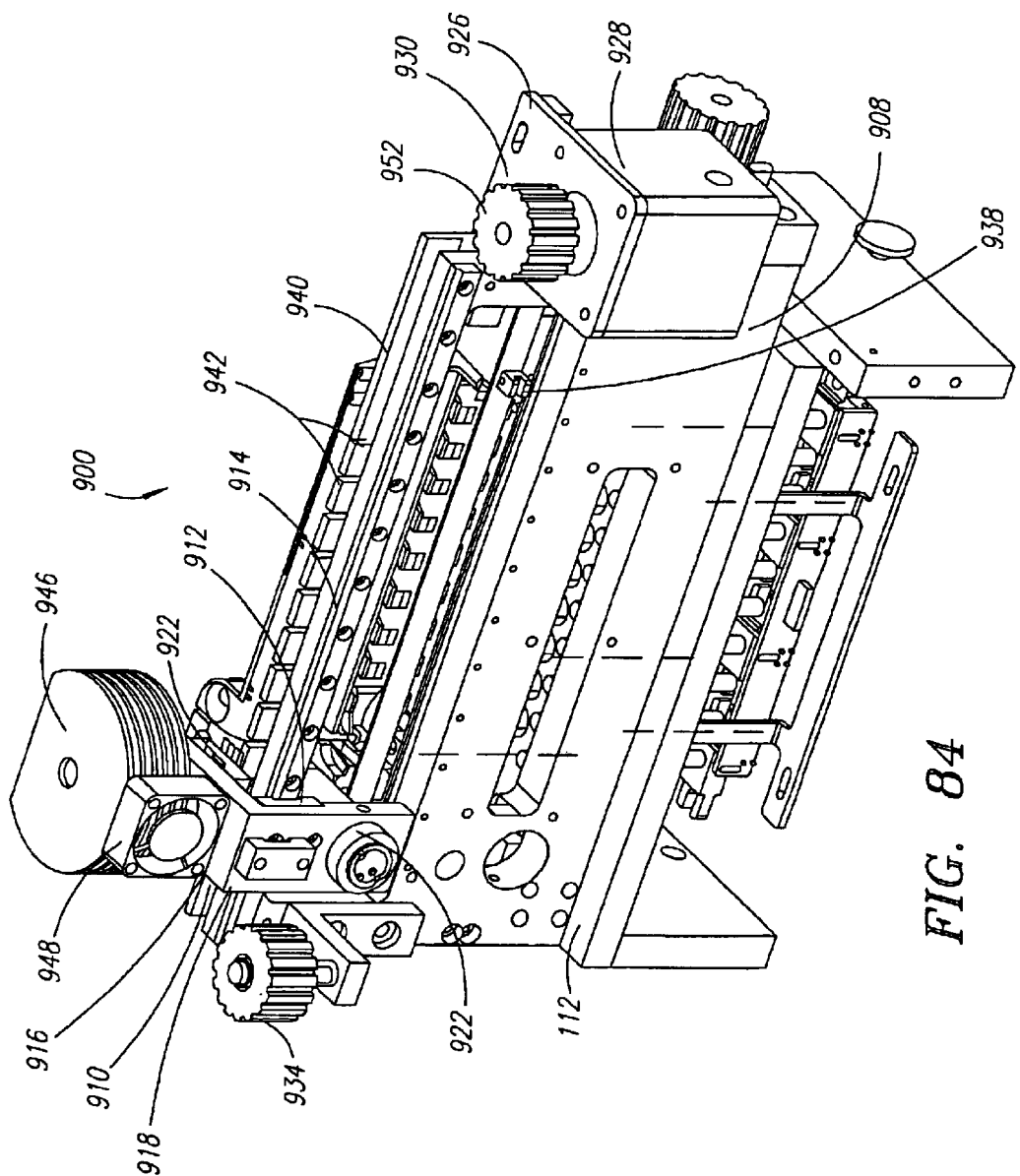
FIG. 84 is a front-right perspective view of the immunoassay scanning assembly, particularly showing the scanner head mechanism in a home position.
Figure 85:
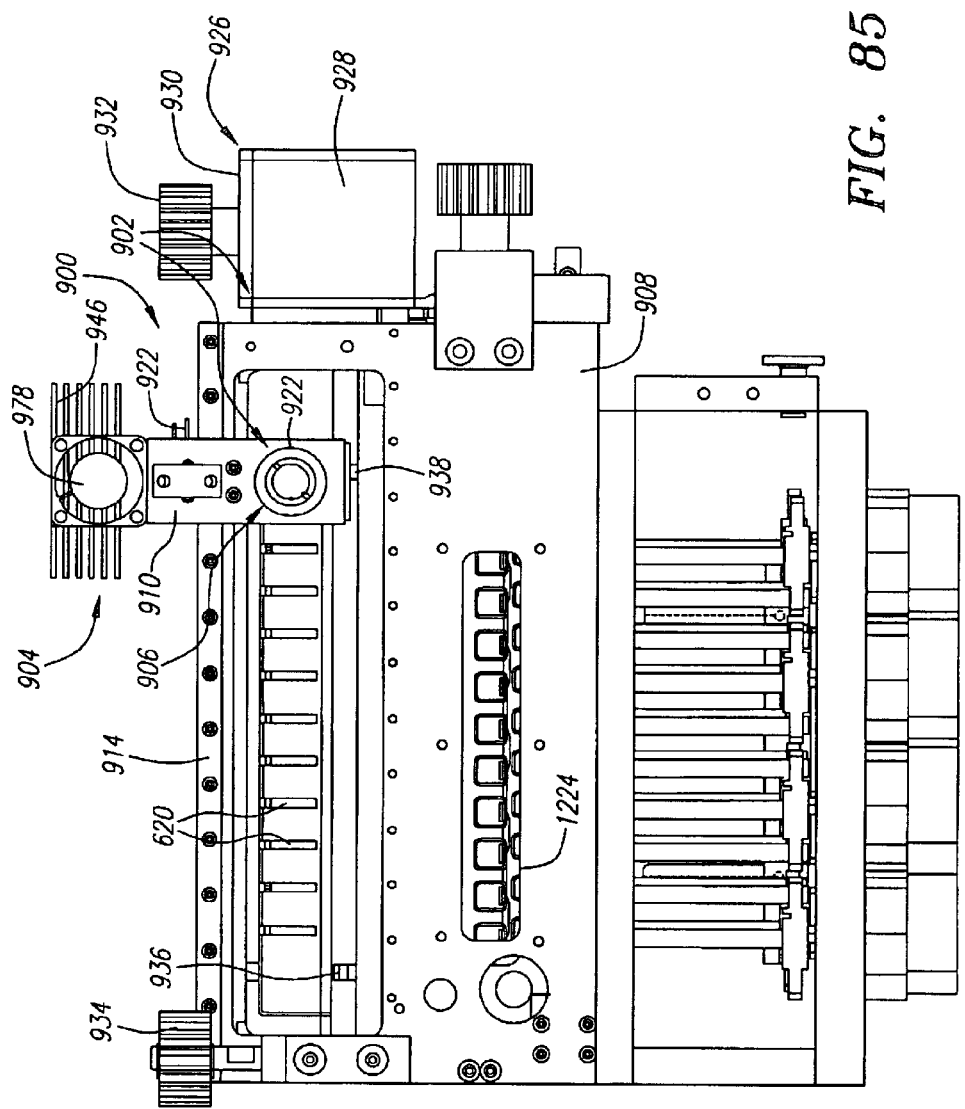
FIG. 85 is a front view of the immunoassay scanning assembly.

Referring to FIGS. 64, 65, and 81, the buffer post-wash is performed to push the remaining sample through the immunoassay reaction chambers 616 and read cells 620. Specifically, the rotary valve 610 is placed into the buffer post-wash configuration, which in the illustrated embodiment, is the same as the sample flow configuration. The buffer drive assemblies 734 are automatically operated again, further pushing the buffer dispense plungers 658 up within the buffer chambers 614. The remaining buffer is dispensed out of the buffer chambers 614, through the rigid tubes 650, buffer entry dispense ports 684, buffer post-wash channels 722, exit dispense ports 686, reaction chambers 616, read cells 620, and finally into the waste chamber 622. This is performed until the entirety of the buffer has been dispensed from the buffer chambers 614. The volume of the buffer chambers 614, and the speed of the buffer dispense plungers 658, are such that buffer continues to flow through the immunoassay reaction chambers 616 even after the sample is no longer flowing. In this manner, the buffer will push any remaining sample residing in the rotary valve 610 out through the immunoassay reaction chambers 616 and read cells 620, providing for a more efficient use of the sample.

The flow of the buffer through the immunoassay reaction chambers 616 are of a suitable flow rate and volume. For example, a flow rate of 100 $\mu$L/min and 250 $\mu$L volume for all of the drug-of-abuse has been determined to be suitable. Thus, in this case, it will take about 2 ½ minutes to complete the buffer post-wash.

Prior to the ejection of the cassette 152 from the test console 102, automatic operation of the sample drive assemblies 732 move the sample dispense plunger drivers 764 downward, disengaging them from the sample distribution chambers 612 and cassette carriage 302 until they are back in their home positions. Likewise, automatic operation of the buffer drive assemblies 734 moves the buffer dispense plunger drivers 764 downward, disengaging them from the buffer chambers 614 and cassette carriage 302 until they are back in their home positions.

VII. Optical Flow Immunoassay Scanning Assembly

Referring generally to FIGS. 13, and 82–88, the system 100 comprises an optical flow immunoassay scanning assembly 900, the purpose of which is to measure the amount of labeled antigen, and specifically fluorescent CY5 dye, flowing through each of the optical read cells 620. In performing this function, the optical flow immunoassay assembly 600 includes a dynamic scanning assembly 902, an optical excitation assembly 904, and an optical detection assembly 906.

A. Dynamic Scanning Assembly

The purpose of the dynamic scanning assembly 902 is to translate the positions of the optical excitation assembly 904 and optical detection assembly 906, so that they can interact with the optical read cells 620 of the flow immunoassay assembly 600. To this end, the dynamic scanning assembly 902 comprises a vertically extending rigid mechanical bench 908 mounted to the top flange 116 of the main base 114. The dynamic scanning assembly 902 further includes a scanner head mechanism 910 that rides on top of the mechanical bench 908. Specifically, the dynamic scanning assembly 902 includes a runner 912, which is mounted to the scanner head mechanism 910, and a rail 914, which is mounted to the top of the mechanical bench 908. Thus, the runner 912 rides on the rail 914, such that the scanner head mechanism 910 rides smoothly along the top of the mechanical bench 908.

The scanner head mechanism 910 includes a horizontal flange 916 and a vertical flange 918 for mounting various components. Specifically, the horizontal flange 916 extends along the top of the chemistry cassette 152 when loaded into the test console 102, and includes a laser aperture 918 (shown best in FIG. 13) with which the optical excitation assembly 904 is associated to interact with the optical read cells 620. The horizontal flange 916 is used to mount a position sensor 920, which as will be described in further detail below, aids in determining the location of the scanner head mechanism 910 in relation to each optical read cell 620. In addition, the previously described runner 912 is mounted to the vertical flange 918. The vertical flange 918 extends along the front of the chemistry cassette 152 when loaded into the test console 102 and includes a detector aperture 922 with which the optical detection assembly 906 is associated to interact with the optical read cells 620. The vertical flange 918 comprises a sensor actuator 924 (shown best in FIG. 13), which as will be described below, aid in determining the extreme limits of the scanner head mechanism 910 in relation to the mechanical bench 908.

The dynamic scanning assembly 902 further includes a scanning drive assembly 926, which automatically scans the scanner head mechanism 910 in relation to the mechanical bench 908, and thus, the loaded cassette 152. The scanning drive assembly 926 includes a rotational stepper motor 928 and a motor mount 930, which affixed the motor 928 to the mechanical bench 908. The scanning drive assembly 926 further includes a driver pulley 932, which is rotatably mounted to the motor 928, and an idler pulley 934, which is rotatably mounted to the front of the mechanical bench 908. The scanning drive assembly 926 further includes a circular, notched drive belt (not shown) mounted around the respective driver and idler pulleys 932 and 934. The scanner head mechanism 910 is affixed to the drive belt, such that operation of the motor 928 moves the drive belt, thus linearly translating the scanner head mechanism 910 in relation to the mechanical bench 908, which linear translation is ensured by the rail and runner arrangement.

It should be noted that one scan cycle of the dynamic scanning assembly 902 consists of one scan in the forward direction (left-to-right, referred to simply as the "forward scan") immediately followed by one scan in the reverse direction (right-to-left, referred to simply as the "reverse scan"). To ensure that the scanner head mechanism 910 does not translate to far, the scanning drive assembly 926 includes a scanner home position sensor 936, which is mounted to one end of the mechanical bench 908, and a scanner end position sensor 938, which is mounted to the other end of the mechanical bench 908, to independently indicate the position of the scanner head mechanism 910 near the extreme limits of travel during each scan cycle. The sensor actuator 924 mounted to the vertical flange 918 of the scanner head mechanism 910 triggers the scanner home and end position sensors 936 and 938 to facilitate this determination. The forward and reverse scans of the scanner head mechanism 910 are performed under control of the CPU 204 (FIG. 12). Specifically, the CPU 204 generates instructions used to program the I/O controller 206 for the motor 928, which in the illustrated embodiment, is performed at a linear rate of 20 cm/s, thus performing a single scan of all ten channels in one second (1 s).

To indicate the location of the optical read cells 620, the scanning drive assembly 926 further includes an indexed flange 940, which is mounted to the front of the mechanical bench 908, and the position sensor 922, which, as previously described, is mounted to the horizontal flange 916 of the scanner head mechanism 910. To this end, the indexed flange 940 comprises notches 942 (ten, in the illustrated embodiment) that are spaced apart the same distance in which the optical read cells 620 are spaced apart, i.e., each notch 942 spaced from an adjacent notch 942 a distance equal to the distance in which each optical read cell 620 is spaced from an adjacent read cell 620. Thus, when the position sensor 922 associated with the scanner head mechanism 910 senses a notch 942 within indexed flange 940, a certain portion of the scanner head mechanism 910 will be aligned with a read cell 620, which as will be described in further detail below, indicates that the optical read cell 620 is currently being scanned.

B. Optical Excitation Assembly

The purpose of the optical excitation assembly 904 is to provide constant wavelength, constant intensity light to the optical read cells 620, so that each of the labeled antigen, and specifically fluorescent CY5 dye, flowing therethrough are excited by photons of the correct wavelength. To this end, the optical excitation assembly 904 comprises a laser module 944 (best shown in FIG. 13), which is mounted within the laser aperture 918 formed through the horizontal flange 916 of the scanner head mechanism 910. The optical excitation assembly 904 further includes a heat sink 946 and fan 948, which provide heatsinking functionality to the optical excitation assembly 904.

Figure 86:
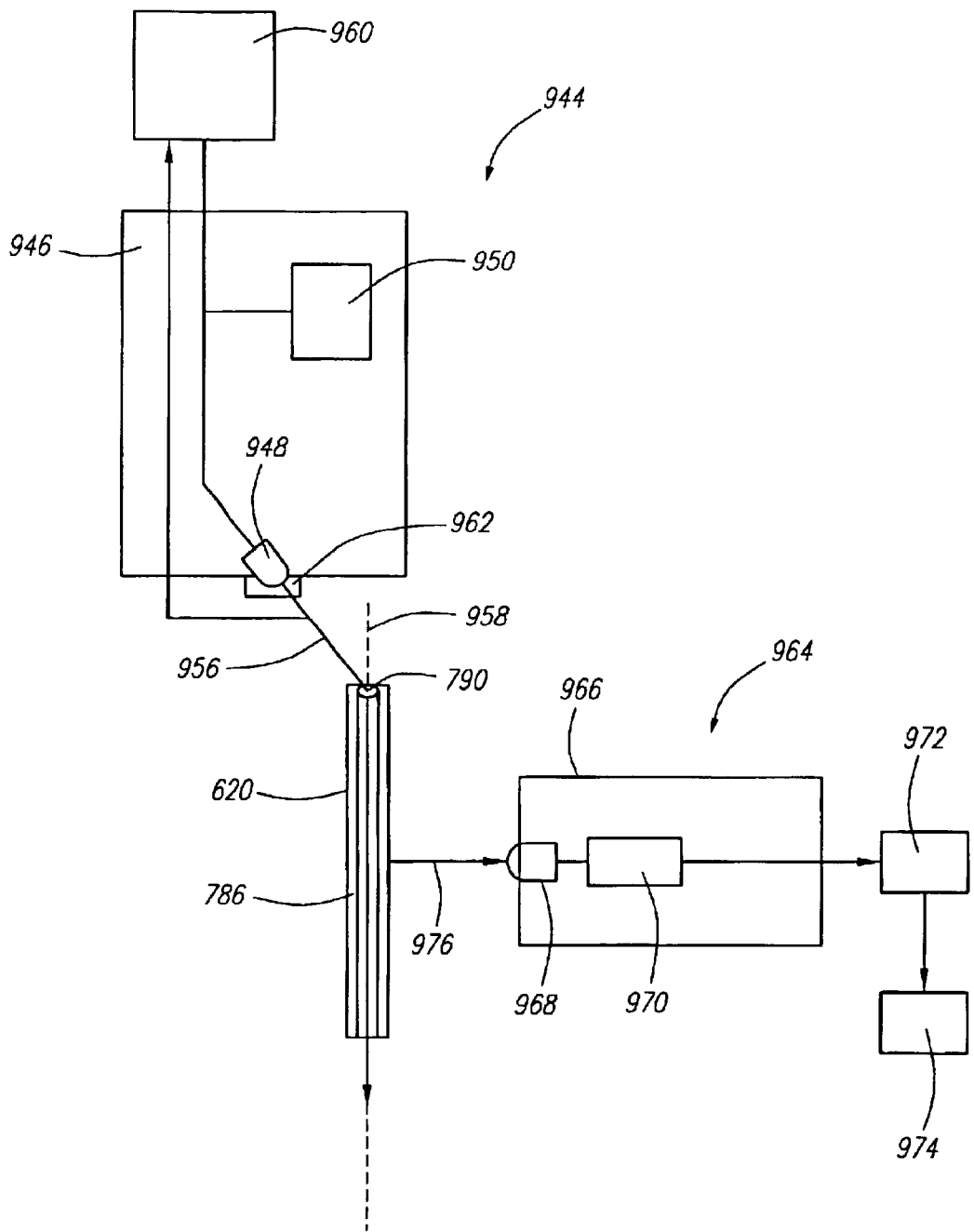
FIG. 86 is a schematic diagram of an optical excitation assembly and optical detection assembly associated with an optical read cell of the immunoassay reaction assembly.

As illustrated in FIG. 86, the laser module 944 includes a modular housing 950, which contains a laser source 952 and a thermocontroller 954 that are configured to provide constant output controlled laser energy to the optical read cells 620. The laser source 952 is rigidly mounted within the modular housing 950, which aligns the laser source 952 with the optical transmission port 790 of the read cell 620. Thus, the laser source 952 transmits laser energy through the optical transmission port 790 of each read cell 620, and through the corresponding lumen 786.

In the illustrated embodiment, the laser source 952 is mounted, such that the resultant laser beam 956 intersects the longitudinal axis 958 of the read cell lumen 786 at an oblique entry angle. If this oblique angle is, e.g., 45° 0 a two times (2×) overscan of each optical read cell 620 in the vertical axis (and many times overscan in the horizontal axis due to the linear translation of the scanner head mechanism 910) is provided. This assures that some portion of the cross-section of the laser beam 956 intersects the transmission ports 790 of the read cell lumens 786, even if some displacement of the optical read cells 620 along the length of the cassette 152 exists, e.g., if the cassette 152 is slightly warped, or otherwise due to manufacturing tolerances in the injection molded plastic read cell assembly 618. The laser source 952 specifically comprises a 5 mW solid-state laser diode that nominally operates at 636 nm and has a resultant laser beam 956 with a 2 mm×4 mm rectangular beam profile.

Thus, operation of the dynamic scanning assembly 902, mechanically scans the resultant laser beam across each optical read cell 620 through the transmission port 790 and down the longitudinal axis of the lumen 786, thereby illuminating the sample stream, as well as the walls of the optical read cells 620, with laser light. Thus, at a linear scan rate of 20 cm/s, some portion of each 2 mm wide optical read cell 620 will be exposed to the laser beam for approximately 0.020 s.

The thermocontroller 950 controls the temperature of the heat sink 946, thereby controlling the operating wavelength of the laser source 948. The thermocontroller 950 is a 4W Peltier thermocontroller, which ensures that the output wavelength of the laser source 948 is maintained substantially constant. The optical excitation assembly 904 further includes a laser controller 960 to control the operating current of the laser source 948. The laser controller 960 comprises an internal reference optical diode (not shown) that samples a small portion of the laser output and provides a reference voltage that is input to the laser controller 960 and used to control the current to the laser source 948 as a feedback signal from an amplifier (not shown) in the laser controller 960.

The optical excitation assembly 904 further comprises a laser filter 962, which is mounted between the laser source 948 and the optical read cell 620 to provide adequate rejection of scattered light produced by the turbid saliva samples (turbidity of human saliva samples can vary by as much as 20-to-1) and by the read cell assembly 618. Since solid-state laser diodes typically contain a light emitting diode (LED) with a high-Q resonant cavity, the LED produces a relatively low intensity broad band of radiation approximately 200 nm in width on which is superimposed a high intensity, narrow band (≅±1 nm) of resonant laser energy. For example, the laser energy can be about $10^6$ ( a million times, or 6 orders of magnitude) more intense than the low energy broadband radiation. Consequently, the low energy broadband radiation of a solid-state laser diode is typically ignored. Since fluorescence, however, is $10^4$–$10^5$ times less intense than scattering due to the low efficiency of the fluorescent radiation process, scattered light outside the nominal laser wavelength that reaches the laser source 948 from the sample can be even more intense than the fluorescent light generated within each optical read cell 620.

Thus, in order to eliminate significant error due to light scattering by the sample, and thereby ensure that detected light is due to the fluorescence of CY5 dye found within the optical read cell 620, rather than to high turbidity of the saliva sample, scattered light must be highly rejected from the optical detection assembly 906. To this end, the laser filter 962 comprises a 636 nm±5 nm FWHM (full width at half maximum height) bandpass filter with steep rolloff (20 db) of its bandpass, thus assuring that light outside the desired excitation band is prevented from reaching the optical read cells 620, and ultimately the optical detection assembly 906. Further, the laser filter 962 is preferably mounted at an oblique angle off of its normal axis, e.g., 5°, so that the reflected light from the front and back surfaces of the laser filter 962 cannot reenter the resonant laser cavity and modulate the laser activity of the laser source 948.

C. Optical Detection Assembly

The purpose of the optical detection assembly 906 is to detect the excited labeled antigen, and specifically fluorescent radiation from the CY5 dye, and produce a voltage signal that is directly proportional to the concentration of dye in the optical read cell 620, and thus directly proportional to the concentration of target drug analyte in the sample. To this end, the optical detection assembly 906 comprises an optical detector module 964 mounted within the detector aperture 922 formed through the vertical flange 918 of the scanner head mechanism 910. The optical detector module 964 includes a modular housing 966, which contains an optical detector 968 and an integral high-gain preamplifier 970 (shown in FIG. 86). The optical detector 968 includes a silicon diode, and the high-gain preamplifier 970 is mounted on the same dye to minimize noise and thermal effects of the high impedance detector circuit. The high-gain integral preamplifier 970 has a 600 MΩ internal feedback resistor (not shown), giving the circuit a relatively large internal gain. The optical detector 968 is mounted within the modular housing 966, such that its sensing beam 976 intersects the optical read cells 620 at an angle-transverse to the longitudinal axes of the optical read cells 620. In the illustrated embodiment, this transverse angle is 90° to maximize the amount of light sensed by the optical detector 968.

The optical detection assembly 906 further comprises an external amplifier 972, which takes the preamplified signal (e.g., $10^4$ gain) from the preamplifier 970, and amplifies it by an additional factor, e.g., $10^2$. The combined detector circuitry gain has a gain of one million ($10^6$ gain) in order to produce an output voltage of 1.4 volts for a CY5 dye concentration of $1.0 \times 10^{-9}$ M. This is a combined gain within a factor of 2 of what is obtainable with a highly sensitive photomultiplier tube detector. Thus, the power supply for optical detection assembly 906 preferably has a very low noise.

It should be noted that CY5 dye molecules absorb photons most efficiently at 650 mn ($\lambda_{ex\ max}$=650 nm) and emit fluorescent photons most efficiently at 655 nm ($\lambda_{em\ max}$=655 nm). This gives a Stokes shift of only 5 nm, which is a relatively demanding optical requirement. As a result, the optical detection assembly 906 must be capable of detecting fluorescent photons with great sensitivity, while simultaneously rejecting incident light photons with high selectivity. To this end, the optical detection assembly 906 comprises a three-stage filter 974, which includes two stages of 670 nm bandpass filters (±5 nm FWHM) to permit detection of fluorescent photons, and a single stage 655 nm reject filter, which rejects light <655 nm and passes light >655 nm with a steep slope between the two. Together these filters reject incident photons of scattered light (<655 nm) while passing photons of fluorescent light (>655 nm) with at least 50% efficiency for the three-stage filter 974.

Together, the optical excitation assembly 904 and optical detection assembly 906 provide a Stokes shift of approximately 35 nm (670 nm–635 nm). While this is only about 50% as sensitive for fluorescent light detection as the optimal 5 nm Stokes shift, it does permit acceptable rejection of scattered light (>$10^8$:1 limit). This is equivalent to a background light of about $10^{-12}$ M (i.e., 1 pM) CY5 dye. The combined optical excitation and optical detection assemblies 904 and 906 has a linear dynamic range of about $10^{-11}$ to $5 \times 10^{-9}$ M CY5 dye or about 2.5 decades of linear response to CY5 dye molecules. The flow immunoassay assembly 600 has been optimized, so that the cutoff points for each of the assay occur well within this range of CY5 dye concentration.

D. Optical Flow Immunoassay Scanning Assembly-Operation

Having now described the detail structure of the optical flow immunoassay scanning assembly 900, its operation will now be described. During the afore-described buffer pre-wash, sample dispense, and buffer post-wash cycles, the optical flow immunoassay scanning assembly 900 senses any displaced labeled antigen flowing through the read cells 620 and processes this information accordingly.

Specifically, the scanning drive assembly 926 is operated to translate the scanner head mechanism 910, and thus, the laser beam of the laser source 948 and sensing beam of the optical detector 968 simultaneously across the immunoassay flow channels. That is, the laser source 948 transmits laser energy at an oblique entry angle, e.g., 45°, to the longitudinal axes of the read cells 620 lumens. The laser energy enters the optical transmission ports 790 of the read cell lumens 786, which is then transmitted down the longitudinal axes 958 of the read cells lumens 786. In response, any fluorescent labeled antigen flowing through the optical read cells 620 is excited into fluorescence, which optical energy is in turn transversely emitted from the fluoresced labeled antigen through the walls of the read cells 620. At the same time, the optical detector 968 senses the transversely emitted optical energy at an angle substantially perpendicular to the longitudinal axes of the read cell lumens 786.

Figure 87:
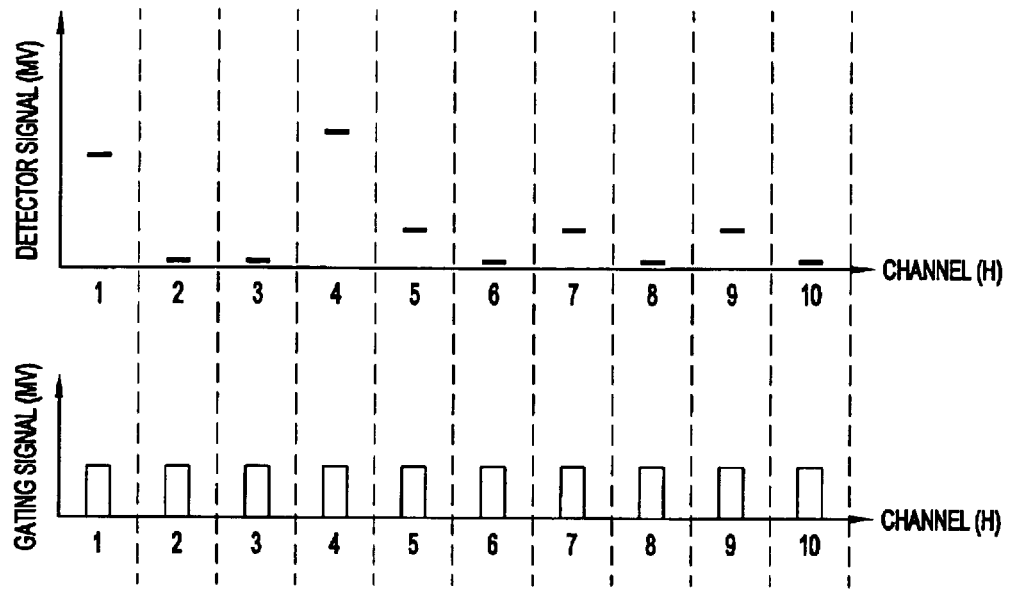
FIG. 87 is a diagram plotting the gated voltage levels of a measured reaction within the channels of the immunoassay reaction assembly as measured by the immunoassay scanning assembly during a single scan.

Referring to FIG. 87, the optical detector 968 outputs a signal indicative of the sensed fluorescence level of the optical energy, which is then received by the CPU 204 (FIG. 12). Because the optical detector 968 scans through the immunoassay flow channels, a discrete output signal is generated for each of the immunoassay flow channels during a single scan. As illustrated in FIG. 87, the CPU 204 takes these discrete output signals and constructs, for each immunoassay flow channel, a fluorescence magnitude well waveform over time, i.e., over several forward and reverse scans.

The position sensor 922 is gated to the CPU 204, such that the CPU 204 only processes the data for each immunoassay reaction chamber when a corresponding optical read cell 620 is detected, i.e., when the sensing beam of the optical detector 968 intersects the corresponding optical read cell 620. That is, as the position sensor 922 senses a position indicator 942, which in the illustrated embodiment is a notch, it outputs a high signal to the CPU 204, indicating that the sensing beam 976 of the optical detector 968 is currently passing through the corresponding optical read cell 620. As long as this signal is high, the CPU 204 processes the output signal received from the optical detector 968. In contrast, when the position sensor 922 no longer senses a position indicator 942, it outputs a low signal to the CPU 204, indicating that the sensing beam of the optical detector 968 is currently passing through a region between optical read cells 620. As long as the signal is low, the CPU 204 will not process the output signal received from the optical detector 968.

Figure 88:
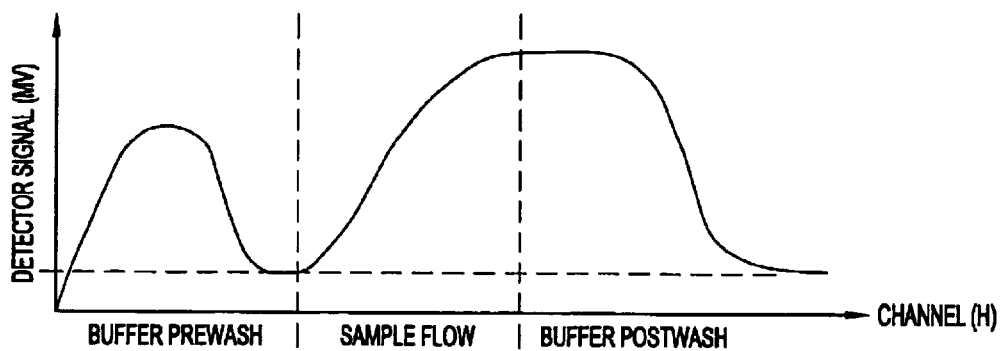
FIG. 88 is a diagram plotting the voltage level of a measured reaction within a channel of the immunoassay reaction assembly during the buffer pre-wash, sample flow, and buffer post wash processes.
Figure 89:
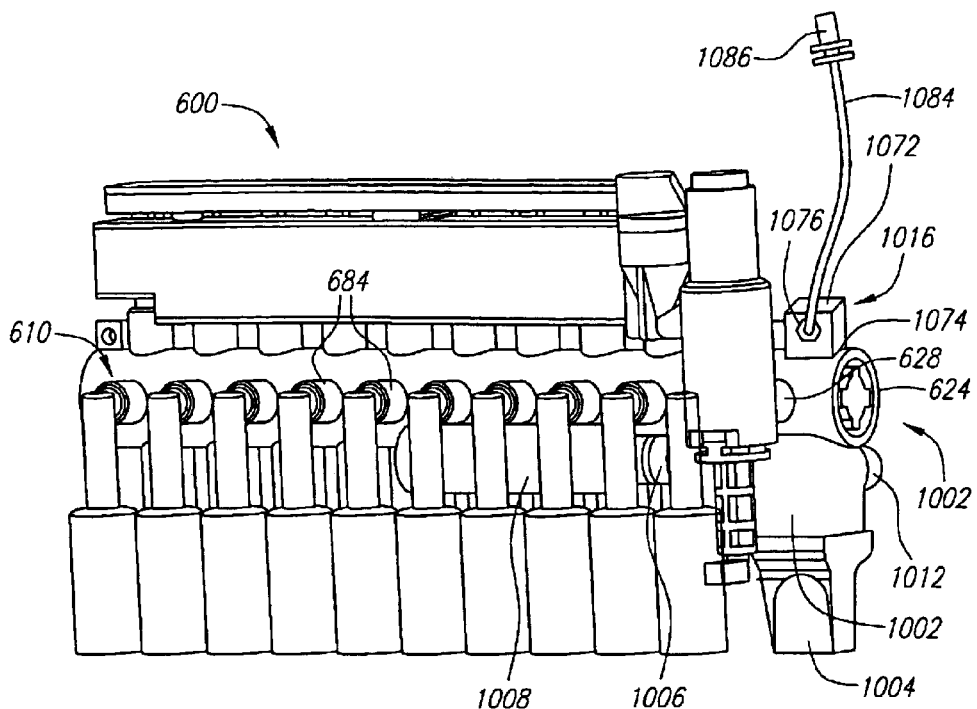
FIG. 89 is a rear-right perspective view of the cassette portion of an alcohol reaction assembly mechanically associated with the cassette portion of the immunoassay flow assembly.
Figure 90:
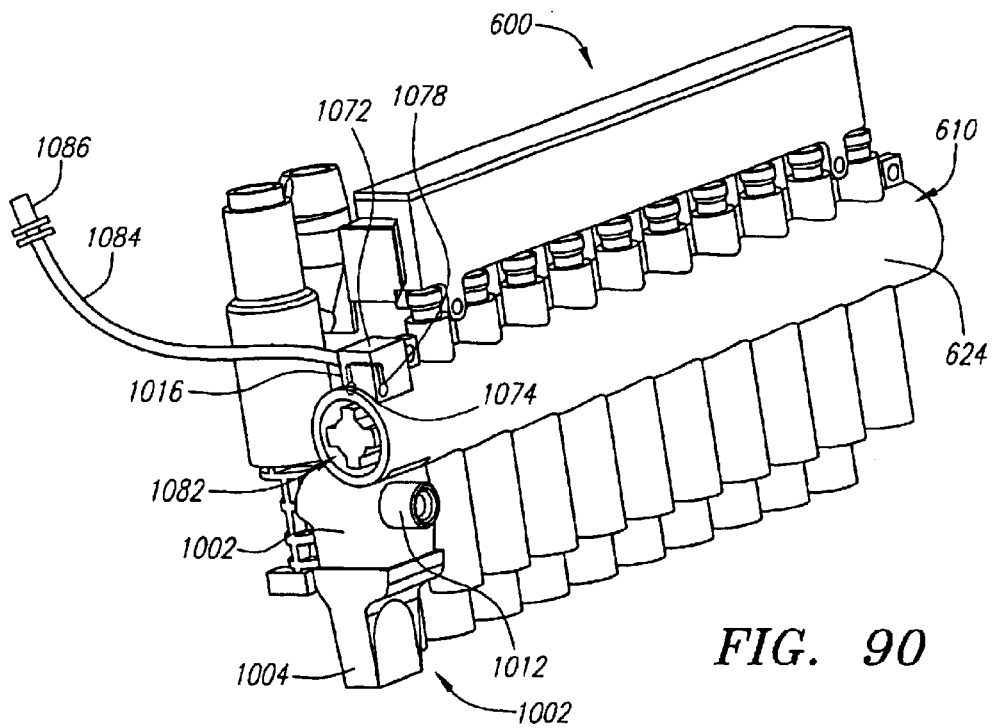
FIG. 90 is a front-left perspective view of the cassette portion of an alcohol reaction assembly mechanically associated with the cassette portion of the immunoassay flow assembly.
Figure 91:
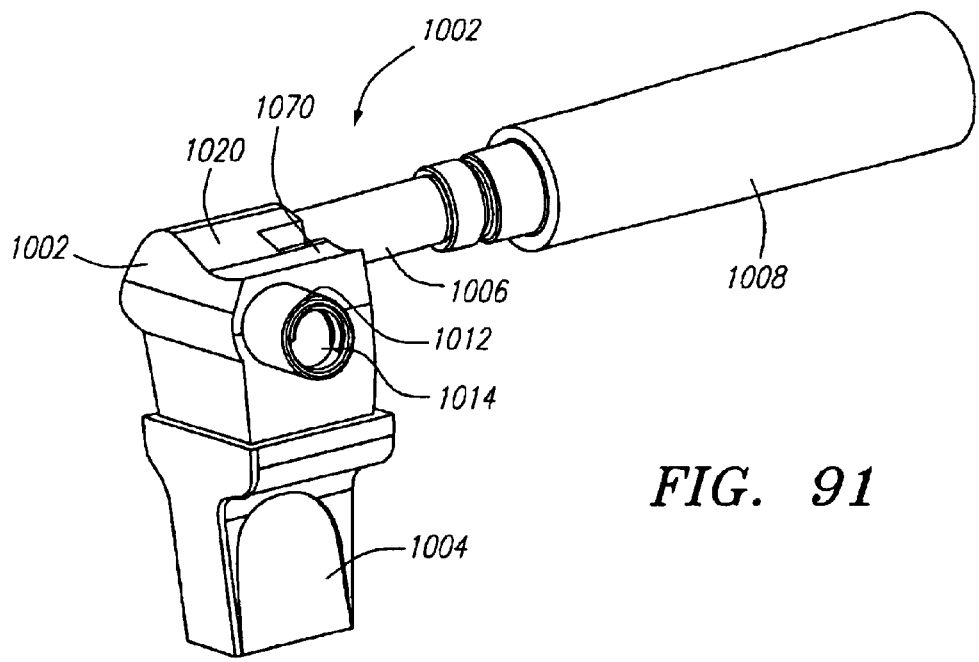
FIG. 91 is front perspective view of the cassette portion of the alcohol reaction assembly.
Figure 92:
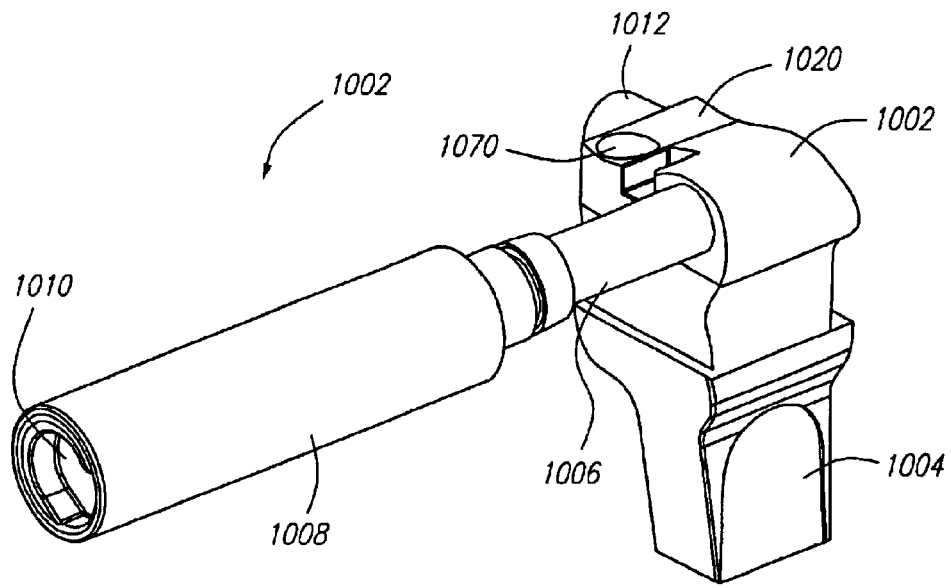
FIG. 92 is a rear perspective view of the cassette portion of the alcohol reaction assembly.

Turning now to the analysis of the detector signals, during the buffer pre-wash, the buffer is flowed through the immunoassay reaction chambers 616 to wash out any displaced labeled antigen from the immunoassay reaction chambers. The analyte detectable sample solution is then flowed through the read cells 620. The buffer pre-wash continues until all immunoassay flow channels have caused the requisite volume of buffer to flow through the immunoassay reaction chambers 616, so that each has come to equilibrium, as demonstrated by each immunoassay flow channel having achieved a constant background fluorescence level readout of approximately 100 mV. As previously discussed, the illustrated embodiment flows 400 µl of buffer from the buffer chambers 614, which has been found to achieve equilibrium. This phenomenon is illustrated in FIG. 88, which shows a sharp increase in the fluorescence level detected from the excited labeled antigen, and a drop off of the fluorescence level to a fluorescence reference level when the immunoassay reaction chamber 616 comes to equilibrium. The fluorescence reference level is used to establish normalization parameters for each of the respective immunoassay flow channels by using the immunoassay flow channel having the greatest mean intensity as a reference value of 1.000 and determining the ratio of each immunoassay flow channel to this reference immunoassay flow channel. This provides a separate normalization parameter for each immunoassay flow channel. For example, Table 1 illustrates exemplary pre-wash reference values for five immunoassay flow channels and the respective calculated normalization factors for each. As shown, immunoassay flow channel #3 exhibits the greatest mean fluorescence reference level, and is thus assigned a normalization factor of 1.00. The remaining immunoassay flow channels exhibit lesser fluorescent levels, and are thus assigned a normalization factor less than 1.00.

During sample flow after the buffer pre-wash, the sample is flowed through the immunoassay reaction chambers 616, which if it contains the target drug analyte, displaces any remaining bound labeled antigen from the corresponding immunoassay reaction chamber 616. In any event, the analyte detectable sample solution then flows through the read cells 620. The sample flow continues until all of the sample has flowed from the sample distribution chambers 612. If the sample does contain the target drug analyte, the detected fluorescent level will increase to a relatively high level, as illustrated in FIG. 88. If the sample does not contain the target drug analyte, the detected fluorescent level will remain at the relatively low reference level.

After sample flow is completed, buffer post-wash is performed until all of the remaining sample has been pushed through the immunoassay flow channels and into the waste chamber 622. As previously discussed, the illustrated embodiment flows 250 µl more of buffer from the buffer chambers 614, which has been found to be suitable to push the remaining sample through the immunoassay flow channels. In the case, where the sample does contain the target drug analyte, the detected fluorescence level will eventually decrease to the relatively low reference level when the sample has indeed been flowed out of the read cells 620, as illustrated in FIG. 88. Of course if the sample does not contain the target drug analyte, the detected fluorescence level will have already been at the relatively low reference level, and will remain as such through the duration of the buffer post-wash.

After the buffer post-wash is completed, the amount of target drug analyte within the sample is quantified by first obtaining the mean fluorescent intensity of each of the immunoassay flow channels. The mean intensity of each of the immunoassay flow channels is then divided by their respective normalization factors, providing for a ratiometric readout that tends to cancel channel-to-channel optical differences arising from slight optical differences caused by manufacturing tolerances in the injection molded plastic optical read cell assembly 618. Table 1 illustrates exemplary sample mean values for the sample for the five immunoassay flow channels, and the and the calculated ratiometric values for each. It is noted that although the means signal values for immunoassay flow channels #'s 1, 4, and 5 were less than that of immunoassay flow channel #3, their ratiometric output signals are greater than that of immunoassay flow channel #3 due to their relatively low channel normalization factors.

TABLE 1

| Channel No. | Ch. #1 | Ch. #2 | Ch. #3 | Ch. #4 | Ch. #5 |
|---|---|---|---|---|---|
| Mean Pre-wash Reference Value | 95 mV | 98 mV | 100 mV | 97 mV | 99 mV |
| Channel Normalization Factor | 0.950 | 0.980 | 1.00 | 0.970 | 0.990 |
| Sample Mean Value | 1500 mV | 1450 mV | 1570 mV | 1533 mV | 1610 mV |
| Ratiometric Value | 1579 | 1480 | 1570 | 1580 | 1626 |

It is noted that since immunoassay agglomerization reactions require minutes/hours to reach completion, and the continuous flow immunoassay reactions used in the system 100 occur within 3–5 minutes, the reactions are performed in kinetic/dynamic mode far from equilibrium conditions. Nevertheless, careful control of reaction parameters ensures that the concentration of the labeled antigen in the analyte detectable sample solution is representative of the original concentration of the target drug analyte contained in the original pure saliva sample. As previously discussed, appropriate proportionality constants permitting calibration of each of the immunoassay flow channels are contained in the barcode information, which can be used in addition to the previously discussed internally measured channel-to-channel normalization factors.

VIII. Alcohol Detection Assembly

Referring to FIGS. 6–8 and 89–96, the system 100 comprises an alcohol detection assembly 1000, the purpose of which is to conduct a quantitative analysis of the concentration of ethanol in the buffer sample solution and determine the mass-per-volume percentage (% w/v) of ethanol in the original sample of collected, undiluted saliva. In the illustrated embodiment, the alcohol detection assembly 1000 conducts an endpoint alcohol dehydrogenase (ADH) enzymatic assay on the sample in order to quantitatively detect the alcohol in the sample. The alcohol detection assembly 1000 generally comprises an alcohol reaction assembly 1002 and an alcohol reader assembly 1004.

A. Alcohol Reaction Assembly-Cassette Portion

The purpose of the alcohol reaction assembly 1002 is to provide a reaction between any alcohol in the sample and reagents, and then presenting this reaction for analysis. Referring specifically to FIGS. 89–96, the portion of the alcohol detection assembly 1000 associated with the cassette 152 is illustrated. As can be seen, the alcohol detection assembly 1000 is integrated with the previously described flow immunoassay assembly 600, and specifically, the rotary valve 610, which is operated to dispense the same sample to the alcohol detection assembly 1000 as is distributed to the flow immunoassay assembly 600. The alcohol detection assembly 1000 generally includes a manifold 1002, an alcohol reaction chamber 1004, a reagent chamber 1006, a buffer chamber 1008 with an associated buffer dispense plunger 1010, a calibrator chamber 1012 with an associated calibrator dispense plunger 1014, a sample chamber 1015 (which is the same as the through channel 706(1) shown in FIG. 55), and a vent/air flow assembly 1016.

The manifold 1002 is configured to provide the necessary interface, e.g., fluid and air transfer, between the alcohol reaction chamber 1004 and the other components. Specifically, the manifold 1002 comprises a main body 1018 that is composed of a suitable material, such as polycarbonate. The manifold main body 1018 is mounted to the bottom of the stator 624 of the rotary valve 610 underneath the sample feed port 628, which as will be described in further detail below, allows for indirect receipt of the sample from the feed port 628. To the end, the manifold main body 1018 includes an arcuate surface 1020 that complements the outer surface of the stator 624. The various channels disposed within the manifold 1002 will be described in further detail below.

Figure 93:
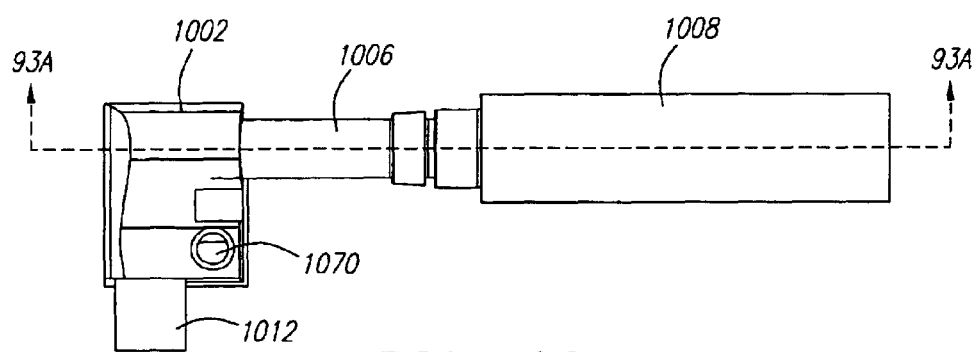
FIG. 93 is a top view of the cassette portion of the alcohol reaction assembly.
Figure 93A:
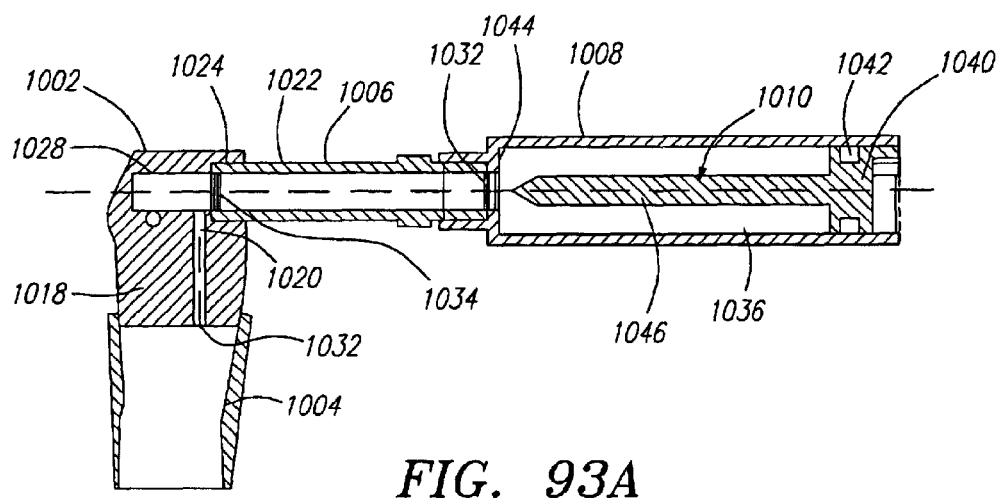
FIG. 93A is a longitudinal-sectional view taken along the line 93A—93A of FIG. 93.
Figure 95:
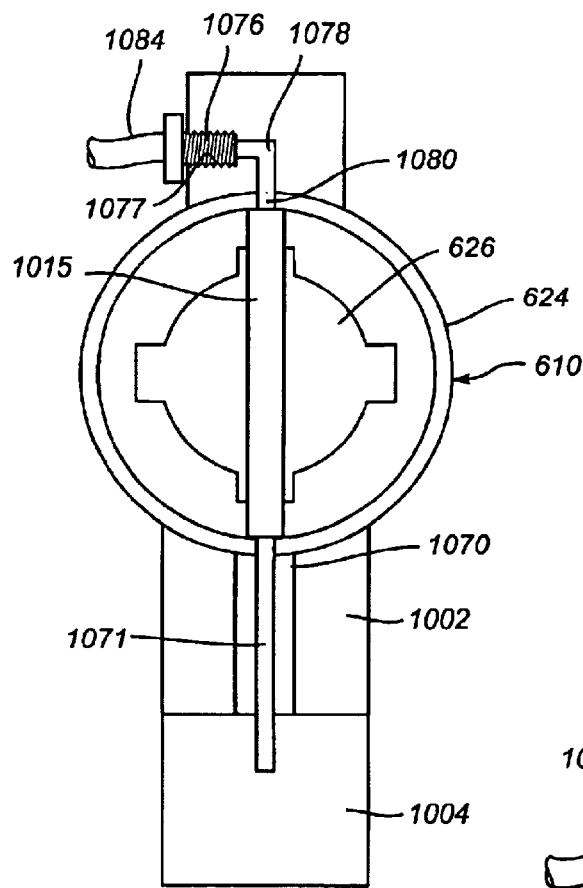
FIG. 95 is a cross-sectional view of the cassette portion of the alcohol reaction assembly when the rotary valve is in the sample flow/buffer post-wash configuration.
Figure 96:
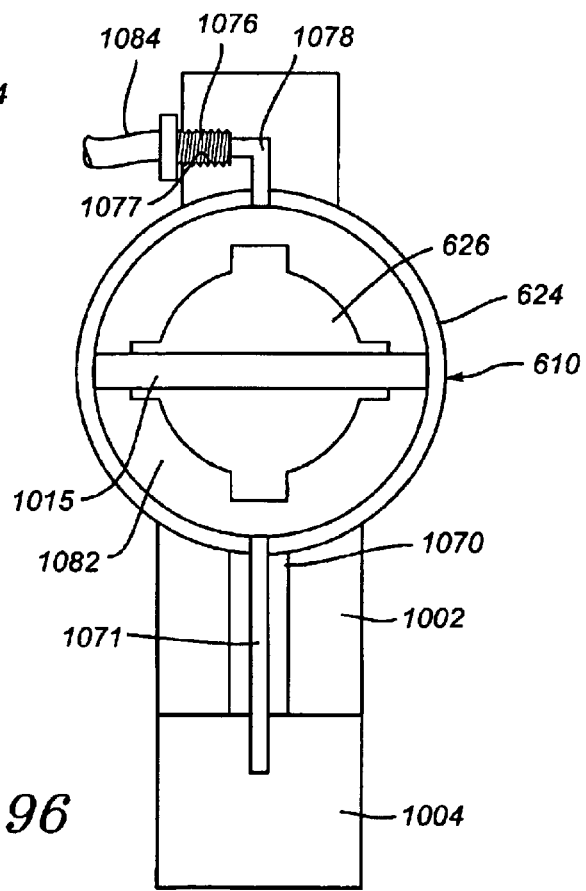
FIG. 96 is a cross-sectional view of the cassette portion of the alcohol reaction assembly when the rotary valve is clocked in the sample distribution/buffer pre-wash configuration.

Referring specifically to FIG. 93A, the reagent chamber 1006 comprises a cylindrical column 1022 composed of a suitable chemically insert material, such as injection molded polypropylene polymer. The reagent chamber 1006 is configured to provide the components that react in the presence of alcohol to produce an alcohol indicator. In the illustrated embodiment, the reagent chamber 1006 contains dry alcohol reagent, which is specifically produced by disposing 0.2 mM N-acetyl cyseine, 1.8 $\mu$M nicotinamide adenine dinucleotide (NAD), 500 U/ml alcohol dehydrogenase (ADH), 0.01 M phosphate buffer (pH=7.5), 0.01% BSA, and 2% trehalose, and lyophilizing the components to stabilize them during transportation and storage of the cassette 152. The reagent chamber 1006 is in fluid communication with the alcohol reaction chamber 1004 through the manifold 1002. To this end, the manifold 1002 is seated within a reaction chamber seat 1024 formed within the manifold 1002. The manifold 1002 comprises a reagent channel 1026 that extends perpendicularly between a stylus bore 1028, which extends from the reagent chamber seat 1028, and a reagent exit port 1030 leading to the alcohol reaction chamber 1004. To prevent permeation of water vapor, a pair of puncturable seals 1032 and 1034 are bonded at the opposite ends of the reagent chamber 1006. The seals 1032 and 1034 are composed of a suitable material, such as an aluminum foil-lined/polymer bilayer seal.

The buffer chamber 1008 is longitudinally disposed along the side of the rotary valve 610 underneath the buffer chamber seats 684, and is configured to rehydrate the lyophilized reagent within the reagent chamber 1006. The buffer chamber 1008 is cylindrical-shaped and is composed of a suitable material, e.g., injection molded polypropylene. The buffer chamber 1008 is in fluid communication with the reagent chamber 1006, and to this end, is suitably mated with the extreme end of the reagent chamber 1006. As with the other buffer chambers, the walls of the buffer chamber 1008 are sufficiently thick and impermeable to water vapor during the storage lifetime of the cassette 152. The buffer chamber 1008 has a 1 ml capacity and contains a buffer solution suitable for reconstituting the reagents within the reaction chamber 1005, e.g., 0.6 M TRIS/0.4 M lysine buffer (pH=9.7).

Referring specifically to FIG. 93A, the buffer chamber 1008 comprises a cylindrical bearing surface 1038 with which the associated buffer dispense plunger 1010 sealingly mates. The buffer dispense plunger 1010 comprises a rigid plunger head 1040, which includes an O-ring groove 1042 for seating of an O-ring (not shown). The O-ring of the buffer dispense plunger 1010 facilitates a sealing relationship between the buffer dispense plunger 1010 and the bearing surface 1036 of the buffer chamber 1008. Originally, the buffer dispense plunger 1010 is disposed within the buffer chamber 1008 at its extreme end, while a puncturable seal 1042 is bonded to the end of the buffer chamber 1008 opposite the buffer dispense plunger 1010. The combination of the buffer dispense plunger 1010 and seal 1042 prevent water vapor from escaping the confines of the buffer chamber 1008 during storage of the cassette 152. The seal 1042 is composed of a suitable material, such as an aluminum foil-lined/polymer bilayer seal.

The buffer dispense plunger 1010 further includes a stylus 1046, which is configured to puncture the seal 1044 at the other end of the buffer chamber 1008. Movement of the buffer dispense plunger 1010 towards the seal 1044, causes the stylus 1046 to puncture the seal 1044, allowing the buffer to flow from the buffer chamber 1008 through the reagent chamber 1006. During the buffer dispensing process, the stylus 1046 extends through the reagent chamber 1006 and reagent chamber seat 1028 (after puncturing the seals 1032 and 1034), coming to rest in the stylus bore 1028 at the end of the dispensing process. The flow of buffer through the reagent chamber 1006 rehydrates the lyophilized reagent, producing a reconstituted reagent therein, which is in turn, dispensed into the alcohol reaction chamber 1004.

Referring specifically to FIG. 94A, the calibrator chamber 1012 contains a calibrator solution having a known quantity of alcohol, which in the illustrated embodiment, is 0.1 ml calibrator selection with a concentration of 0.01% concentration of alcohol. injection molded polypropylene. The calibrator chamber 1012 is in fluid communication with the alcohol reaction chamber 1004 via the manifold 1002. To this end, the manifold 1002 includes a calibrator chamber seat 1048 in which one end of the calibrator chamber 1012 is seated. The manifold 1002 further includes an alcohol channel 1050 perpendicularly extending between a stylus bore 1028, which extends from the seat 1048, and an alcohol exit port 1054 leading to the alcohol reaction chamber 1004.

The calibrator chamber 1012 comprises a cylindrical bearing surface 1056 with which the associated calibrator dispense plunger 1014 sealingly mates. The calibrator dispense plunger 1014 comprises a rigid plunger head 1058, which includes an O-ring groove 1060 for seating of an O-ring (not shown). The O-ring of the calibrator dispense plunger 1014 facilitates a sealing relationship between the calibrator dispense plunger 1014 and the bearing surface 1056 of the calibrator chamber 1012. Originally, the calibrator dispense plunger 1014 is disposed within the calibrator chamber 1012 at its extreme end, while a puncturable seal 1062 is bonded within the calibrator chamber 1012 opposite the calibrator dispense plunger 1014. The combination of the calibrator dispense plunger 1014 and seal 1062 prevent the calibrator solution from escaping the confines of the calibrator chamber 1012 and manifold 1002 during storage of the cassette 152. The seal 1062 is composed of a suitable material, such as an aluminum foil-lined/polymer bilayer seal.

The calibrator dispense plunger 1014 further includes a stylus 1064, which is configured to puncture the seal 1062 at the other end of the calibrator chamber 1012. Movement of the calibrator dispense plunger 1014 towards the seal 1062, causes the stylus 1064 to puncture the seal 1062 and extend through an aperture 1066 at the end of the calibrator chamber 1012, allowing the calibrator solution to flow through the alcohol channel 1050 into the alcohol reaction chamber 1004. At the end of the alcohol dispensing process, the stylus 1064 comes to rest in the stylus bore 1052.

The sample chamber 1015 is the same as the through channel 706(1) (shown in FIG. 59) that extends through the rotor 626 and forms part of the feed channel 712 in the flow immunoassay assembly 600. In the illustrated embodiment, the sample chamber 1015 contains 20 μl of sample. When the rotary valve 610 is clocked in the sample flow/buffer post-wash configuration, the sample chamber 1015 is rotated to a vertical position, where it placed into fluid communication with the alcohol reaction chamber 1004, thereby acting as a shear valve. Specifically, the sample chamber 1015 communicates with a sample dispense port 1068 disposed through the bottom of the stator 624 (shown in FIG. 59). The manifold includes an access channel 1070 through which a sample/vent tube 1071 extends. One end of the sample/vent tube 1071 is connected to the sample dispense port 1068, while the other end of the sample/vent tube 1071 extends into the alcohol reaction chamber 1004. The sample remains in the sample chamber 1015 even when in the vertical position, due to the surface tension of the sample. As will be described in further detail below, the sample is forced out of the sample chamber 1015 into the alcohol reaction chamber 1004 using air pressure, as will be described below.

The alcohol reaction chamber 1004 is configured to collect the sample from the sample chamber 1015, the alcohol from the calibrator chamber 1012, and the reconstituted reagent solution from the reagent chamber 1006, and exhibit the analyte detectable sample solution to the alcohol reader assembly 1004 for calibration and detection of the alcohol within the sample. It is noted that the reagent solution, which contains NAD and ADH will react with the alcohol to produce an optical energy absorbing substance, and specifically, NAD with high energy hydrogen (NADH). As will be described in further detail below, the optical energy absorbed by the NADH can be optically detected by the alcohol reader assembly 1004 to perform the calibration and detection functions. To this end, the reaction chamber 1004 is composed of a suitably clear material, such as, acrylic polymer, and is rectangular in shape, which in the illustrated embodiment, has a pathlength of 0.500 cm, a width of 0.8 cm, and a height of 2.5 cm. The top of the reaction chamber 1004 is open and is friction fit around the bottom of the manifold main body 1018.

The vent/air flow assembly 1016 is configured to perform three functions: (1) provide venting of air from the alcohol reaction chamber 1004 during the dispensing processes; (2) providing air flow to the sample chamber 1015 to dispense the slug of sample into the alcohol reaction chamber 1004; and (3) sealing the sample within the sample chamber 1015 and alcohol reaction chamber 1004 after the cassette 152 is discarded. Specifically, the vent/air flow assembly 1016 comprises a vent manifold 1072 composed of a suitable material, such as polycarbonate. The vent manifold 1072 is mounted to the top of the stator 624 of the rotary valve 610 above the sample feed port 628. To the end, the vent manifold 1072 includes an arcuate surface 1074 that complements the outer surface of the stator 624.

The vent/air flow assembly 1016 further comprises a channeled barb fitting 1076 that is screwed into vent seat 1077 formed within the vent manifold 1072. The vent manifold 1072 includes a vent channel 1078, which extends from the vent seat 1077 down through the vent manifold 1072, where it communicates with an air entry port 1080 disposed through the stator 624. When the rotary valve 610 is clocked in the sample flow/buffer post-wash configuration (FIG. 95), thereby vertically positioning the sample chamber 1015, the top of the sample chamber 1015 is aligned with and communicates with the air entry port 1080 located at the top of the stator 624, and the bottom of the sample chamber 1015, as previously described, is aligned with and communicates with the sample dispense port 1068 located at the bottom of the stator 624, which as will be described in further detail below, facilitates conveyance of air flow through the sample chamber 1015 to dispense the sample into the alcohol reaction chamber 1004. In contrast, when the rotary valve 610 is clocked in the sample distribution/buffer pre-wash configuration (FIG. 96), the air entry port 1080 and sample dispense port 1068 are exposed to the space 1082 within the stator 624, as will be described in further detail below, facilitating venting of air from the alcohol reaction chamber 1004.

The vent/air flow assembly 1016 further includes a flexible conduit 1084, such as Tygon tubing, one of which is mated to the vent fitting 1076. The vent/air flow assembly 1016 further includes a vent/air flow port 1086, which is suitably affixed to the other end of the flexible conduit 1084. The flexible conduit 1084 is of a suitable length, e.g., 13 cm., to allow the vent/air flow port 1086 to be mounted within an vent/air flow port mounting aperture 188 on the side of the cassette case 154 (FIG. 3). Optionally, the vent/air flow port 1086 may be self-sealing in that it includes a tightly disposed a hydrophobic seal (not shown), which allows air to pass therethrough, while preventing the biologically hazardous saliva from leaking out of the cassette 152 after its disposal following use.

Thus, when the rotary valve 610 is clocked in the sample flow/buffer post-wash configuration (FIG. 95), the vent/air flow port 1086 is placed into communication with the alcohol reaction chamber 1004 via the flexible conduit 1084, vent fitting 1076, vent channel 1078, air entry port 1080, sample chamber 1015, sample dispense port 1068, and sample/vent tube 1071, thereby facilitating the dispensing of the sample from the sample chamber 1015 into the alcohol reaction chamber 1004 when air is blown into the vent/air flow port 1086. When the rotary valve 610 is clocked in the sample distribution/buffer pre-wash configuration (FIG. 96), the vent/air flow port 1086 is placed into communication with the alcohol reaction chamber 1004 via the flexible conduit 1084, vent fitting 1076, vent channel 716, air entry port 1080, the interior of the stator 624, the sample dispense port 1068, and the sample/vent tube 1071, thereby facilitating the venting of air out through the alcohol reaction chamber 1004 during the dispensing process.

B. Alcohol Reaction Assembly-Tester Portion

Having just described the portion of the alcohol reaction assembly 1002 associated with the cassette 152, the portion of the alcohol reaction assembly 1002 associated with the test console 102 will be discussed. Referring to FIGS. 6–8, 13, and 14, the alcohol reaction assembly 1002 further includes a buffer driver 1102, calibrator drive assembly 1104, a vacuum port connector 1106, the previously described cassette loading assembly 300 and vacuum pump 456, and a mixing drive assembly 1110.

The buffer driver 1002 (best shown in FIG. 14), which is affixed to the pin alignment flange 750 in a manner that aligns the buffer driver 1002 with the buffer dispense plunger 1010 disposed within the buffer chamber 1008. Thus, as the cassette loading assembly 300 is operated to load the cassette 152 into the test console 102, the buffer driver 1002 engages and displaces the buffer dispense plunger 1010 within the buffer chamber 1008. A buffer driver access opening 190 is formed on the side of the cassette case 154 (shown in FIG. 3), thereby allowing the buffer driver 1002 to engage the buffer dispense plunger 1010.

The calibrator drive assembly 1104 includes a linear stepper buffer motor 1114, which is mounted to the motor mount 1116, and a calibrator driver 1118, which is aligned with the calibrator dispense plunger 1014 within the calibrator chamber 1012 when the cassette 152 is loaded into the test console 102. Thus, when the calibrator driver 1118 is driven towards the cassette 152, it engages and displaces the calibrator dispense plunger 1014 within the calibrator chamber 1012. A calibrator chamber access opening 192 is formed on the front 156 of the cassette case 154 (shown in FIGS. 3 and 4), thereby allowing the calibrator driver 1118 to engage the calibrator dispense plunger 1014.

The vent/air flow port connector 1106 is mounted within an aperture 1112 disposed within the pin alignment flange 750 (best shown in FIGS. 13 and 14). In the illustrated embodiment, the vent/air flow port connector 1106 is similar to the previously described vacuum port connector 450. Thus, the vent/air flow port connector 1106 is composed of a compliant silicone rubber in the form of bellows, a compliant rim of which forms a tight vacuum seal when engaged with the cassette vent/air flow port. In the illustrated embodiment, the vent/air flow port connector 1106 is 1.5 cm in length, and 1 cm in diameter, with its compliant rim 2 mm in width.

The afore-described cassette loading assembly 300 is used as the vent/air flow port drive assembly. Thus, as the cassette 152 is loaded into the test console 102, the vent/air flow port connector 1106 is engaged with the vent/air flow port 1086 located on the side of the cassette case 154, so that the compliant rim of the connector and the vent/air flow port 1086 coincide and provide a tight seal. The previously described vent/air flow port mounting aperture 188 (shown in FIG. 3) allows vent/air flow port connector 1106 to engage the vent/air flow port 1086.

The other end of the vent/air flow port connector 1106 is connected to vacuum tubing 1120, which is composed of a suitable material, such as Tygon tubing. The vacuum tubing 1120 is in turn connected to one port of a vacuum outlet filter 1122, which is composed of a suitable material, such as 0.1 μm diameter port microporous hydrophilic PTFE. The other port of the outlet filter 1122 is connected to a vacuum outlet port 1124 of the vacuum pump 456. Thus, the vacuum pump 456 can be operated to create positive pressure within the vent/air flow assembly 1016. It should be noted that the vent/air flow port drive assembly 1108 and vacuum pump 456 are both operated under control of a CPU 204 and I/O controller 206 (FIG. 12). A vent/air flow port drive home sensor (generally shown in FIG. 12) is used to provide independent confirmation that the vent/air flow port drive assembly 1108 has moved from or into its home position.

The mixing drive assembly 1110 includes a rotary mixing motor 1126, which is mounted to the inside of the door 310, and a mixing coupling (not shown) that is rotatably coupled to the mixing motor 1126, which is located adjacent the alcohol reaction chamber 1004 when the cassette 152 is loaded into the test console 102. The mixing coupling contains two magnets (not shown), which when rotated by the mixing motor 1126 magnetically interact with a ferrous element (not shown) within the alcohol reaction chamber 1004. In the illustrated embodiment, the ferrous element is a 1.6 mm diameter stainless steel ball. It should be noted that the mixing drive motor assembly 1110 is operated under control of a CPU 204 and I/O controller 206 (FIG. 12). A mixing motor 1126 home sensor (generally shown in FIG. 12) is used to provide independent confirmation that the coupling is in the home position, i.e., the magnet is located at it lowest point to ensure that the ferrous element is disposed in the bottom portion of the alcohol reaction chamber 1102, so that dispensing operations are not interfered with.

C. Alcohol Reader Assembly

The purpose of the alcohol reader assembly 1004 is to measure the reaction that takes place in the alcohol reaction chamber 1004 and to quantify any alcohol contained in the sample based on this measured reactions. In the illustrated embodiment, the alcohol reader assembly 1004 uses spectrophotometry to determine the absorbance level of the reacted solution, which absorbance level is proportional to the amount of alcohol in the reacted solution. To this end, the alcohol reader assembly 1004 generally comprises an optical transmission assembly 1150, an optical detection assembly 1152, and processing circuitry, which in the illustrated embodiment, is the CPU 204.

The optical transmission assembly 1150 comprises an optical transmission module 1154 and a mount 1156 mounted to the main base side flange 120. The mount 1156 has an aperture 1158 through which the optical transmission module 1154 is mounted. The optical transmission module 1154 includes a housing 1160 in which there is housed an optical source (not shown) that is aligned with and is configured to transmit optical energy through the alcohol reaction chamber 1004, and thus the analyte detectable sample solution, from the rear 158 of the cassette case 154. An optical viewing window 194 is formed through the cassette case 154 (shown in FIGS. 3 and 4) to expose the alcohol reaction chamber 1004 on both sides of the cassette case 154, thereby allowing the transmission of optical energy from the rear 158 of the cassette case 154 where the optical transmission assembly 1 50, out the front 156 of the cassette case 154.

The optical transmission assembly 1150 further includes a optical bandpass filter (not shown) housed within the housing 1160, so that the optical energy passing through the alcohol reaction chamber 1004 and analyte detectable sample solution exhibits approximately monochromatic light of suitable wavelength. In the illustrated embodiment, the optical source comprises a 0.75 mW UV light emitting diode (LED) with maximum light emission at 375 nm, and the optical bandpass filter passes an optical frequency of 365 nm (±5 nm FWHM). The optical transmission assembly 1150 further comprises an optical 50:50 splitter 1160, which splits the energy beam from the optical bandpass filter into two energy beams, one of which is a reference energy beam that bypasses the alcohol reaction chamber 1004, and the other of which is the energy beam that passes through the alcohol reaction chamber 1004. As will be described, in further detail below, the reference energy beam is used to ensure that the optical source transmits a uniform quantity of optical energy through the alcohol reaction chamber 1004.

The optical detection assembly 1152 comprises a first optical detection module 1164 located at the front 156 of the cassette case 154 adjacent the optical viewing window 194. The optical detection module 1164 is mounted within an aperture 1166 formed within the mechanical bench 908, such that it receives the optical energy beam transmitted through the alcohol reaction chamber 1004. The optical detection assembly 1152 further comprises a second optical detection module 1168 mounted within a beam splitter 1170 in which the optical transmission module 1164 is associated. Thus, the second optical detection module 1168 receives half of the optical energy from the optical transmission module 1154 in the form of a reference optical energy beam.

In the illustrated embodiment, each of the optical detection modules 1164 and 1168 comprises a blue-sensitive silicon diode. The first optical detection module 1164 receives the energy beam from the alcohol reaction chamber 1004 and outputs a signal indicative of the amount of optical energy received by it. As will be described in further detail, this output signal is processed by the CPU 204 to calibrate the alcohol detection assembly 1000 and quantify the amount of alcohol in the sample. The second optical detection module 1168 receives the reference energy beam directly from the optical transmission module 1154 and also outputs a signal indicative of the amount of optical energy received by it. This output signal is used as feed back to a voltage-controlled current source controller module (not shown), which ensures that the optical transmission module 1154 is outputting a uniform optical energy intensity.

D. Alcohol Detection Assembly-Operation

Having now described the detail structure of the alcohol detection assembly 1000, its operation will now be described. In general, the alcohol detection assembly 1000 reacts the sample with the reagent solution to produce an alcohol detectable sample solution having an alcohol indicator. In the illustrated embodiment, any alcohol within the sample is reacted in the presence of NAD, using ADH to effect the oxidation of the alcohol to acetaldehyde with a simultaneous reduction of NAD to NADH. When reacted to completion, a number of moles of NADH equal to the number of moles of alcohol is produced. Thus, the concentration of NADH is proportional to the concentration of alcohol within the sample.

The concentration of the NADH in the alcohol detectable sample solution can be measured by determining the change in absorbance between the blank reagent solution, which does not contain alcohol, and the alcohol detectable sample solution, which does contain alcohol if the sample does. That is, according to the Beer-Lambert Law (commonly known as Beer's law), the common logarithm of the intensity of signal (i.e., voltage output) from an optical detector is inversely proportional to the concentration of NADH in the alcohol detectable sample solution, To eliminate any unknown parameters from the sample quantification calculation, the system is first calibrated by reacting the calibrator solution with the reagent solution to produce an alcohol detectable calibrator solution.

Thus, the concentration of alcohol in the sample can be calculated using the following equations:

$$F=C/(A_1-A_0);$$

$$P=F*(A_2-A_0)*1.02,$$

where F is the calibration factor; C is the concentration of alcohol in the alcohol detector calibrator solution, which is 0.001 in the illustrated embodiment; A0 is the measured absorbance of the blank reagent solution, A1 is the measured absorbance of the alcohol detectable calibrator solution, A2 is the measured absorbance of the alcohol detectable calibrator solution; and P is the weight-per-volume concentration of alcohol in the alcohol detector sample solution. It is noted that the factor 1.02 corrects for the dilution of the alcohol detectable sample solution by the sample. The weight-per-volume concentration of alcohol in original sample can then be obtained from the weight-per-volume concentration of alcohol in the alcohol detector sample solution (P), keeping in mind that the buffered sample solution dispensed in the alcohol reaction chamber 1004 has been diluted 1:1 by a buffer.

Thus, as will now be described in further detail, the alcohol detection assembly 1000 is operated to (1) produce and measure the absorbance of the blank reagent solution; (2) produce and measure the absorbance of the alcohol detectable calibrator solution; and (3) produce and measure the absorbance of the alcohol detectable sample solution.

The blank reagent solution is produced by operating the cassette loading assembly 300 to move the cassette carriage 302, and thus the cassette 152, towards the buffer driver 1002 affixed within the test console 102. As the buffer driver 1002 engages and displaces the buffer dispense plunger 1010 within the buffer chamber 1008, the stylus 1046 punctures the seal 1044 in the buffer chamber 1008, and the seals 1032 and 1034 in the reagent chamber 1006. This allows the buffer to flow through the alcohol reaction chamber 1004, thereby hydrating the dry reagent, and exiting the reagent chamber 1006 as reconstituted reagent solution. The blank reagent solution then flows through the reagent channel 1026 within the manifold 1002 and into the reagent chamber 1006 via the reagent exit port 1030. The mixing drive assembly 1110 is then operated for a period of time, e.g., 1 minute, to move the ferrous element within the alcohol reaction chamber 1004, thereby quantitatively mixing the blank reagent solution.

The absorbance of the blank reagent solution is measured by operating the alcohol detection assembly 1000. Specifically, optical energy is transmitted from the optical transmission module 1154 through the blank reagent solution, where it is received by the first optical detection module 1164. The first optical detection module 1164 then outputs a signal, which is received and used by the CPU 204 to determine the absorbance of the blank reagent solution. It is noted that the second optical detection module 1168 continuously receives the reference optical energy to provide feedback and effect uniform transmission of optical energy from the optical source.

The alcohol detectable calibrator solution is produced by operating the calibrator drive assembly 1104 to move the calibrator driver 1118 into engagement with the calibrator dispense plunger 1014, which is displaced within the calibrator chamber 1012. During displacement of the calibrator dispense plunger 1014, the stylus 1064 punctures the seal 1062 within the calibration chamber 1012, allowing the calibrator solution to flow from the calibrator chamber 1012, through the alcohol channel 1050 within the manifold 1002, and into the alcohol reaction chamber 1004 via the alcohol exit port 1054. The mixing drive assembly 1110 is again operated for a period of time, e.g., 1 minute, to move the ferrous element within the alcohol reaction chamber 1004, thereby mixing the unreacted calibrator solution and the blank reagent solution to form a fully reacted alcohol detectable calibrator solution.

The absorbance of the alcohol detectable calibrator solution is measured by operating the alcohol detection assembly 1000 again. Specifically, optical energy is transmitted from the optical module 1154 through the alcohol detectable calibrator solution, where it is received by the first optical detection module 1164. The first optical detection module 1164 then outputs a signal, which is received and used by the CPU 204 to determine the absorbance of the alcohol detectable calibrator solution.

The alcohol detectable sample solution is produced by operating the rotary valve drive assembly 730 to clock the rotary valve 610 into the sample flow/buffer post-wash configuration, thereby placing the sample chamber 1015 into the vertical position. The vent/air flow connector drive assembly is operated to engage the vent/air flow port connector with the vent/air flow port 1086. It is noted that this can be performed during the previous steps. The vacuum pump 456 is then operated to provide a short burst of compressed air, e.g., 1 second, to force air through the vent/air flow assembly 1016, and thus, the sample out of the sample chamber 1015, through the sample/vent tube 1071 and into the alcohol reaction chamber 1004. The mixing drive assembly 1110 is then operated to move the ferrous element within the alcohol reaction chamber 1004, thereby mixing the unreacted sample and the alcohol detectable calibrator solution to form a fully reacted alcohol detectable sample solution. It is noted that if the sample contains alcohol, additional NADH is produced.

The absorbance of the alcohol detectable sample solution is measured by again operating the alcohol detection assembly 1000. Specifically, optical energy is transmitted from the optical module 1154 through the alcohol detectable calibrator solution, where it is received by the first optical detection module 1164. The first optical detection module 1164 then outputs a signal, which is received and used by the CPU 204 to determine the absorbance of the alcohol detectable sample solution.

With knowledge of the measured absorbances of the blank reagent solution ($A_1$), alcohol detectable calibrator solution ($A_2$), and alcohol detectable sample solution ($A_3$), as well as the known mass of alcohol in the calibrator solution (M), the CPU 204 calculates the weight-per-volume percentage of alcohol in the alcohol detectable sample solution (P), and thus, the original sample.

IX. Temperature Control Assembly

Figure 7:
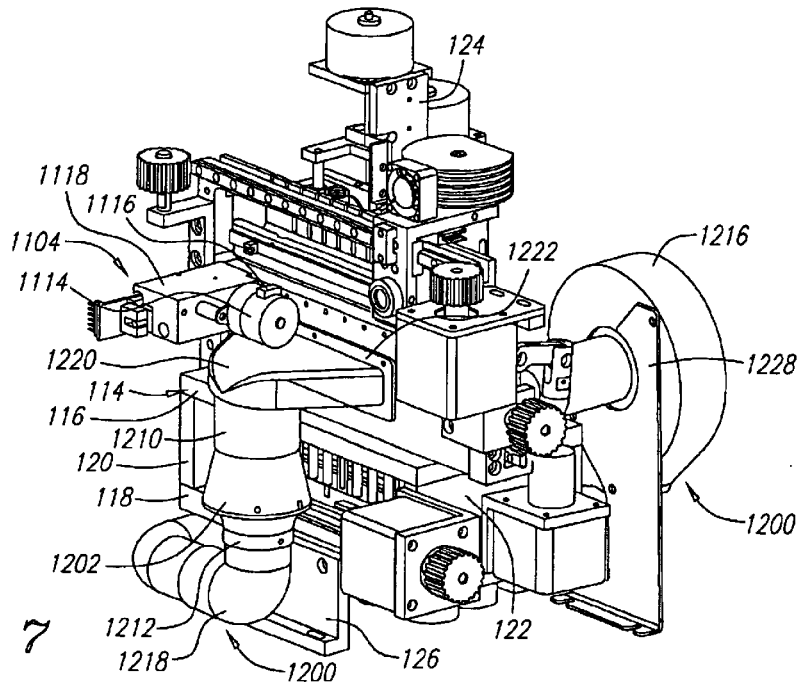
FIG. 7 is a front-right perspective view of the inner components of the test console with the cassette assembly.
Figure 97:
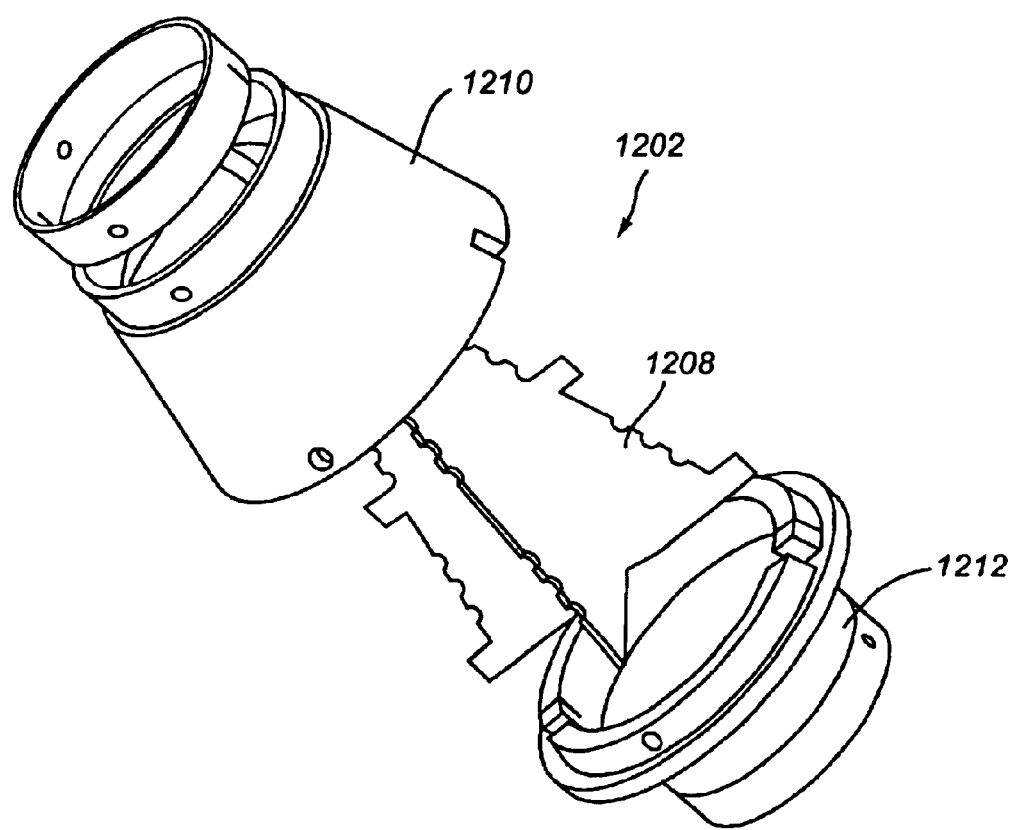
FIG. 97 is a perspective view of a heater assembly for use in a temperature control assembly of the test console.
Figure 98:
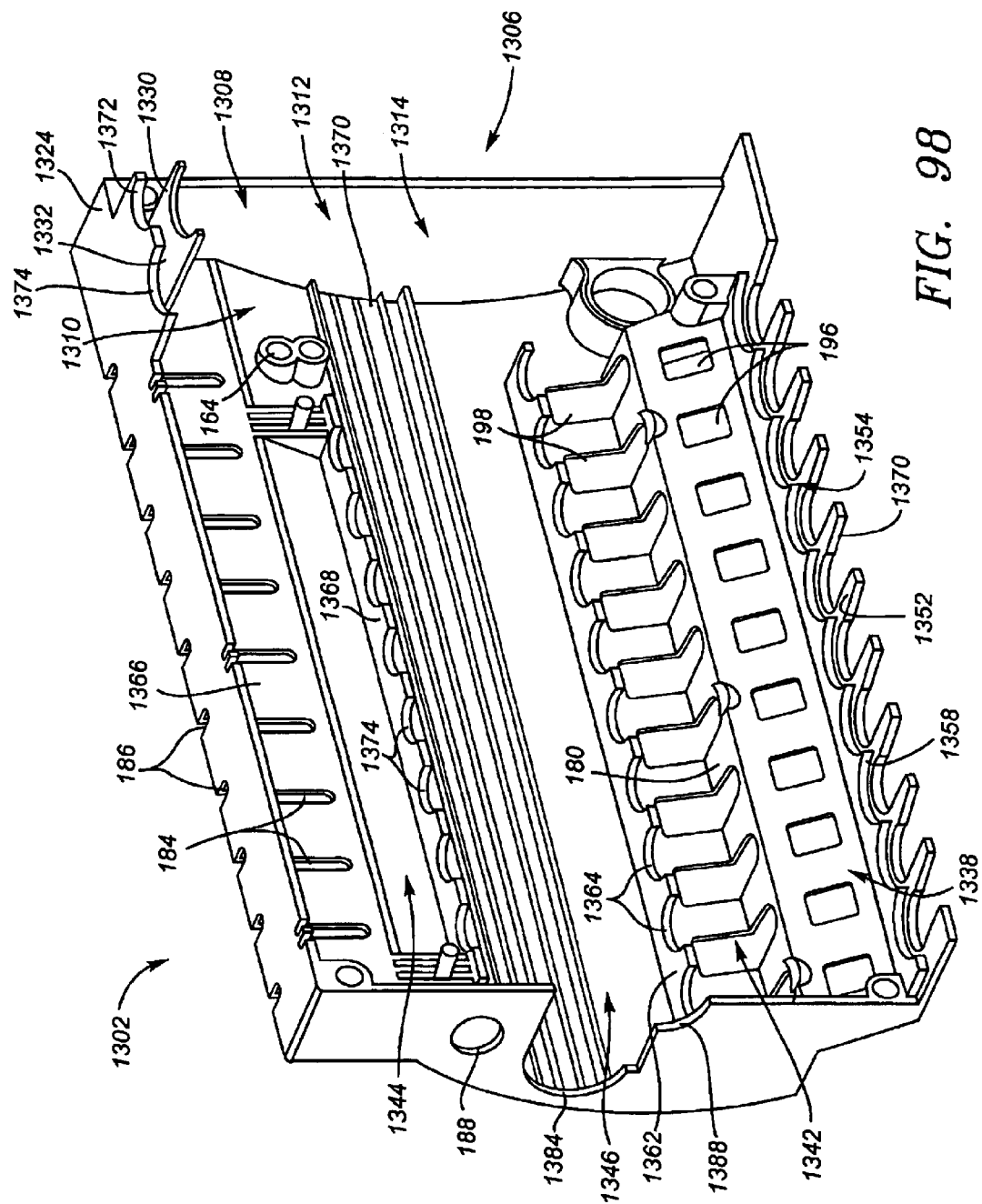
FIG. 98 is a perspective view of the inside of a front panel used to construct a cassette case of the cassette assembly.
Figure 99:
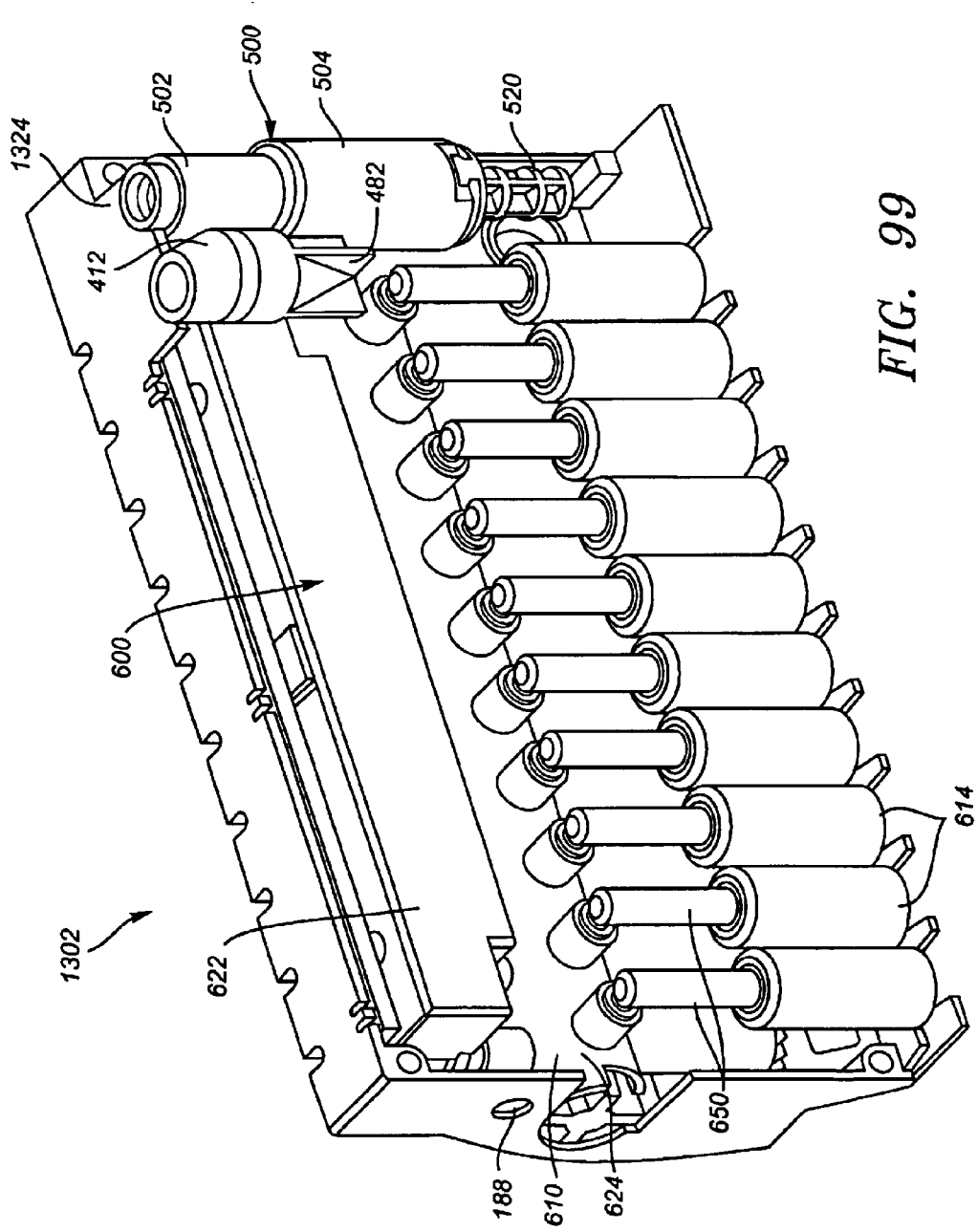
FIG. 99 is a perspective view of the front panel with the cassette portion of the immunoassay flow assembly mounted therein.
Figure 100:
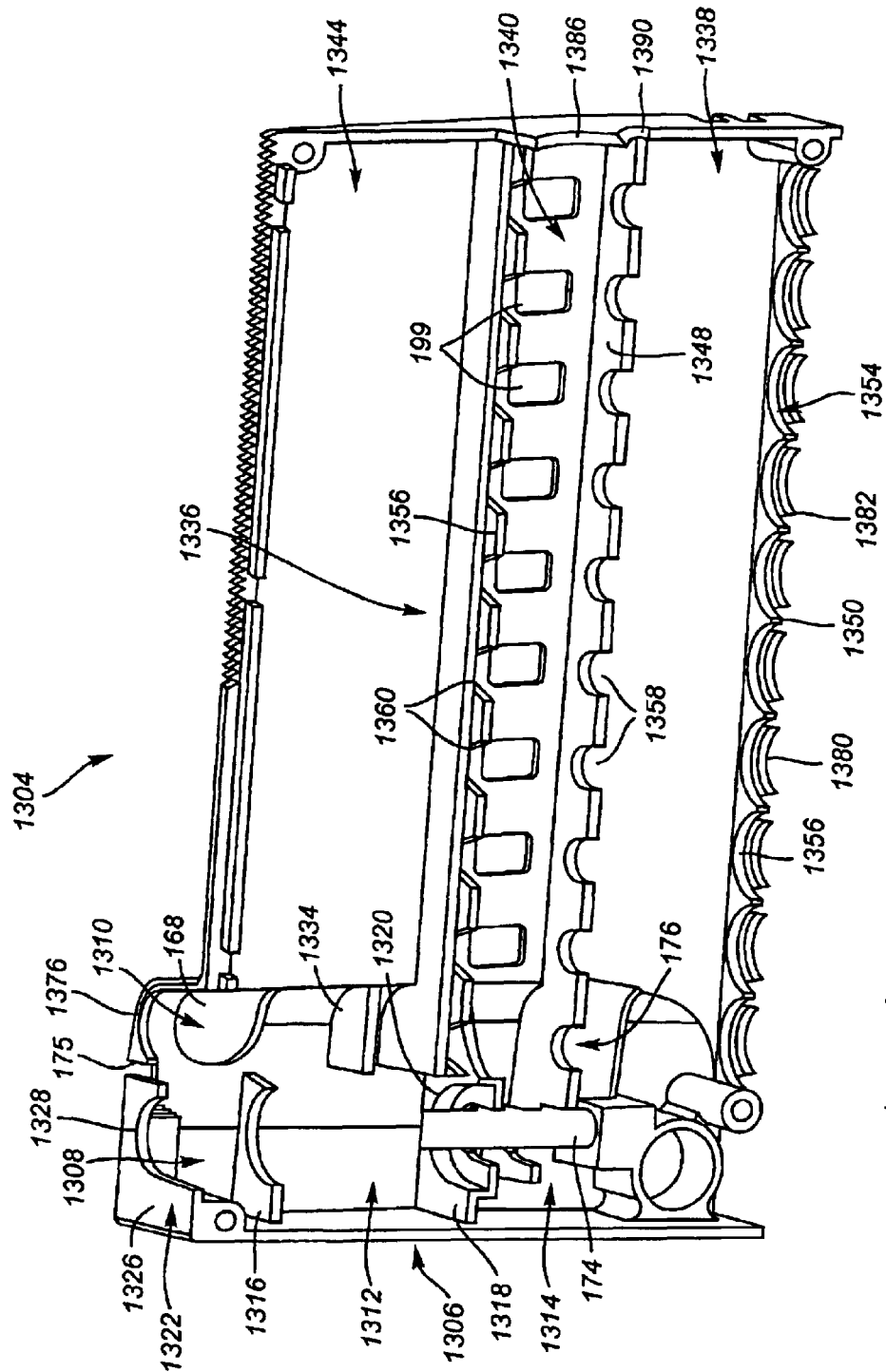
FIG. 100 is a perspective view of the inside of a rear panel used to constructed the cassette case.
Figure 101:
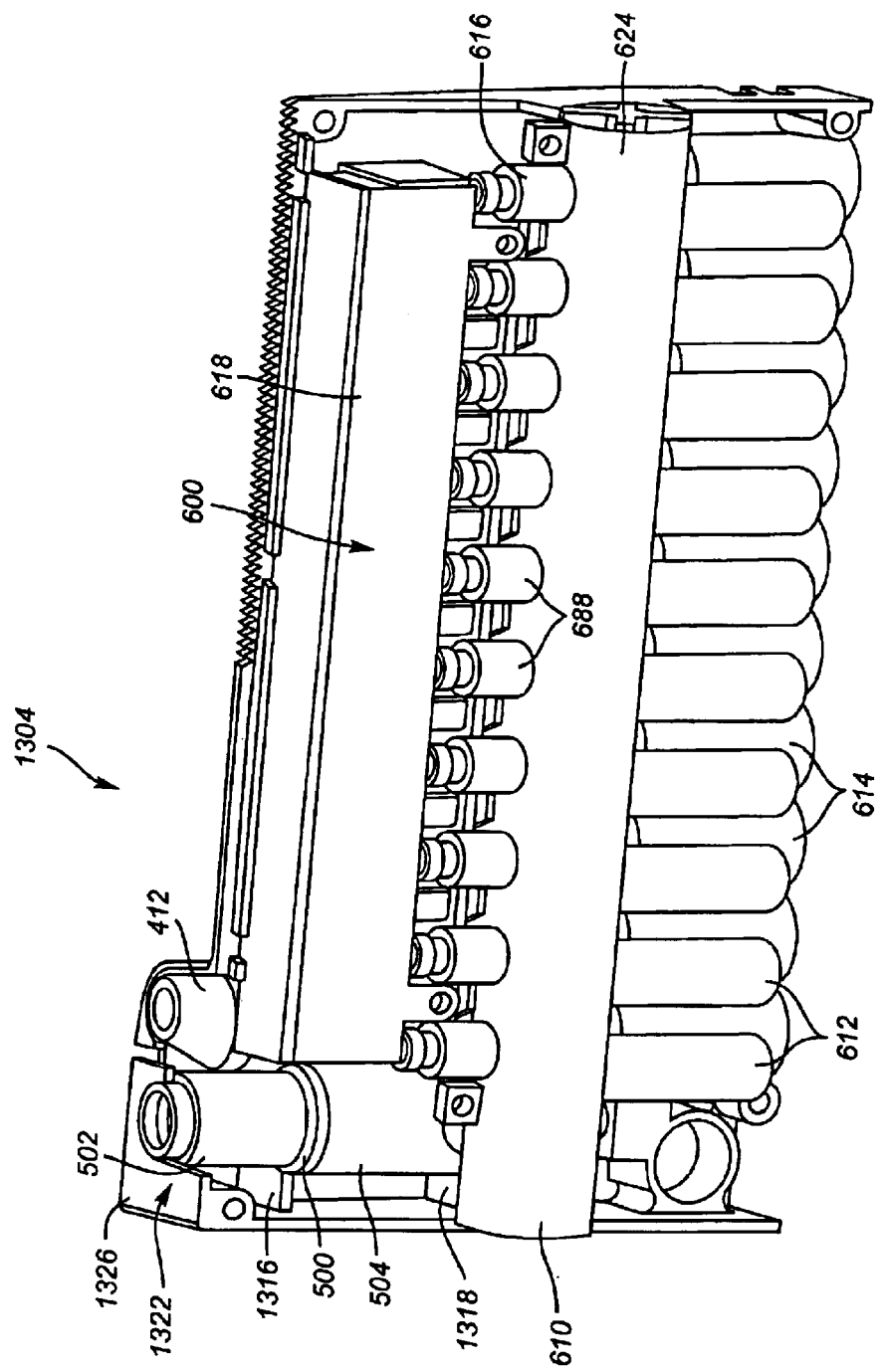
FIG. 101 is a perspective view of the rear panel with the cassette portion of the immunoassay flow assembly mounted therein.

Referring to FIGS. 7, 8, and 97, the system 100 comprises a temperature control assembly 1200, the purpose of which is to bring the internal assemblies of the cassette 152 to a desired controlled constant temperature, thus providing consistency and predictability to the chemical reactions that occur within the cassette 152. The temperature control assembly 1200 is an independent hardware-only assembly that functions independently of the CPU 204. This permits temperature control to function continuously while the CPU 204 performs other housekeeping functions, such as sensor QC control tests.

The temperature control assembly 1200 includes a heater assembly 1202 and a heater controller (not shown) that periodically turns the heater assembly 1202 on and off to maintain the temperature of the system 100 as measured by temperature sensors (not shown) disposed at strategic locations within the test console 102. The heater assembly 1202 includes internal heating elements 1208, a heat shroud adapter 1210, and a heat vent adapter 1212. The temperature control assembly 1200 further includes a cooler (not shown), which remains on to provide a constant level of cooling of the cassette 152 sufficient to lower the ambient temperature of the cassette 152 from its maximum initial ambient temperature (10–40° C. in the illustrated embodiment) to the desired cassette control temperature (37° C. in the illustrated embodiment).

The temperature control assembly 1200 further include a fan 1216, which is mounted to a fan bracket 1228, a flexible heat vent 1218, and a heat shroud 1220 to provide recirculation of the controlled temperature air. One end of the heat vent 1218 is connected to the fan 1216, while the other end of the heat vent 1218 is connected to the heat vent adapter 1212 of the heater assembly 1202. The heat shroud adapter 1210 of the heater assembly 1202 is in turn connected to the heat shroud 1220. The heat shroud 1220 tapers to a rectangular tapered end 1222, which mates with a complementary rectangular opening 1224 (FIG. 85) formed in the mechanical bench 908 of the dynamic scanning assembly 902. A complementary rectangular opening 1226 (FIG. 14) is also formned in the front support flange 304 of the cassette carriage 302. Thus, the rectangular tapered end 1222 of the heat shroud 1220 aligns with various openings formed in the cassette case 154 for providing thermal access to the internal components with the cassette 152.

Figure 4:
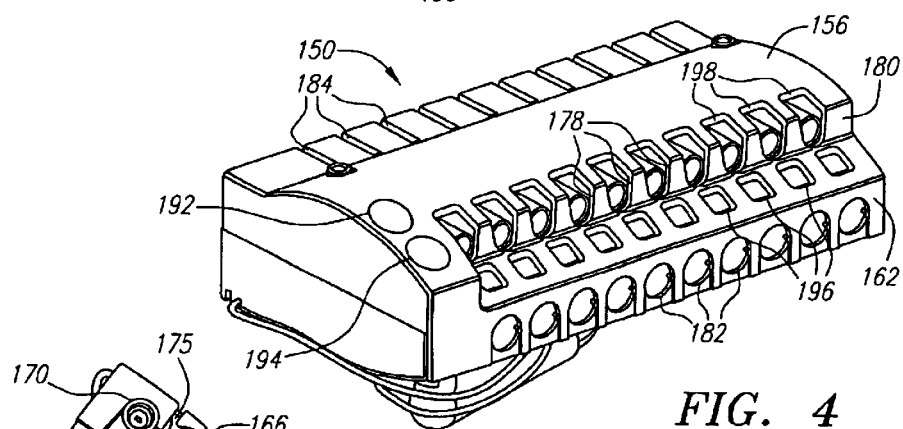
FIG. 4 is a bottom-left perspective view of the cassette assembly.

Referring to FIGS. 3–5, a first series of heat vents 196 is formed on the front 156 of the cassette case 154 adjacent the buffer chambers 614. A second series of heat vents 198 is formed on the front 156 of the cassette case 154 adjacent the sample distribution chambers 612. A third series of heat vents 199 is formed on the rear 158 of the cassette case adjacent the angled rigid tubes 650 of the buffer chambers 614. Thus, thermally controlled air exiting the rectangular tapered end 1222 of the heat shroud 1220 enters the cassette case 154 through the first and second series of heat vents 196 and 198, thereby exposing the internal components of the chemistry cassette 152 to the air, which then exits the cassette case 154 out through the third series of heat vents 199 on the rear 158 of the cassette case 154.

In the illustrated embodiment, the heater assembly 1202 comprises a 350 W resistive heater, and the heater controller is a proportional/differential/integral solid-state heater controller. The temperature sensors are thermistors that are placed in mechanical contact With the cassette case 154, thereby providing intimate thermal conductivity with the cassette case 154, or alternatively, IR-sensitive thermocouples or thermopiles (shown as thermopile 1214 in FIG. 9) that are optically coupled to the buffer chambers 614 near the middle of the cassette 152. Thus, if the cassette 152 is determined to be below the desired temperature, the heater controller places the temperature control assembly 1200 in heat mode by turning on the heater assembly 1202. As a result, heat proportional to the difference between the desired cassette temperature and the ambient measured temperature of the cassette case 154 is produced.

The heater controller controls the amount of heat added to the constantly recirculating air through the closed loop temperature control assembly 1200 by incorporating sufficient anticipation to ramp down the heat added to the temperature control assembly 1200, so that the temperature of the cassette 152 does not stray outside (i.e., overshoot or undershoot) a transitional temperature range (e.g., ±2° C.) on the initial thermal cycle, and does not stray outside a lesser steady-state temperature range (e.g., ±1° C.) during subsequent thermal cycles. Once the temperature of the cassette 152 is determined to be in this smaller range, only sufficient heat is added to keep the cassette 152 within the control range, which provides a counteracting effect to the constantly operating cooler 1208.

X. Cassette Case

Turning now to FIGS. 98–101, the internal structural details of the cassette case 154 will now be described. The cassette case 154 can be generally divided into front and rear panels 1302 and 1304 that fit together in a clam-shell fashion. For the purposes of this discussion, the relative terms "upward" and "downward" will respectively mean towards the top and bottom sides of the cassette case; "leftward" and "rightward" will respectively mean towards the left and right sides of the cassette case looking towards the back of the cassette case 154; and "forward" and "rearward" means towards the front and back of the cassette case 154.

The cassette case 154 comprises an internal mixing assembly compartment 1306, which is formed when the front and rear panels 1302 and 1304 are mated together. The mixing assembly compartment 1306 can be divided into a separate buffer chamber compartment 1308, sample collection chamber compartment 1310, mixing chamber compartment 1312, and sample dispense plunger compartment 1314, which respectively contain and support the buffer chamber 502, sample collection chamber 412, mixing chamber 504, and plunger body 520 of the mixing assembly 500. It will appreciated that structure disclosed as providing mechanical support to a particular component of the mixing assembly 500 will provide similar mechanical support to the entire mixing assembly 500 to some extent, since the mixing assembly 500 can, in general, be considered a rigid body.

The mixing chamber compartment 1312 comprises first and second support flanges 1316 and 1318, which extend from the rear panel 1304 at the top and bottom of the mixing chamber compartment 1312. The bottom surface of the first flange 1316 abuts the top of the mixing chamber 504, and the top surface of the second flange 1318 abuts the bottom of the mixing chamber 504, thereby supporting the mixing chamber 504 in the presence of force applied to it in the upward and downward directions. Of significance is the prevention of the upward and downward movement of the mixing chamber 504 when the sample and buffer drive assemblies 732 and 734 are operably associated with mixing assembly 500. The sample dispense plunger compartment 1314 further comprises an actuate opening 1320 provided within the second flange 1318 through which the sample dispense plunger body 520 is disposed.

The buffer chamber compartment 1308 comprises the afore-described first support flange 1316 and a third support flange 1322, which is formed by complementary support flange sections 1324 and 1326 extending from the tops of the front and rear panels 1302 and 1304. An arcuate seat 1328 is formed within the flange section 1326, and an opposing arcuate seat 1330 is formed within a fourth flange 1332 extending from the front panel 1302. Thus, when the front and rear panels 1302 and 1304 are mated together, the arcuate section 1330 receives the bottom of the buffer chamber 502, and the arcuate section 1328 receives the top of the buffer chamber 502, thereby supporting the buffer chamber 502 in the presence of force applied to it in the leftward, rightward, forward, and rearward directions.

The sample collection chamber compartment 1310 comprises the afore-described third support flange 1322, and a fifth support flange 1334 extending from the rear panel 1304 at the bottom of the sample collection chamber compartment 1310. The chamber stand 482 of the sample collection chamber 412 rests on the fifth support flange 1334, thereby supporting the sample collection chamber 412 in the presence of force applied to it in the downward direction. Of significance is the prevention of any downward movement of the sample collection chamber 412 when the vacuum port connector 450 is operably associated with the mixing assembly 500. As a result, any shear or bending stress otherwise created between the sample dispense port 530 and the sample inlet port 506 of the mixing chamber 504 is minimized.

The cassette case 154 further comprises an internal flow immunoassay assembly compartment 1336, which is formed when the front and rear panels 1302 and 1304 are mated together. The flow immunoassay assembly compartment 1336 can be divided into a separate buffer chamber, rigid tube, distribution chamber, upper chamber, and rotary valve compartments 1338, 1340, 1342, 1344, and 1346, which respectively contain the buffer chambers 614, the rigid tubes 650, the sample distribution chambers 612, the immunoassay reaction chambers 616, read cell assembly 618 and waste chamber 622, and the rotary valve 610. It will appreciated that structure disclosed as providing mechanical support to a particular component of the flow immunoassay assembly 600 will provide similar mechanical support to the entire flow immunoassay assembly 600 to some extent, since the flow immunoassay assembly 600 can, in general, be considered a rigid body.

The buffer chamber compartment 1338 comprises sixth and seventh support flanges 1348 and 1350, which extend from the rear panel 1304 at the top and bottom of the buffer chamber compartment 1338. The bottom surface of the sixth support flange 1348 abuts the top of the buffer chambers 614, and the top surface of the seventh support flange 1350 abuts the bottom of the buffer chambers 614, thereby supporting the buffer chambers 614 in the presence of force applied to them in the upward and downward directions. Significantly, upward movement of the buffer chambers 614 are prevented when the buffer drive assemblies 734 are in operable association with the flow immunoassay assembly 600. An eighth flange 1352 extends from the front panel 1302 at the bottom of the buffer chamber compartment 1338. The buffer chamber compartment 1338 comprises a series often buffer chamber seats 1354, which are formed from a series of ten arcuate openings 1356 formed on top of the seventh flange 1350 and a complementary series of ten arcuate ledges 1358 formed on the eighth flange 1352 at the bottom of the front panel 1302. When the front and rear panels 1302 and 1304 are mated together, the complementary arcuate openings 1356 and ledges 1358 abut each other to form the completed buffer chamber seats 1352. Thus, the bottoms of the buffer chambers 614 can be seated within the corresponding seats 1352, thereby supporting the buffer chambers 614 in the presence of force applied to them in the leftward, rightward, forward, and rearward directions.

The rigid tube compartment 1340 comprises the afore-described sixth support flange 1348 and a ninth support flange 1356, which extend from the rear panel 1304 at the top and bottom of the rigid tube compartment 1340. The bottom surface of the ninth support flange 1356 abuts the angled portion of the rigid tubes 650, thereby supporting the rigid tubes 650 in the presence of force applied to them in the upward direction. Of significance, upward movement of the rigid tubes 650 is prevented when the buffer drive assemblies 734 are in operable association with the flow immunoassay assembly 600. The rigid tube compartment 1340 also comprises a first and second series of ten arcuate seats 1358 and 1360 respectively formed in the sixth and ninth support flanges 1348 and 1356 at the bottom and top of the rigid tube compartment 1340. The first and second series of arcuate seats 1358 and 1360 receive the rigid tubes 650 at their top and bottom, thereby supporting the rigid tubes 650, and thus further supporting the flow immunoassay assembly 600 in the left, right, and back lateral directions.

The sample distribution chamber compartment 1342 comprises the previously described ledge 180, which is formed by the front panel 1302. The top surface of the ledge 180 abuts the bottom of the sample distribution chambers 612, thereby supporting the sample distribution chambers 612 in the presence of force applied to them in the downward direction. The sample distribution chamber compartment 1342 also comprises a tenth flange 1362 extending from the front panel 1302 in the middle of the sample distribution chamber compartment. A series often arcuate seats 1364 are formed in the tenth flange 1362, and receive the sample distribution chambers 612, thereby supporting the sample distribution chambers 612 in the presence of force applied to them in the leftward and rightward directions.

The upper chamber compartment 1344 comprises a front wall 1366 an eleventh flange 1368 formed by the upper portion of the front panel 1302, and a ridge 1370 formed on the upper portion of the rear panel 1304. The front surface of the read cell assembly 618 abuts the surface of the front wall 1366, and the top back surface of the read cell assembly 618 abuts the ledge 180. Thus, the read cell assembly 618 is supported against any force applied to it in the forward and rearward directions. The bottom surface of the eleventh flange 1368 abuts the top of the read cell assembly 618, thereby supporting the read cell assembly 618 against any force applied to it in the upward direction. Significantly, the upward movement of the read cell assembly 618 is prevented when the sample drive assemblies 732 are operably associated with the flow immunoassay assembly 600.

The rotary valve compartment 1346 comprises an annular relief 1370 formed within the inner surface of the front panel 1302. The annular relief 1370 receives one side of the cylindrical wall 668 of the stator 624, thereby supporting the rotary valve 610 in the presence of force applied to it in the forward direction. The rotary valve compartment 1346 also a series of ten arcuate seats 1374 that are formed in the eleventh flange 1368, and receive the immunoassay reaction chamber seats 688 of the stator 624, thereby supporting the rotary valve 610 in the presence of force applied to it in the leftward and rightward directions.

The cassette case 154 further comprises various openings for providing thermal access to the various components of the flow immunoassay assembly 600, including the previously mentioned first, second, and third series of heat vents 196, 198, and 199, which are formed on the front and rear panel 1302 and 1304. The cassette case 154 also comprises the previously described pair of homing pin holes 164 on the front panel 1302. The cassette case 154 further comprises various openings for providing access to the internal components of the chemistry cassette 152, including the previously mentioned vertical access slot 174, horizontal access slot 172, routing slot 175, sample distribution chamber access openings 178, sensor access opening 168, optical read slits 184, optical excitation apertures 186, vent/air flow port mounting aperture 188, calibrator chamber access opening 192, and optical viewing window 194. These openings can be easily understood from a review of the intact cassette case 154, and will not be discussed further.

The cassette case 154 further includes the previously mentioned buffer chamber access opening 170, vacuum port access opening 166, buffer chamber access openings 182, rotary valve access opening 176, and buffer driver access opening 190 which will now be described in further detail. The buffer chamber access opening 170 and vacuum port access opening 166 are formed by cooperation between the front and rear panels 1302 and 1304. Specifically, the buffer chamber access opening 176 is formed from the previously described arcuate opening 1328 formed in the flange section 1326 of the rear panel 1304, and a complementary arcuate opening 1372 formed on the flange section 1324 of the front panel 1302 when the front and rear panels 1302 and 1304 are mated together. The vacuum port access opening 166 is also formed from complementary arcuate openings 1374 and 1376 formed within the flange sections 1324 and 1326 when the front and rear panels 1302 and 1304 are mated together.

The buffer chamber access openings 182 are formed from arcuate openings 1378 formed in the eighth flange 1352 at the bottom of the buffer chamber compartment 1308, and complementary arcuate openings 1380 formed in a thirteen flange 1382 directly below the seventh flange 1350 when the front and rear panels 1302 and 1304 are mated together. The rotary valve access opening 176 is formed from complementary arcuate openings 1384 and 1386 within the side walls of the front and rear panels 1302 and 1304 when mated together. The buffer driver access opening 190 is formed from complementary arcuate openings 1388 and 1390 within the side walls of the front and rear panels 1302 and 1304 when mated together. In addition, a series of five guiding holes (not shown) extend through the cassette case 154 in longitudinal alignment with buffer drive access opening 190, thus receiving the buffer driver 1002 when inserted into the buffer driver access opening 190. The guiding holes are formed from complementary arcuate openings (not shown) formed from opposing flanges (not shown) extending respectively from the inside surfaces of the front and rear panels 1302 and 1304.

XI. User Interface Assembly

Referring to FIG. 1, the system 100 includes a user interface 150 for providing information to, and receiving information from, an administrator/operator. The user interface 150 includes an LCD display screen 152, which displays menu items, information request prompts, and test results to the operator, and an internal printer 154, which provides the test results on hardcopy upon request by the operator. The user interface 150 further includes a keyboard (not shown) and keys 156 for entering requested information into the system 100. The keys 156 include (1) a set of alpha-numeric keys 158 for entering numerical information into the user interface 150; (2) a set of arrow keys 160 for scrolling between menu items; and (3) a set of four soft function keys 162, which, depending on the menu item displayed, may be assigned "cont," "accept," "menu," "return," "cancel," "previous," "next," "back," "yes," "no," "print," or "done" functions, which appear at the bottom of the display screen 152 for viewing by the administrator/operator.

Specifically, depression of the following soft function keys 162 will provide the following functions: (1) "cont" will accept a selected menu item (highlighted by manipulation of the arrow keys 160) and take the user to the next screen or menu; (2) "accept" will accept the properly entered information and take the user to the next screen or menu; (3)

"menu" will take the user back to the main menu if in the test mode or the administration menu if in the administration mode; (4) "return" will return the user to the next higher level menu; (5) "cancel" will place the system in cancel mode; (6) "previous" will take the user to a previous same level menu or screen; (7) "next" will take the user to the next same level menu or screen; (8) "back" will return the user to a previously selected same level menu or screen; (9) "yes" will give an affirmative answer to a posed question and take the user to the next menu or screen; (10) "no" will give a negative answer to a posed question and take the user to the next menu or screen; (11) "print" will print test results; and (12) "done" will be return the user to the main menu. The CPU 204 is programmed to implement the menu-driven user interface 150.

XII. System and User Level Operation

Figure 102:
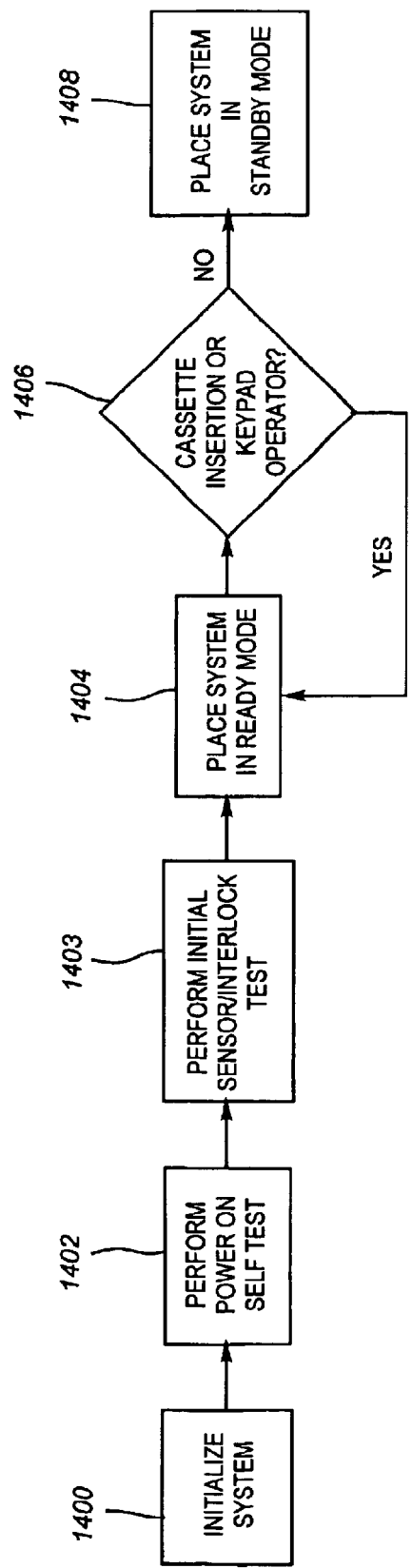
FIG. 102 is a flow diagram illustrating the initialization process of the system.

Having described the detailed structure and operation of the assemblies of the system 100, the overall operation of the system 100 will now be described. Referring to FIG. 102, the system 100 runs through a battery of tests and monitoring processes. The system 100 is first initialized at action block 1400, e.g., immediately upon power-up (cold-start), or after any interruption of normal operations or system reset (warm-start). During system initialization, the CPU 204 performs an initialization process in which all software variable parameters are initialized, including counters and pointers to data tables, with values necessary for correction operation of the software. The core BIOS provides the initialization of all hardware resources and provides a flag to the power on self-test that the initialization process has occurred satisfactorily.

At action block 1402, the CPU 204 performs a power on self-test during which the various assemblies are tested to determine that the test console 102 is capable of performing the desired functions for its correct operation. Any failure of a assembly component causes a QC message to indicate the type of failure and not allow the operator to run a test. Immediately following successful completion of the power on self-test, the CPU 204, at action block 1404, performs an initial sensor/interlock test during which all of the sensors will be read by the CPU 204 for proper initial state/operation.

Following the completion of the foregoing tests, the system 100 is placed into a Ready mode at action block 1408 during which all assemblies are fully powered and chemical testing can be initiated immediately upon insertion of a cassette 152 into the cassette port 106 on the front of the test console 102. If no cassette insertion or keypad or keyboard operation is sensed within a predetermined period of time (decision block 1406), e.g., 5 minutes, the CPU 204 will place the system 100 into Standby mode (action block 1408) during which only the cassette port 106 and the keypad/keyboard ports are power on. Insertion of the chemistry cassette 152 or pressing any key on the keypad or keyboard will cause the CPU 204 to place the system 100 back into Ready mode (action block 1404).

When the system 100 is placed into Ready or Standby mode, the CPU 204 continuously monitors power supply voltages and sensor/interlock functions for satisfactory operation. A fault in any of the power supply voltages and sensor/interlock functions generates a fault condition, which generates an error flag on the display screen 152 and halts any further analytical operation of the test console 102 until the fault condition has been cleared. Any error flags indicative of faults in the system 100 are permanently logged into the nonvolatile memory of the reader device. Further, during idle operation time, the test console 102 will periodically perform a diagnostic self test to determine proper function of the various assemblies and certify the system's ability to conduct the testing functions. In the event that a new cassette 152 is inserted into the test console 102, any diagnostic self-test currently underway will be cancelled, and the test console 102 will then immediately return to its normal Ready (analytical) mode of operation.

Figure 103B:
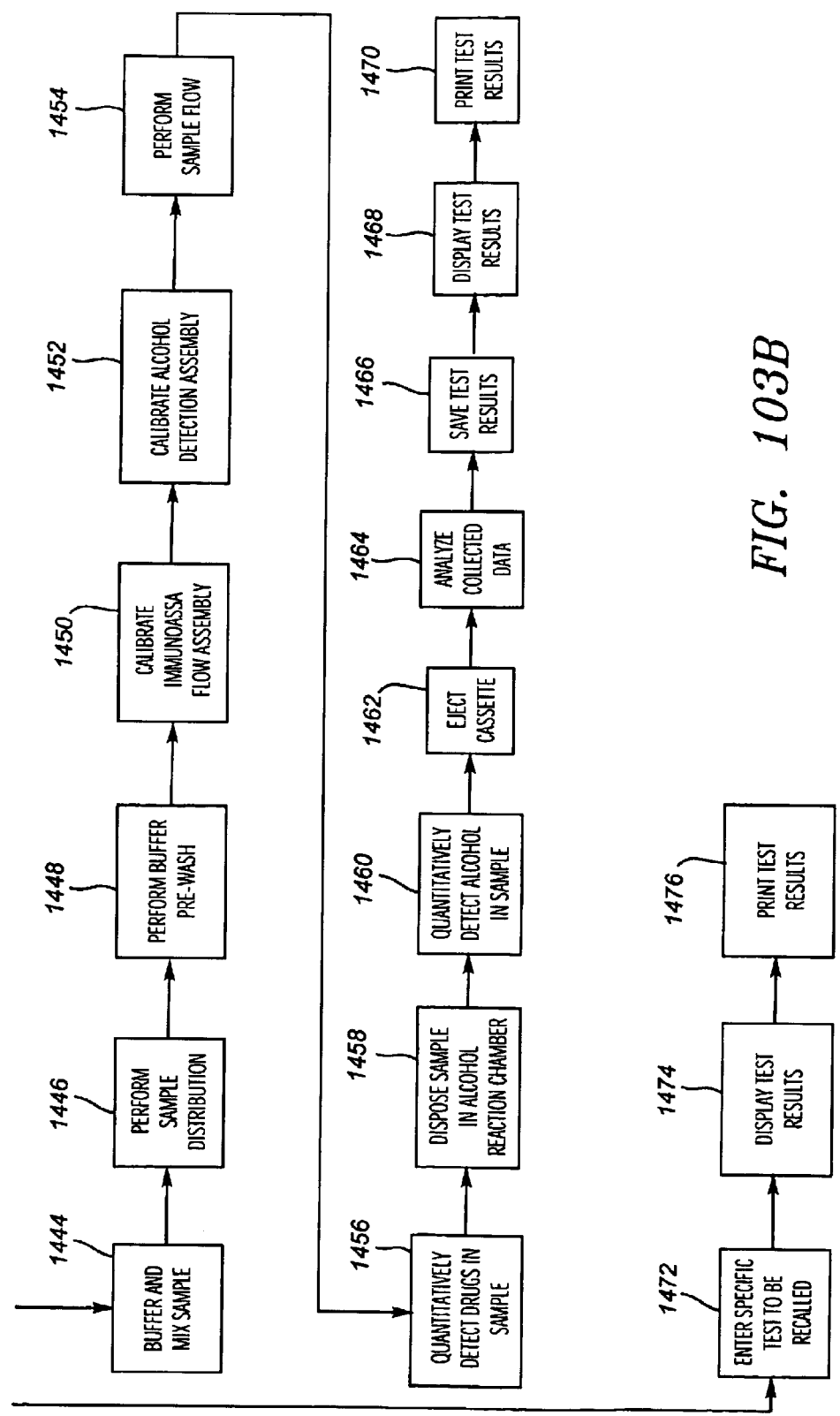
FIG. 103 is a flow diagram illustrating the administration, operation, and recall modes of the system.

Referring now to FIG. 103, once the system 100 has been powered on and has run through various initialization tests, the administrator/operator is given the option to place the system 100 in an administrative mode, an operation mode, and a recall mode (action block 1410). In the administration mode, an authorized administrator may define the operational parameters of the system 100, e.g., record specific operator and facility information, customize test panels, change the test parameters, setup display and printer options, etc. In the operation mode, an authorized operator may input test subject information and conduct tests using the system 100, but may not alter predefined parameters that change the function of the system 100 (which can only be accomplished by the administrator). In the recall mode, an authorized operator may recall previously performed and stored tests along with corresponding subject information.

If at action block 1410, the user selects the "Administrative Mode," the system 100 first prompts the operator/administrator for his or her user name and password (action block 1412). Thus, only authorized administrators can modify the operational parameters of the system 100. Upon entry of his or her correct user name and password, the system 100 is prompted to select a specific language (e.g., English, Spanish, French, and German) that the operator will use to communicate with the system 100 (action block 1414). In alternative embodiments, the specific language will not be selectable, but rather will default to the language of the country in which the system 100 is ultimately shipped. Upon selection of the language, the system 100 prompts the administrator to select the type of administration information (e.g., facility information, general setup information, date/time information, authorized operator, test panel, units/threshold, and output option information) to be programmed into the system 100 (action block 1416).

Specifically, selection of the "Facility" choice prompts the administrator to enter facility specific information, such as the name and location of the facility where the test is being run, as well as any comments. Selection of the "General Setup" choice prompts the administrator to input general setup information, such as whether an operator password and/or subject identification information is required. For example, if test results are to be used as evidentiary purposes, e.g., at a police station or workplace, the administrator would likely require an operator password and subject information to be entered. If, on the other hand, the test results are to be used merely to determine the state of the test subject, e.g., in an emergency hospital room, the administrator would likely not require an operator password and subject information to be entered. The administrator may also select whether an operator must enter the operator password/subject identification at the beginning of every test. Selection of the "Date/Time" choice prompts the administrator to enter date/time information, such as the current date, time, and daylight savings information.

Selection of the "Authorized Operator" choice prompts the administrator to further select the operators authorized to operate the system 100. Specifically, the administrator may add an operator to a list of those authorized to operate the system 100 by entering an operator user ID and associated password that is to be assigned to the added operator. The administrator may select whether the added operator also has administrative privileges, i.e., whether the operator can modify the administrative parameters of the system 100. The administrator may also remove an operator from the authorization list.

Selection of the "Test Panel" choice prompts the administrator to further select the specific tests that are to be run within each of a multitude of specific test panels. Thus, the system 100 allows the administrator to customize test panels that are to be run on the system 100. These test panels can be preprogrammed into the system 100, but ultimately can be modified by the administrator. For example, the administrator may customize the test panels to a workplace environment. Here, the workplace test panels may include, e.g., pre-employment, post-accident, random, or reasonable cause (the name of which has been preprogrammed or typed in by the administrator), as well as custom tests. It should be noted, however, that the system 100 can be customized to other scenarios besides the workplace, e.g., at a police station or hospital emergency room. Selection of one of the test panels, whether it be specifically named or one the custom test panels, allows the administrator to select the specific drugs that are to be tested for the selected test panel.

Selection of the "Units/Threshold" prompts the administrator to input unit and threshold information for each of the list of specific tests that can be run on the system 100. Selection of the "Output Option" prompts the administrator to further select how the test results will be exhibited and stored. For example, the administrator may select the type of data that will be displayed as the test results, e.g., quantitative, threshold level, interpretative, or no display at all. Likewise, the administrator may select the type of data that will be printed as the test results, e.g., quantitative, threshold level, or interpretative. Additionally, the administrator may select other types of information to be printed, e.g., operator signature line, subject signature line, select the number of copies to be printed; and the specific printer that will be used to print the test results, e.g., internal printer, parallel printer, or serial printer. The administrator may also select if the test results will be saved internally within the system 100 or externally to, e.g., another computer via an RS232 port If at action block 1410, the user selects the "Operation Mode," the operator, if previously required by the administrator, enters an operator ID and password, as well as the subject name and ID (action block 1420). Upon correct entry of this information, the operator selects one of the specific test panels to be run on the system 100 (action block 1422). If the operator only desires to collect a sample for subsequent testing at a laboratory, the operator will select a confirmatory test. Once a test panel, if any, has been selected, the chemistry cassette 152 is loaded into the test console 102 (action block 1424) (See Section II). By virtue of the loading action of the chemistry cassette 152, the buffer drive assembly 1102 is operated to hydrate the dry reagent within the alcohol reagent chamber 1006 of the alcohol reaction assembly 1002, producing and dispensing the alcohol reagent solution within the alcohol reaction chamber 1004 of the alcohol reaction assembly 1002 (action block 1426) (Section VIII.D). All of the drive assemblies are then placed into their home position (action block 1428). Once the chemistry cassette 152 has been loaded, it is brought from its ambient temperature (10–40° C.) to the optimum operating temperature (37° C.) (action block 1430) (See Section IX). At the same time, the system 100 determines if the chemistry cassette 152 has been previously used (decision block 1432). If the chemistry cassette 152 has been previously used, the cassette loading assembly 300 is operated to eject the chemistry cassette 152 from the test console 102, and the system 100, via the user interface 150, informs the operator that the chemistry cassette 152 has been previously used and to load another chemistry cassette 152 (action block 1434). If the chemistry cassette 152 has not been previously used, the system 100 customizes the operational parameters of the test console 102 to the specific chemistry cassette 152 and calibrates the test panel (action block 1436) (See Section III).

The sample collection assembly 400 is then operated to collect the saliva sample from the test subject (action block 1438) (See Section IV.C). The system 100 determines whether the cassette is a confirmation cassette (decision block 1440). If it is, the confirmation cassette is ejected and processed accordingly (action block 1442). It should be noted that if the cassette is a confirmation cassette, action block 1426 will not have been completed since there is no test to be run. If the cassette is not a confirmation cassette, the sample is buffered and mixed at action block 1444 (See Section V.C). The sample collection assembly 400 is then operated to dispense the sample into the flow immunoassay assembly 600, and specifically, to distribute the sample amongst the multitude of immunoassay flow paths within the sample distribution chambers 612, i.e., the sample distribution is performed (action block 1446) (See Section VI.C). Simultaneous with the sample distribution, the sample/buffer flow assembly 602 of the immunoassay flow assembly 600, and specifically, the buffer drive assemblies 576, is operated to flow the buffer through the immunoassay flow paths to prepare the immunoassay reaction chambers 616, i.e., the buffer pre-wash is performed (action block 1448) (See Section VI.C). During the buffer pre-wash, the optical flow immunoassay scanning assembly 900 is operated to calibrate the immunoassay flow paths (action block 1450) (See Section VII.D). During the buffer pre-wash, the alcohol detection assembly 1000 is also calibrated by (1) operating the alcohol reader assembly 1004 to measure the absorbance of the alcohol reagent solution previously dispensed within the alcohol reaction chamber 1004; (2) operating the alcohol reaction assembly 1002 to dispense the calibrator solution into the alcohol reaction chamber 1004 to react with the alcohol reagent solution and produce the alcohol detectable calibrator solution; and (3) operating the alcohol reader assembly 1004 again to measure the absorbance of the alcohol detection calibrator solution (action block 1452) (See Section VIII.D). The sample/buffer flow assembly 602 of the immunoassay flow assembly 600, and specifically, the sample drive assemblies 574, is then operated to flow the sample through the immunoassay flow paths to react within the immunoassay reaction chambers 616, i.e., the sample flow is performed (action block 1454) (See Section VI.C). During sample flow, the optical flow immunoassay scanning assembly 900 is operated to quantitatively detect the presence of any drug analytes within the sample (action block 1456) (See Section VII.D). During sample flow, the vent/air flow assembly 1016 of the alcohol reaction assembly 1002 is also operated to dispense the sample within the alcohol reaction chamber 1004 to react with the alcohol reagent solution, thereby producing the alcohol detectable sample solution (action block 1458) (See Section VIII.D). The alcohol reader assembly 1004 is then operated to quantitatively detect the presence of alcohol within the sample (action block 1460) (See Section VIII.D).

Once the test is complete, the cassette loading assembly 300 is operated to eject the chemistry cassette 152 from the test console 102, which is then discarded (action block 1462). The system 100 then analyzes the collected data (action block 1464), saves the results (action block 1466), and then displays the results of the test (action block 1468), and optionally, the operator prints the results (action block 1470).

If at action block 1410, the user selects the "Recall Mode," the user enters the specific test to be recalled (action block 1472), and the system 100 displays the results of the recalled test (action block 1474), and optionally, prints the results (action block 1476).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims. All publications, patents, and patent applications cited herein are hereby incorporated by reference in their entirety for all purposes.

What is claimed:

1. A sample collection assembly for collecting a sample from a mouth, comprising: a sample collection body configured for being placed within said mouth, said sample collection body having an outer surface and an inner surface; a bore and one or more pores; and a conduit disposed within said bore in fluid communication with said one or more pores; and wherein the outer surface of said sample collection body is hydrophilic and the inner surface of said sample collection body is hydrophobic.

2. The sample collection assembly of claim 1, wherein said conduit is bonded within said bore.

3. The sample collection assembly of claim 1, further comprising a hand piece having a tip on which said sample collection body is mounted.

4. The sample collection assembly of claim 3, wherein said sample collection body comprises a rear surface that is bonded to a front surface of said hand piece tip.

5. The sample collection assembly of claim 3, wherein said conduit extends through said hand piece.

6. The sample collection assembly of claim 1, wherein said conduit is flexible.

7. The sample collection assembly of claim 1, wherein said one or more pores comprises a plurality of pores.

8. The sample collection assembly of claim 1, wherein said one or more pores comprises a plurality of micropores.

9. The sample collection assembly of claim 8, wherein said plurality of micropores have a pore size of 135 $\mu$m or less.

10. The sample collection assembly of claim 1, wherein said hydrophobic sample collection body comprises high density polyethylene.

11. The sample collection assembly of claim 1, wherein said sample collection body is hemi-dome shaped.

12. A sample collection assembly for collecting a sample from a mouth; comprising: a sample collection body configured for being placed within said mouth, said sample collection body having an outer surface and an inner surface; a bore and one or more pores; and a conduit bonded within said bore in fluid communication with said one or more pores, wherein an adhesive force between said conduit and said bore is greater than a cohesive force of said sample collection body; and wherein the outer surface of said sample collection body is hydrophilic and the inner surface of said sample collection body is hydrophobic.

13. The sample collection assembly of claim 12, further comprising a hand piece having a tip on which said sample collection body is mounted, wherein said sample collection body comprises a rear surface that is bonded to a front surface of said hand piece tip, and an adhesive force between said rear surface of said sample collection body and said front surface of said hand piece tip.

14. The sample collection assembly of claim 13, wherein said conduit extends through said hand piece.

15. The sample collection assembly of claim 12, wherein said conduit is flexible.

16. The sample collection assembly of claim 12, wherein said one or more pores comprises a plurality of pores.

17. The sample collection assembly of claim 12, wherein said one or more pores comprises a plurality of micropores.

18. The sample collection assembly of claim 17, wherein said plurality of micropores have a pore size of 135 $\mu$m or less.

19. The sample collection assembly of claim 12, wherein said hydrophobic sample collection body comprises high density polyethylene.

20. The sample collection assembly of claim 1, wherein said sample collection body is hemi-dome shaped.

21. A sample collection assembly for collecting a sample from a mouth, comprising: a sample collection body configured for being placed within said mouth, said sample collection body having an outer surface and an inner surface; a bore and one or more pores; a sample collection chamber; a conduit in fluid communication between said one or more pores of said sample collection tip and said sample collection chamber; and a pump configured to pump sample from said one or more pores of said sample collection body, through said conduit, and into said sample collection chamber; and wherein the outer surface of said sample collection body is hydrophilic and the inner surface of said sample collection body is hydrophobic.

22. The sample collection assembly of claim 21, wherein said conduit is bonded within said bore, wherein an adhesive force between said conduit and said bore is greater than a cohesive force of said sample collection body.

23. The sample collection assembly of claim 21, further comprising a hand piece having a tip on which said sample collection body is mounted, wherein said sample collection body comprises a rear surface that is bonded to a front surface of said hand piece tip, and an adhesive force between said rear surface of said sample collection body and said front surface of said hand piece tip.

24. The sample collection assembly of claim 23, wherein said conduit extends through said hand piece.

25. The sample collection assembly of claim 21, wherein said conduit is flexible.

26. The sample collection assembly of claim 21, wherein said one or more pores comprises a plurality of pores.

27. The sample collection assembly of claim 21, wherein said one or more pores comprises a plurality of micropores.

28. The sample collection assembly of claim 27, wherein said plurality of micropores have a pore size of 135 $\mu$m or less.

29. The sample collection assembly of claim 21, wherein said hydrophobic sample collection body comprises high density polyethylene.

30. The sample collection assembly of claim 21, wherein said sample collection body is hemi-dome shaped.

* * * * *